(12) United States Patent
Lee et al.

(10) Patent No.: US 12,219,869 B2
(45) Date of Patent: Feb. 4, 2025

(54) COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Seungjae Lee, Suwon-si (KR); Seonyeong Gwak, Suwon-si (KR); Jinhyun Lui, Suwon-si (KR); Chang Ju Shin, Suwon-si (KR); Jongwoo Won, Suwon-si (KR); Youngkyoung Jo, Suwon-si (KR); Hyung Sun Kim, Suwon-si (KR); Hyungyu Lee, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 734 days.

(21) Appl. No.: 17/512,856

(22) Filed: Oct. 28, 2021

(65) Prior Publication Data
US 2022/0140253 A1  May 5, 2022

(30) Foreign Application Priority Data
Nov. 3, 2020  (KR) .................. 10-2020-0145349

(51) Int. Cl.
*H01L 51/50* (2006.01)
*C07D 491/048* (2006.01)
(Continued)

(52) U.S. Cl.
CPC ....... *H10K 85/657* (2023.02); *C07D 491/048* (2013.01); *C09K 11/02* (2013.01);
(Continued)

(58) Field of Classification Search
None
See application file for complete search history.

(56) References Cited

U.S. PATENT DOCUMENTS

| 5,061,569 A | 10/1991 | VanSlyke et al. |
| 2012/0126208 A1 | 5/2012 | Kawamura et al. |

(Continued)

FOREIGN PATENT DOCUMENTS

| CN | 106068261 A | 11/2016 |
| CN | 106133113 A | 11/2016 |

(Continued)

OTHER PUBLICATIONS

Chinese Office Action (including a search report) dated May 23, 2023, of the corresponding Chinese Patent Application No. 202111289394.3.

(Continued)

*Primary Examiner* — Gregory D Clark
(74) *Attorney, Agent, or Firm* — Lee IP Law, P.C.

(57) ABSTRACT

A composition for an organic optoelectronic device, an organic optoelectronic device including the same, and a display device, the composition including a first compound represented by Chemical Formula 1, and a second compound represented by Chemical Formula 2; or a combination of Chemical Formula 3 and Chemical Formula 4, (Continued)

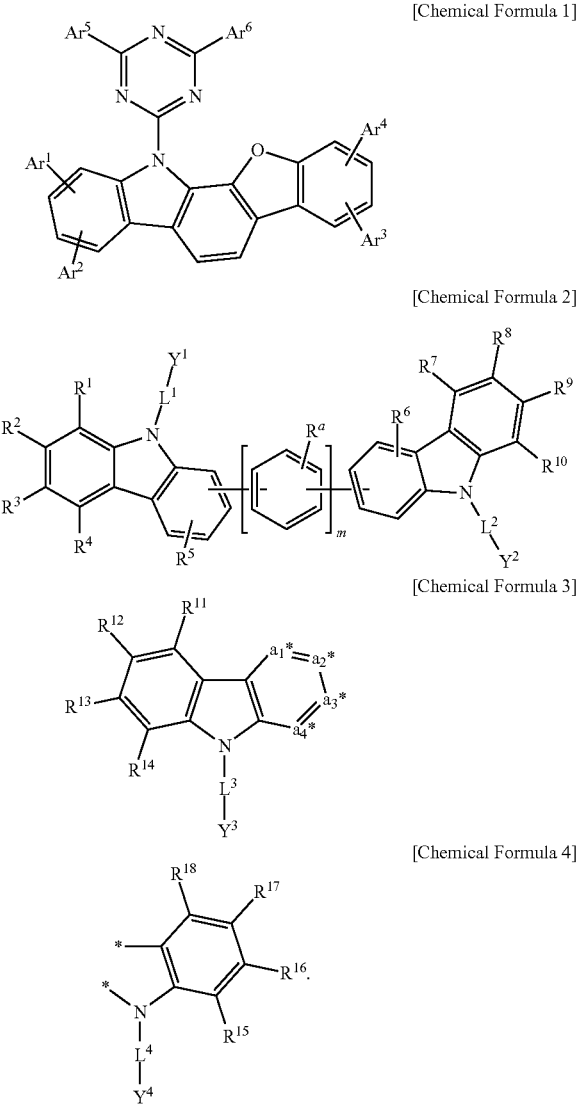

[Chemical Formula 1]

[Chemical Formula 2]

[Chemical Formula 3]

[Chemical Formula 4]

11 Claims, 2 Drawing Sheets

(51) Int. Cl.
C09K 11/02 (2006.01)
C09K 11/06 (2006.01)
H10K 85/60 (2023.01)
H10K 50/11 (2023.01)
H10K 101/00 (2023.01)
H10K 101/10 (2023.01)

(52) U.S. Cl.
CPC ............ *C09K 11/06* (2013.01); *H10K 85/654* (2023.02); *C09K 2211/1007* (2013.01); *C09K 2211/1029* (2013.01); *C09K 2211/185* (2013.01); *H10K 50/11* (2023.02); *H10K 2101/10* (2023.02); *H10K 2101/90* (2023.02)

(56) References Cited

U.S. PATENT DOCUMENTS

| | | |
|---|---|---|
| 2014/0332793 A1 | 11/2014 | Park et al. |
| 2015/0053938 A1 | 2/2015 | Zeng et al. |
| 2016/0351822 A1 | 12/2016 | Lee et al. |
| 2017/0117488 A1 | 4/2017 | Ahn et al. |
| 2017/0141323 A1 | 5/2017 | Miyazaki et al. |
| 2018/0047914 A1* | 2/2018 | Cha ........................ C09K 11/06 |
| 2020/0144512 A1 | 5/2020 | Lin et al. |

FOREIGN PATENT DOCUMENTS

| | | |
|---|---|---|
| CN | 106232772 A | 12/2016 |
| CN | 106661041 A | 5/2017 |
| CN | 107428769 A | 12/2017 |
| CN | 110016059 A | 7/2019 |
| CN | 110364632 A | 10/2019 |
| CN | 110713482 A | 1/2020 |
| CN | 111377931 A | 7/2020 |
| CN | 113429413 A | 9/2021 |
| CN | 115244724 A | 10/2022 |
| JP | 1993-009471 A | 1/1993 |
| JP | 1995-126615 A | 5/1995 |
| JP | 1998-095973 A | 4/1998 |
| JP | 2013-026529 A | 2/2013 |
| KR | 10-2011-0021487 A | 3/2011 |
| KR | 10-2013-0084963 A | 7/2013 |
| KR | 10-2014-0067914 A | 6/2014 |
| KR | 10-1498278 B1 | 2/2015 |
| KR | 10-1502316 B1 | 3/2015 |
| KR | 10-2015-0116776 A | 10/2015 |
| KR | 10-2016-0061292 A | 5/2016 |
| KR | 10-1754715 B1 | 7/2017 |
| KR | 10-1773363 B1 | 8/2017 |
| KR | 10-2018-0099436 A | 9/2018 |
| KR | 10-2019-0064251 A | 6/2019 |
| KR | 10-2019-0110775 A | 10/2019 |
| KR | 10-2019-0134301 A | 12/2019 |
| KR | 10-2020-0002020 A | 1/2020 |
| KR | 10-2020-0088772 A | 7/2020 |
| KR | 10-2022-0005388 A | 1/2022 |
| TW | 202026290 A | 7/2020 |
| WO | WO 1995/009147 A1 | 4/1995 |
| WO | WO 2017/034303 A1 | 3/2017 |
| WO | WO 2020/032424 A1 | 2/2020 |
| WO | WO 2020/032447 A1 | 2/2020 |
| WO | WO 2020/130392 A1 | 6/2020 |

OTHER PUBLICATIONS

Taiwanese Search Report dated Dec. 27, 2022.
Korean Office Action dated Jan. 18, 2024, of the corresponding Korean Patent Application No. 10-2020-0145349.

* cited by examiner

COMPOSITION FOR ORGANIC OPTOELECTRONIC DEVICE, ORGANIC OPTOELECTRONIC DEVICE, AND DISPLAY DEVICE

CROSS-REFERENCE TO RELATED APPLICATION

This application claims priority to and the benefit of Korean Patent Application No. 10-2020-0145349 filed in the Korean Intellectual Property Office on Nov. 3, 2020, the entire contents of which are incorporated herein by reference.

BACKGROUND

1. Field

Embodiments relate to a composition for an organic optoelectronic device, an organic optoelectronic device, and a display device.

2. Description of the Related Art

An organic optoelectronic device (e.g., organic optoelectronic diode) is a device capable of converting electrical energy and optical energy to each other.

Organic optoelectronic devices may be divided into two types according to a principle of operation. One is a photoelectric device that generates electrical energy by separating excitons formed by light energy into electrons and holes, and transferring the electrons and holes to different electrodes, respectively and another is a light emitting device that generates light energy from electrical energy by supplying voltage or current to the electrodes.

Examples of the organic optoelectronic device include an organic photoelectric device, an organic light emitting diode, an organic solar cell, and an organic photoconductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode may be influenced by an organic material between electrodes.

SUMMARY

The embodiments may be realized by providing a composition for an organic optoelectronic device, the composition including a first compound represented by Chemical Formula 1, and a second compound represented by Chemical Formula 2; or a combination of Chemical Formula 3 and Chemical Formula 4,

[Chemical Formula 1]

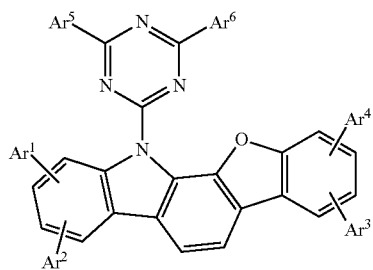

wherein, in Chemical Formula 1, $Ar^1$ to $Ar^4$ are each independently hydrogen, deuterium, or a substituted or unsubstituted C6 to C18 aryl group, at least one of $Ar^1$ to $Ar^4$ being a substituted or unsubstituted C6 to C18 aryl group, and $Ar^5$ and $Ar^6$ are each independently a substituted or unsubstituted C6 to C30 aryl group;

[Chemical Formula 2]

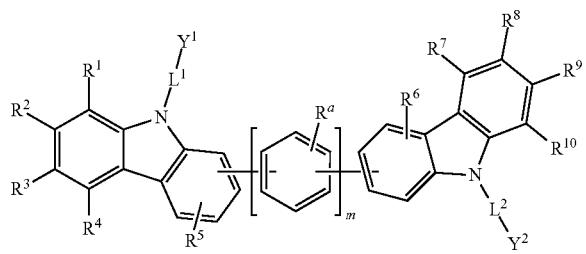

wherein, in Chemical Formula 2, $Y^1$ and $Y^2$ are each independently a substituted or unsubstituted C6 to C20 aryl group or a substituted or unsubstituted C2 to C30 heterocyclic group, $L^1$ and $L^2$ are each independently a single bond or a substituted or unsubstituted C6 to C20 arylene group, $R^a$ and $R^1$ to $R^{10}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group, and m is an integer of 0 to 2;

[Chemical Formula 3]

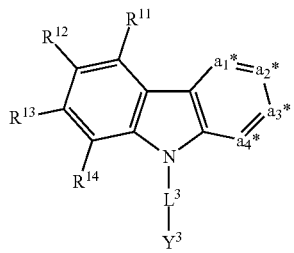

[Chemical Formula 4]

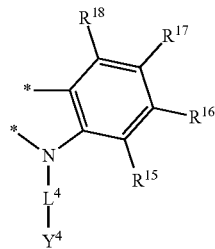

wherein, in Chemical Formulas 3 and 4, $Y^3$ and $Y^4$ are each independently a substituted or unsubstituted C6 to C20 aryl group or a substituted or unsubstituted C2 to C30 heterocyclic group, two adjacent ones of a1* to a4* of Chemical Formula 3 are linking carbons linked at * of Chemical Formula 4, the remaining two of a1* to a4* of Chemical Formula 3, not linked at * of Chemical Formula 4, are C-$L^a$-$R^b$, $L^a$, $L^3$ and $L^4$ are each independently a single bond or a substituted or unsubstituted C6 to C20 arylene group, and $R^b$ and $R^{11}$ to $R^{18}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

The embodiments may be realized by providing an organic optoelectronic device including an anode and a cathode facing each other, and at least one organic layer between the anode and the cathode, wherein the at least one organic layer includes the composition for an organic optoelectronic device according to an embodiment.

The embodiments may be realized by providing a display device including the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
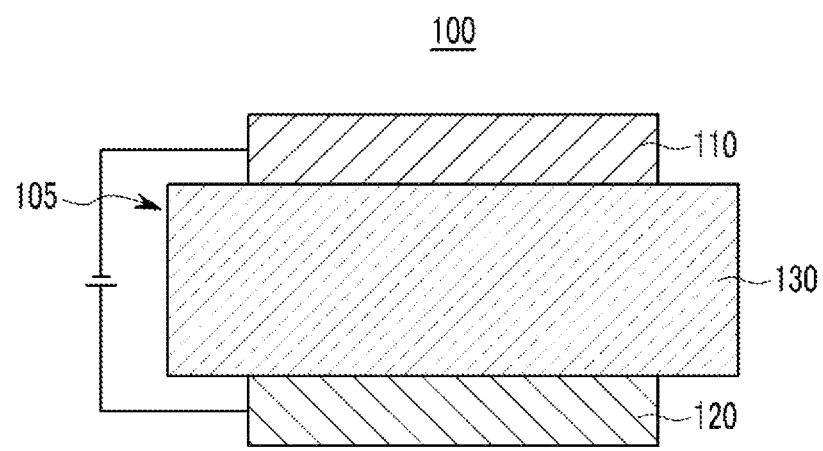
FIGS. 1 to 4 are cross-sectional views of organic light emitting diodes according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In a specific example, the "substituted" refers to replacement of at least one hydrogen of a substituent or a compound by deuterium, a C1 to C20 alkyl group, a C6 to C30 aryl group, or a cyano group. In a specific example, the "substituted" refers to replacement of at least one hydrogen of a substituent or a compound by deuterium, a C1 to C5 alkyl group, a C6 to C18 aryl group, or a cyano group. In a specific example, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group. As used herein, the term "or" is not an exclusive term, e.g., "A or B" would include A, B, or A and B.

As used herein, when a definition is not otherwise provided, "hetero" refers to one including one to three heteroatoms selected from N, O, S, P, and Si, and remaining carbons in one functional group.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (e.g., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

The compound for an organic optoelectronic device according to an embodiment may be represented by Chemical Formula 1.

[Chemical Formula 1]

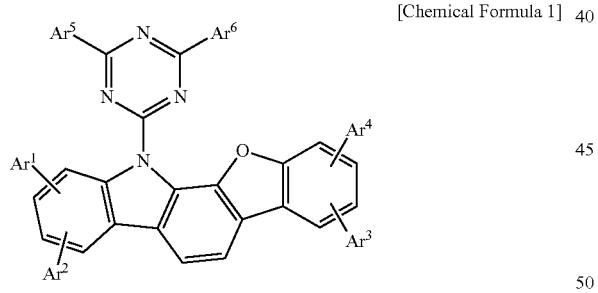

In Chemical Formula 1, $Ar^1$ to $Ar^4$ may each independently be or include, e.g., hydrogen, deuterium, or a substituted or unsubstituted C6 to C18 aryl group. In an implementation, at least one of $Ar^1$ to $Ar^4$ may be, e.g., a substituted or unsubstituted C6 to C18 aryl group.

$Ar^5$ and $Ar^6$ may each independently be or include, e.g., a substituted or unsubstituted C6 to C30 aryl group.

The compound represented by Chemical Formula 1 may have a structure in which a benzofuran moiety is fused at the 1st and 2nd (1- and 2-) positions of a carbazole moiety. In addition, the carbazole moiety is directly substituted with a triazine moiety on the N thereof.

In the compound represented by Chemical Formula 1, the benzofuran moiety may be fused at the 1st and 2nd positions of the carbazole, HOMO/LUMO partition separation may be clearly achieved, and a hole transport region may be expanded through an aryl group of at least one of $Ar^1$ to $Ar^4$, thereby increasing the device life-span and improving a driving voltage and efficiency.

In an implementation, Chemical Formula 1 may be represented by, e.g., one of Chemical Formula 1-1 to Chemical Formula 1-12.

[Chemical Formula 1-1]

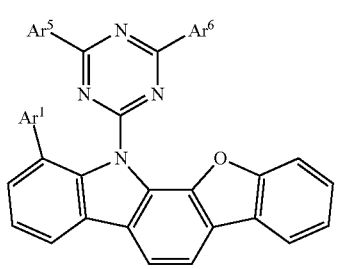

[Chemical Formula 1-2]

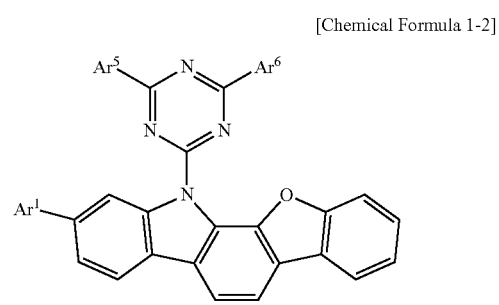

[Chemical Formula 1-3]

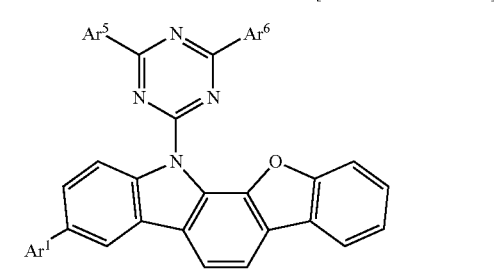

[Chemical Formula 1-4]

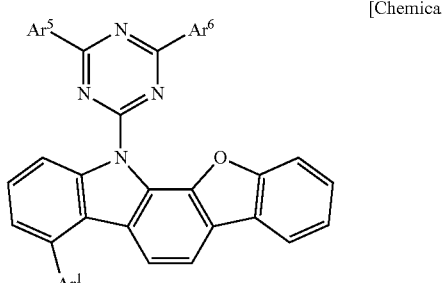

[Chemical Formula 1-5]

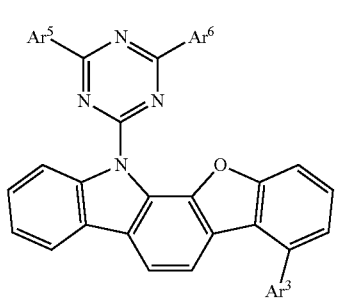

[Chemical Formula 1-6]

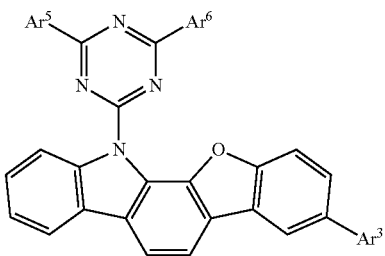

[Chemical Formula 1-7]

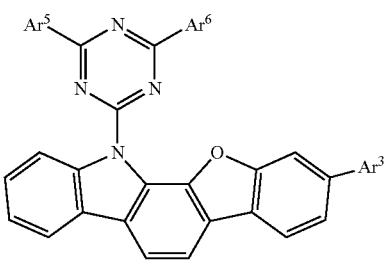

[Chemical Formula 1-8]

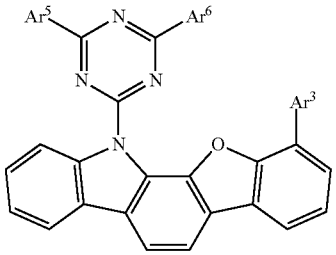

[Chemical Formula 1-9]

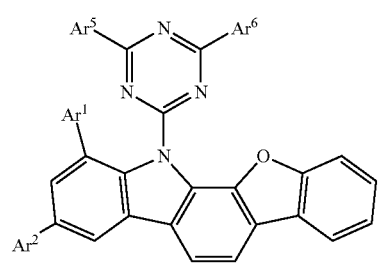

[Chemical Formula 1-10]

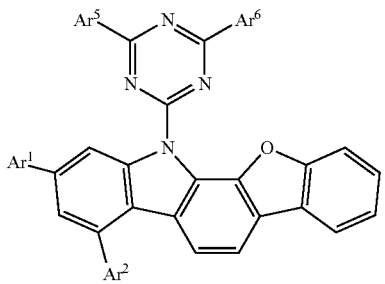

[Chemical Formula 1-11]

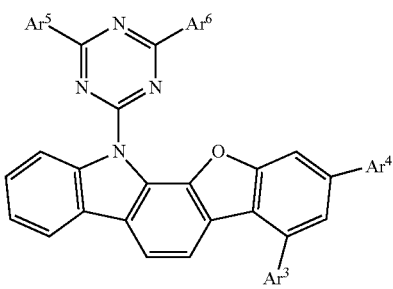

[Chemical Formula 1-12]

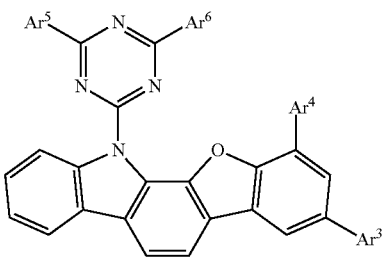

In Chemical Formula 1-1 to Chemical Formula 1-12, $Ar^1$ to $Ar^4$ may each independently be, e.g., a substituted or unsubstituted C6 to C18 aryl group. $Ar^5$ and $Ar^6$ may each independently be, e.g., a substituted or unsubstituted C6 to C30 aryl group.

In an implementation, Chemical Formula 1 may be represented by, e.g., Chemical Formula 1-2, Chemical Formula 1-3, Chemical Formula 1-8, or Chemical Formula 1-9.

In an implementation, at least one of $Ar^1$ to $Ar^4$ may be, e.g., a substituted or unsubstituted C6 to C12 aryl group.

In an implementation, at least one of $Ar^1$ to $Ar^4$ may be, e.g., a substituted or unsubstituted phenyl group or a substituted or unsubstituted biphenyl group.

In an implementation, $Ar^5$ and $Ar^6$ may each independently be, e.g., a substituted or unsubstituted phenyl group or a substituted or unsubstituted biphenyl group.

In an implementation, $Ar^5$ and $Ar^6$ may each independently be, e.g., a substituted or unsubstituted phenyl group, or $Ar^5$ and $Ar^6$ may each independently be, e.g., a substituted or unsubstituted phenyl group, or a substituted or unsubstituted biphenyl group. In an implementation, at least one of $Ar^5$ and $Ar^6$ may be, e.g., a substituted or unsubstituted biphenyl group.

In an implementation, moiety
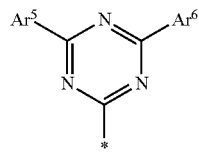
of Chemical Formula 1 may be, e.g., a moiety of Group I.
[Group I]
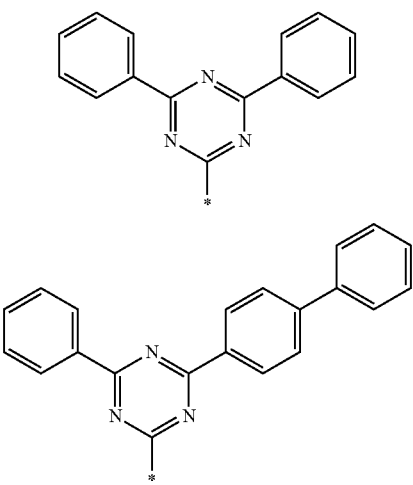
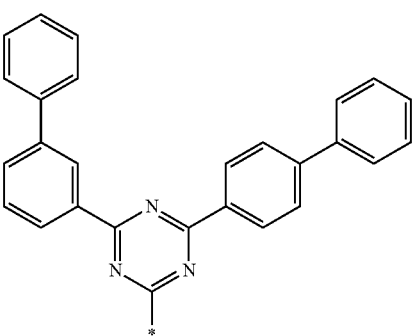
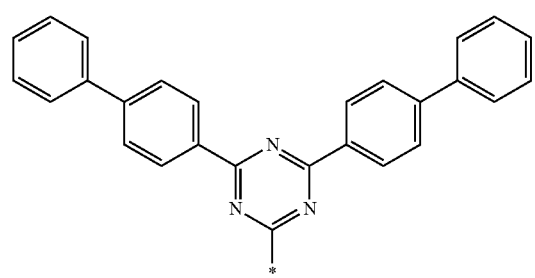
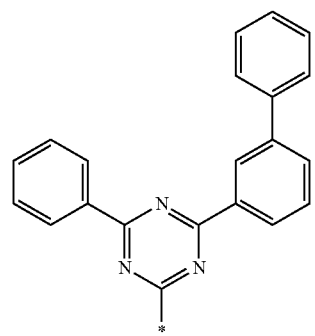
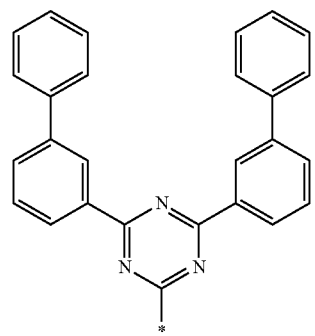
In Group I, * is a linking point (e.g., to N of the carbazole moiety).
In an implementation, the compound represented by Chemical Formula 1 may be, e.g., a compound of Group 1.
[Group 1]
[1]
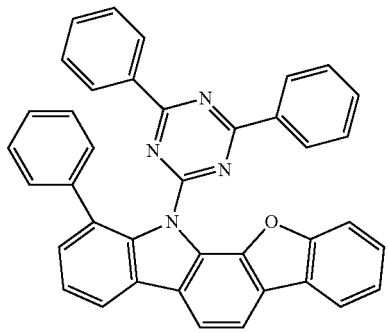
[2]
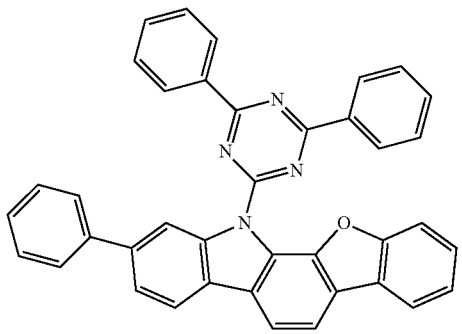

[3]
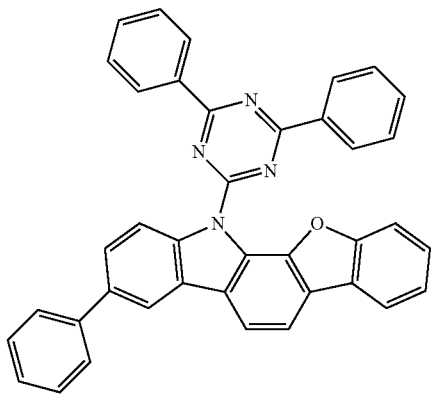
[4]
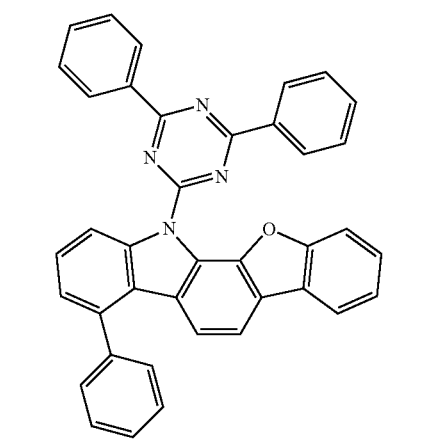
[5]
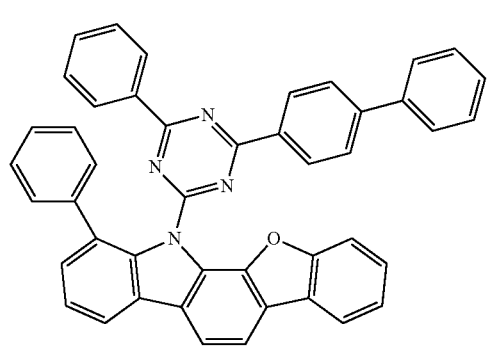
[6]
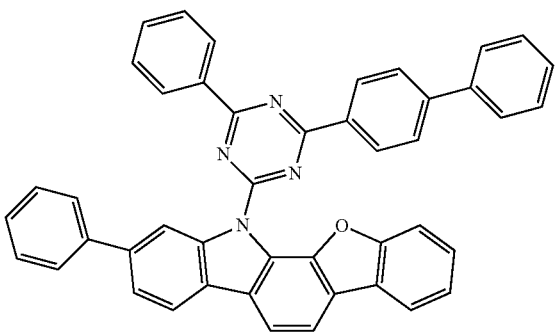
[7]
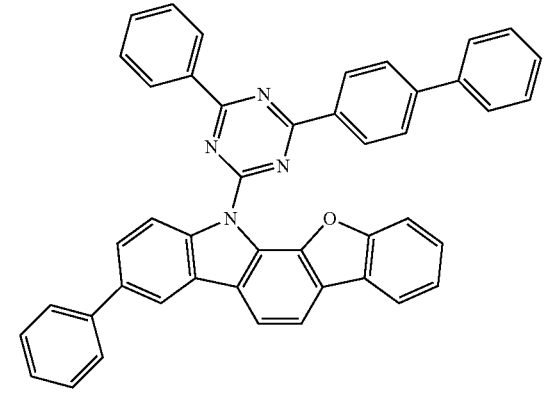
[8]
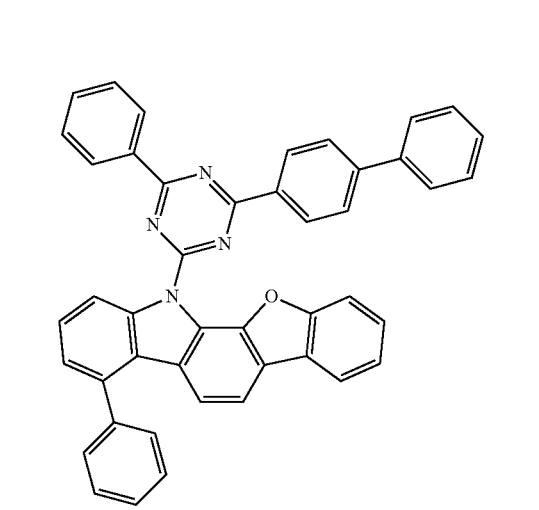
[9]
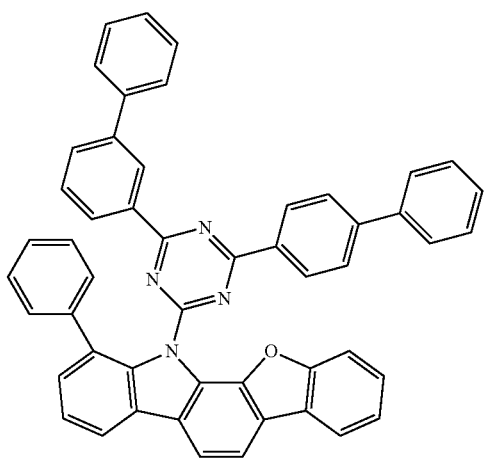

-continued
[10]
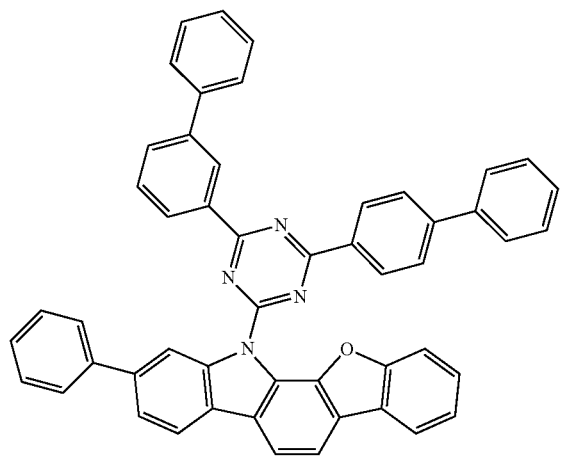
[11]
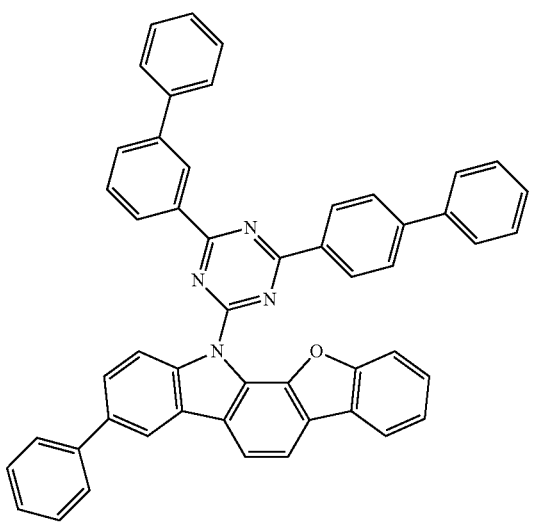
[12]
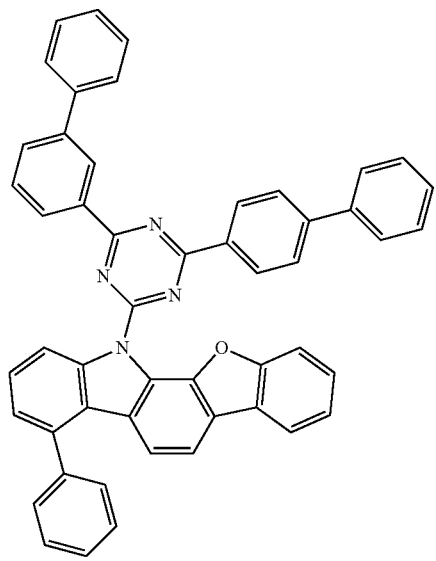
[13]
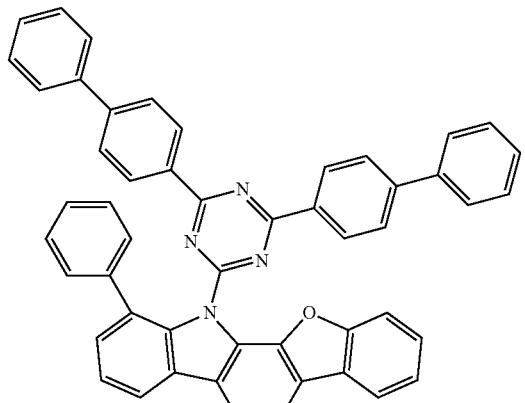
[14]
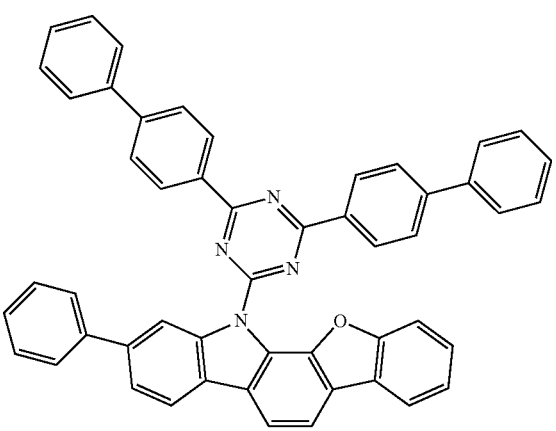
[15]
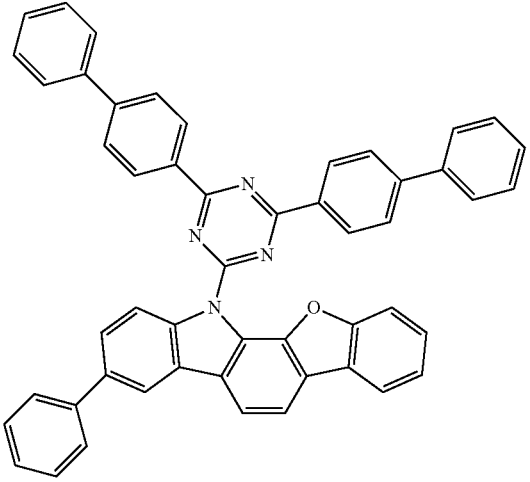

-continued
[16]
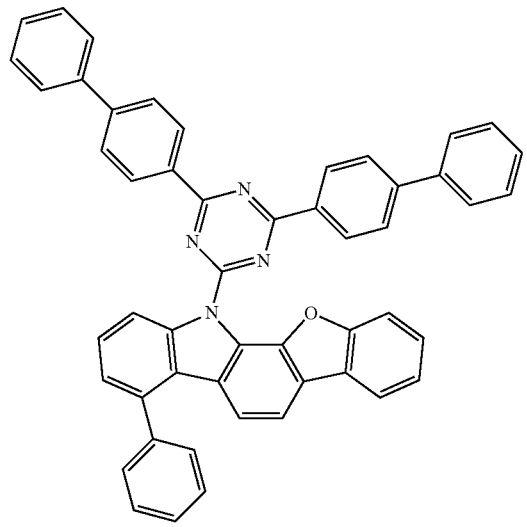
[17]
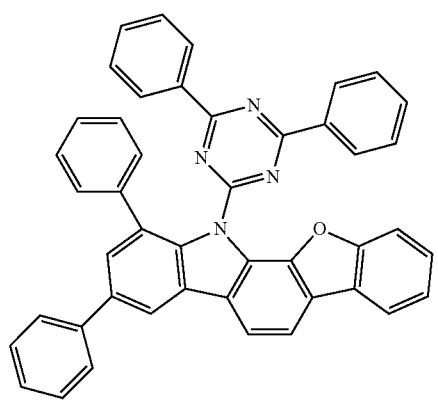
[18]
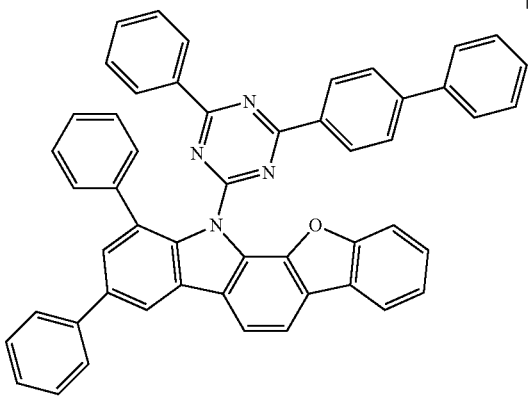
[19]
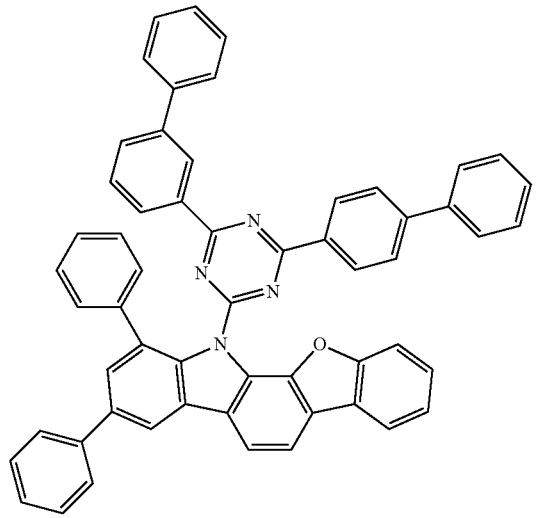
[20]
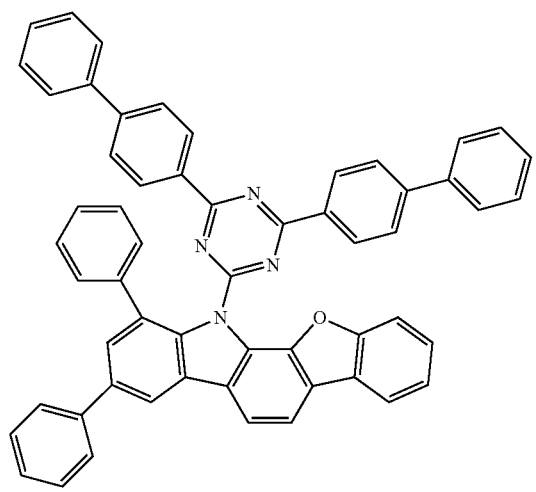
[21]
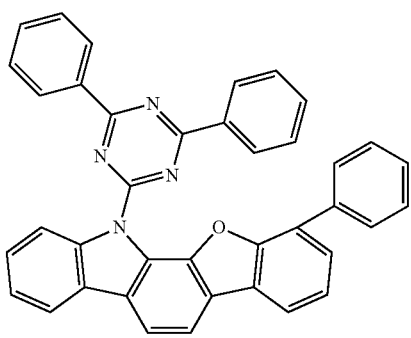

[22]
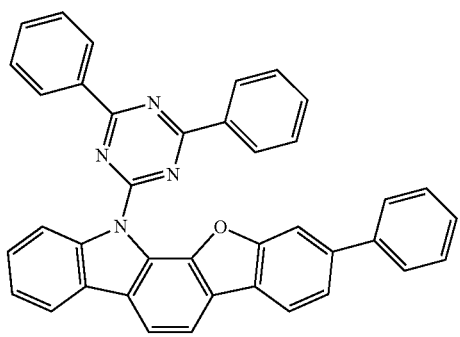
[23]
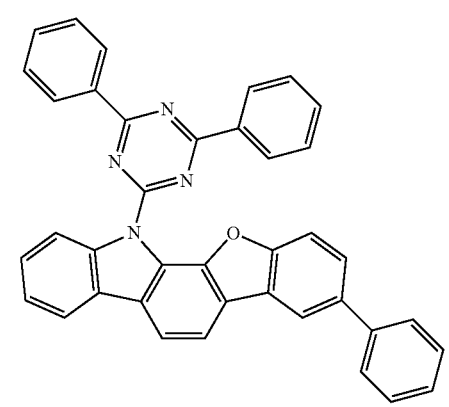
[24]
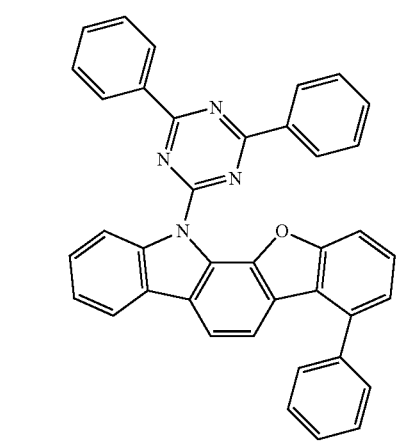
[25]
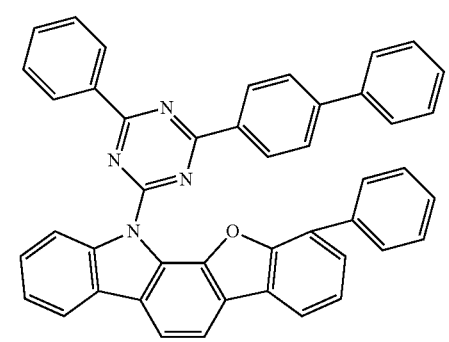
[26]
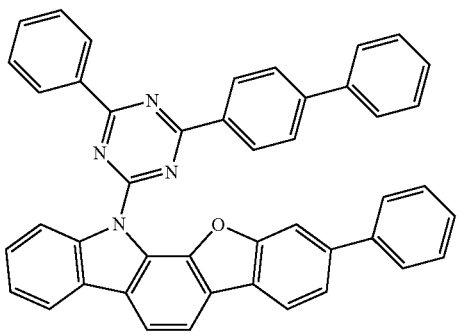
[27]
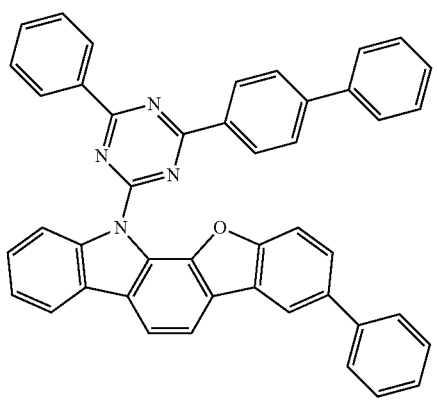
[28]
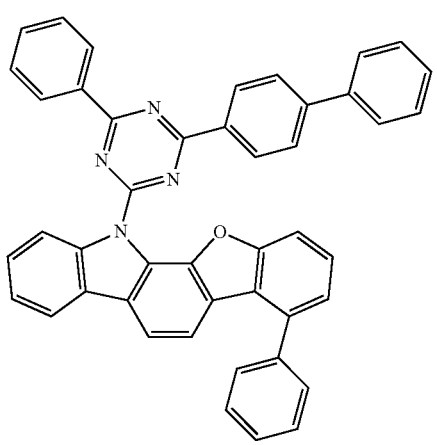
[29]
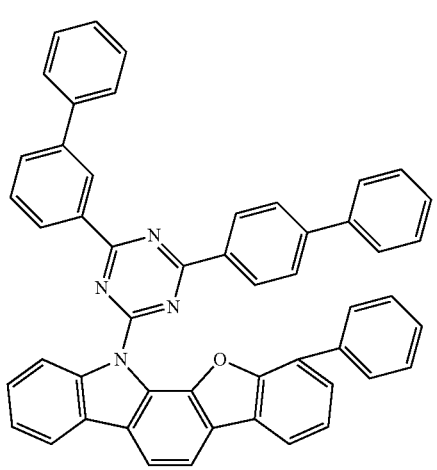

[30]
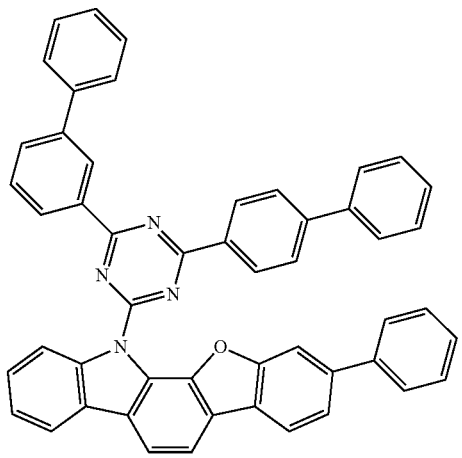
[31]
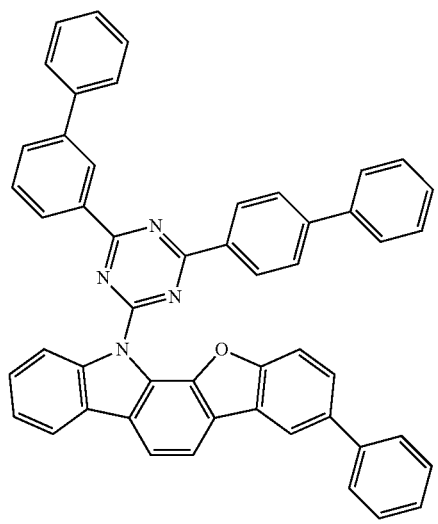
[32]
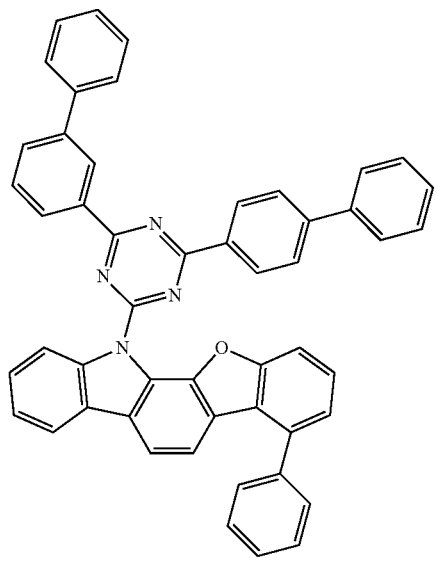
[33]
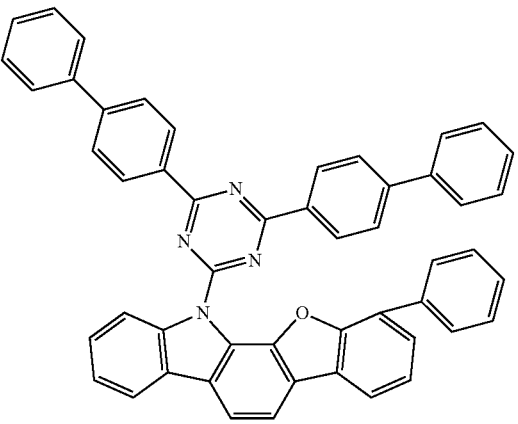
[34]
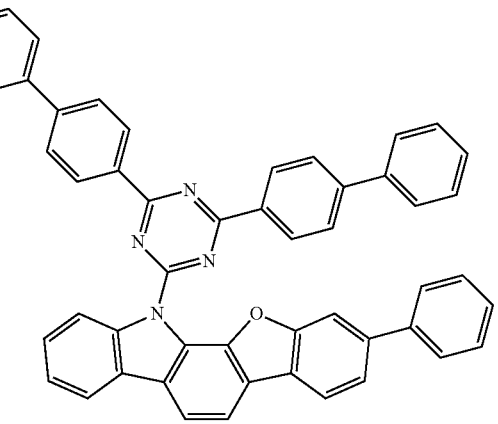
[35]
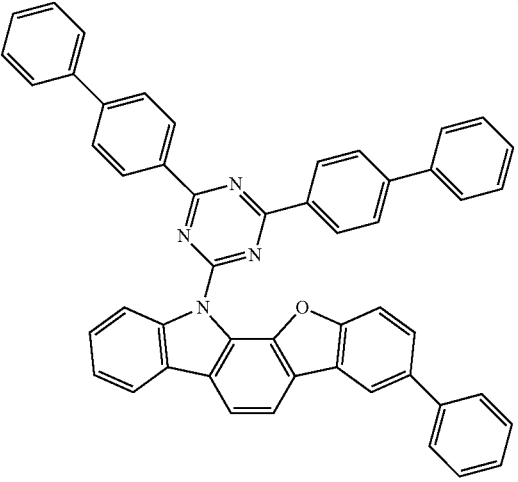

[36]
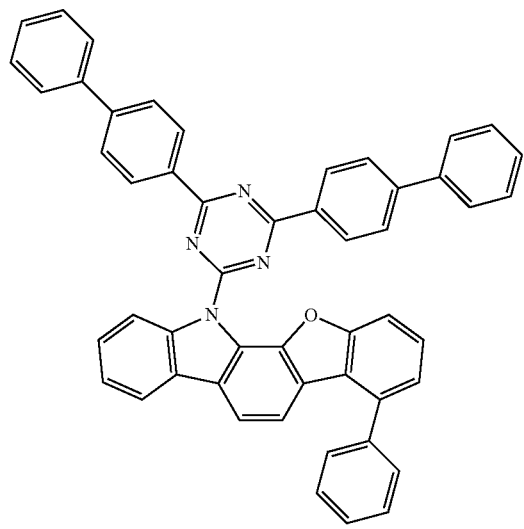
[37]
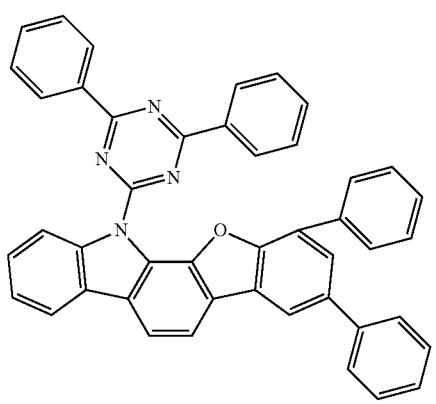
[38]
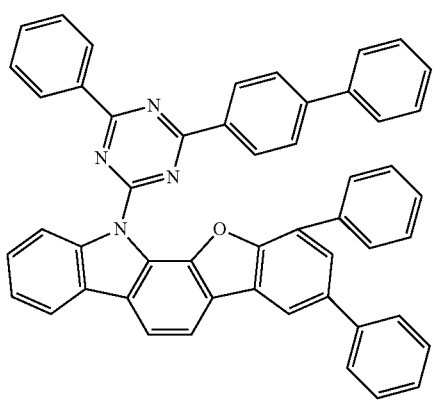
[39]
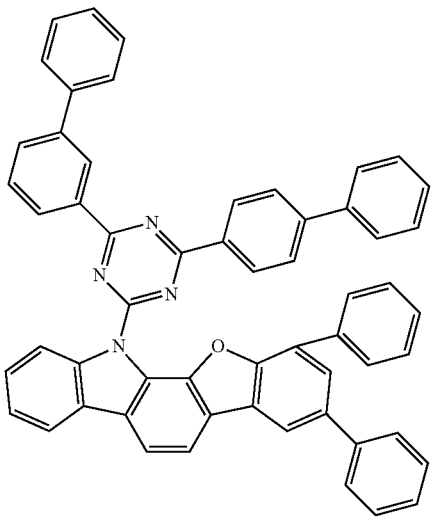
[40]
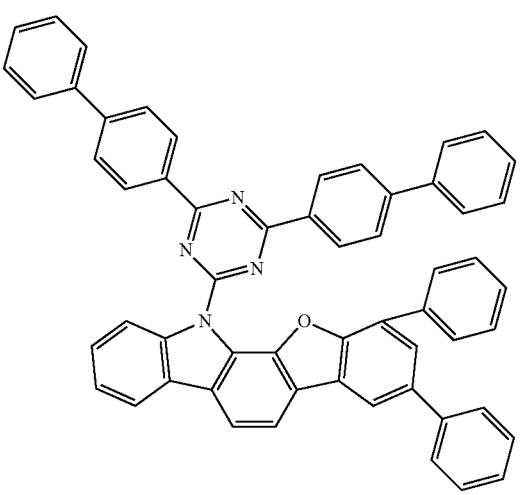
[41]
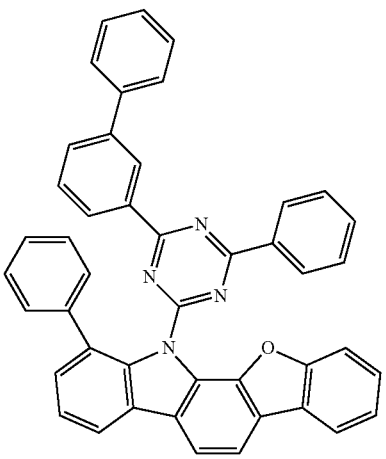

[42]
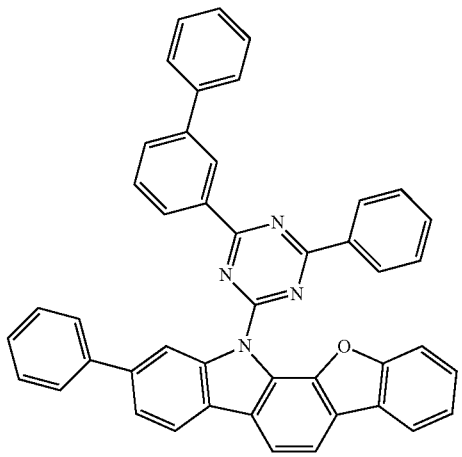
[43]
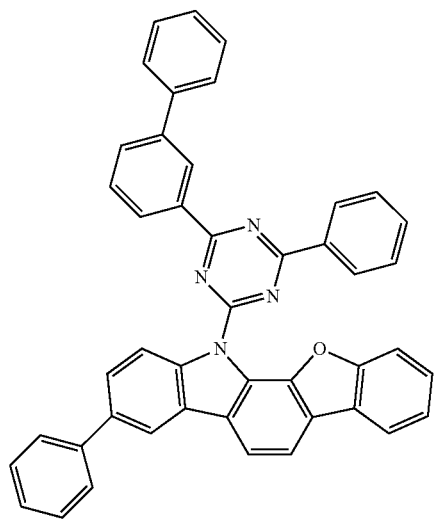
[44]
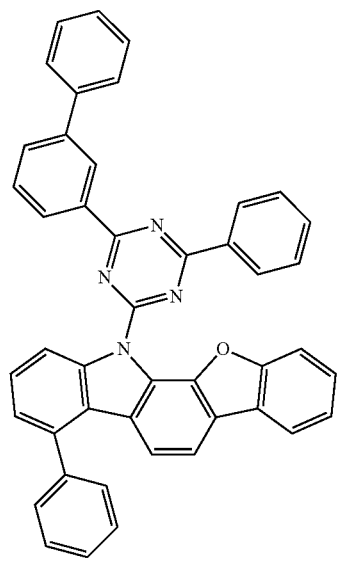
[45]
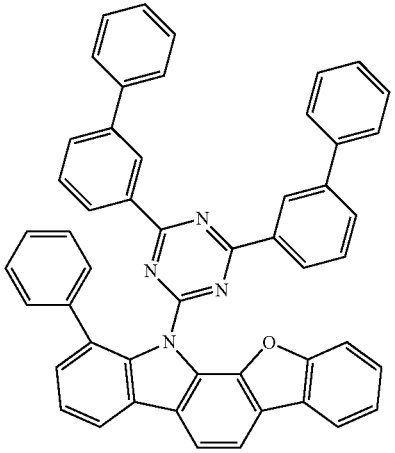
[46]
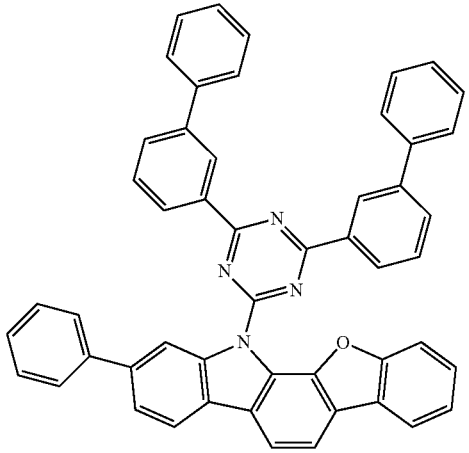
[47]
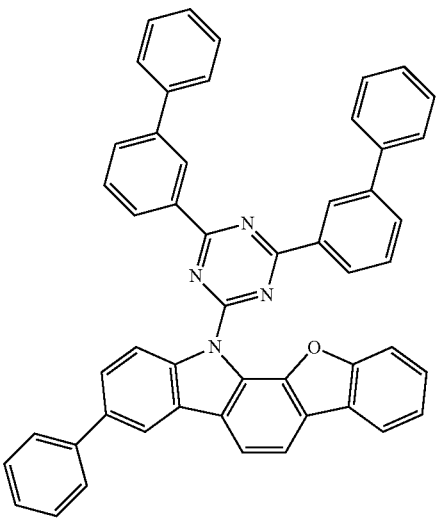

[48]
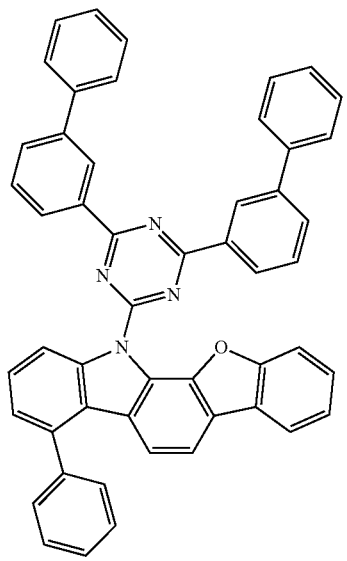
[49]
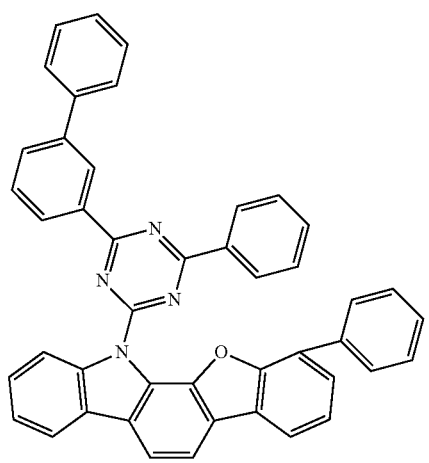
[50]
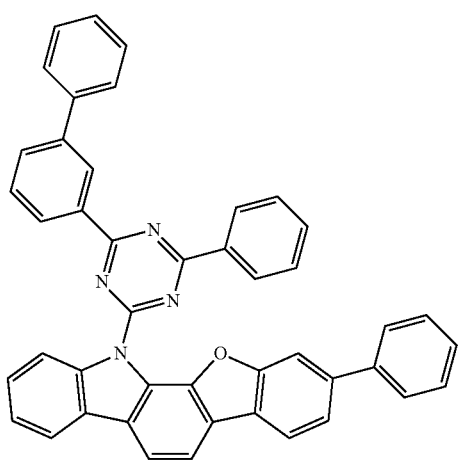
[51]
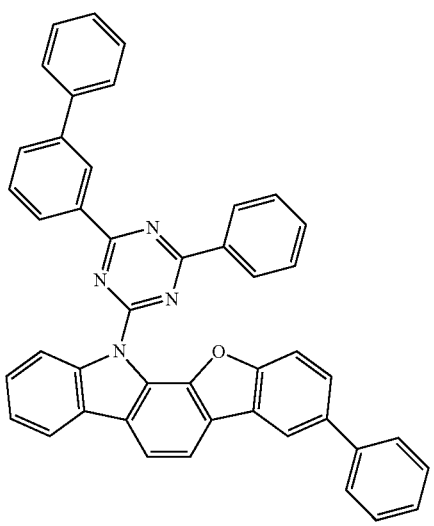
[52]
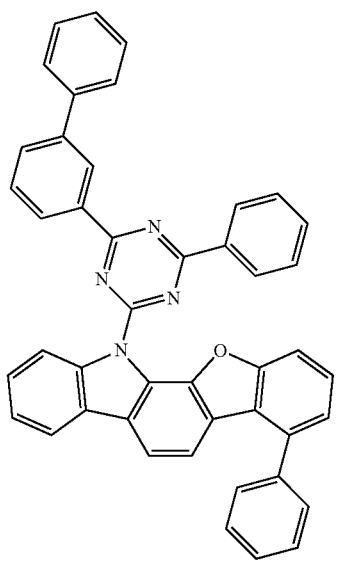
[53]
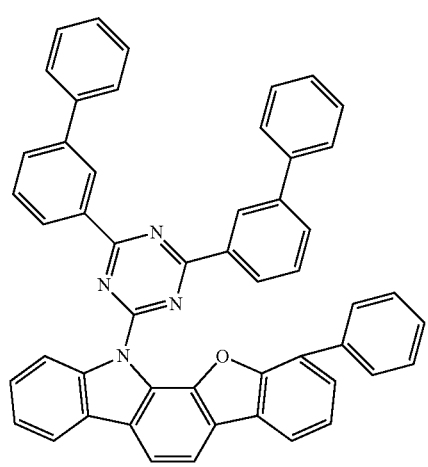

[54]
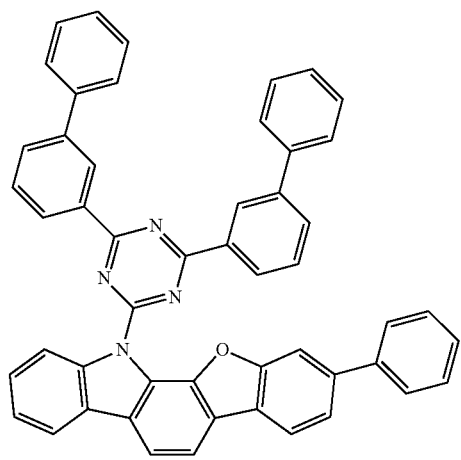
[55]
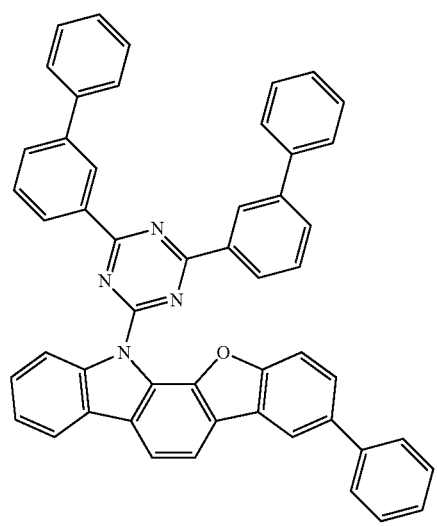
[56]
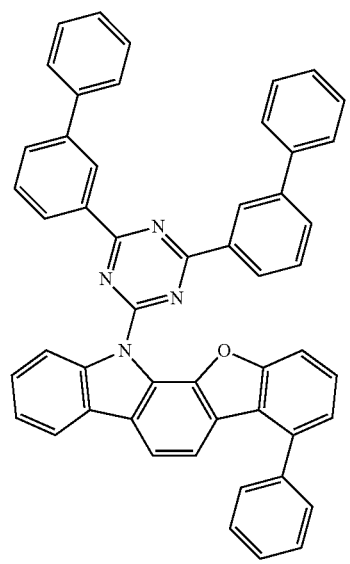
[57]
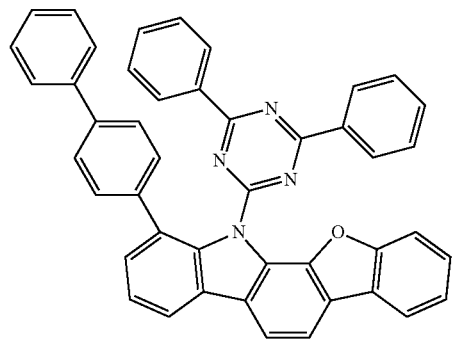
[58]
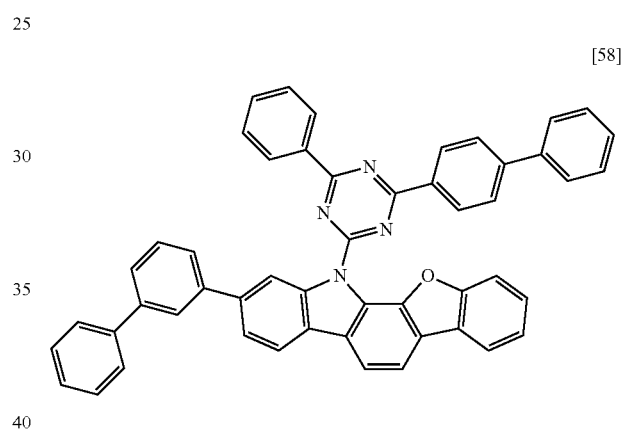
[59]
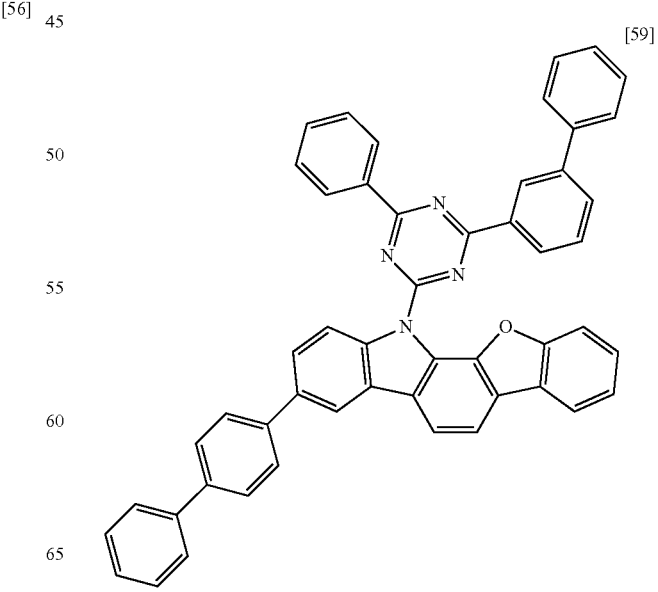

[60]
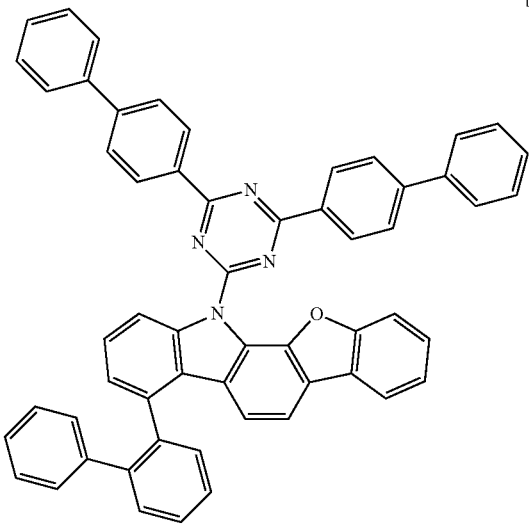
[61]
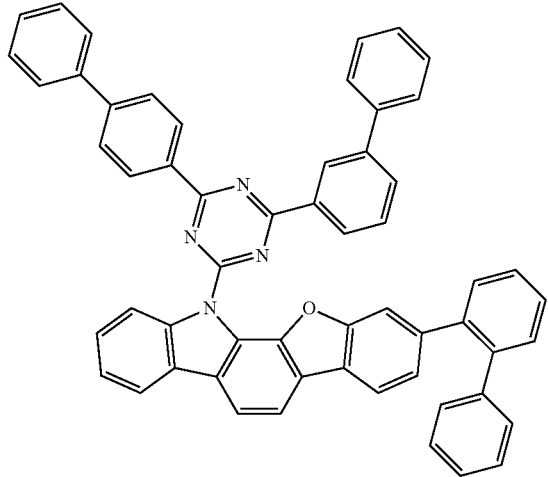
[62]
[63]
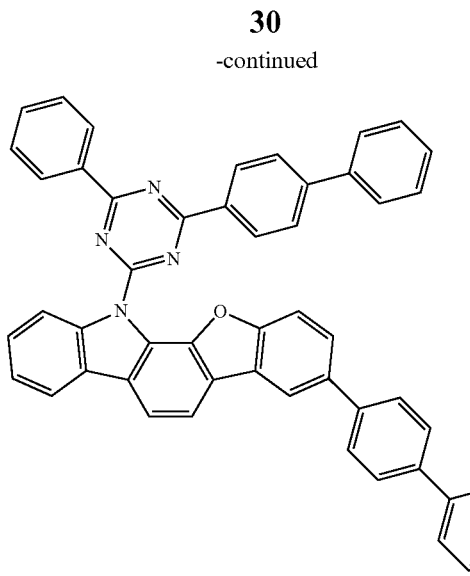
[64]
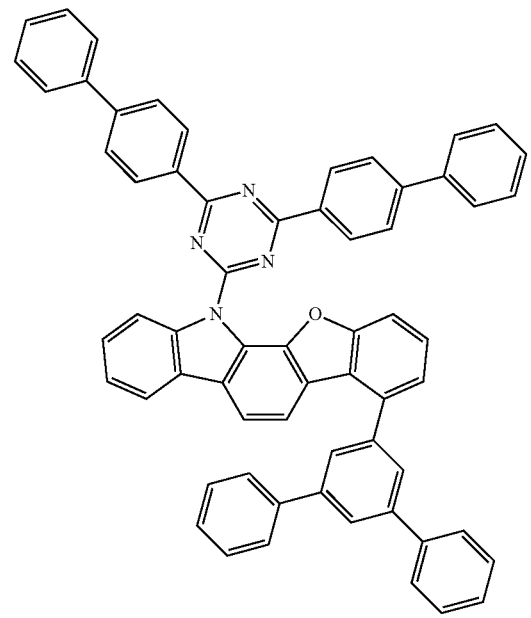
[65]
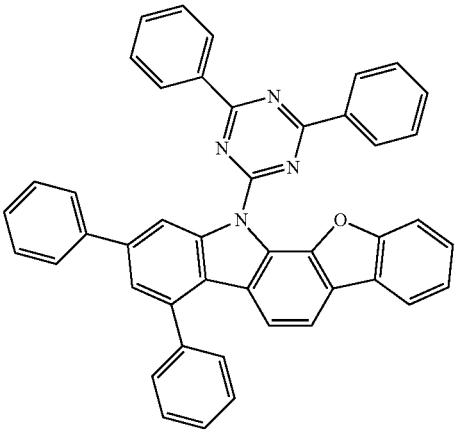

31
-continued
[66]
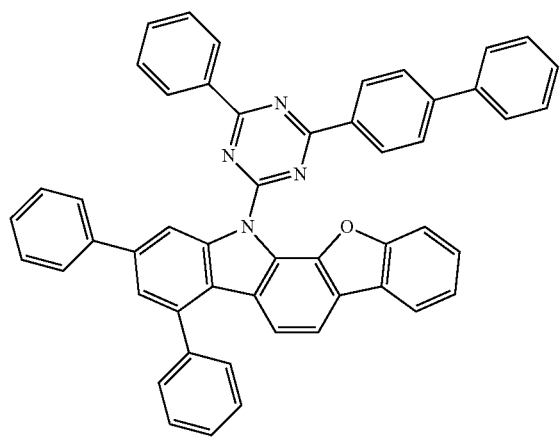
[67]
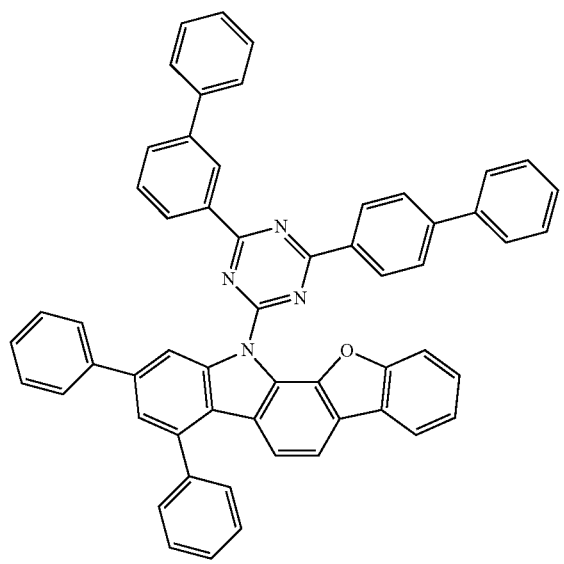
[68]
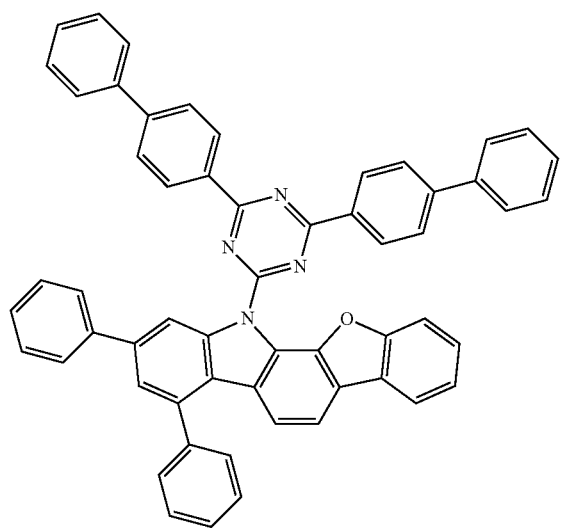
32
-continued
[69]
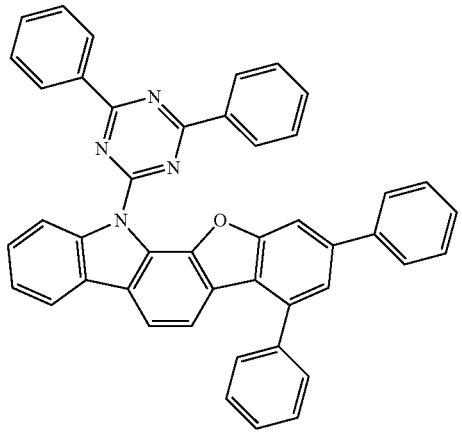
[70]
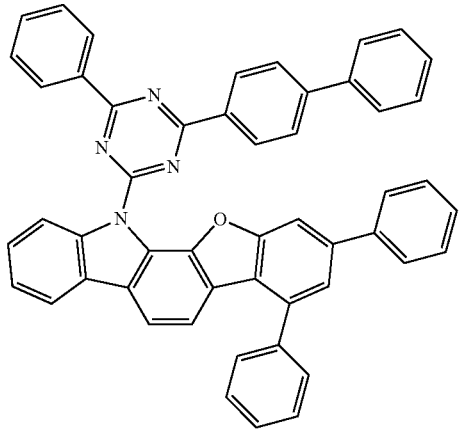
[71]
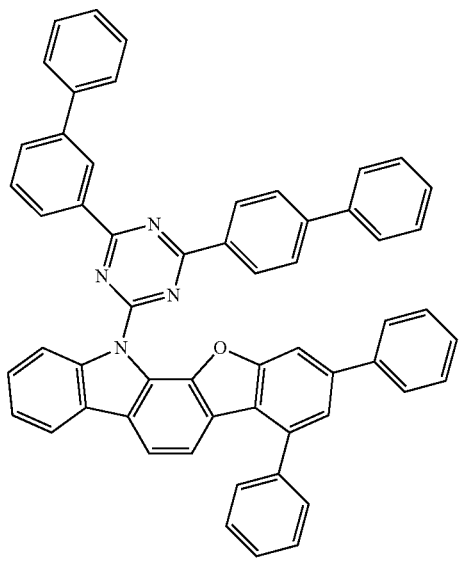

-continued

[72]

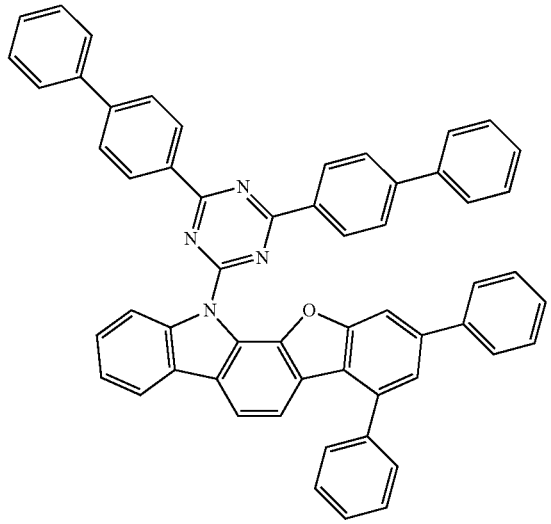

In an implementation, Chemical Formula 1 may be, e.g., represented by Chemical Formula 1-3 or Chemical Formula 1-8.

A composition for an organic optoelectronic device according to another embodiment may include, e.g., a first compound for an organic optoelectronic device and a second compound for an organic optoelectronic device (e.g., a mixture of the first compound and the second compound). In an implementation, the first compound may be, e.g., the aforementioned compound represented by Chemical Formula 1. In an implementation, the second compound may be, e.g., represented by Chemical Formula 2. In an implementation, the second compound may be, e.g., represented by a combination of Chemical Formula 3 and Chemical Formula 4.

[Chemical Formula 2]

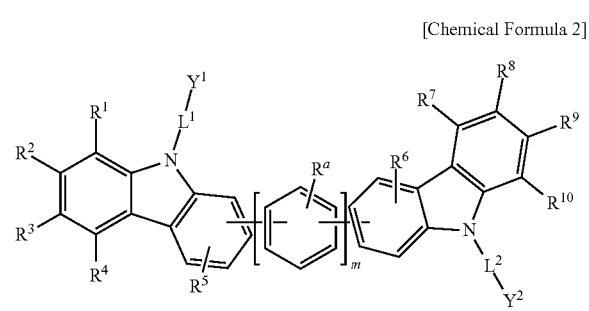

In Chemical Formula 2, $Y^1$ and $Y^2$ may each independently be or include, e.g., a substituted or unsubstituted C6 to C20 aryl group or a substituted or unsubstituted C2 to C30 heterocyclic group.

$L^1$ and $L^2$ may each independently be or include, e.g., a single bond or a substituted or unsubstituted C6 to C20 arylene group, $R^a$ and $R^1$ to $R^{10}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

m may be, e.g., an integer of 0 to 2;

[Chemical Formula 3]

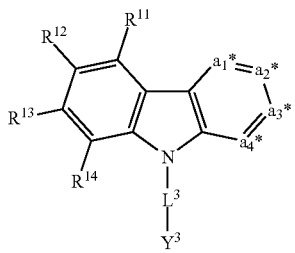

[Chemical Formula 4]

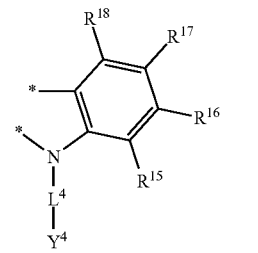

In Chemical Formulas 3 and 4, $Y^3$ and $Y^4$ may each independently be or include, e.g., a substituted or unsubstituted C6 to C20 aryl group or a substituted or unsubstituted C2 to C30 heterocyclic group.

Two adjacent ones of a1* to a4* of Chemical Formula 3 are linking carbons linked at * of Chemical Formula 4. The remaining two of a1* to a4* of Chemical Formula 3, not linked at * of Chemical Formula 4, may be C-$L^a$-$R^b$. As used herein, the term "linking carbon" refers to a shared carbon at which fused rings are linked.

$L^a$, $L^3$ and $L^4$ may each independently be or include, e.g., a single bond or a substituted or unsubstituted C6 to C20 arylene group.

$R^b$ and $R^{11}$ to $R^{18}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

The second compound may be used in the light emitting layer together with the first compound for an organic optoelectronic device to help improve the mobility of charges and improve stability, thereby improving luminous efficiency and life-span characteristics.

In an implementation, $Y^1$ and $Y^2$ of Chemical Formula 2 may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group.

In an implementation, $L^1$ and $L^2$ of Chemical Formula 2 may each independently be, e.g., a single bond, a substituted or unsubstituted phenylene group, or a substituted or unsubstituted biphenylene group.

In an implementation, $R^1$ to $R^{10}$ of Chemical Formula 2 may each independently be, e.g., hydrogen, deuterium, or a substituted or unsubstituted C6 to C12 aryl group.

m may be, e.g., 0 or 1.

In an implementation, "substituted" of Chemical Formula 2 refers to replacement of at least one hydrogen with, e.g., deuterium, a C1 to C4 alkyl group, or a C6 to C18 aryl group.

In an implementation, Chemical Formula 2 may be represented by, e.g., one of Chemical Formula 2-1 to Chemical Formula 2-15.

[Chemical Formula 2-1]

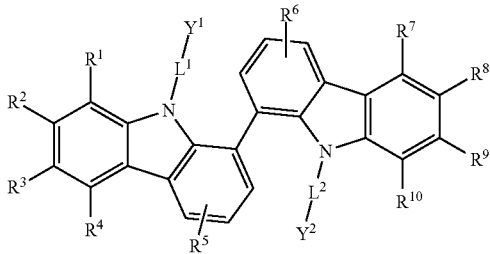

[Chemical Formula 2-2]

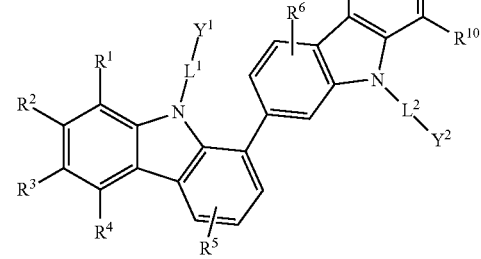

[Chemical Formula 2-3]

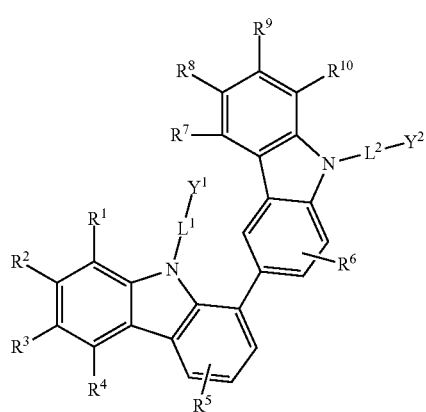

[Chemical Formula 2-4]

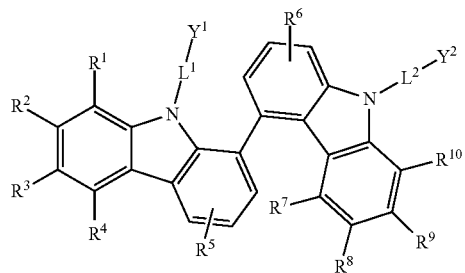

[Chemical Formula 2-5]

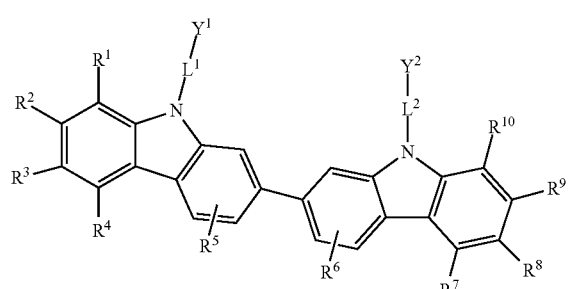

[Chemical Formula 2-6]

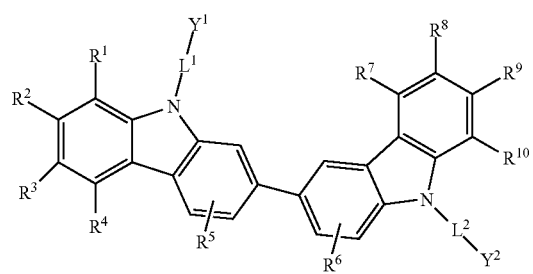

[Chemical Formula 2-7]

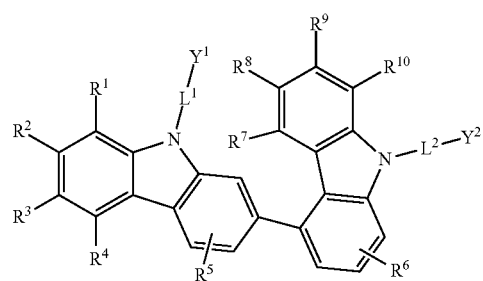

[Chemical Formula 2-8]

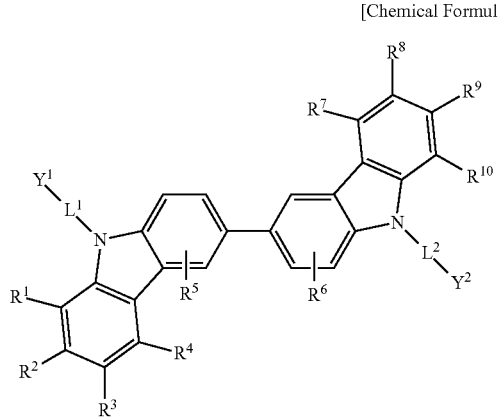

[Chemical Formula 2-9]
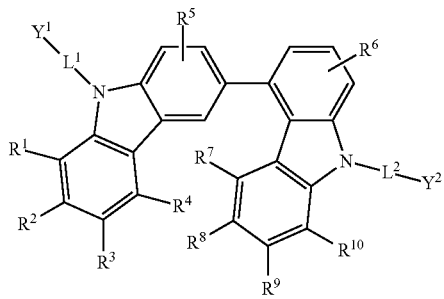
[Chemical Formula 2-10]
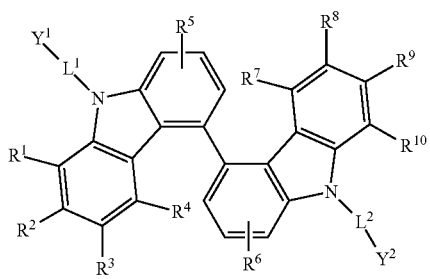
[Chemical Formula 2-11]
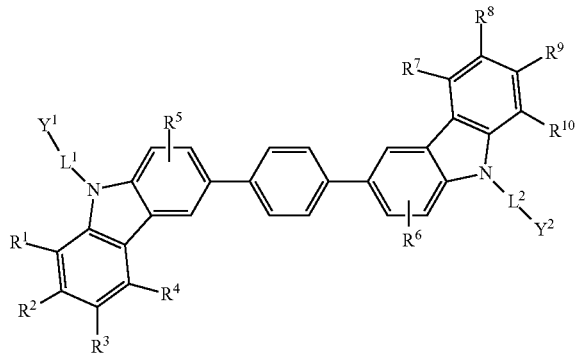
[Chemical Formula 2-12]
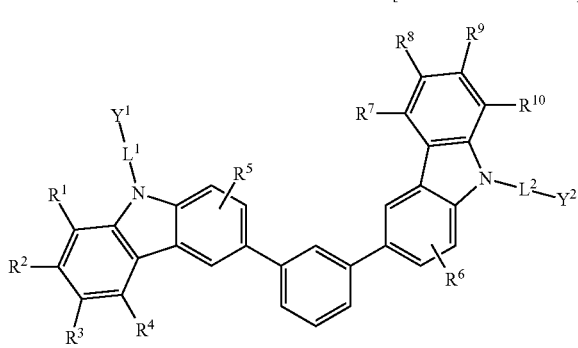
[Chemical Formula 2-13]
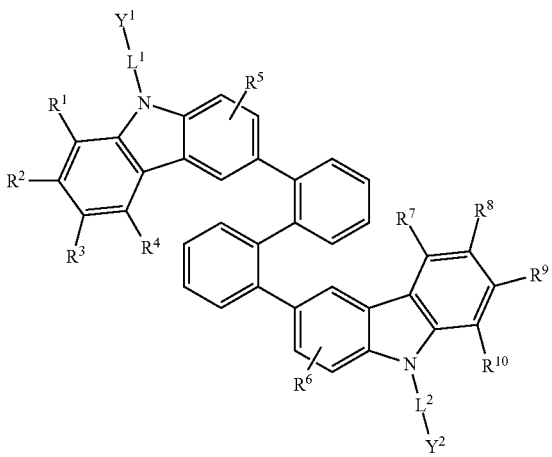
[Chemical Formula 2-14]
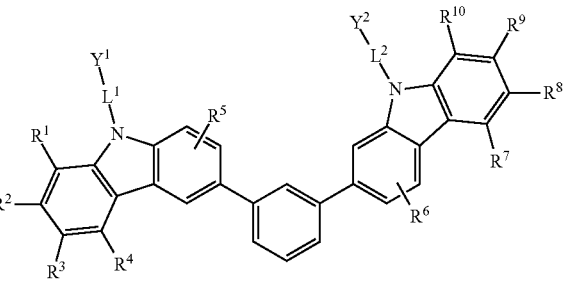
[Chemical Formula 2-15]
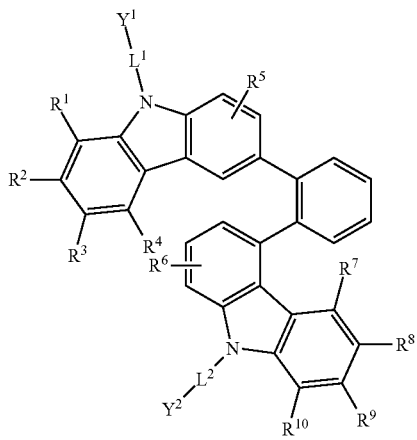
In Chemical Formula 2-1 to Chemical Formula 2-15, $R^1$ to $R^{10}$ may each independently be, e.g., hydrogen or a substituted or unsubstituted C6 to C12 aryl group. Moieties *-$L^1$-$Y^1$ and *-$L^2$-$Y^2$ may each independently be, e.g., a moiety of Group II.
[Group II]
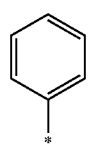
C-1

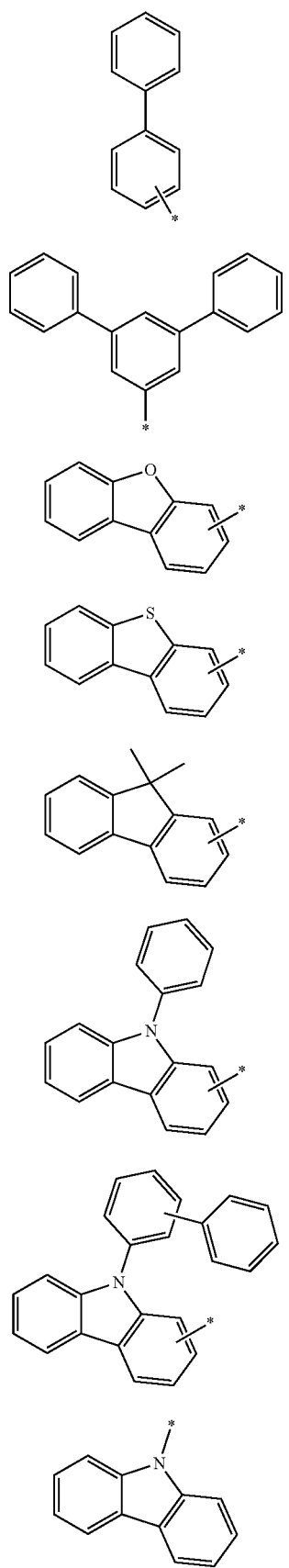
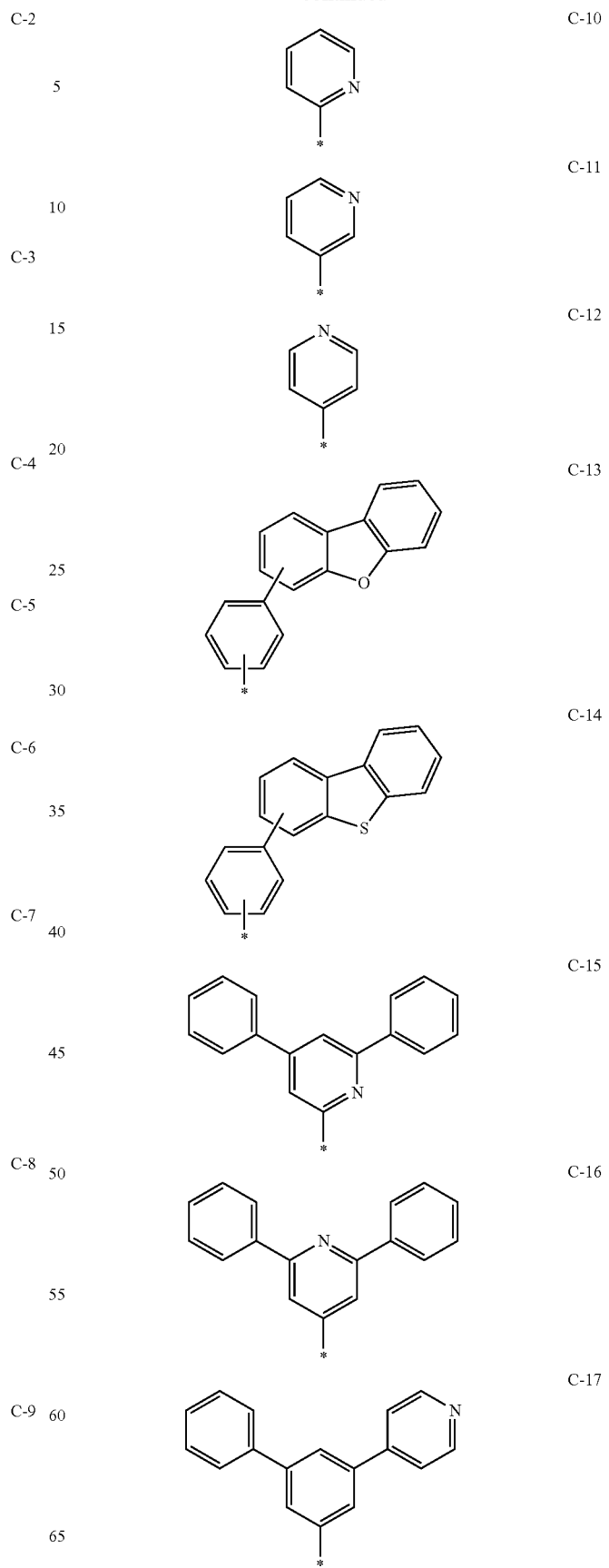

In Group II, * is a linking point (e.g., to N of Chemical Formulae 2-1 to 2-15).

In an implementation, Chemical Formula 2 may be represented by, e.g., Chemical Formula 2-8.

In an implementation, moieties *-L¹-Y¹ and *-L²-Y² of Chemical Formula 2-8 may each independently be a moiety of Group II, e.g., C-1, C-2, C-3, or C-23.

In an implementation, both moieties *-L¹-Y¹ and *-L²-Y² may be, e.g., moieties C-1, C-2, or C-3 of Group II.

In an implementation, the second compound represented by the combination of Chemical Formula 3 and Chemical Formula 4 may be represented by, e.g., Chemical Formula Chemical Formula 3A, Chemical Formula 3B, Chemical Formula 3C, Chemical Formula 3D, or Chemical Formula 3E.

43

-continued

[Chemical Formula 3D]

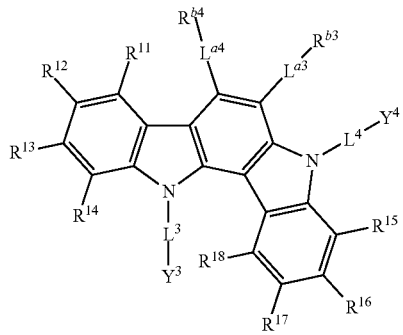

[Chemical Formula 3E]

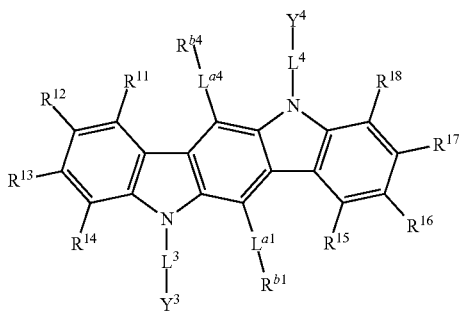

In Chemical Formula 3A to Chemical Formula 3E, $Y^3$, $Y^4$, $L^3$, $L^4$, and $R^{11}$ to $R^{18}$ may be defined the same as those described above.

$L^{a1}$ to $L^{a4}$ may be defined the same as $L^3$ and $L^4$.

$R^{b1}$ to $R^{b4}$ may be defined the same as $R^{11}$ to $R^{18}$.

In an implementation, $Y^3$ and $Y^4$ of Chemical Formulas 3 and 4 may each independently be, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{b1}$ to $R^{b4}$ and $R^{11}$ to $R^{18}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $Y^3$ and $Y^4$ of Chemical Formulas 3 and 4 may each independently be, e.g., a moiety of Group II.

In an implementation, $R^{b1}$ to $R^{b4}$ and $R^{11}$ to $R^{18}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{b1}$ to $R^{b4}$ and $R^{11}$ to $R^{18}$ may each independently be, e.g., hydrogen, deuterium, a cyano group, or a substituted or unsubstituted phenyl group.

44

In an implementation, each of $R^{b1}$ to $R^{b4}$ may be, e.g., hydrogen, and $R^{11}$ to $R^{18}$ may each independently be, e.g., hydrogen or a phenyl group.

In an implementation, the first compound may be represented by, e.g., Chemical Formula 1-3 or Chemical Formula 1-8.

In an implementation, $Ar^1$ and $Ar^3$ may each independently be, e.g., a substituted or unsubstituted phenyl group.

In an implementation, $Ar^5$ and $Ar^6$ may each independently be, e.g., a substituted or unsubstituted phenyl group or $Ar^5$ and $Ar^6$ may each independently be, e.g., a substituted or unsubstituted phenyl group or a substituted or unsubstituted biphenyl group. In an implementation, at least one of $Ar^5$ and $Ar^6$ may be, e.g., a substituted or unsubstituted biphenyl group.

In an implementation, the second compound may be represented by, e.g., Chemical Formula 2-8, and $Y^1$ and $Y^2$ of Chemical Formula 2-8 may each independently be, e.g., a substituted or unsubstituted phenyl group, a substituted or unsubstituted carbazolyl group, a substituted or unsubstituted dibenzofuranyl group, or a substituted or unsubstituted dibenzothiophenyl group, $L^1$ and $L^2$ may each independently be, e.g., a single bond or a substituted or unsubstituted C6 to C20 arylene group, and $R^{15}$ to $R^{24}$ may each independently be, e.g., hydrogen, deuterium, a cyano group, a substituted or unsubstituted phenyl group, a substituted or unsubstituted biphenyl group, a substituted or unsubstituted carbazolyl group, a substituted or unsubstituted dibenzofuranyl group, or a substituted or unsubstituted dibenzothiophenyl group.

In an implementation, the second compound may be represented by, e.g., Chemical Formula 3C, and $L^{a1}$ and $L^{a2}$ of Chemical Formula 3C may be, e.g., a single bond, $L^3$ and $L^4$ may each independently be, e.g., a single bond or a substituted or unsubstituted C6 to C12 arylene group, $R^{11}$ to $R^{18}$, $R^{b1}$ and $R^{b2}$ may each be, e.g., hydrogen, and $Y^3$ and $Y^4$ may each independently be, e.g., a substituted or unsubstituted phenyl group, a substituted or unsubstituted naphthyl group, or a substituted or unsubstituted biphenyl group.

In an implementation, the second compound may be, e.g., a compound of Group 2.

[Group 2]

[A-1]

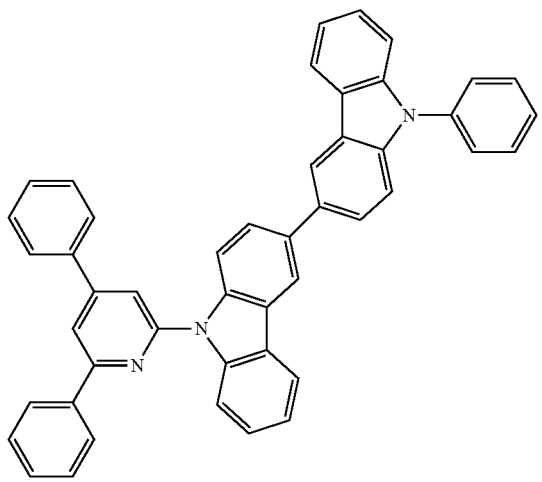

[A-2]
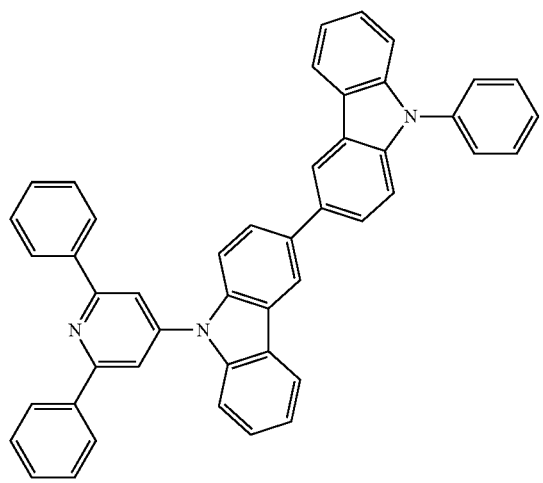
[A-3]
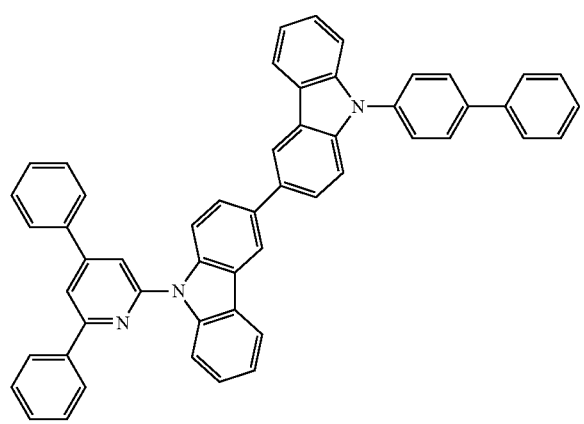
[A-4]
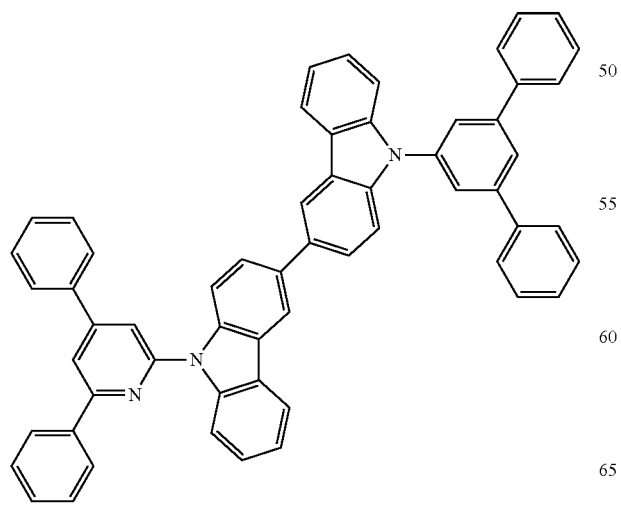
[A-5]
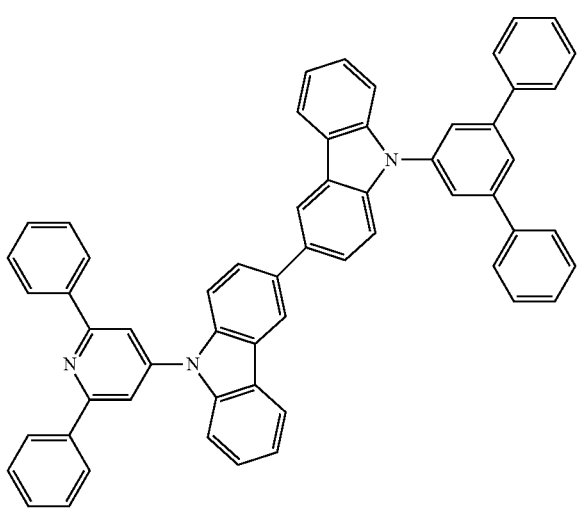
[A-6]
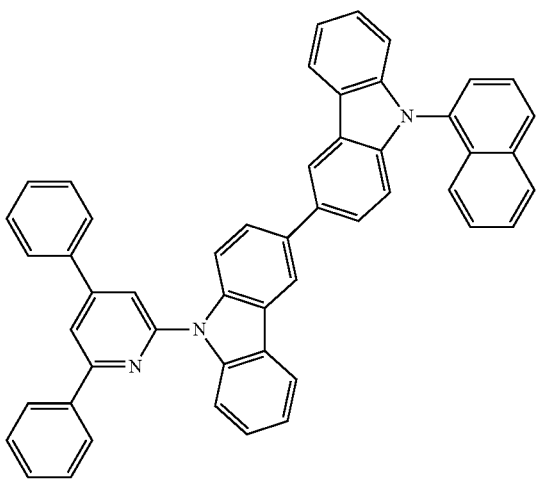
[A-7]
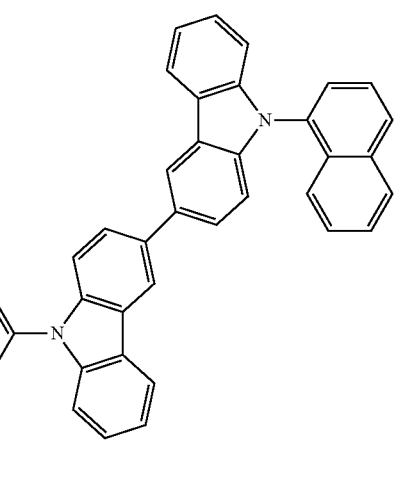

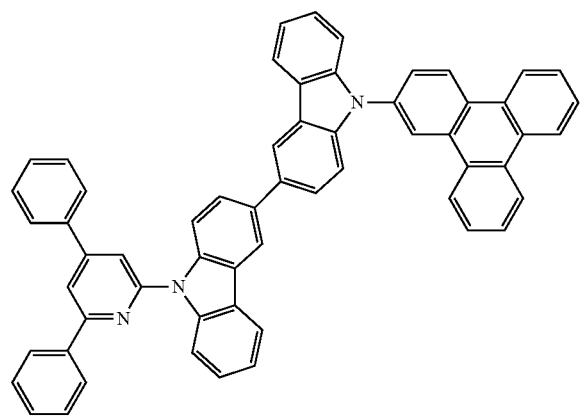
[A-8]
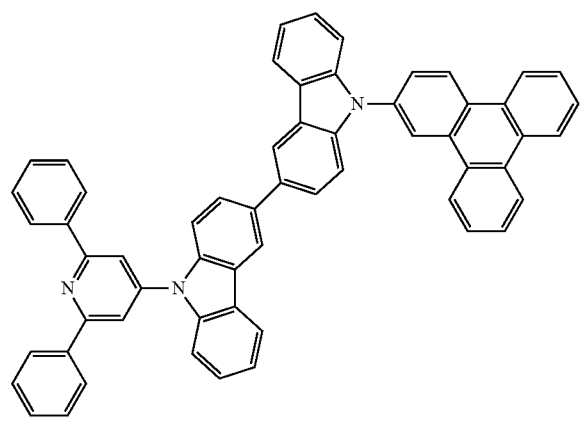
[A-9]
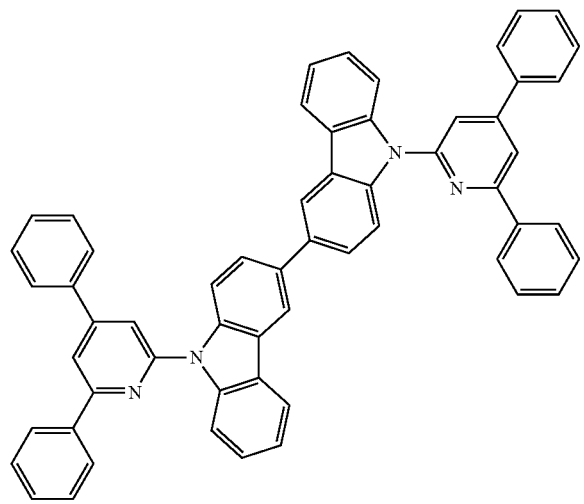
[A-10]
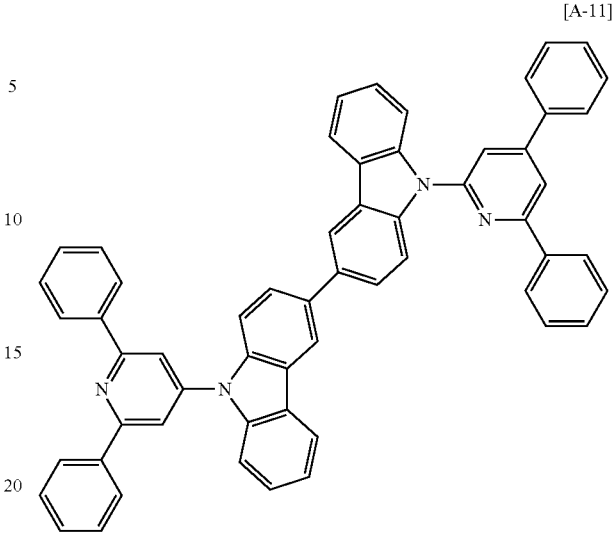
[A-11]
[A-12]
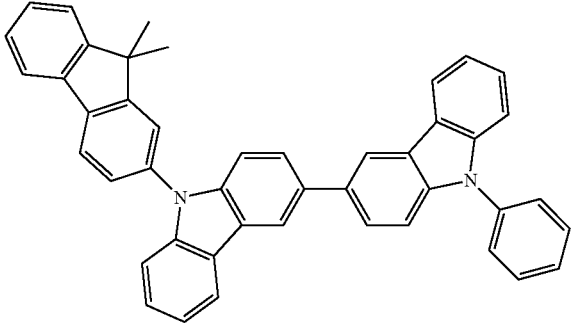
[A-13]

[A-14]
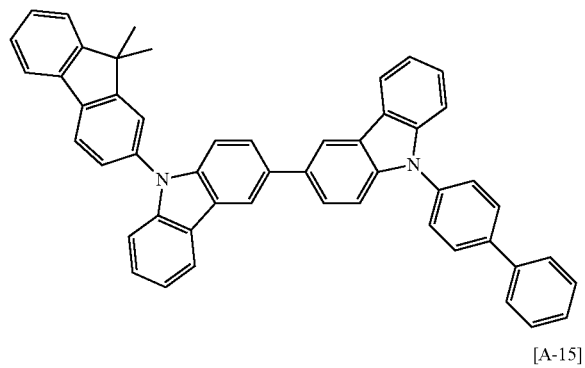
[A-15]
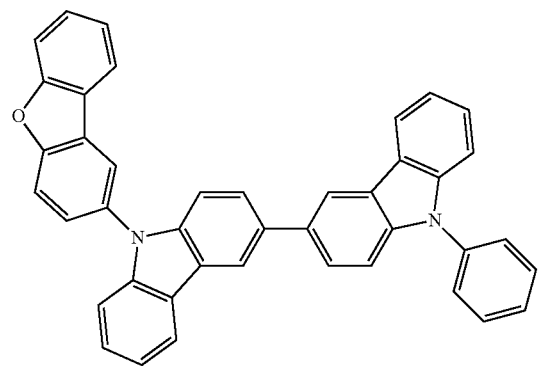
[A-16]
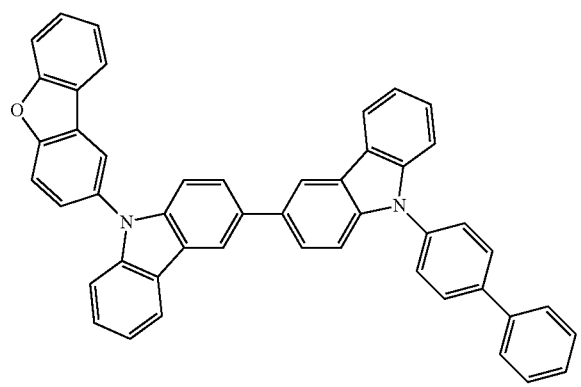
[A-17]
[A-18]
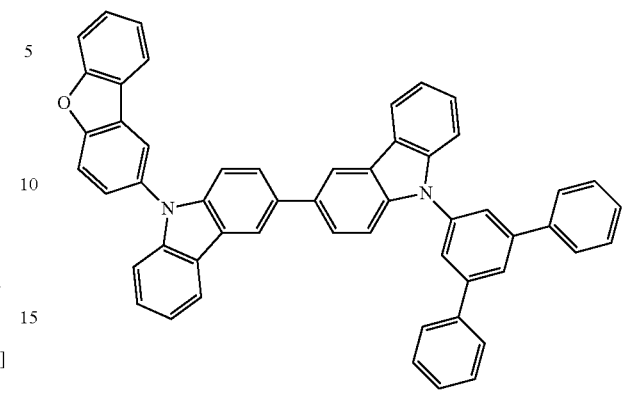
[A-19]
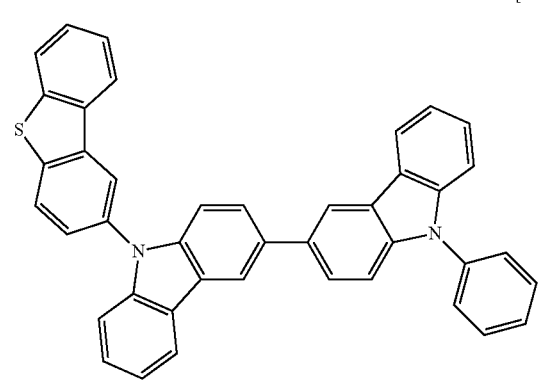
[A-20]
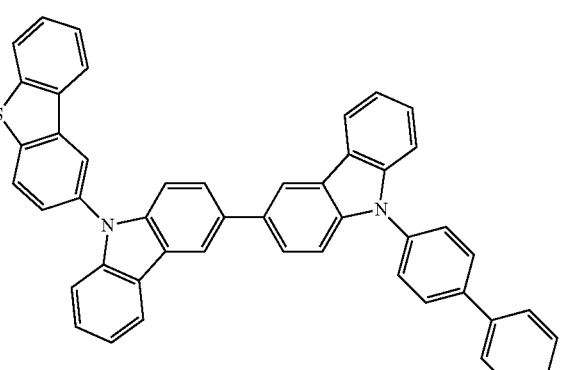
[A-21]
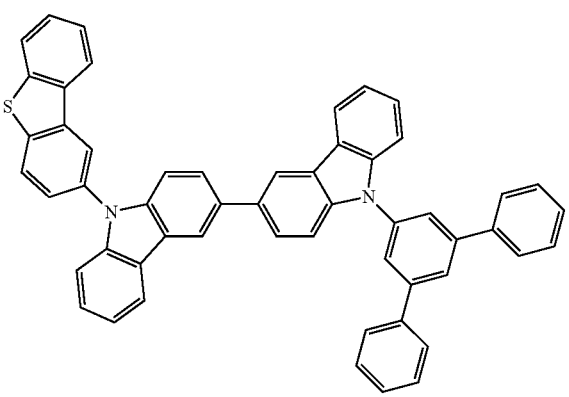

[A-22]
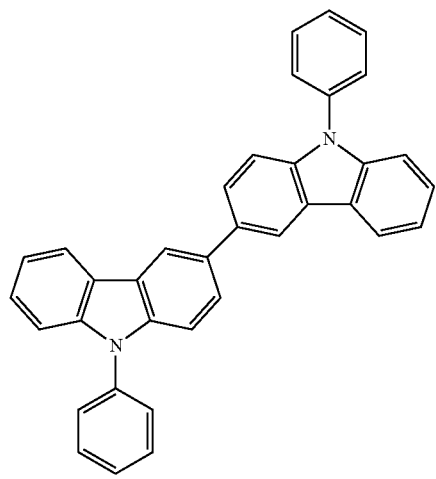
[A-23]
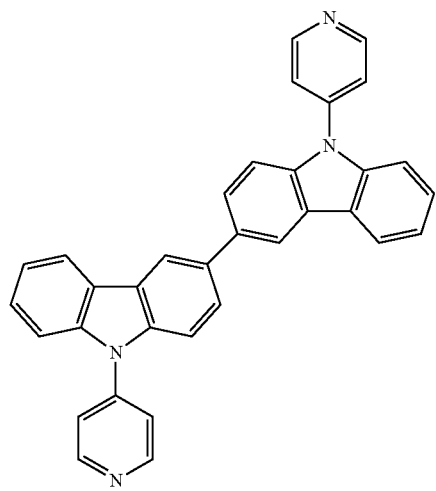
[A-24]
[A-25]
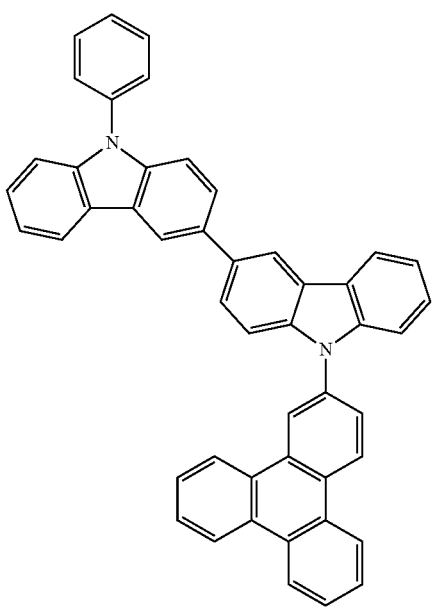
[A-26]
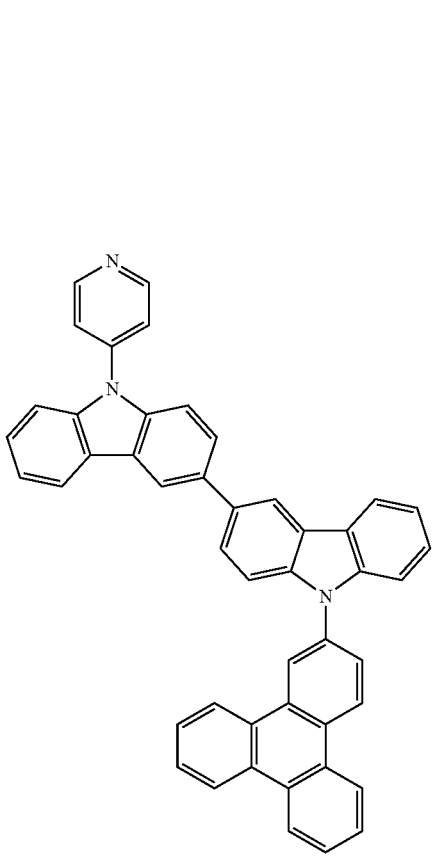

[A-27]
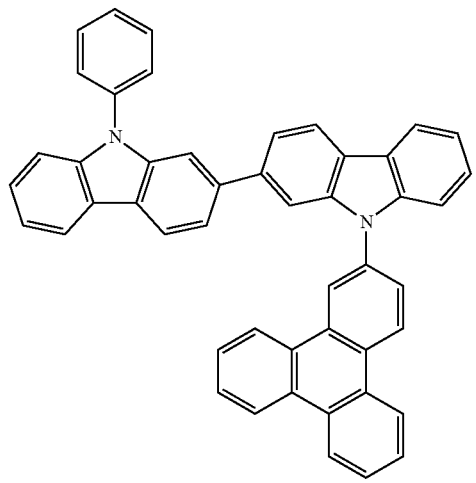
[A-28]
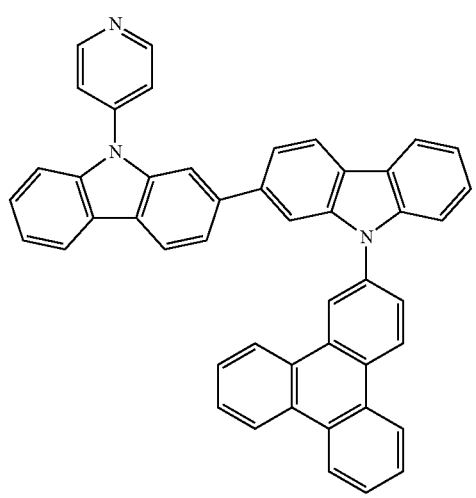
[A-29]
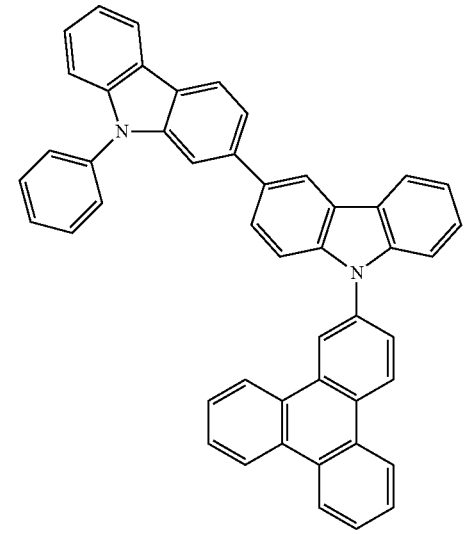
[A-30]
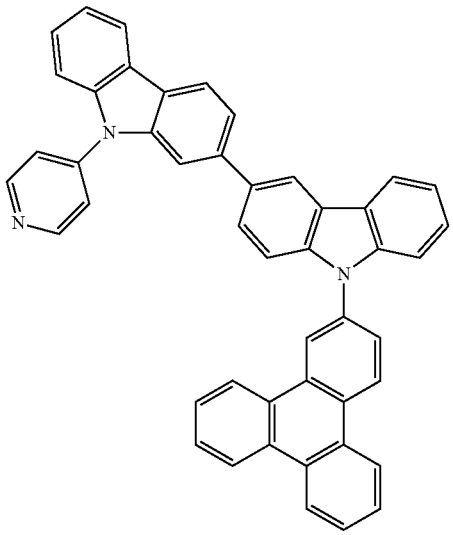
[A-31]
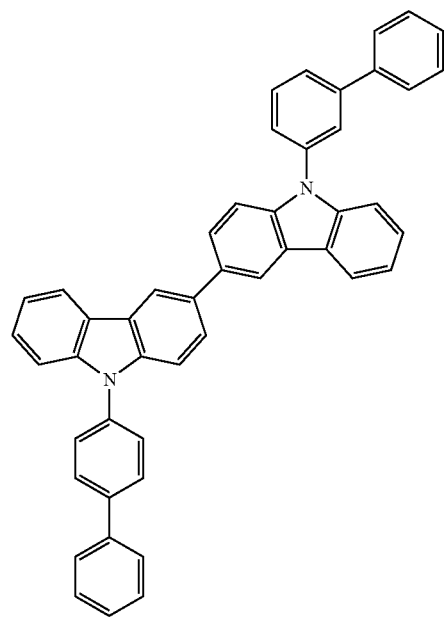

[A-32]
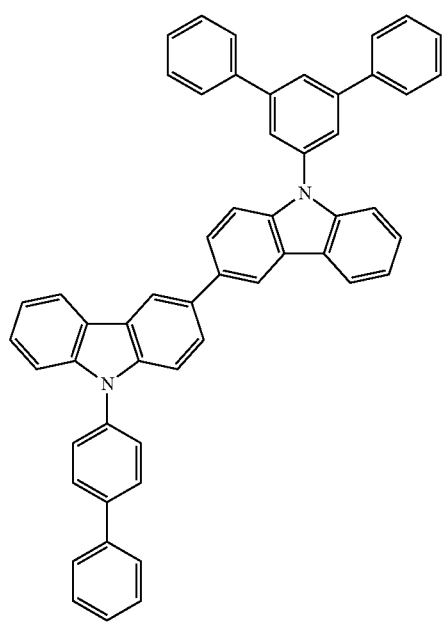
[A-33]
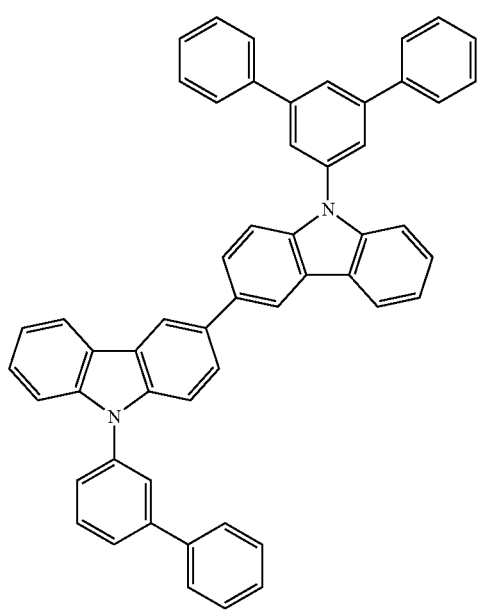
[A-34]
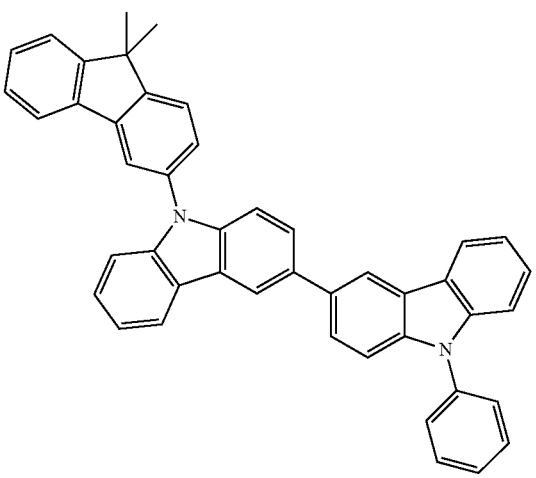
[A-35]
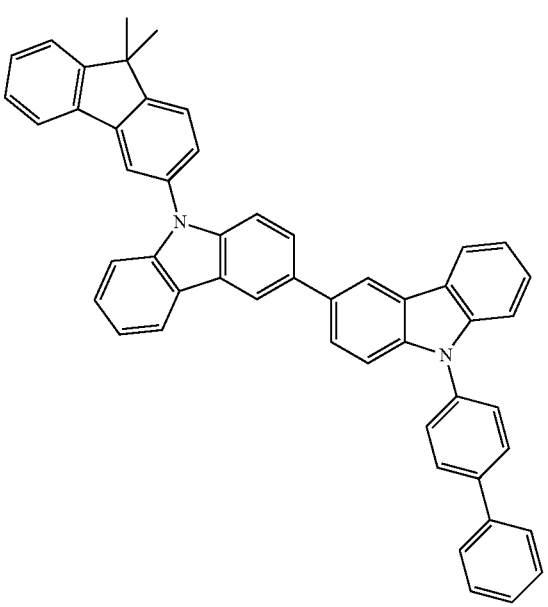
[A-36]
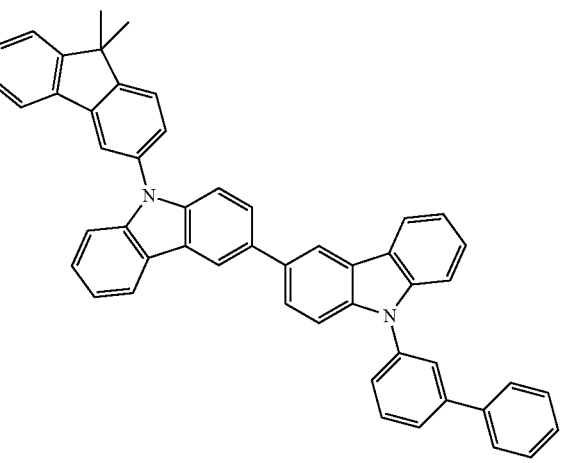

[A-37]
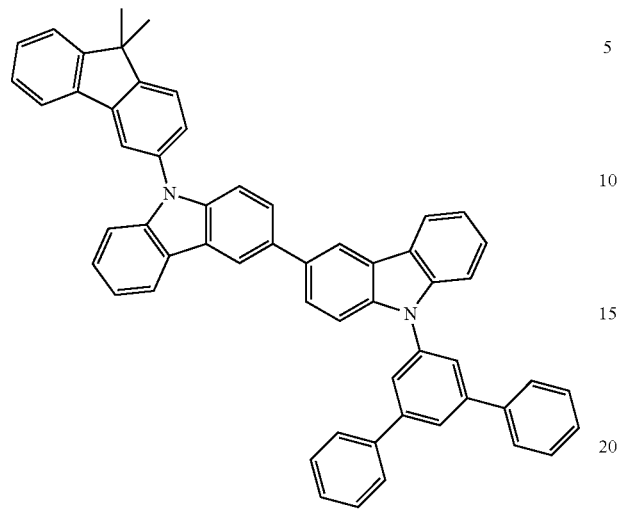
[A-38]
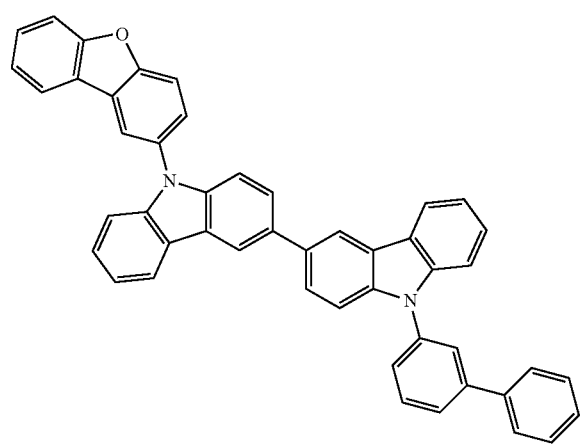
[A-39]
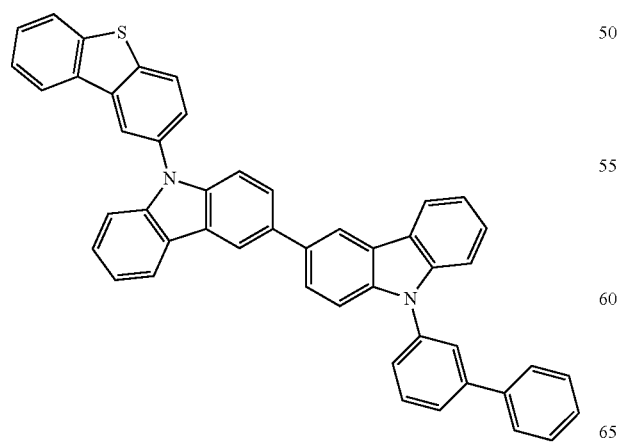
[A-40]
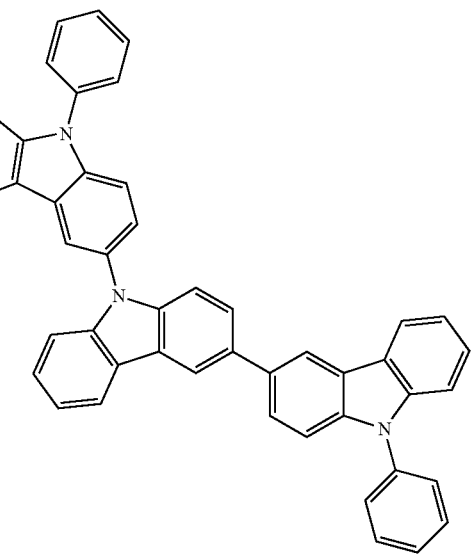
[A-41]
[A-42]
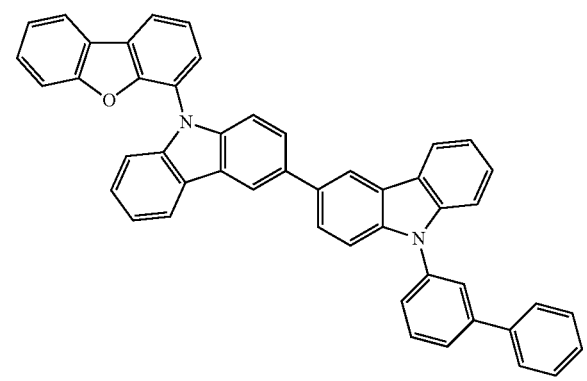

[A-43]
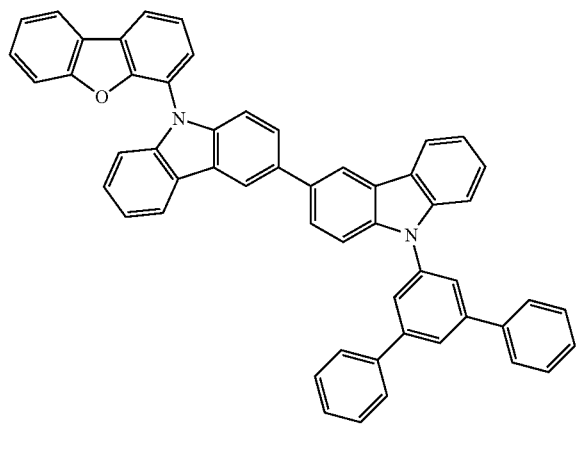
[A-44]
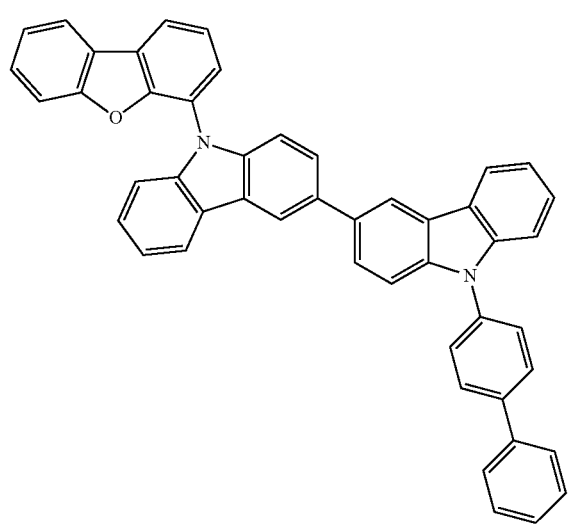
[A-45]
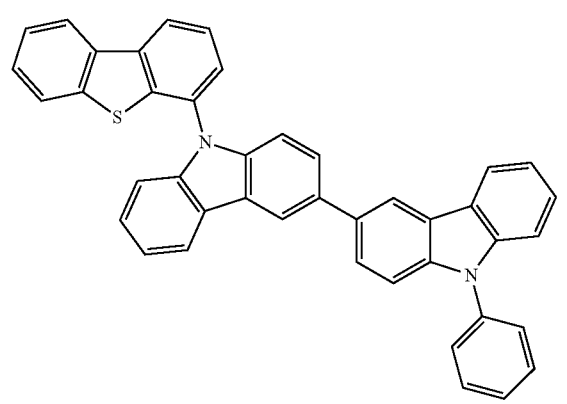
[A-46]
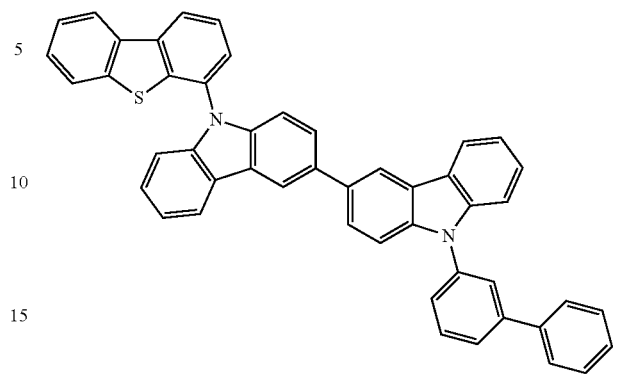
[A-47]
[A-48]
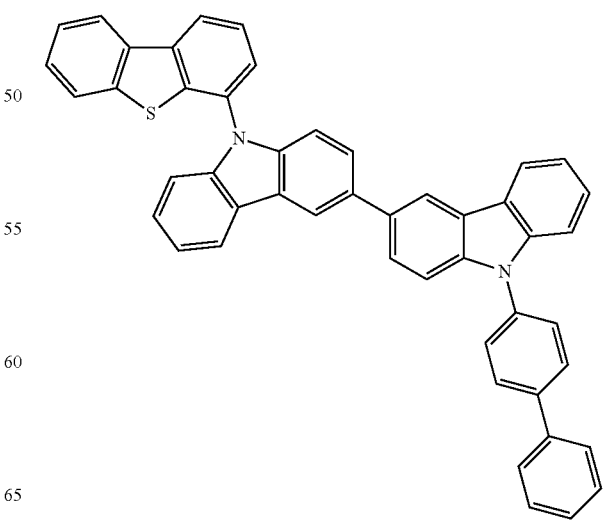

[A-49]
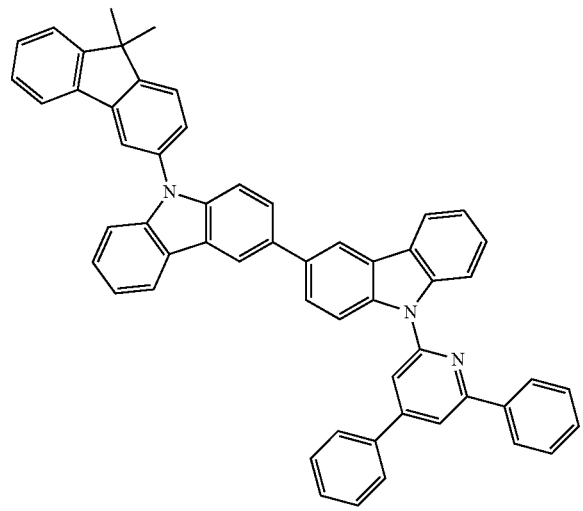
[A-52]
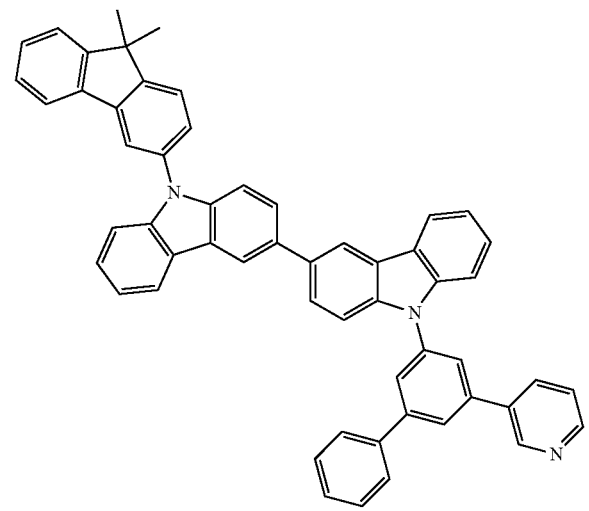
[A-50]
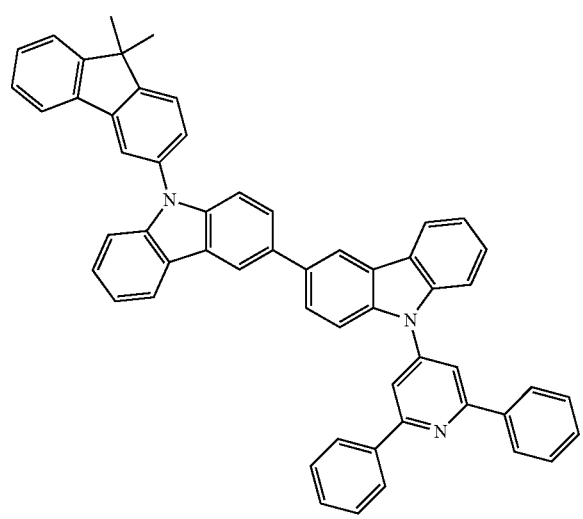
[A-53]
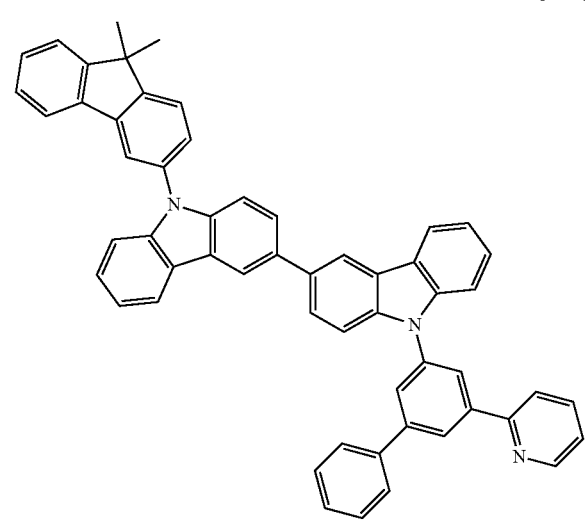
[A-51]
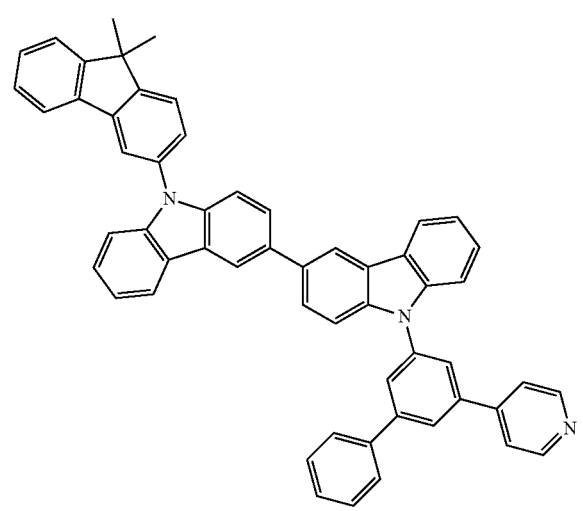
[A-54]
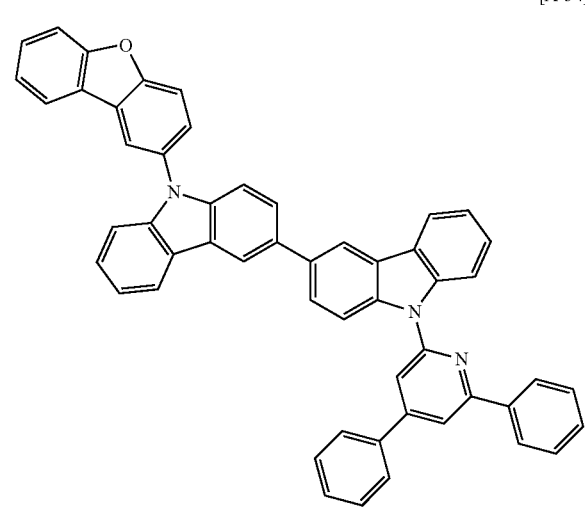

[A-55]
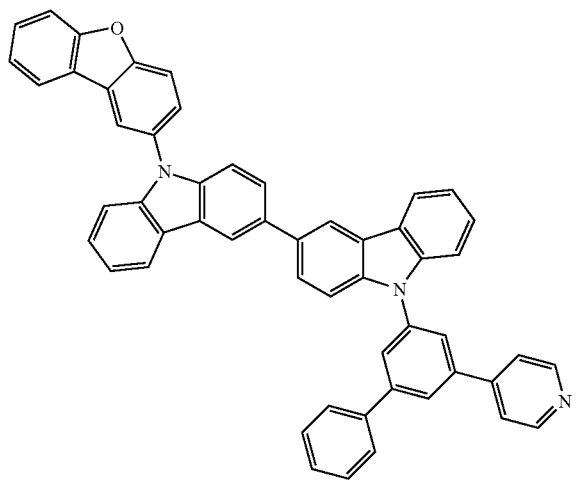
[A-58]
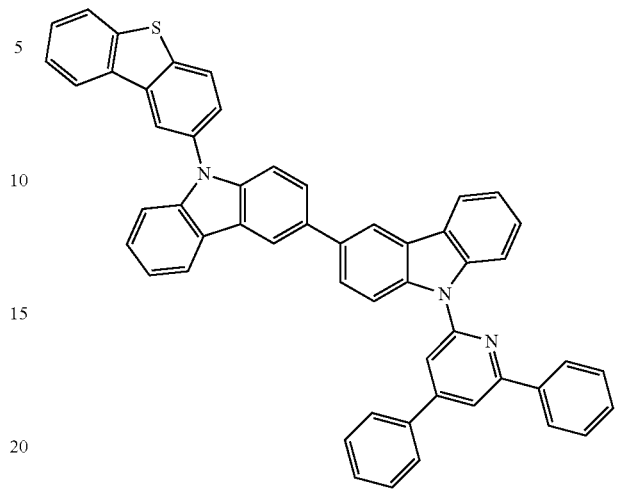
[A-56]
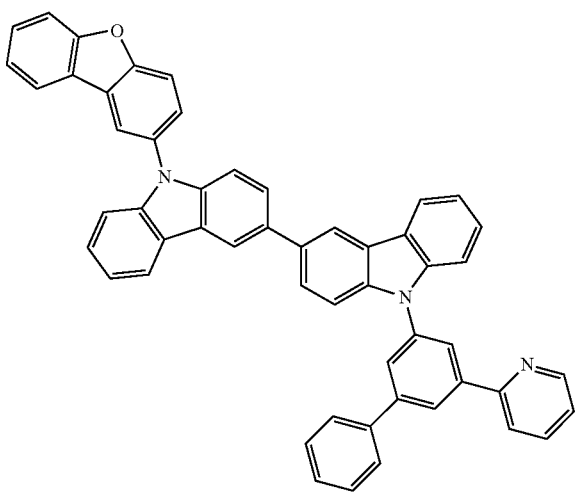
[A-59]
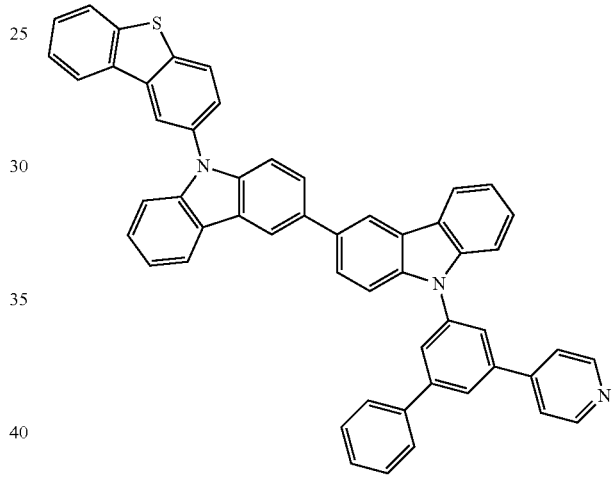
[A-57]
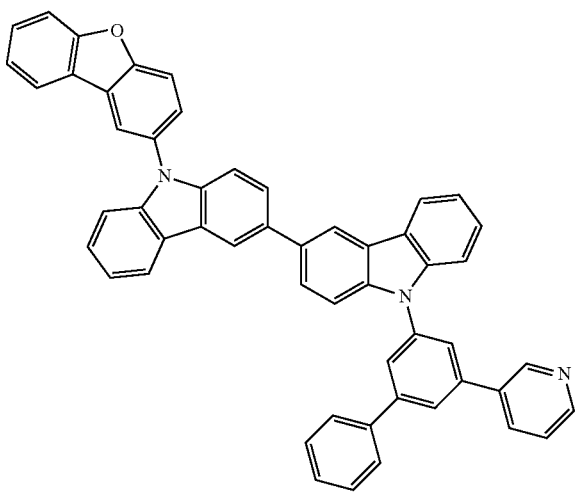
[A-60]
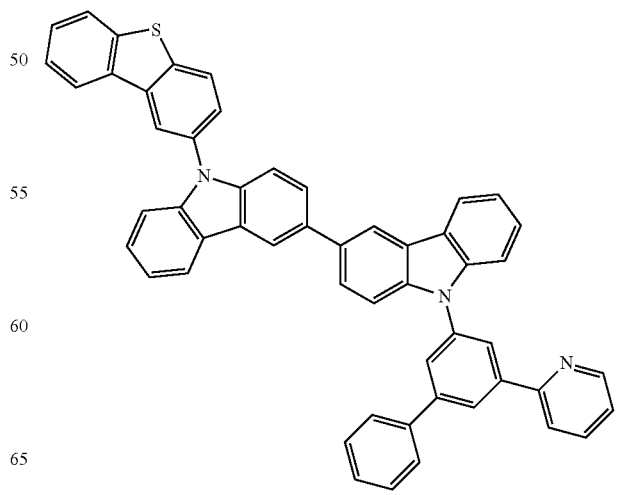

[A-61]
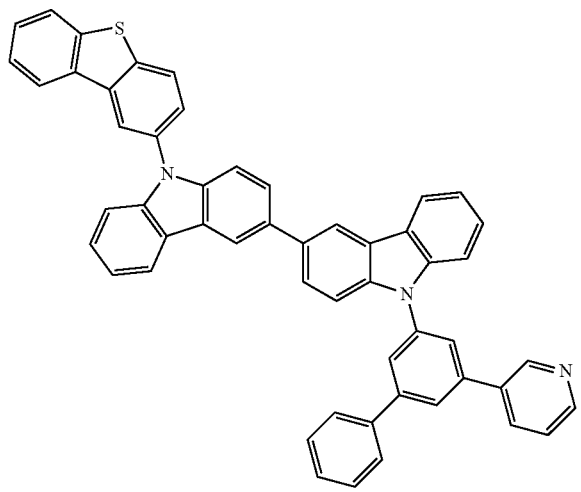
[A-62]
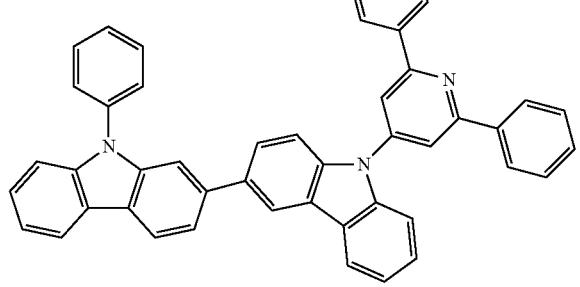
[A-63]
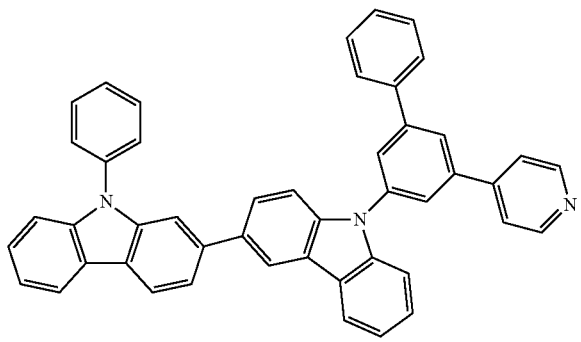
[A-64]
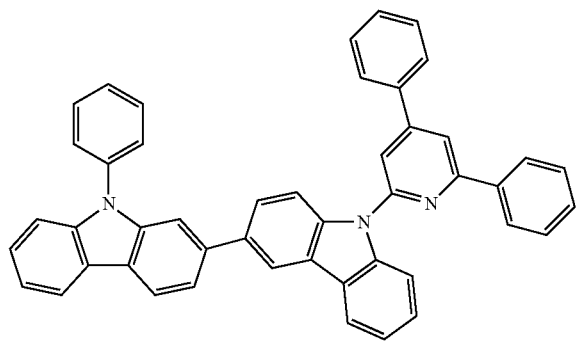
[A-65]
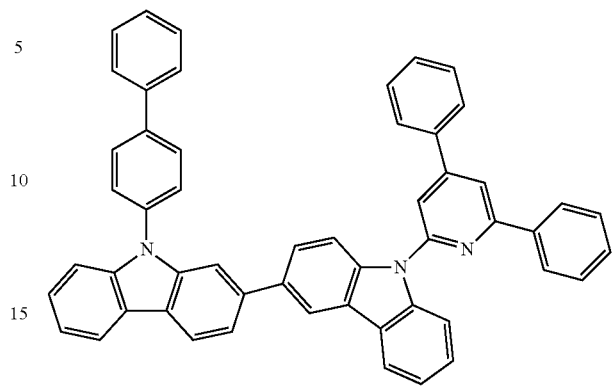
[A-66]
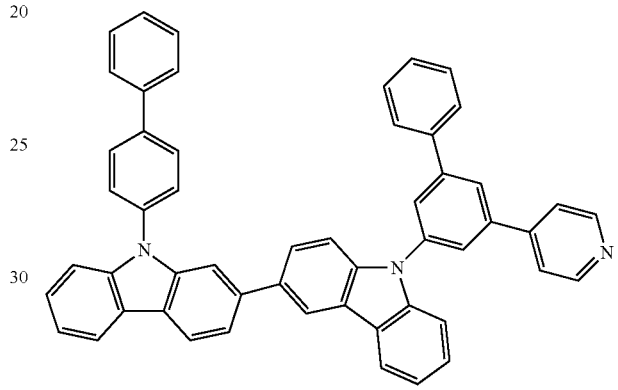
[A-67]
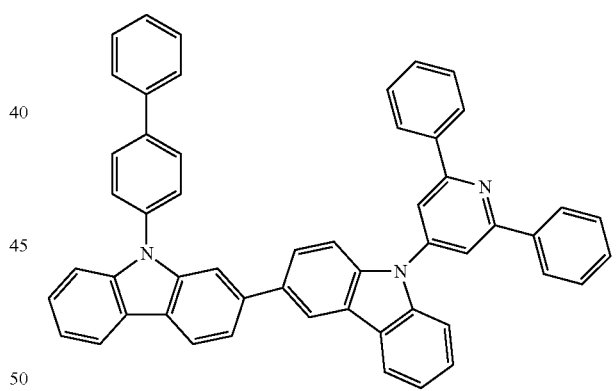
[A-68]
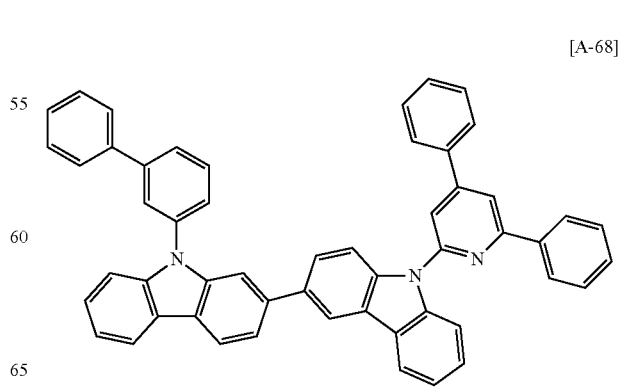

[A-69]
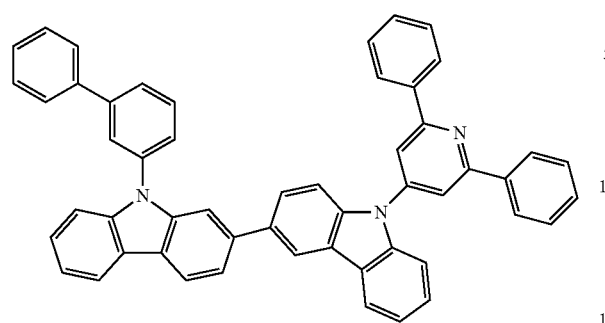
[A-70]
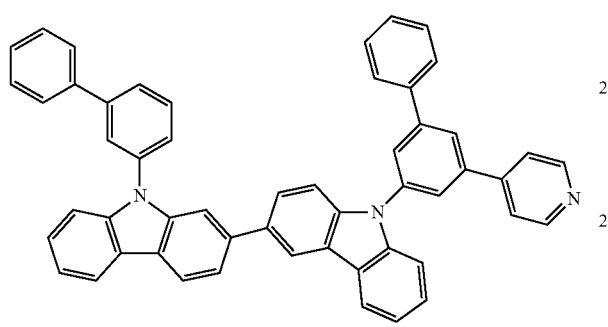
[A-71]
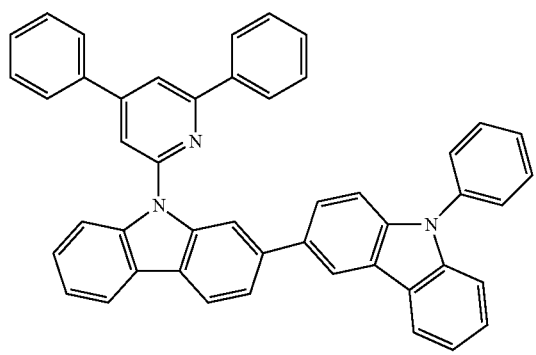
[A-72]
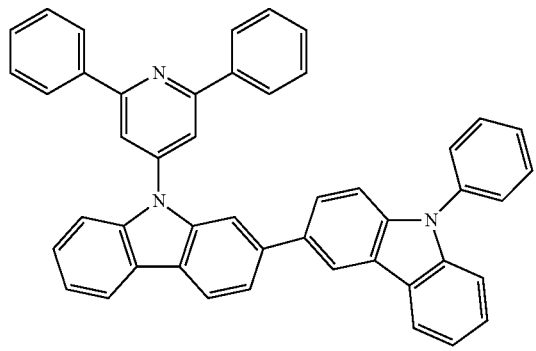
[A-73]
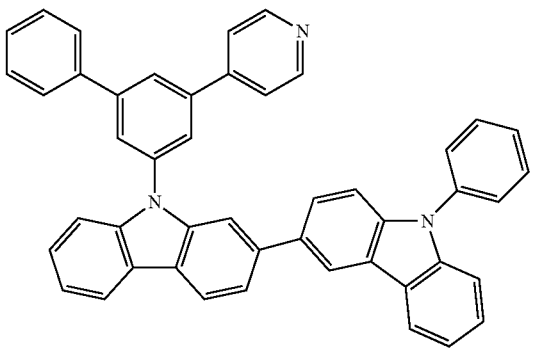
[A-74]
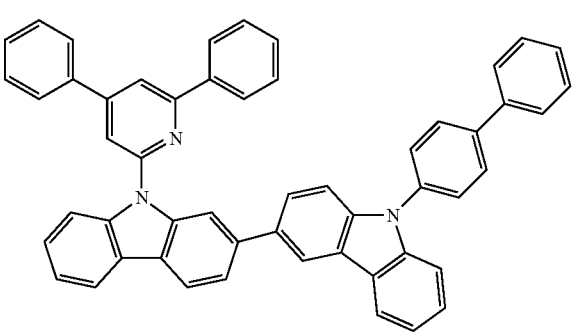
[A-75]
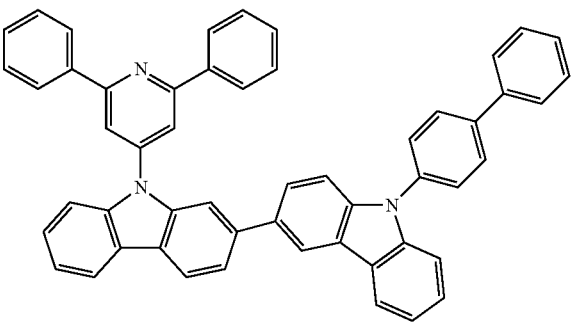
[A-76]
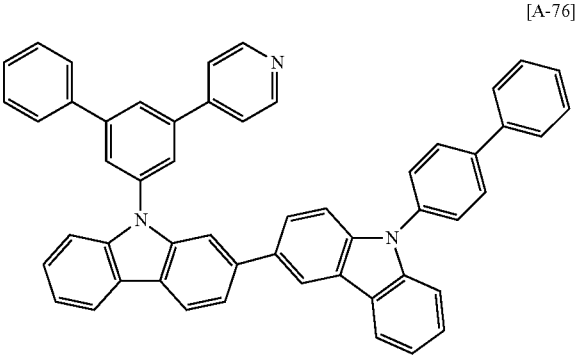

[A-77]
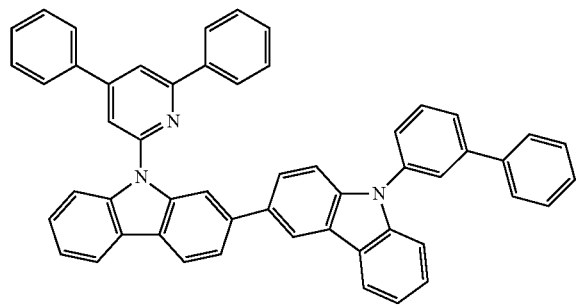
[A-78]
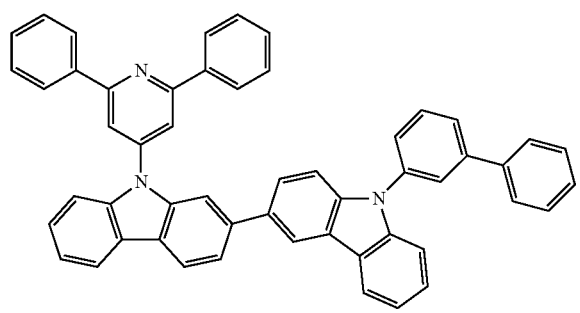
[A-79]
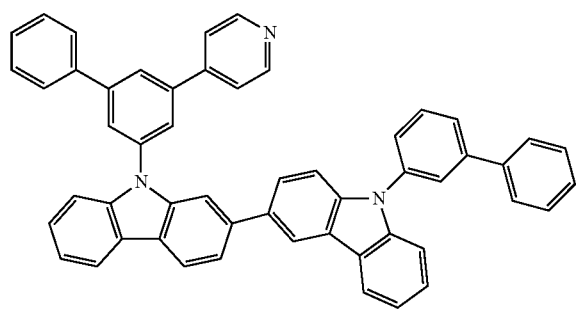
[A-80]
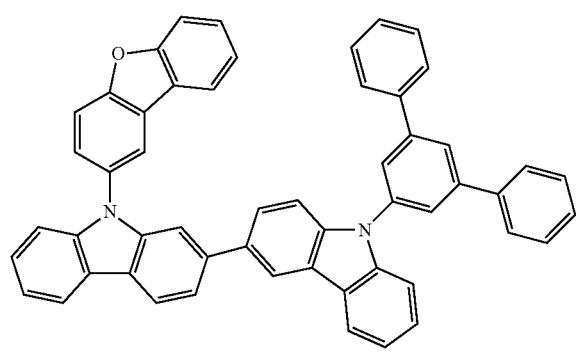
[A-81]
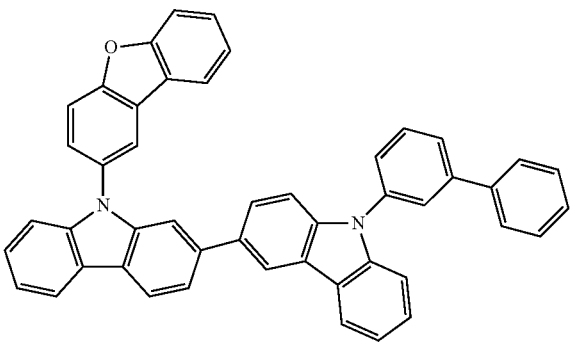
[A-82]
[A-83]
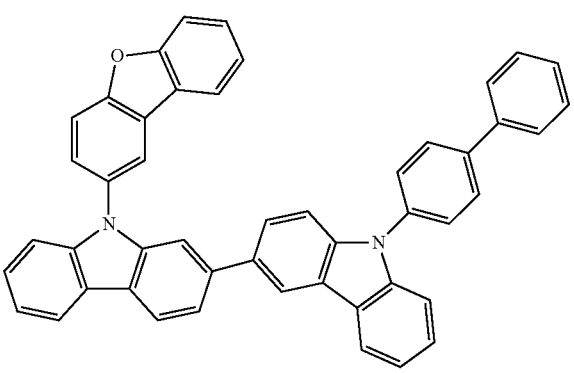
[A-84]
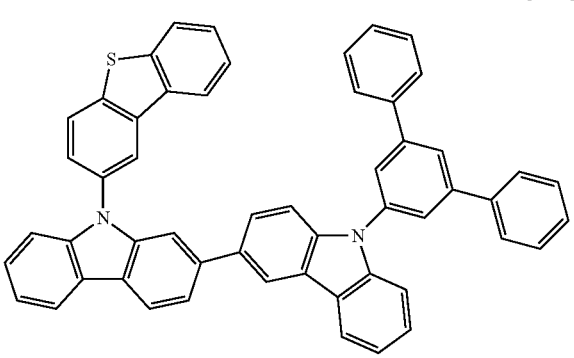

[A-85]
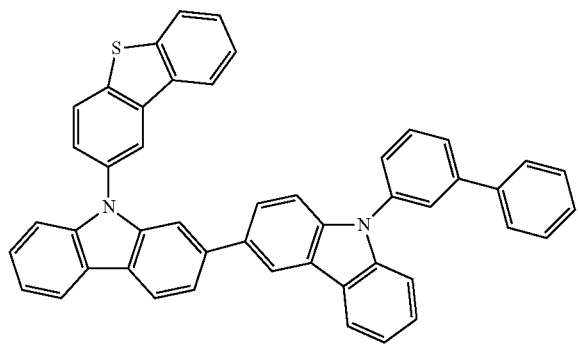
[A-89]
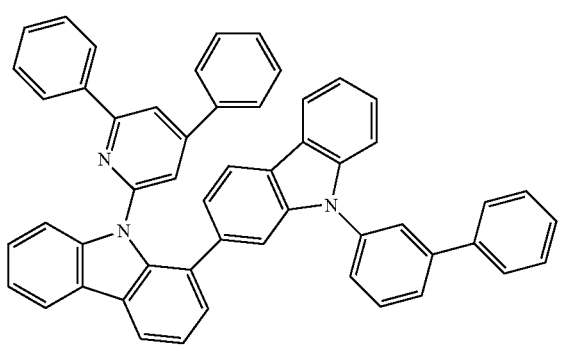
[A-86]
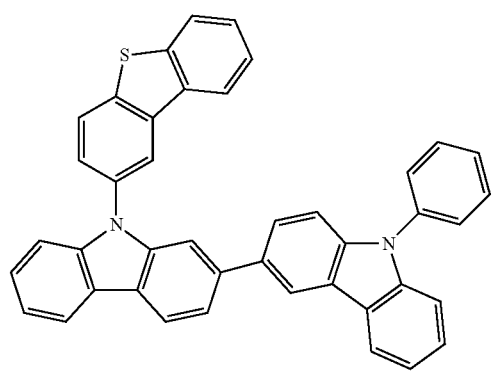
[A-90]
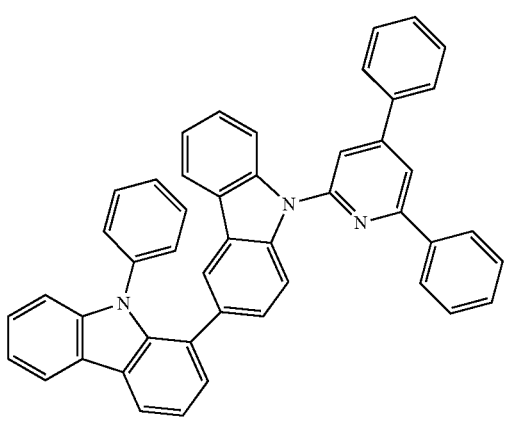
[A-87]
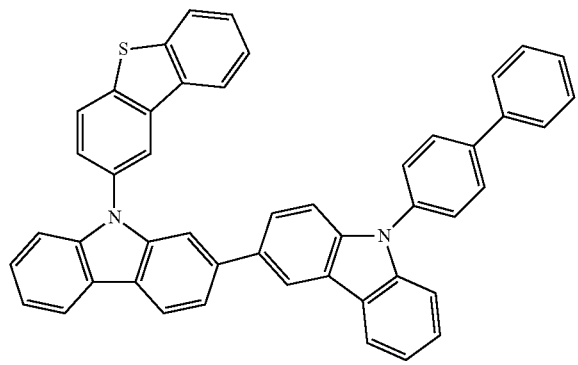
[A-91]
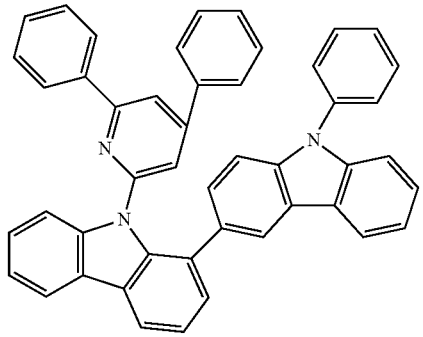
[A-88]
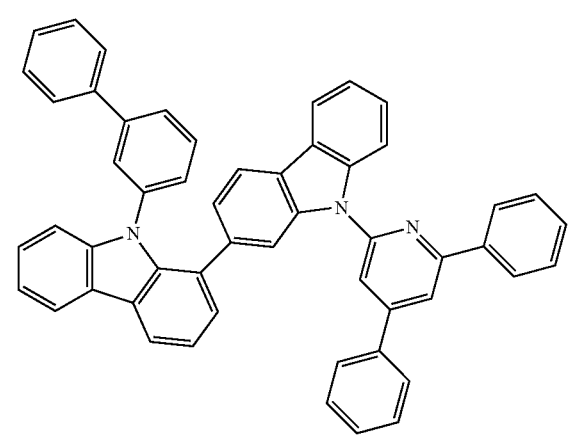
[A-92]
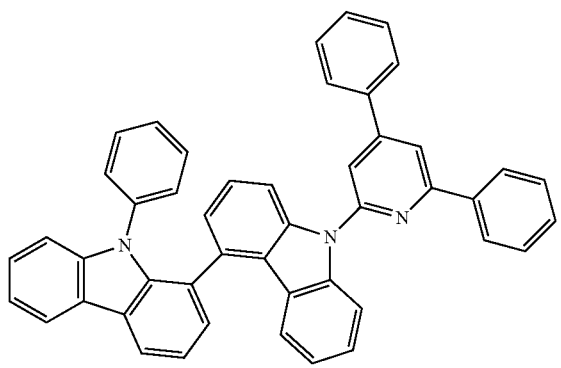

[A-93]
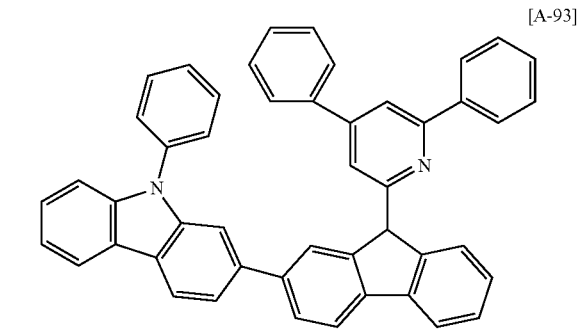
[A-94]
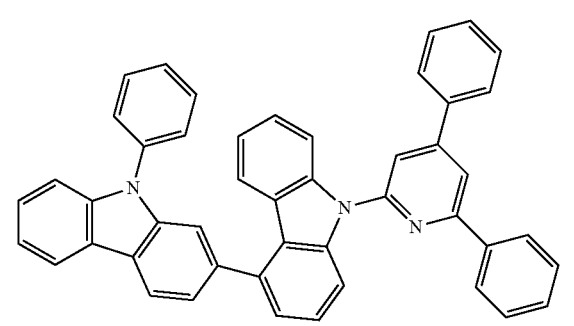
[A-95]
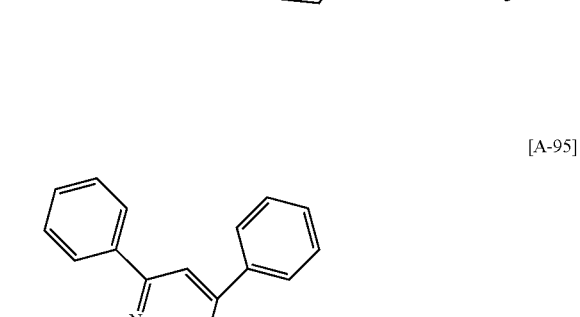
[A-96]
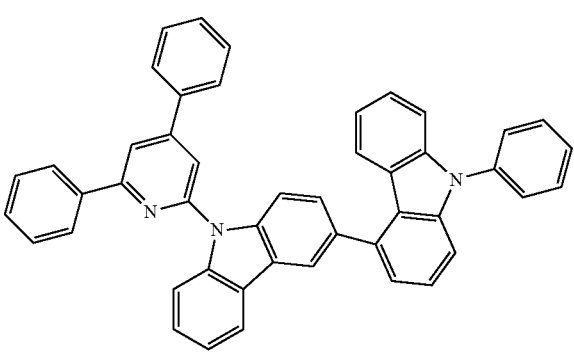
[A-97]
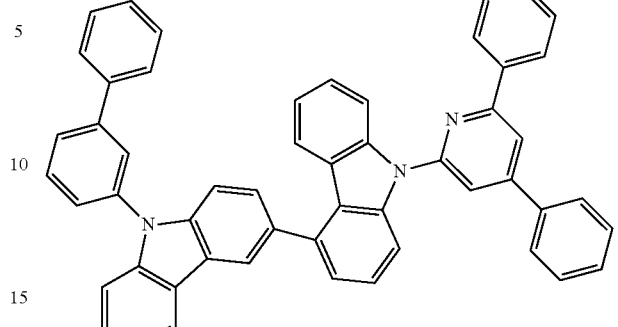
[A-98]
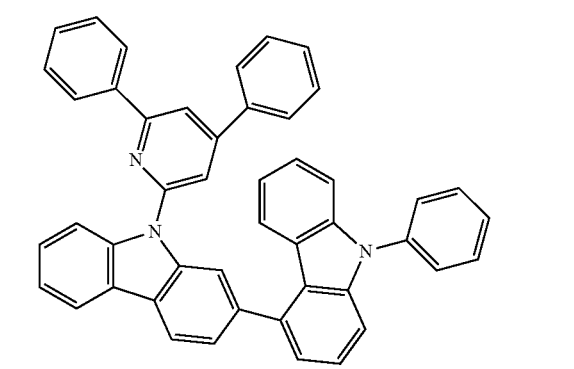
[A-99]
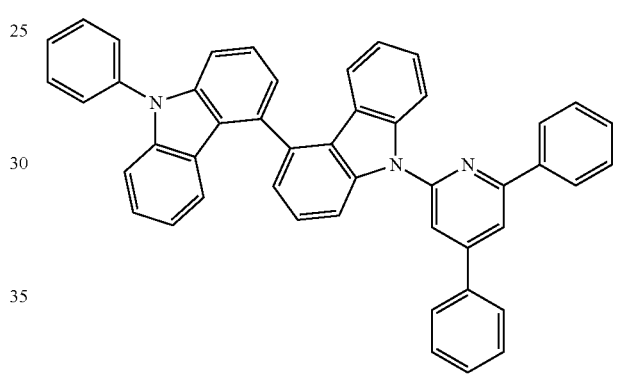

[A-100]
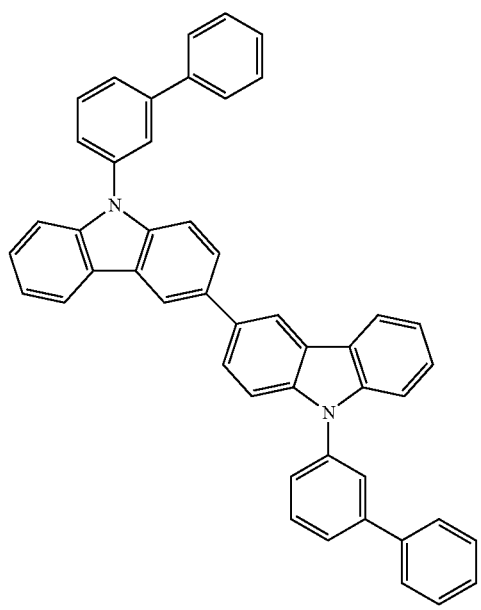
[A-101]
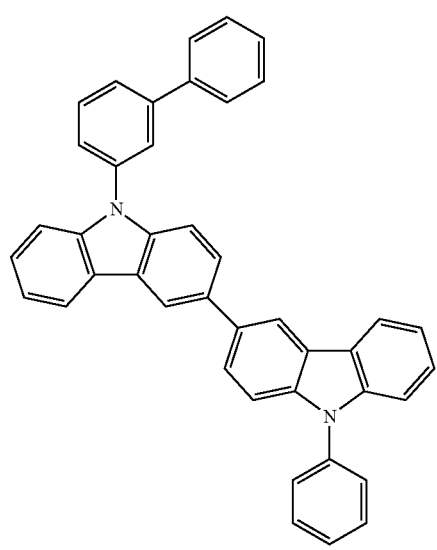
[A-102]
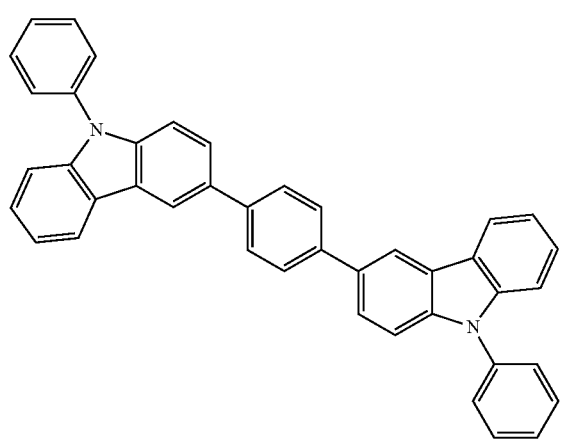
[A-103]
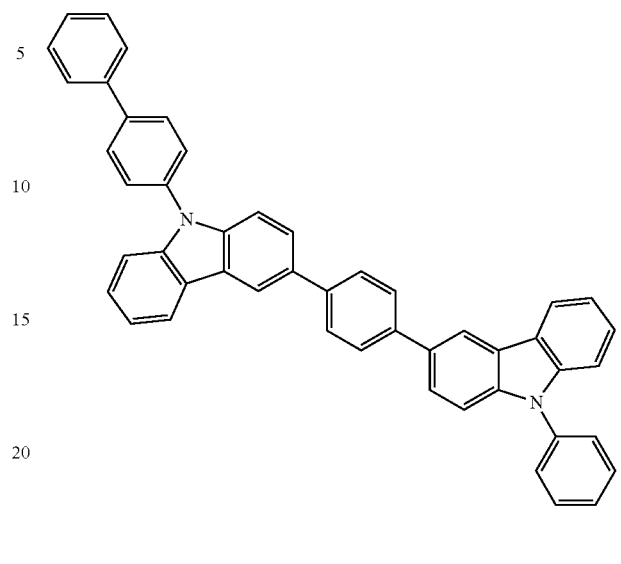
[A-104]
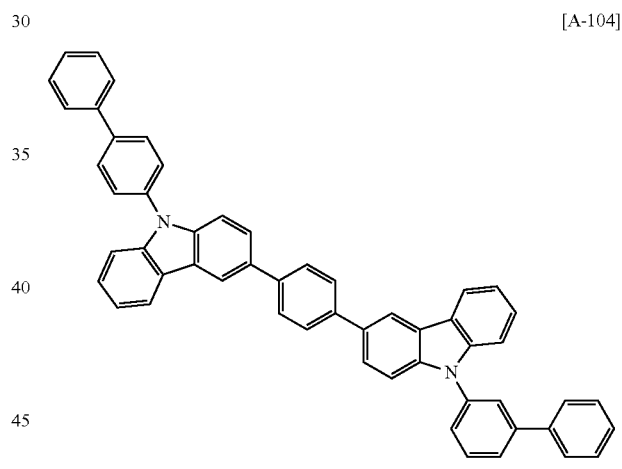
[A-105]
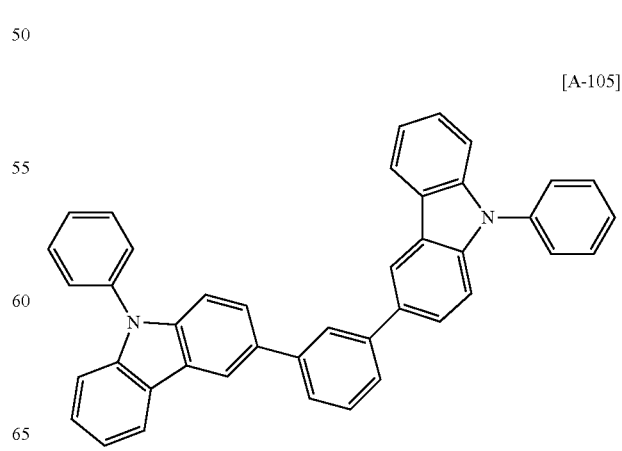

[A-106]
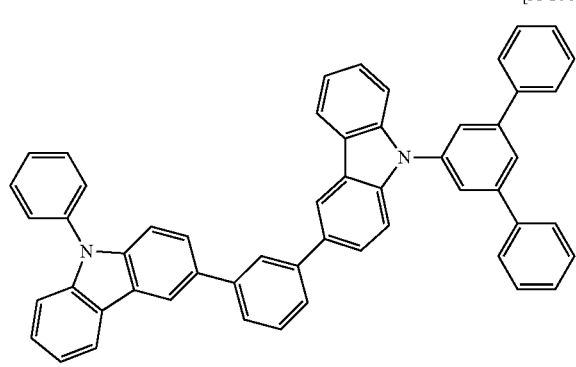
[A-107]
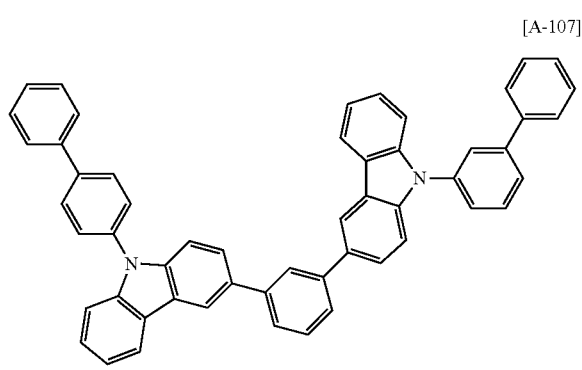
[A-108]
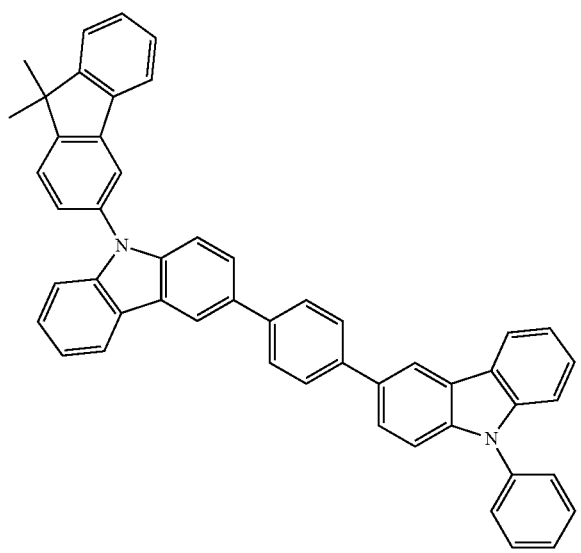
[A-109]
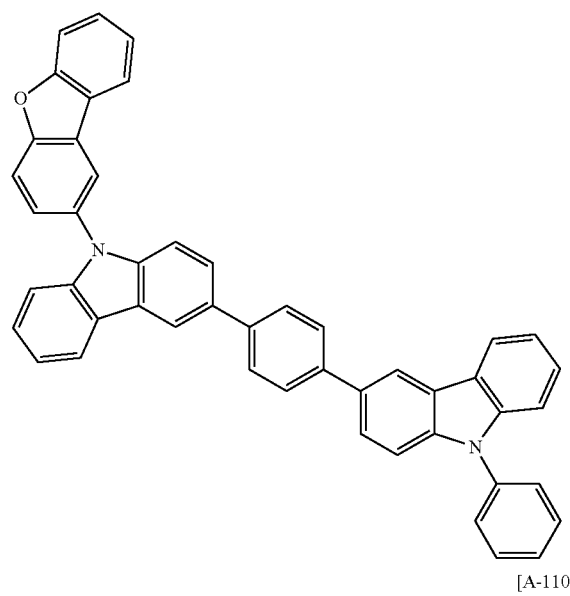
[A-110]
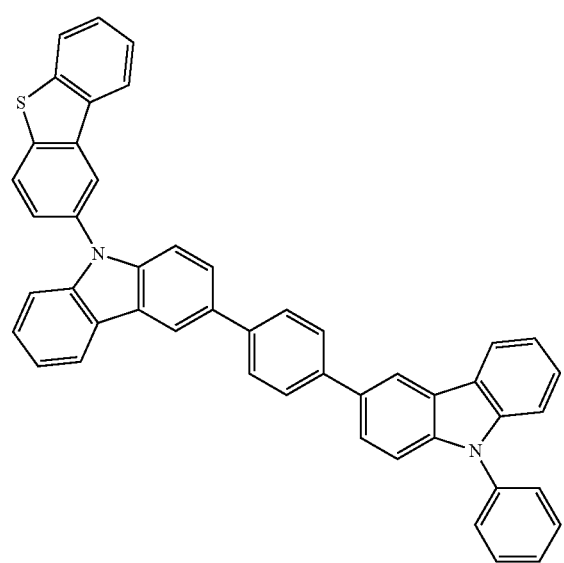
[A-111]
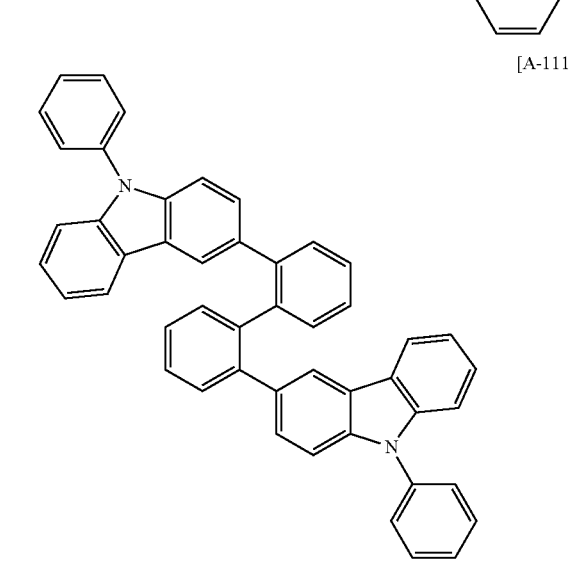

[A-112]
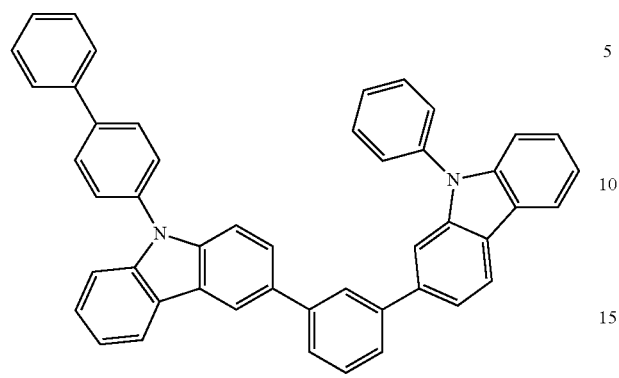
[A-113]
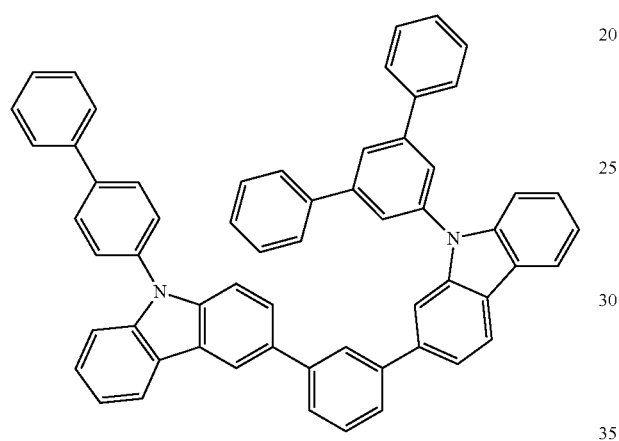
[A-114]
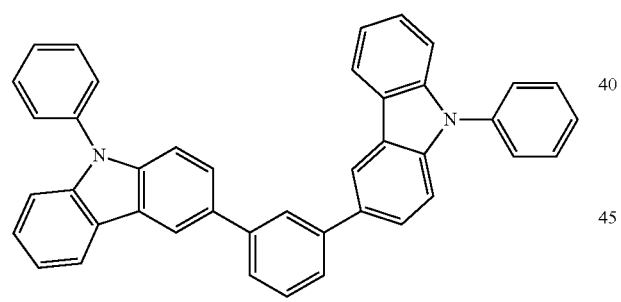
[A-115]
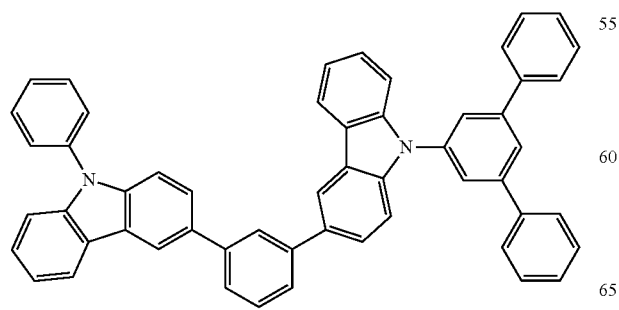
[A-116]
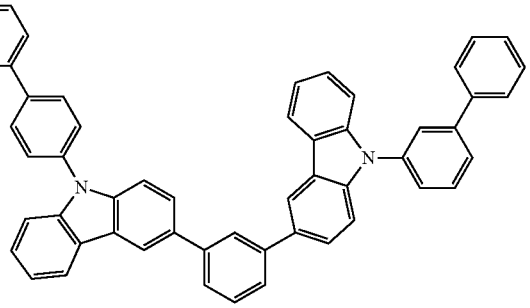
[A-117]
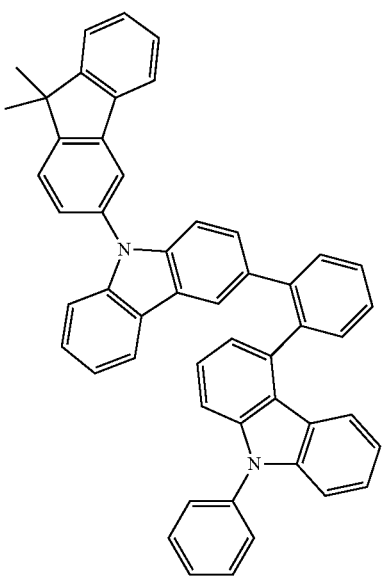
[A-118]
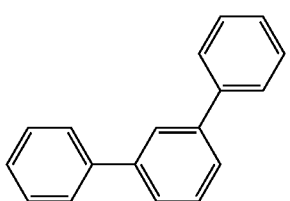

[A-119]
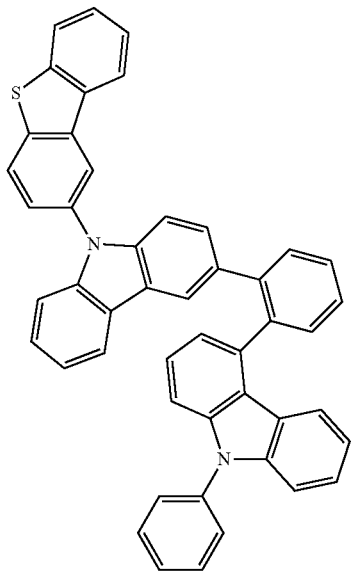
[A-122]
[A-123]
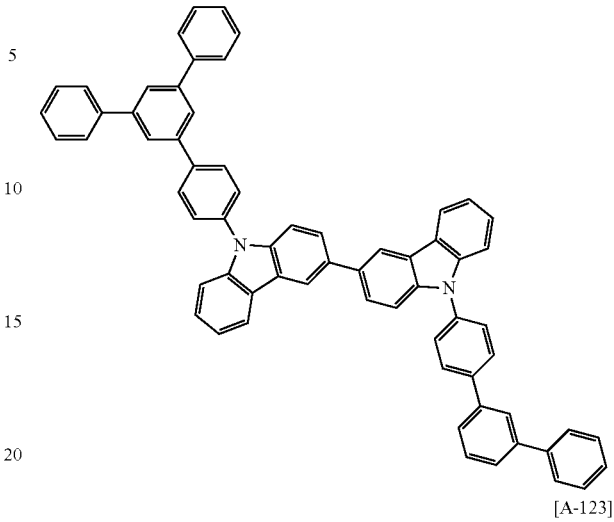
[A-120]
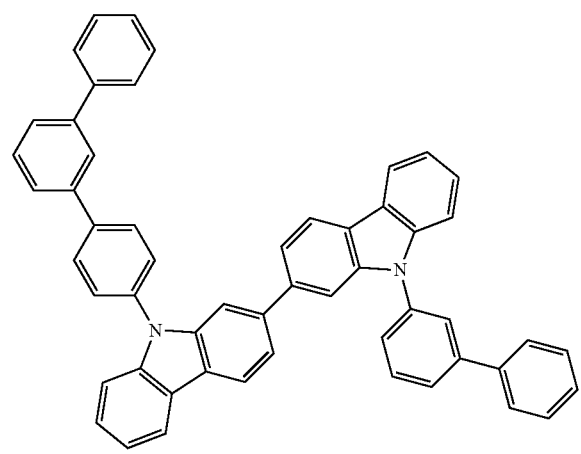
[A-121]
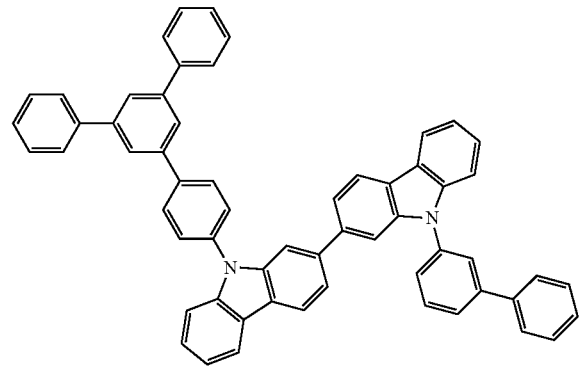
[A-124]
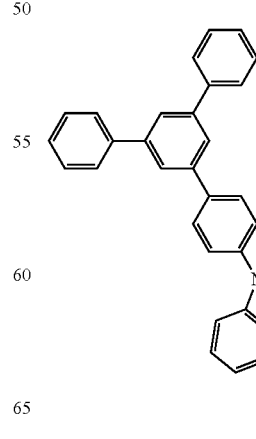

[A-125]
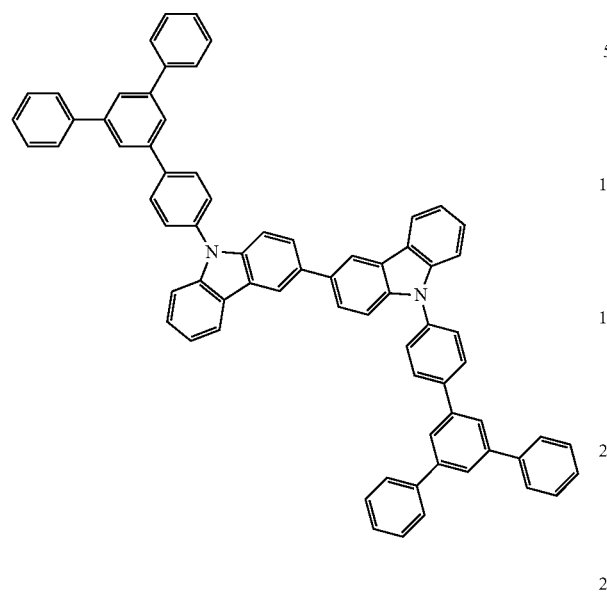
[A-127]
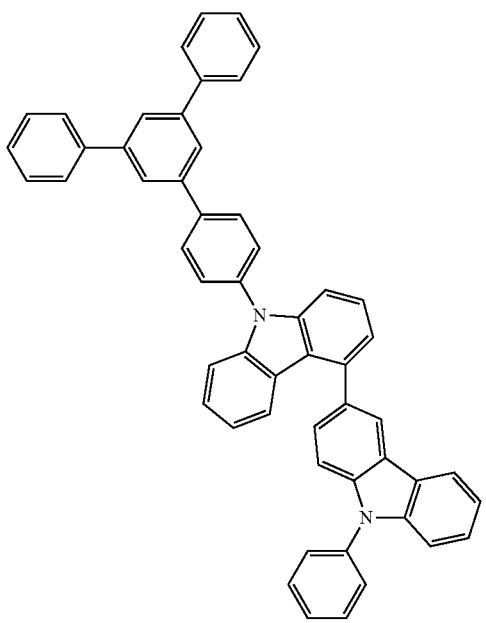
[A-126]
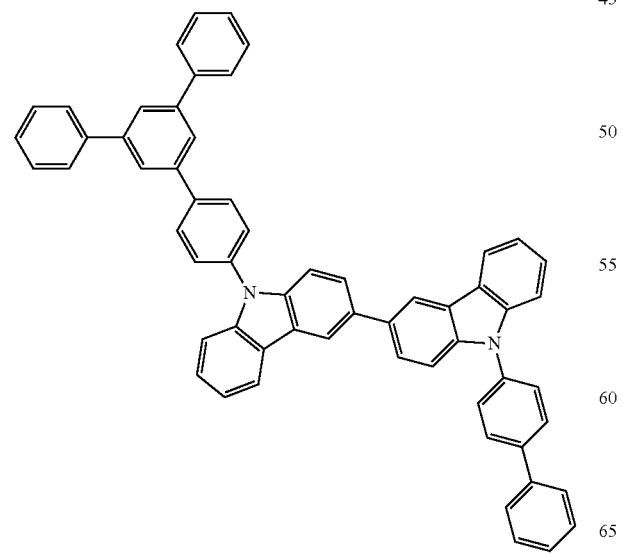
[A-128]
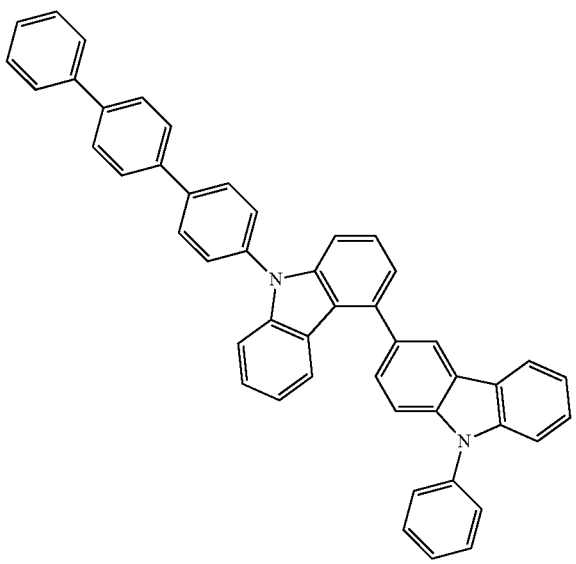

[A-129]
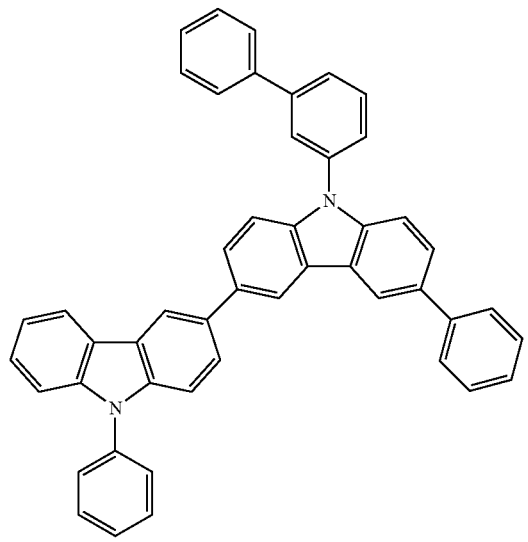
[A-130]
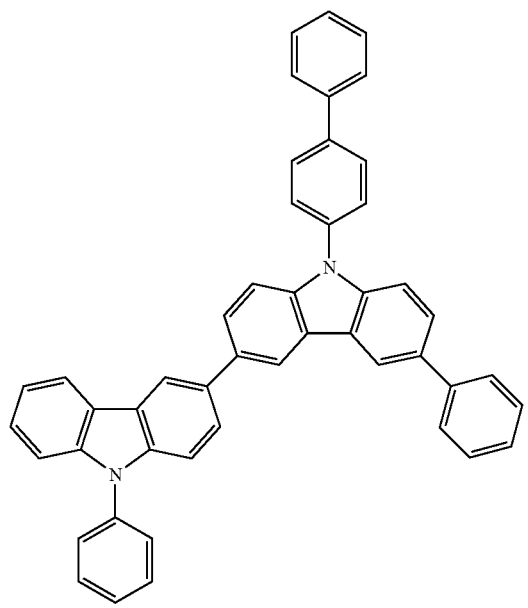
[A-131]
[A-132]
[A-133]
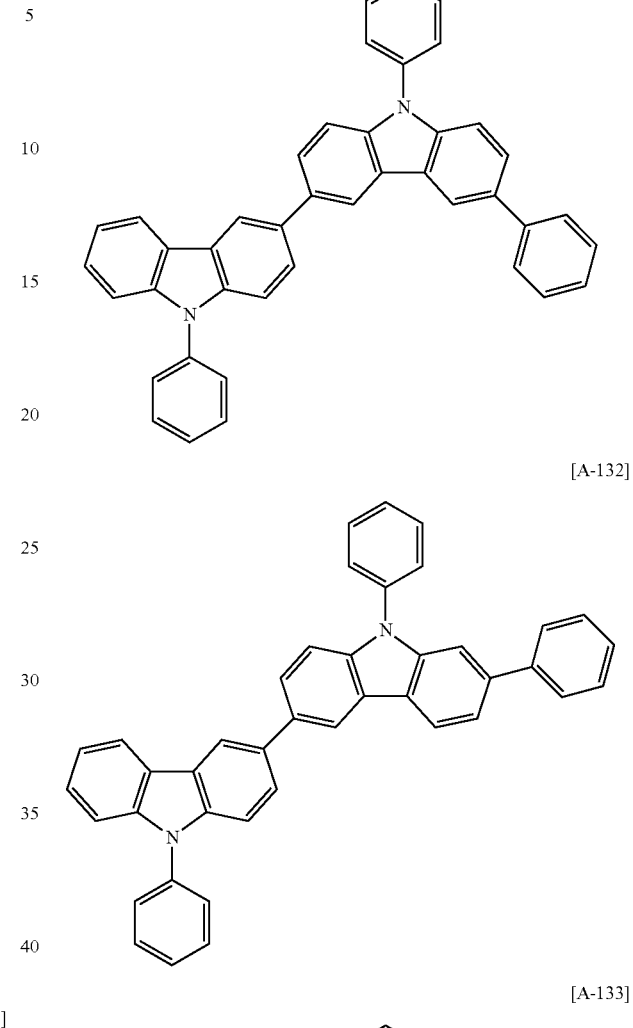

[A-134]
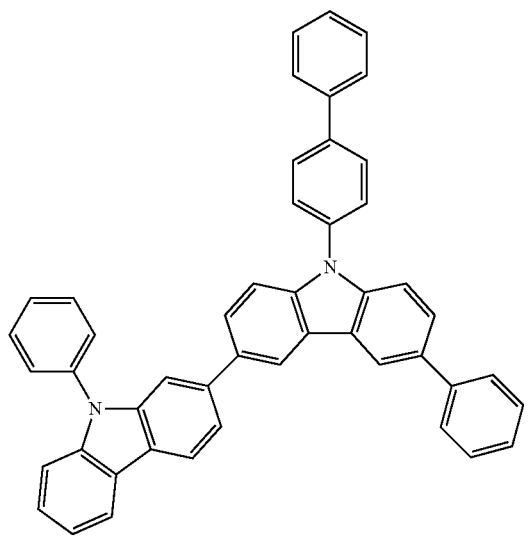
[A-135]
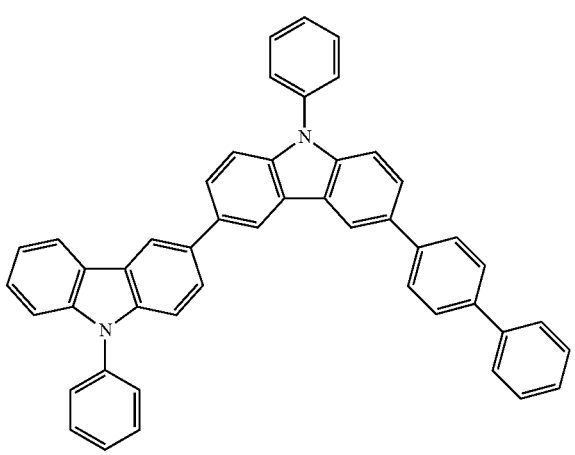
[A-136]
[A-137]
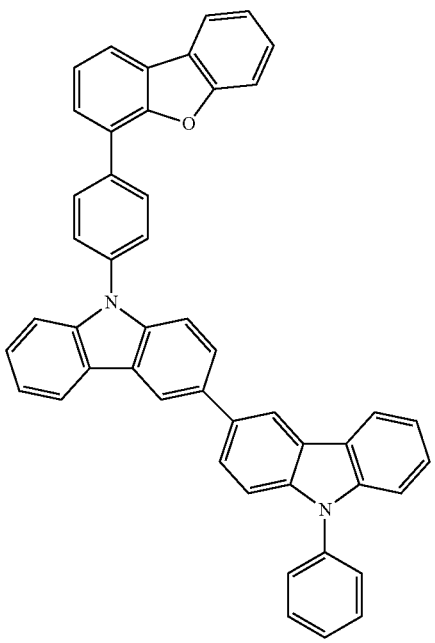
[A-138]
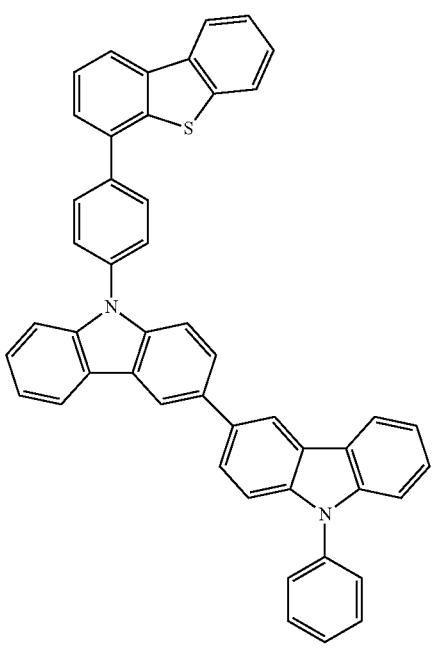
[B-1]
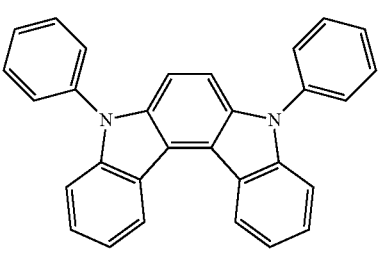

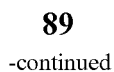
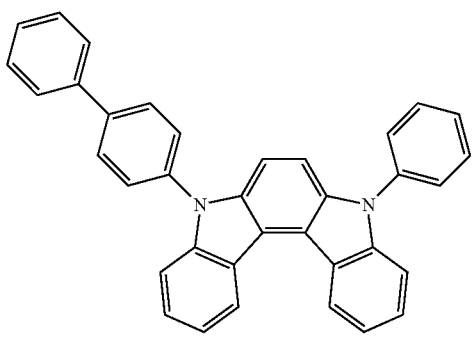
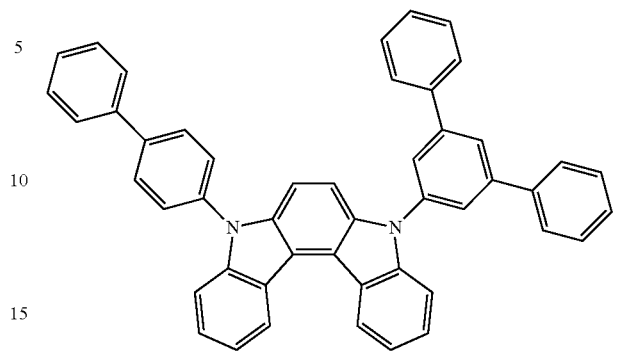
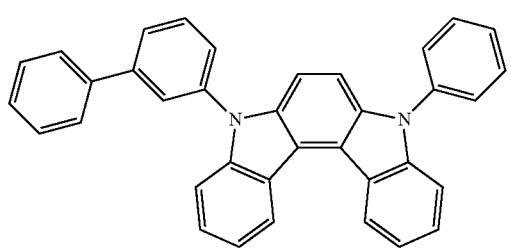
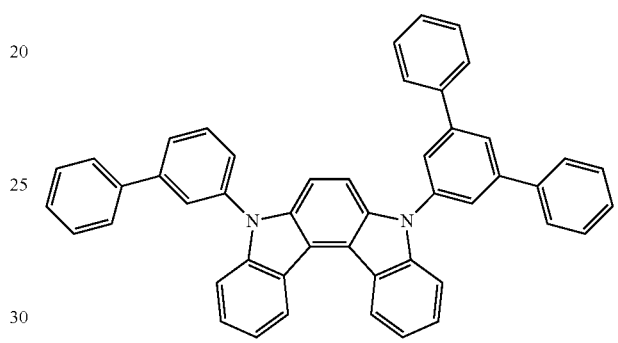
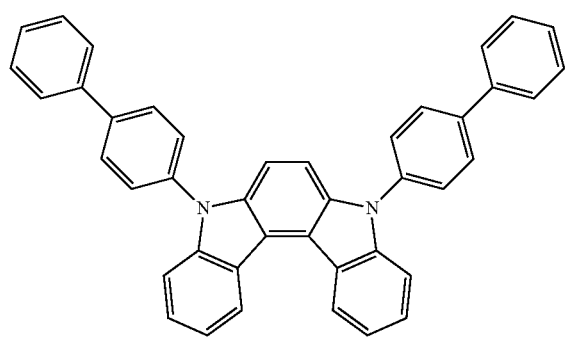
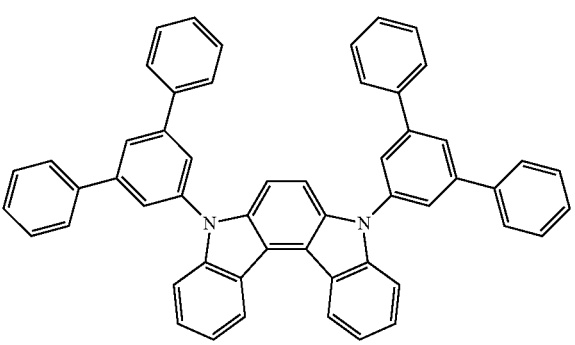
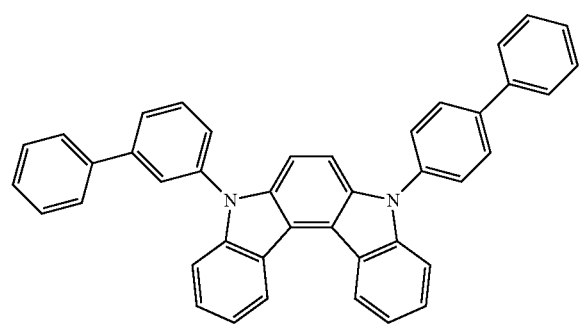
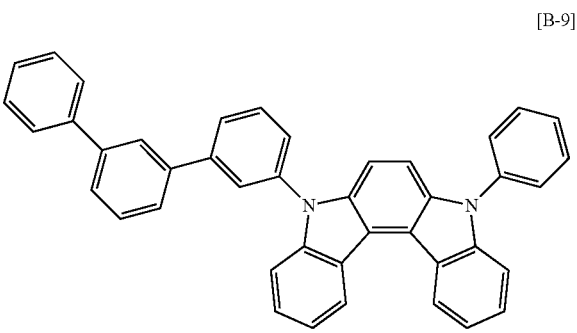

[B-10]
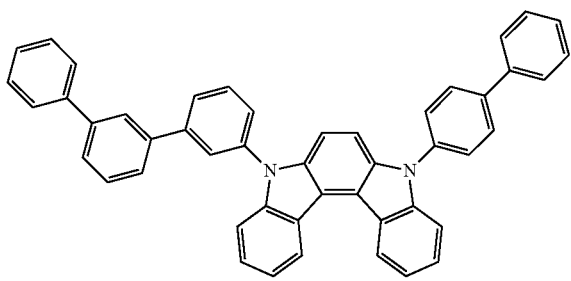
[B-11]
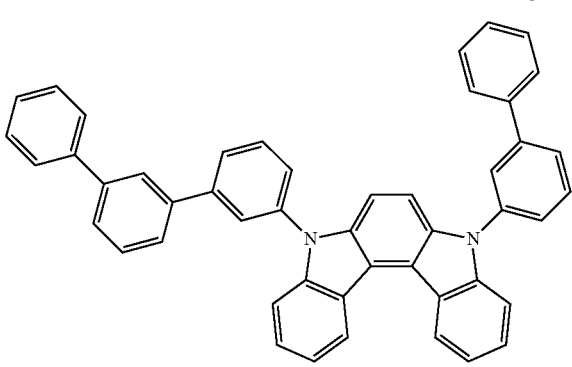
[B-12]
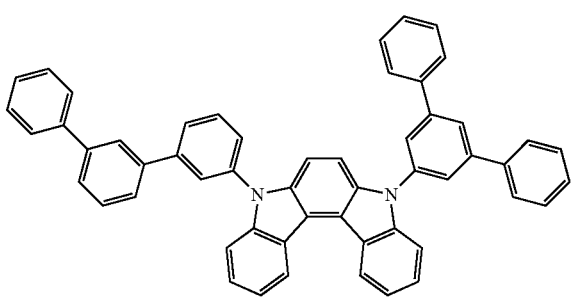
[B-13]
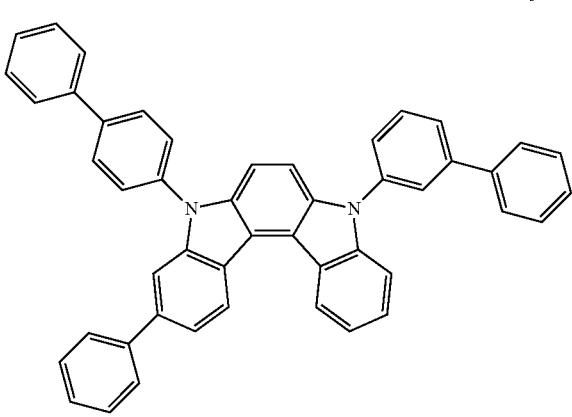
[B-14]
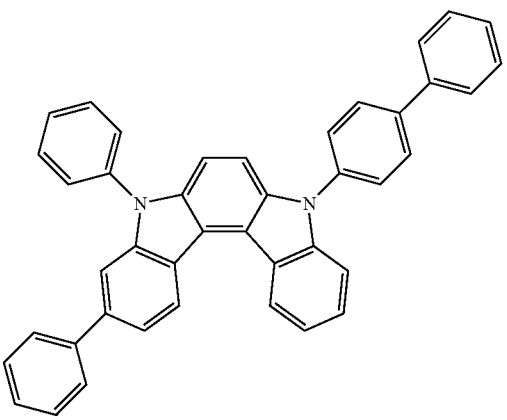
[B-15]
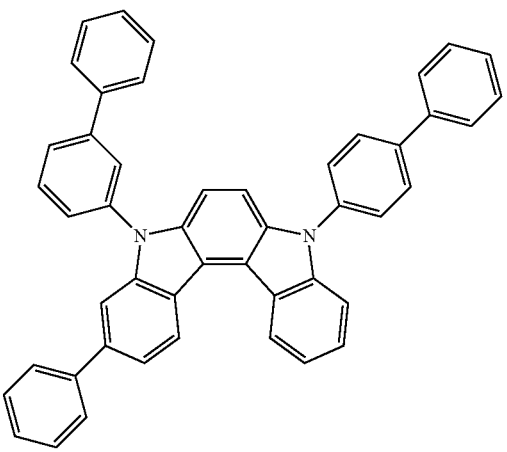
[B-16]
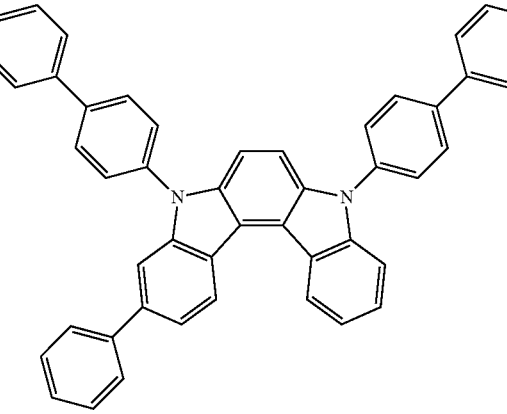

[B-17]
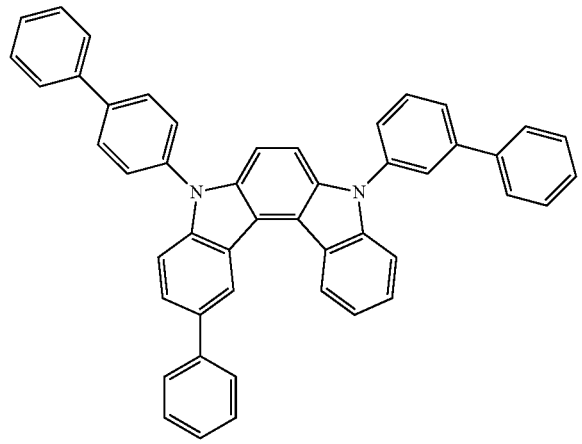
[B-18]
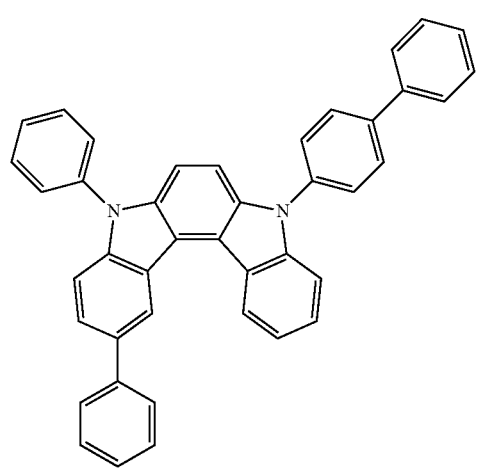
[B-19]
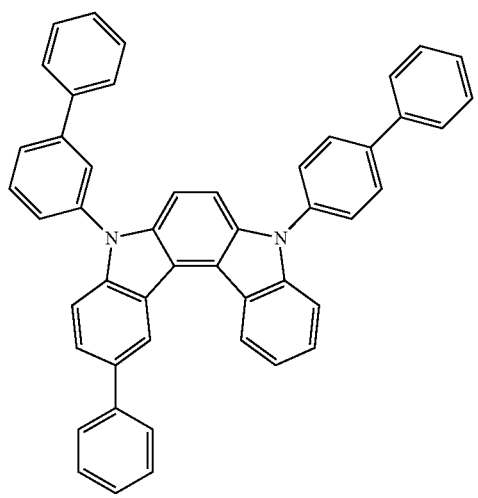
[B-20]
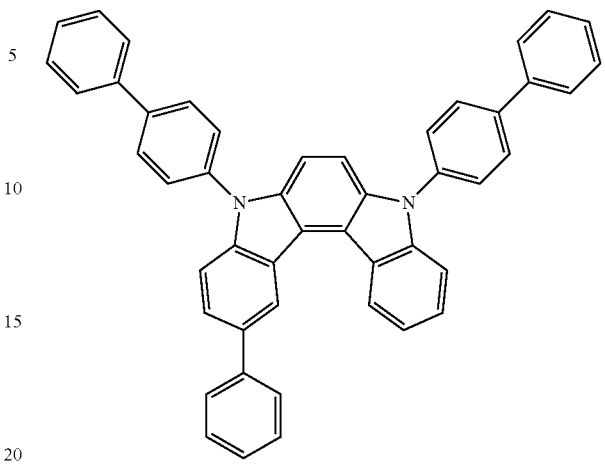
[B-21]
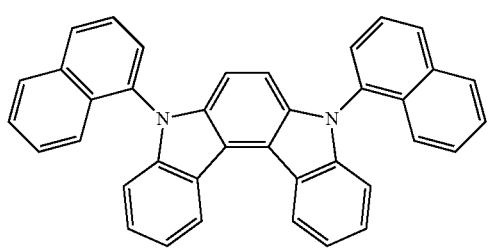
[B-22]
[B-23]
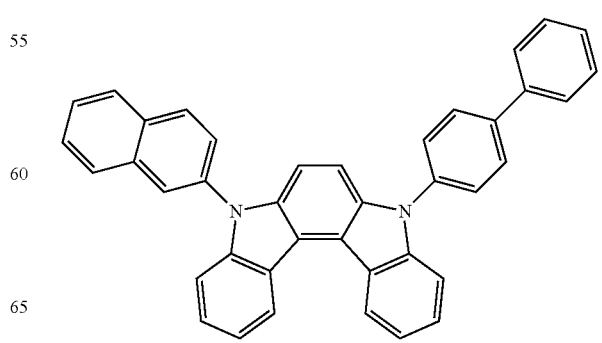

-continued
[B-24]
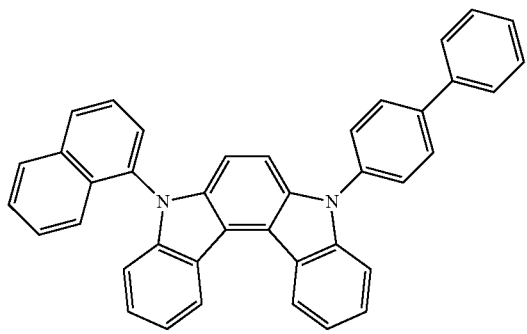
[B-25]
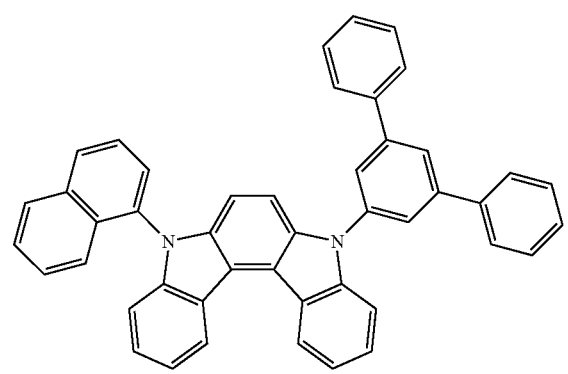
[B-26]
[B-27]
-continued
[B-28]
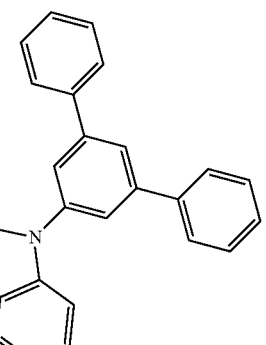
[B-29]
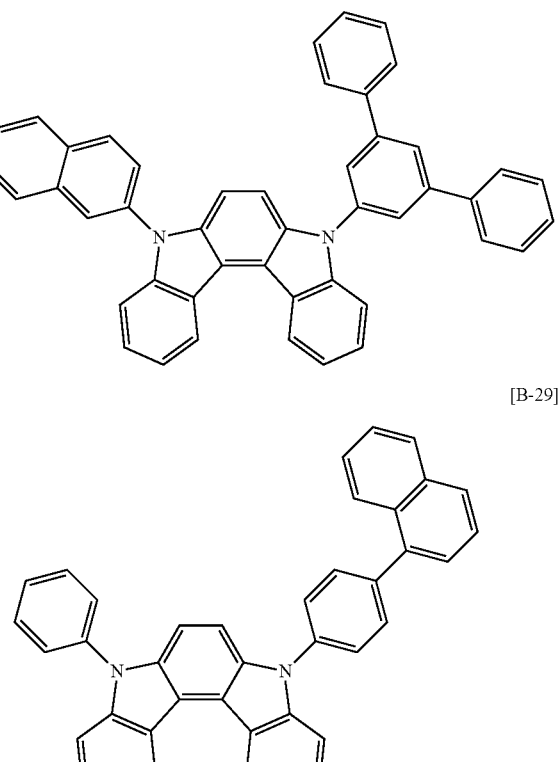
[B-30]
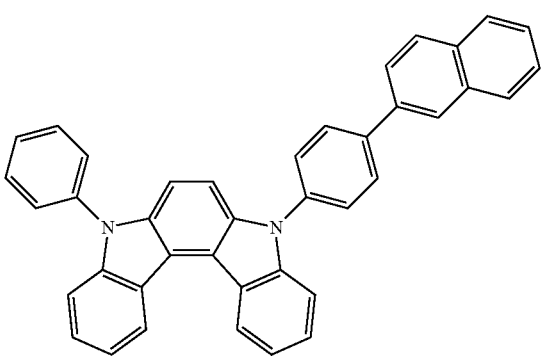
[B-31]
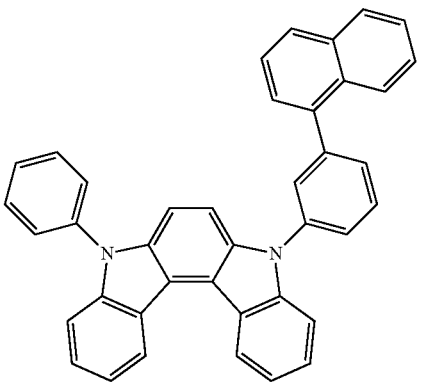

-continued
[B-32]
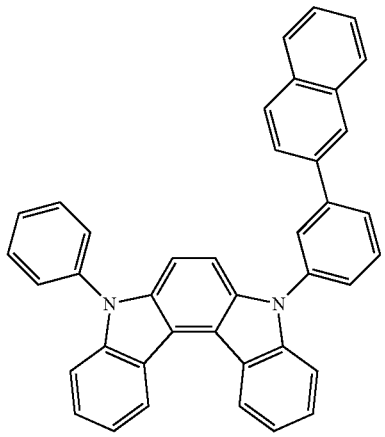
[B-33]
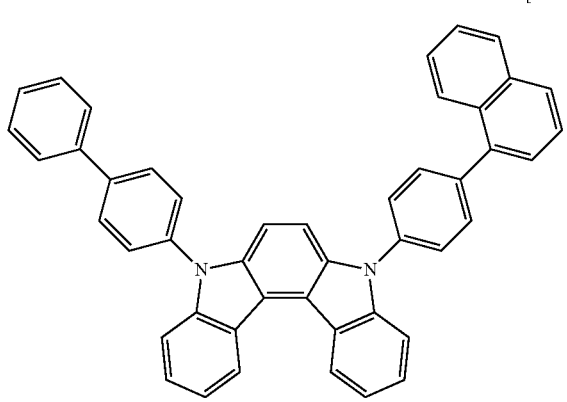
[B-34]
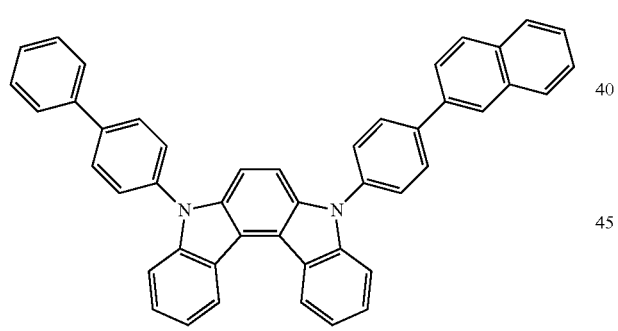
[B-35]
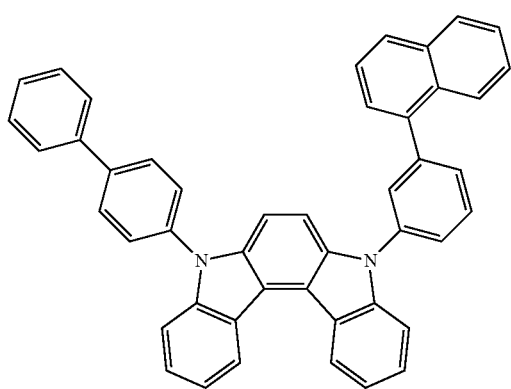
[B-36]
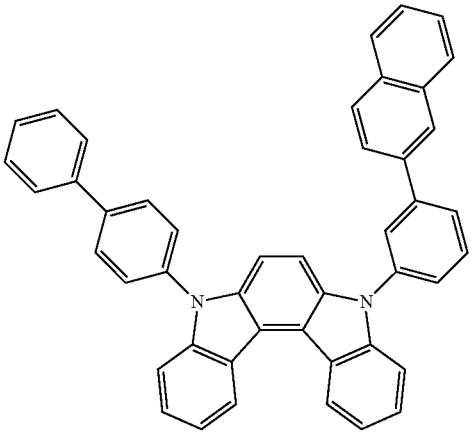
[B-37]
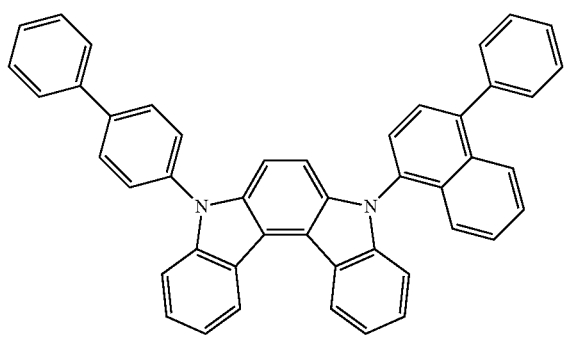
[B-38]
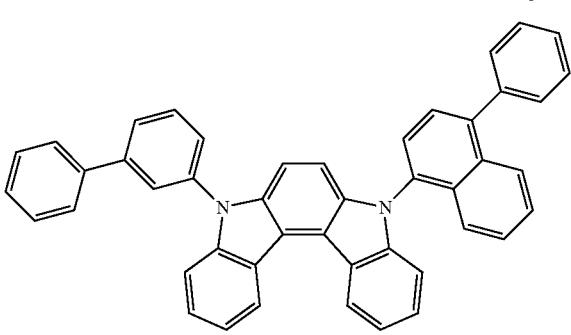
[B-39]
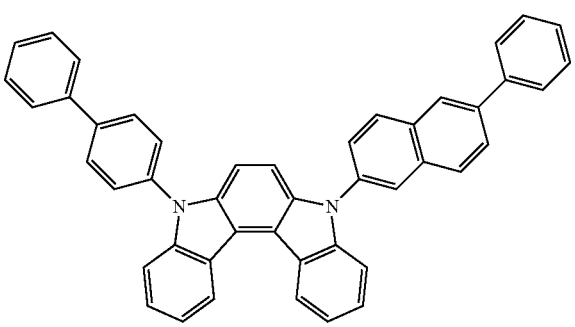

[B-40]
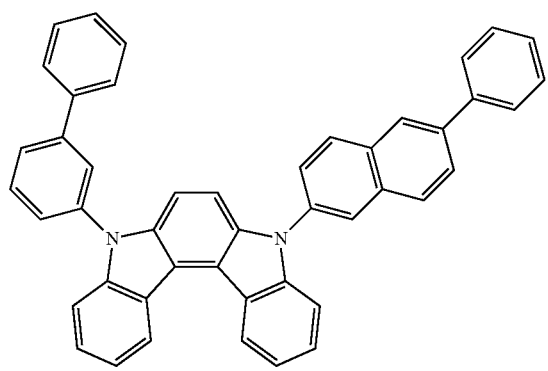
[B-41]
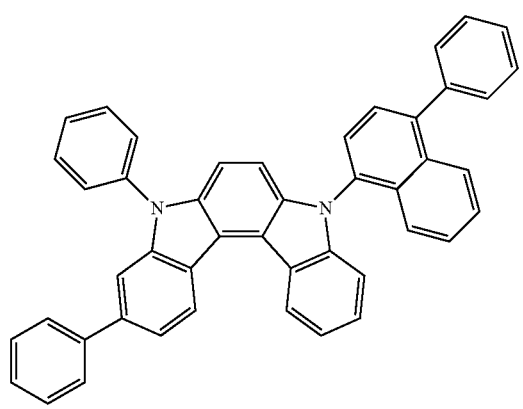
[B-42]
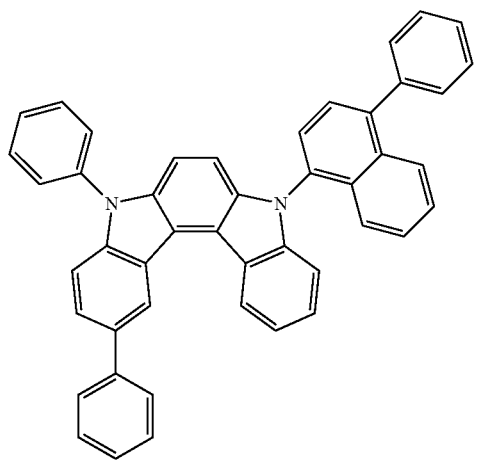
[B-43]
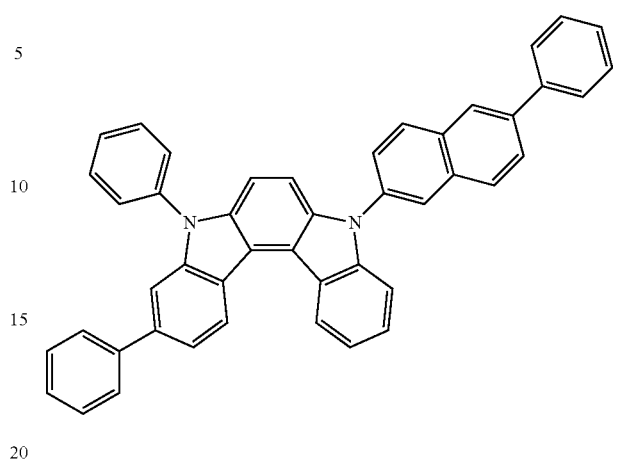
[B-44]
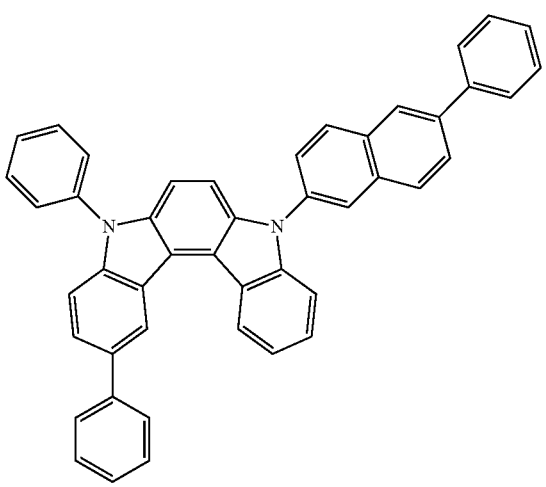
[B-45]
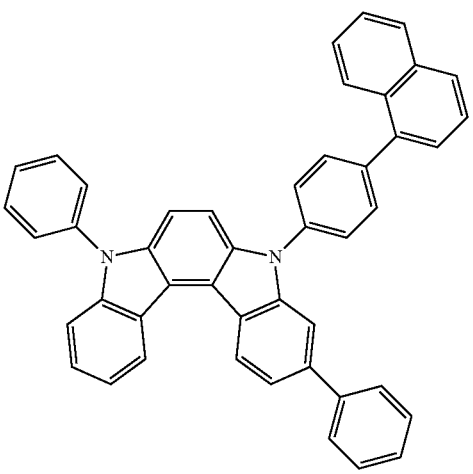

-continued
[B-46]
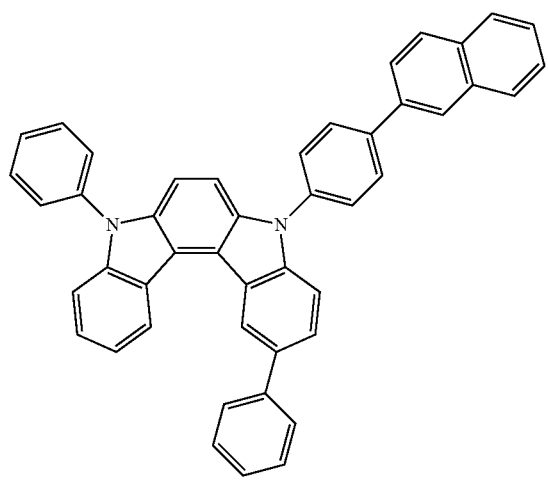
[B-47]
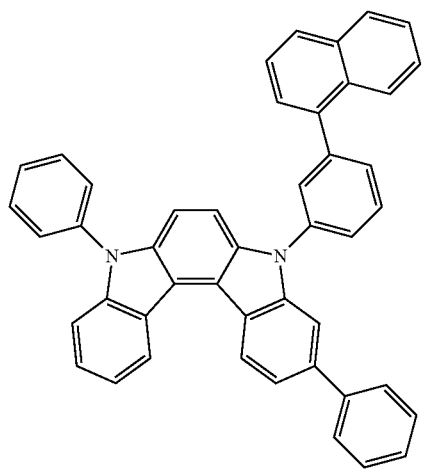
[B-48]
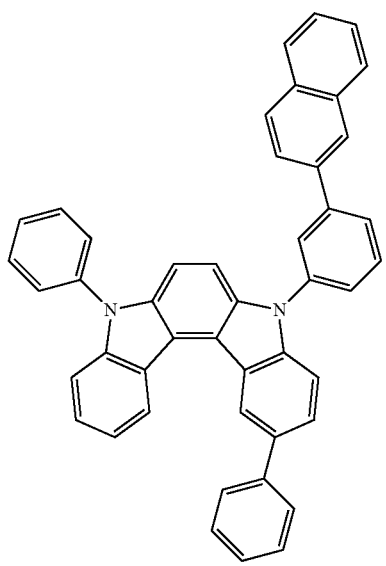
-continued
[B-49]
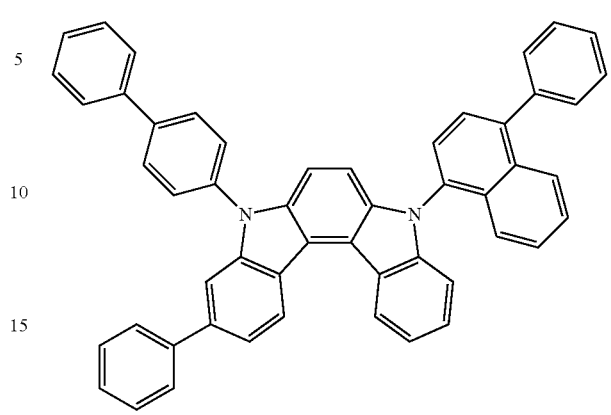
[B-50]
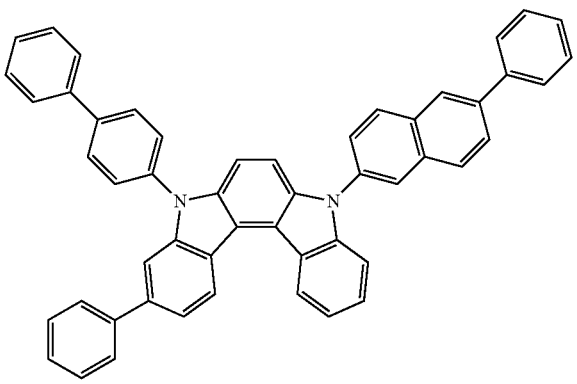
[B-51]

[B-52]

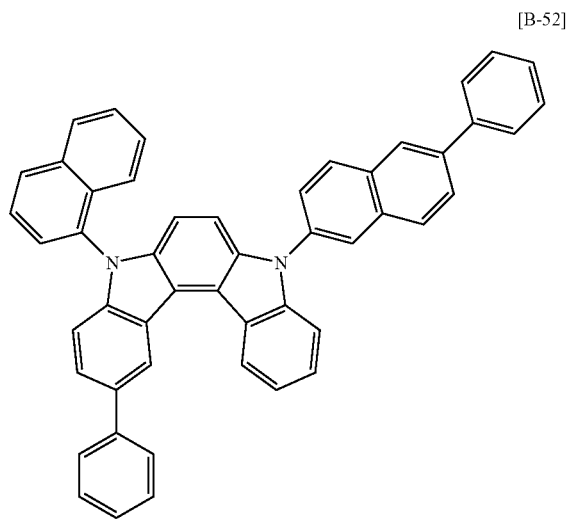

[B-53]

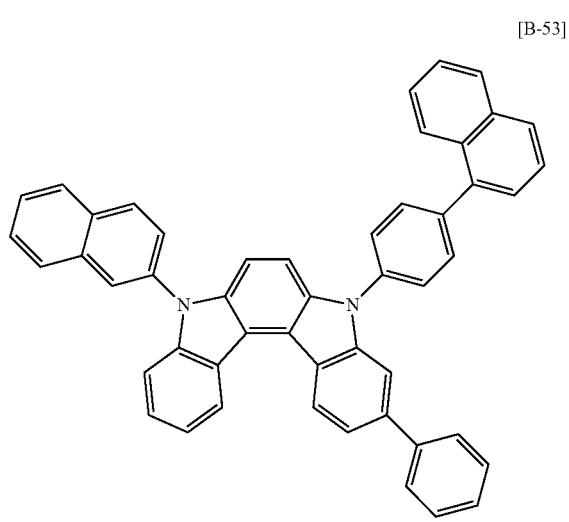

[B-54]

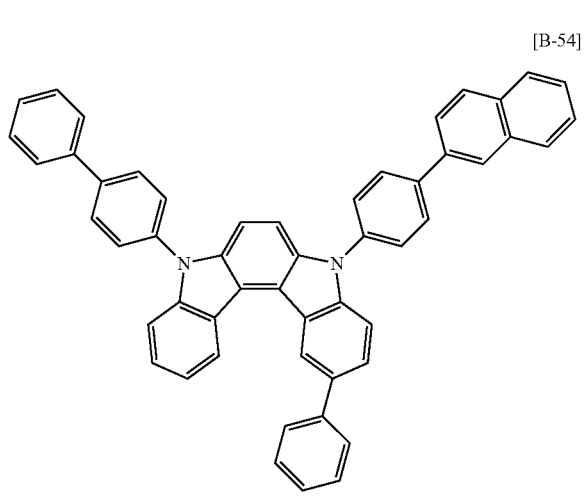

[B-55]

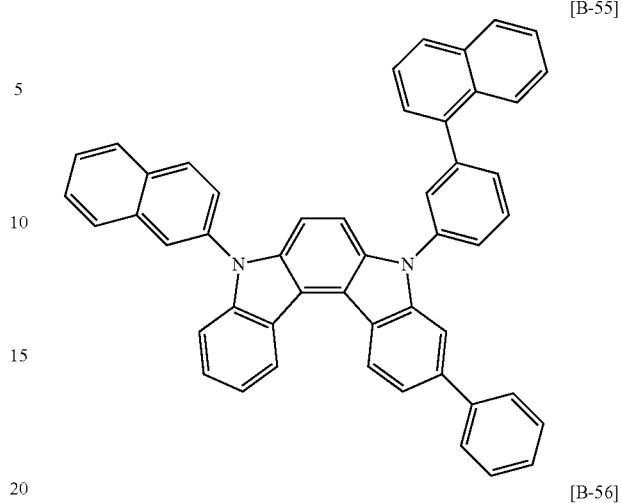

[B-56]

The first compound and the second compound may be included (e.g., mixed), e.g., in a weight ratio of about 1:99 to about 99:1. Within the above range, an appropriate weight ratio may be adjusted using the electron transport capability of the first compound for the organic optoelectronic device and the hole transport capability of the second compound for an organic optoelectronic device to implement bipolar characteristics and to improve the efficiency and life-span. Within the above range, e.g., they may be included in a weight ratio of about 10:90 to about 90:10, about 10:90 to about 80:20, e.g., about 10:90 to about 70:30, about 20:80 to about 70:30, or about 20:80 to about 60:40. In an implementation, they may be included in a weight ratio of, e.g., about 30:70 or about 40:60.

In addition to the aforementioned first compound and second compound, one or more additional compounds may be further included.

The aforementioned compound for an organic optoelectronic device or composition for an organic optoelectronic device may be a composition further including a dopant.

The dopant may be, e.g., a phosphorescent dopant and may be, for example a red, green or blue phosphorescent dopant, for example a red or green phosphorescent dopant.

The dopant is a material mixed with the compound or composition for an organic optoelectronic device in a trace amount to cause light emission, and may be a material such as a metal complex that emits light by multiple excitation into a triplet or more. The dopant may be, e.g., an inorganic, organic, or organic-inorganic compound, and one or more types thereof may be used.

Examples of the dopant may include a phosphorescent dopant and examples of the phosphorescent dopant may include an organic metal compound including Ir, Pt, Os, Ti, Zr, Hf, Eu, Tb, Tm, Fe, Co, Ni, Ru, Rh, Pd, or a combination thereof. In an implementation, the phosphorescent dopant may include, e.g., a compound represented by Chemical Formula Z.

$L^5MX$ [Chemical Formula Z]

In Chemical Formula Z, M may be, e.g., a metal, and $L^5$ and X may each independently be, e.g., a ligand forming a complex with M.

M may be, e.g., Ir, Pt, Os, Ti, Zr, Hf, Eu, Tb, Tm, Fe, Co, Ni, Ru, Rh, Pd, or a combination thereof, and $L^5$ and X may be, e.g., a bidentate ligand.

Hereinafter, an organic optoelectronic device including the aforementioned compound for an organic optoelectronic device or composition for an organic optoelectronic device is described.

The organic optoelectronic device may be a suitable device to convert electrical energy into photoenergy and vice versa, and may be, e.g., an organic photoelectric device, an organic light emitting diode, an organic solar cell, or an organic photoconductor drum.

Herein, an organic light emitting diode as one example of an organic optoelectronic device is described referring to drawings.

FIGS. 1 to 4 are cross-sectional views of organic light emitting diodes according to embodiments.

Referring to FIG. 1, an organic light emitting diode 100 according to an embodiment may include an anode 120 and a cathode 110 facing each other and an organic layer 105 between the anode 120 and cathode 110.

The anode 120 may be made of a conductor having a large work function to help hole injection, and may be, e.g., a metal, a metal oxide or a conductive polymer. The anode 120 may be, e.g., a metal such as nickel, platinum, vanadium, chromium, copper, zinc, gold, or the like, or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, and/or a conductive polymer. The cathode 110 may be, e.g., a metal such as magnesium, calcium, sodium, potassium, titanium, indium, yttrium, lithium, gadolinium, aluminum silver, tin, lead, cesium, barium, or the like, or an alloy thereof; or a multi-layer structure material such as LiF/Al, $LiO_2$/Al, LiF/Ca, or $BaF_2$/Ca.

The organic layer 105 may include the aforementioned compound for an organic optoelectronic device or composition for an organic optoelectronic device.

The organic layer 105 may include the light emitting layer 130, and the light emitting layer 130 may include the aforementioned compound for an organic optoelectronic device or composition for an organic optoelectronic device.

The composition for an organic optoelectronic device further including the dopant may be, e.g., a red light emitting composition.

The light emitting layer 130 may include, e.g., the aforementioned first compound and second compound, respectively, as a phosphorescent host.

The organic layer may further include a charge transport region in addition to the light emitting layer.

Figure 2:
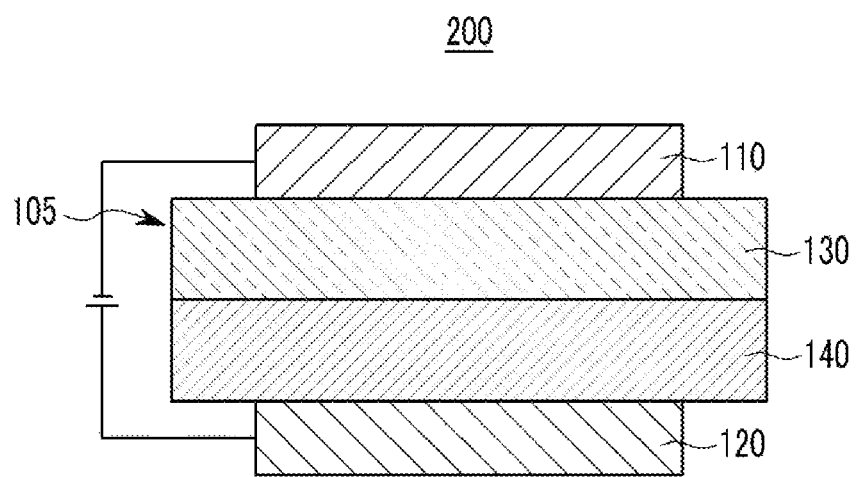

The auxiliary layer may be, e.g., the hole auxiliary layer 140 (see FIG. 2).

Referring to FIG. 2, an organic light emitting diode 200 may further include a hole transport region 140 in addition to the light emitting layer 130. The hole transport region 140 may help further increase hole injection and/or hole mobility between the anode 120 and the light emitting layer 130 and block electrons. In an implementation, the hole transport region 140 may include a hole transport layer between the anode 120 and the light emitting layer 130, and a hole transport auxiliary layer between the light emitting layer 130 and the hole transport layer. In an implementation, a compound of Group E may be included in at least one of the hole transport layer and the hole transport auxiliary layer.

[Group E]

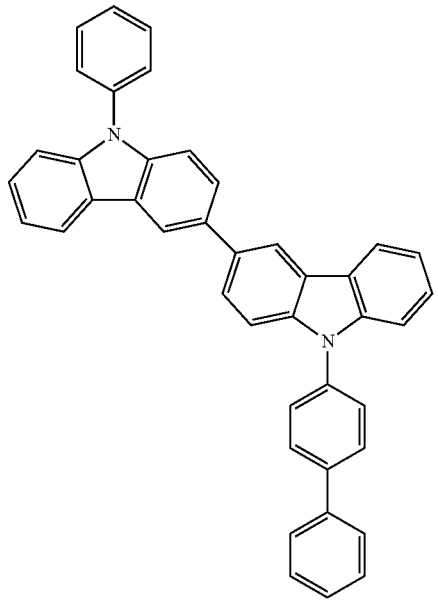

107
-continued
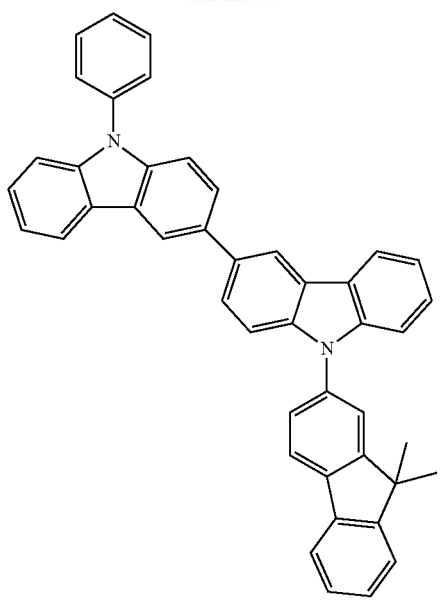
108
-continued
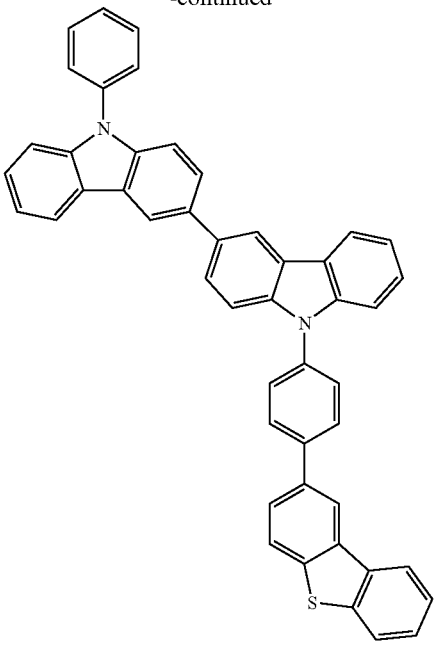
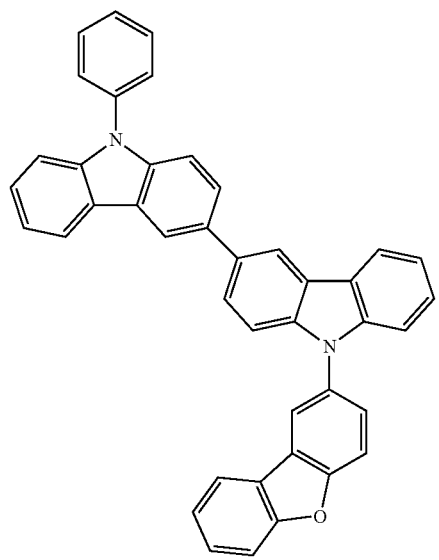
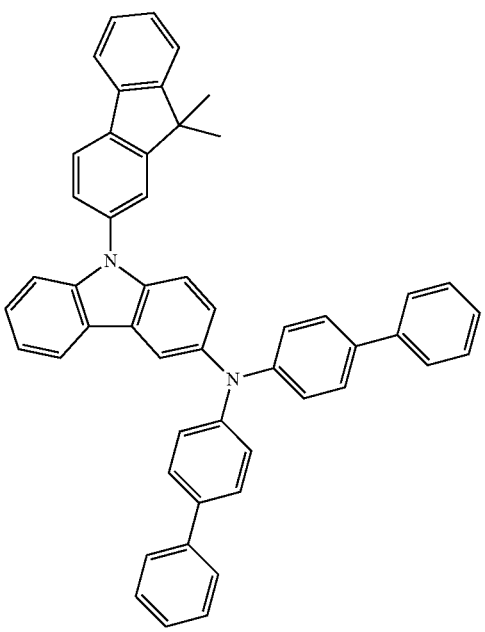

109
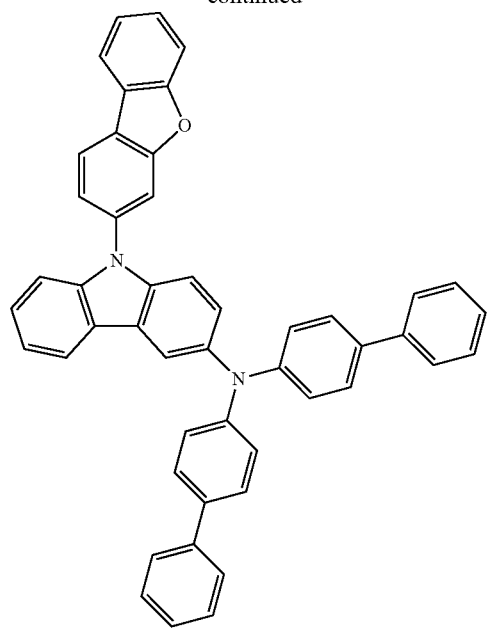
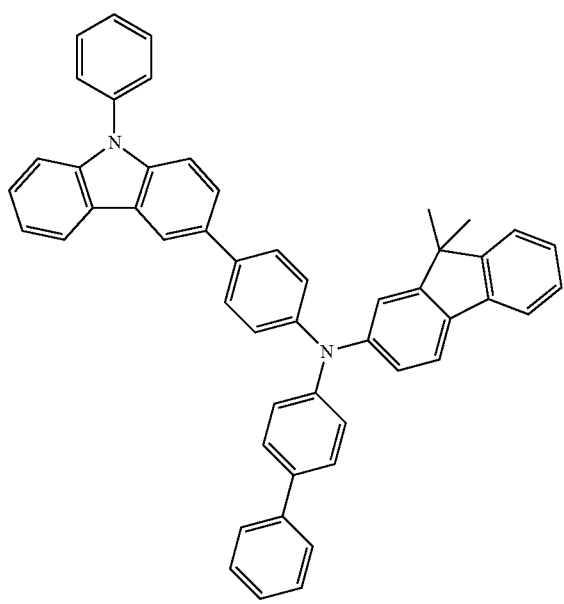
110
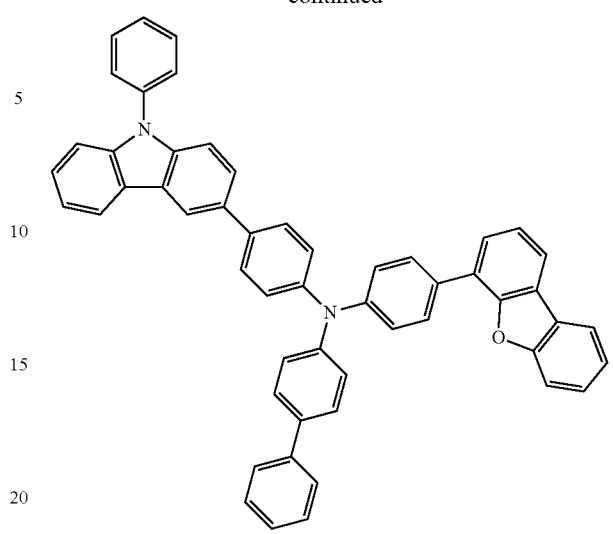
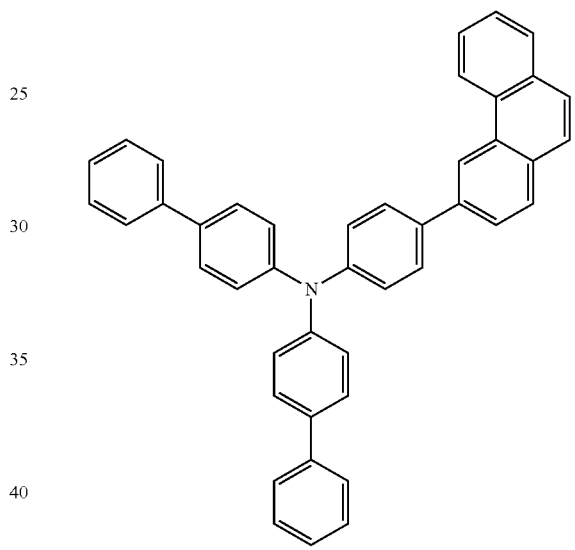
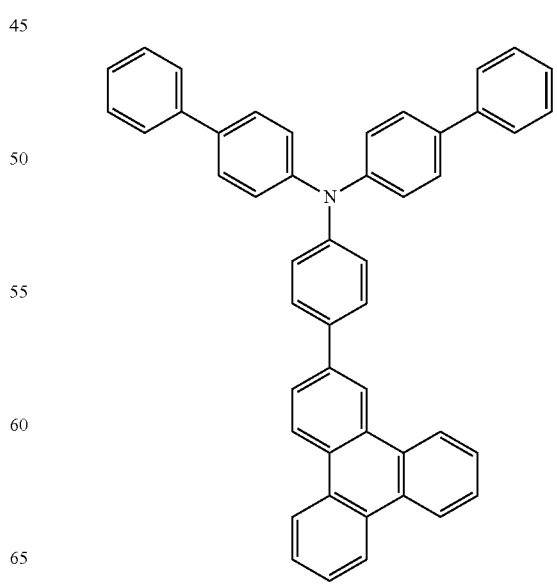

111
-continued
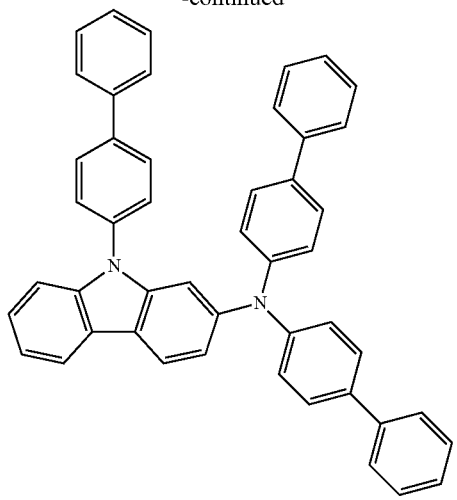
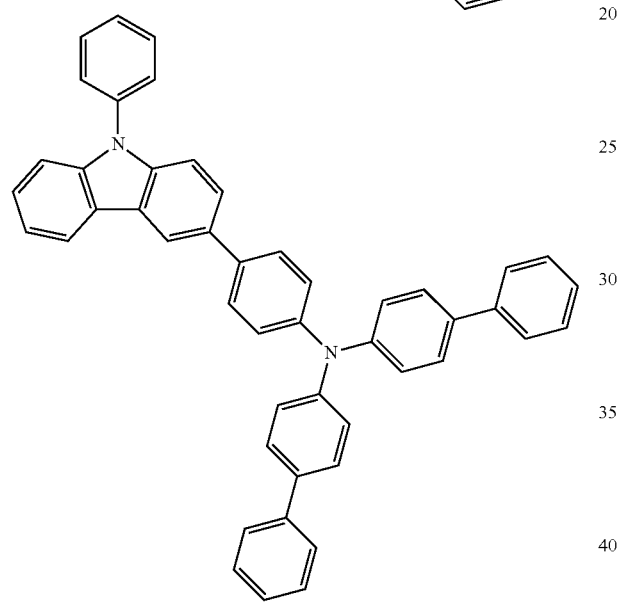
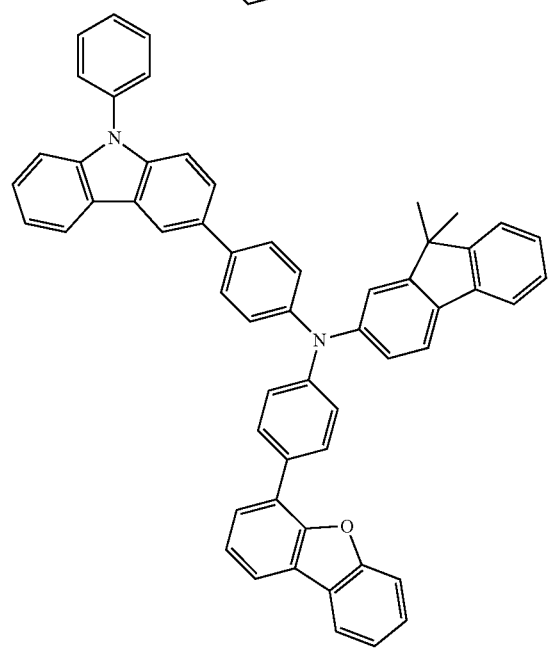
112
-continued
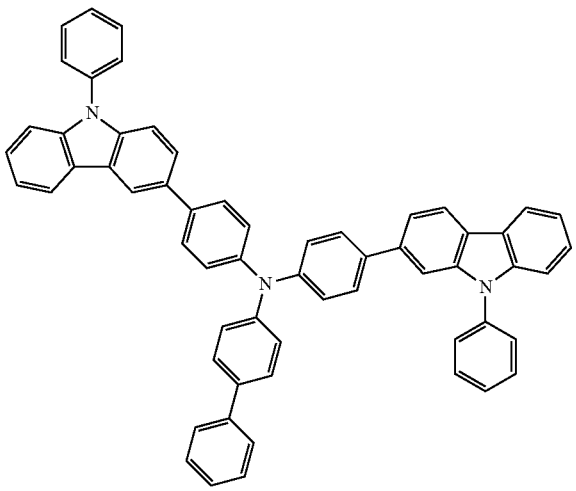
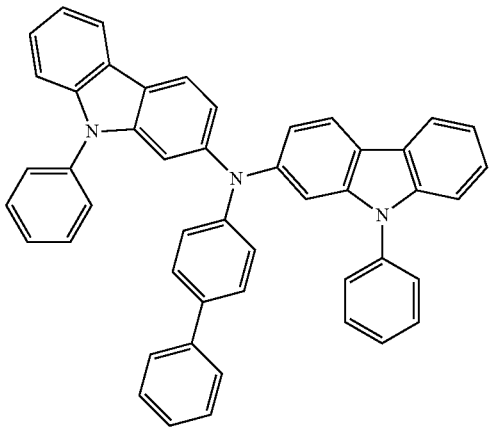
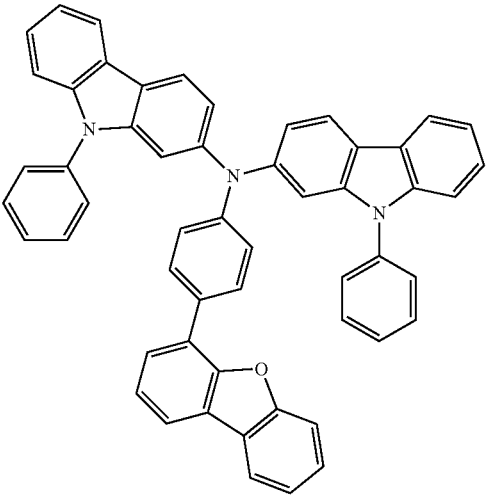

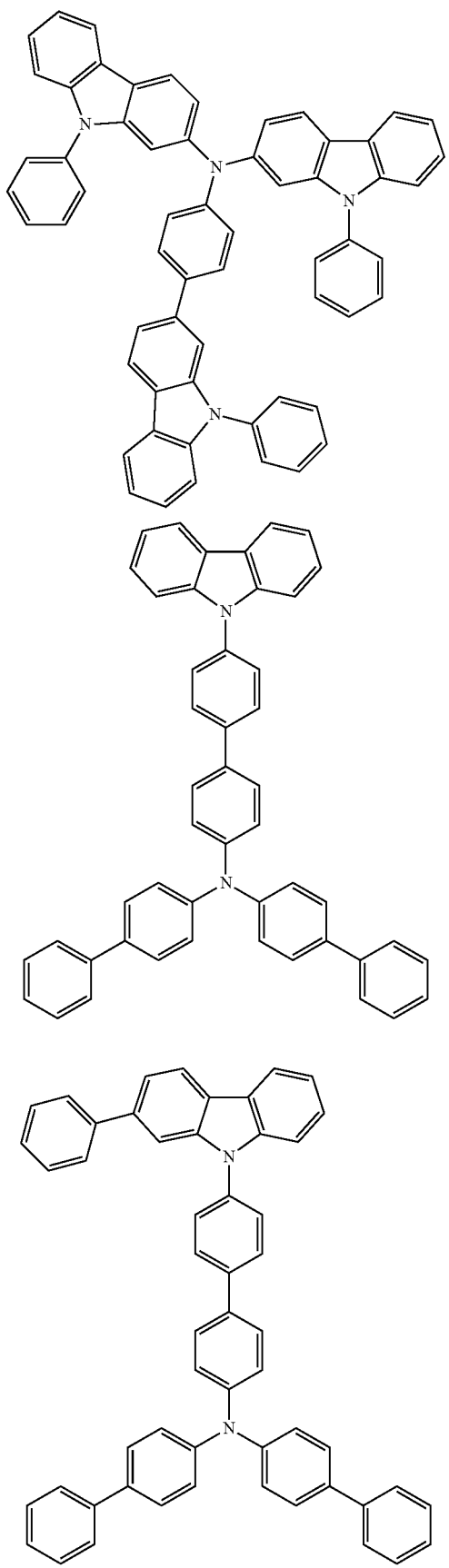
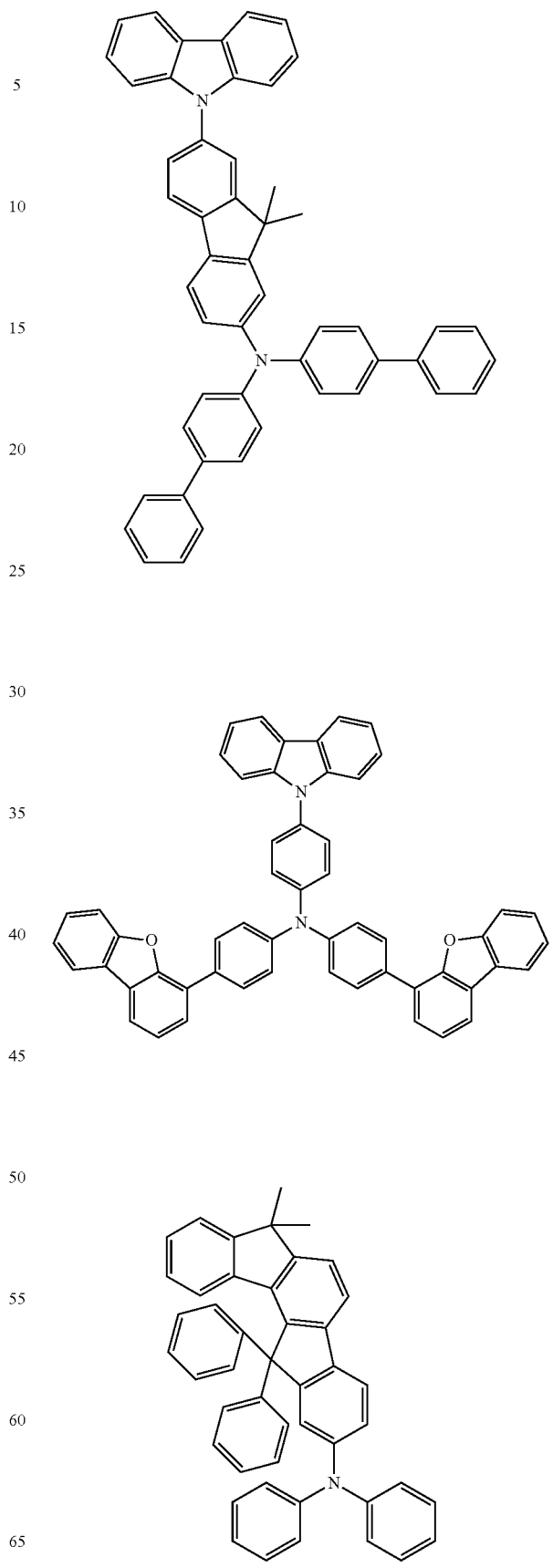

115
-continued
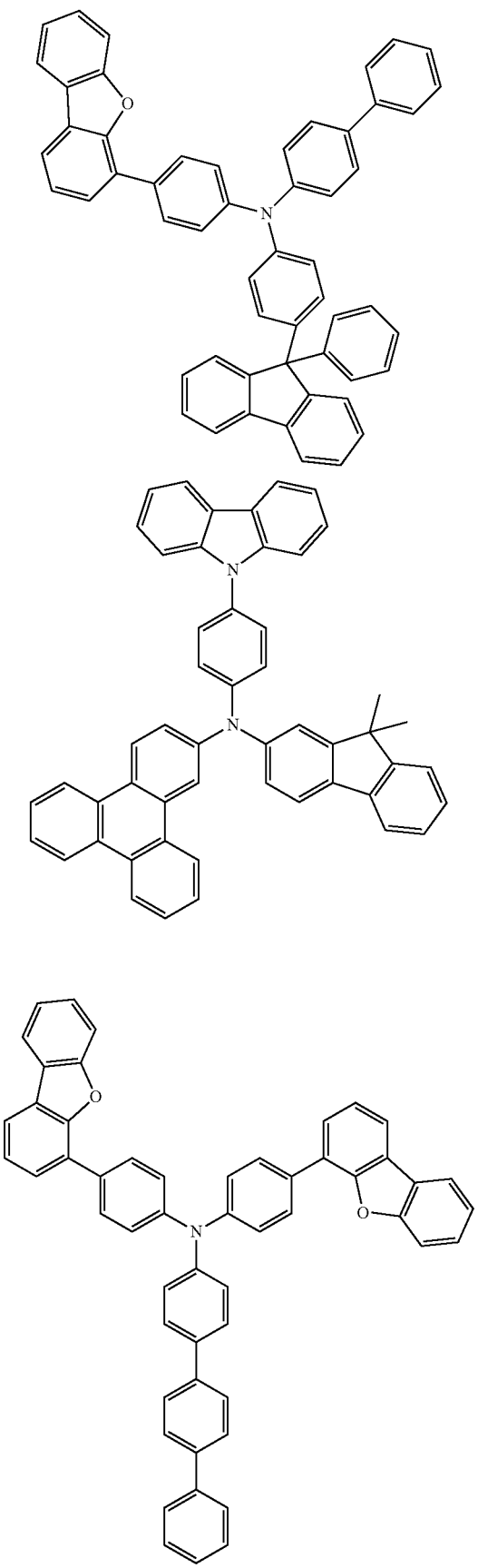
116
-continued
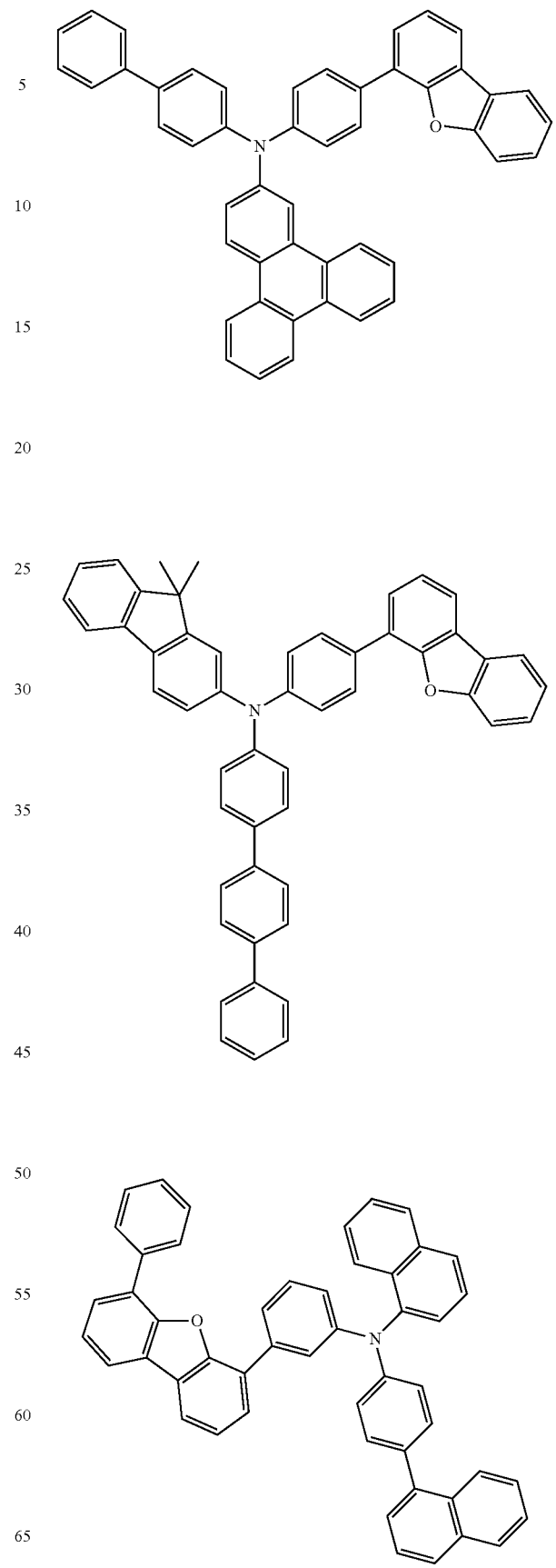

117
-continued
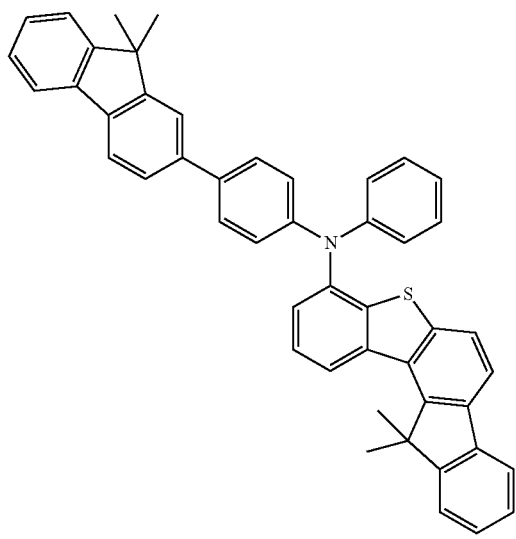
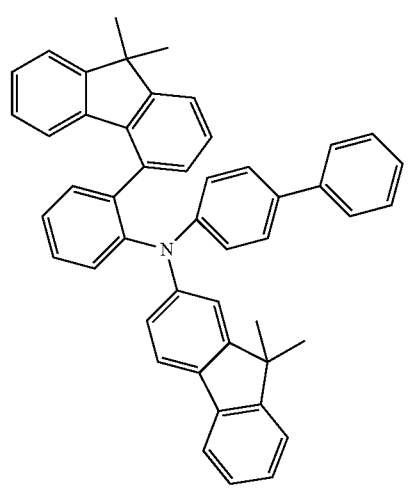
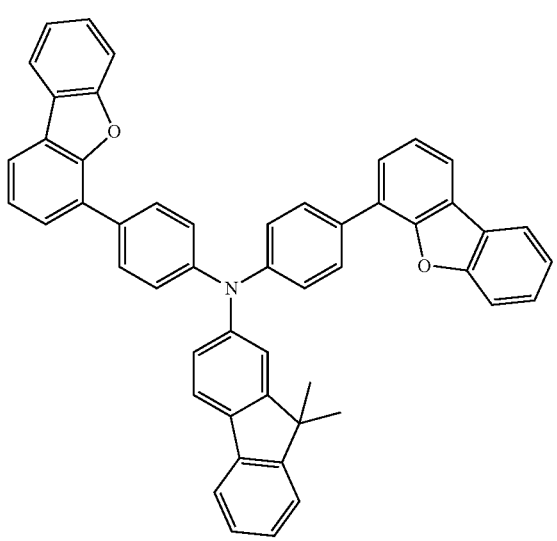
118
-continued
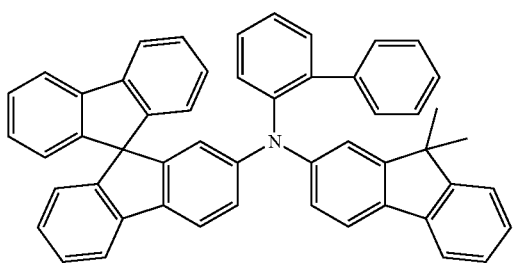
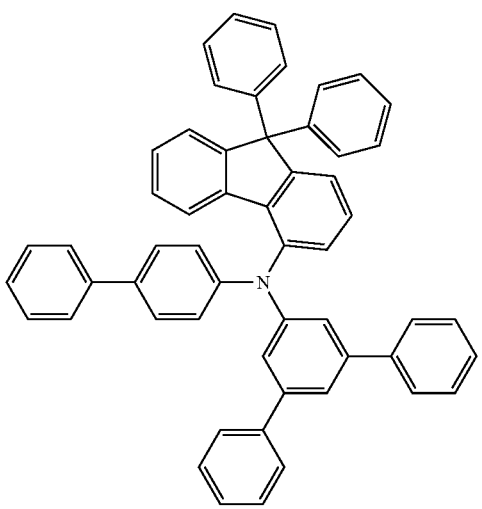
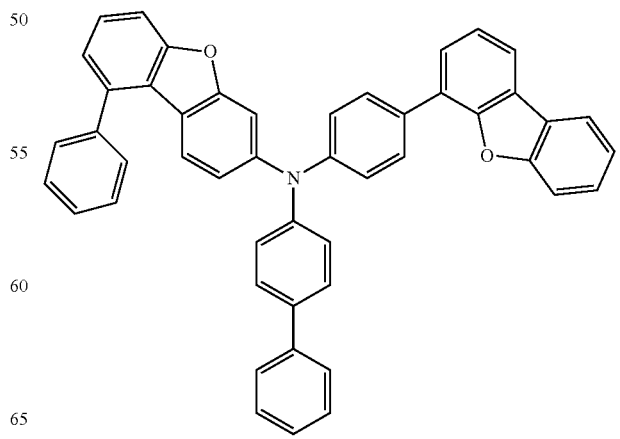

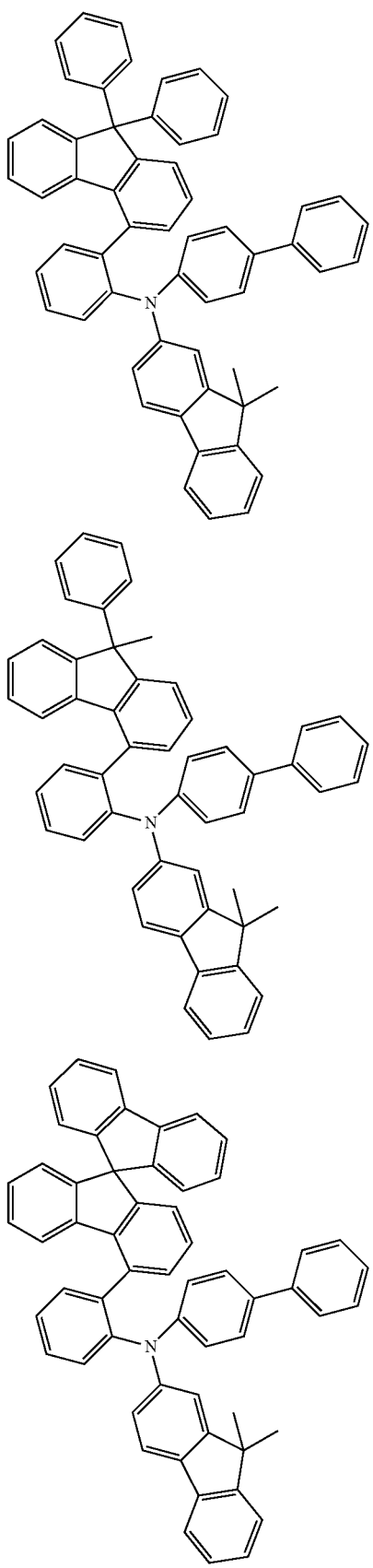
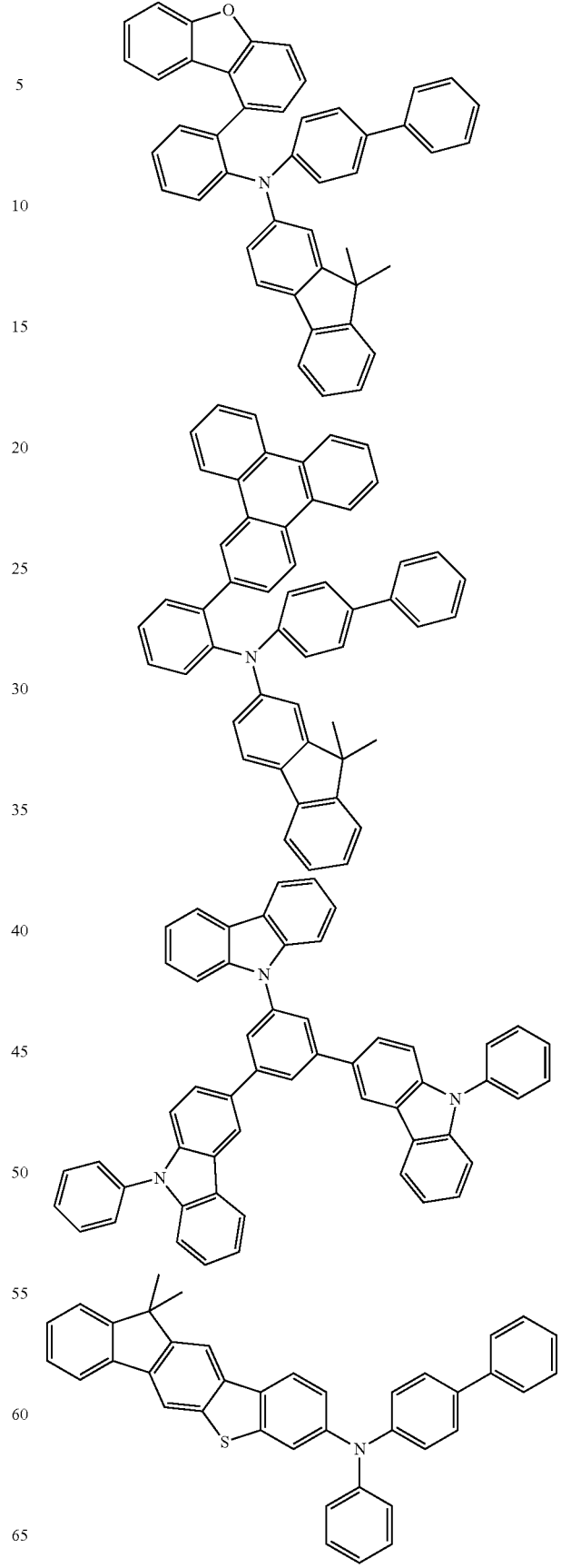

121
-continued
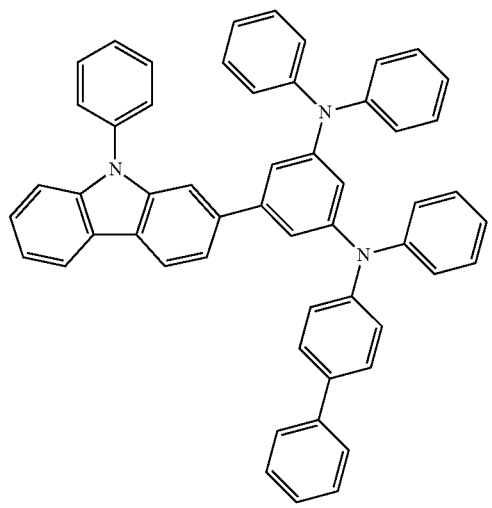
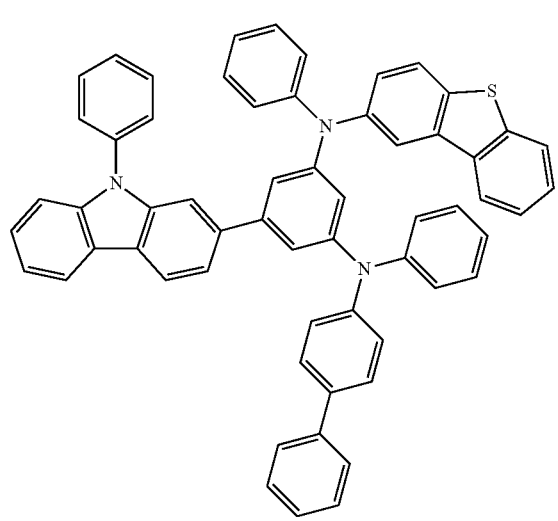
122
-continued
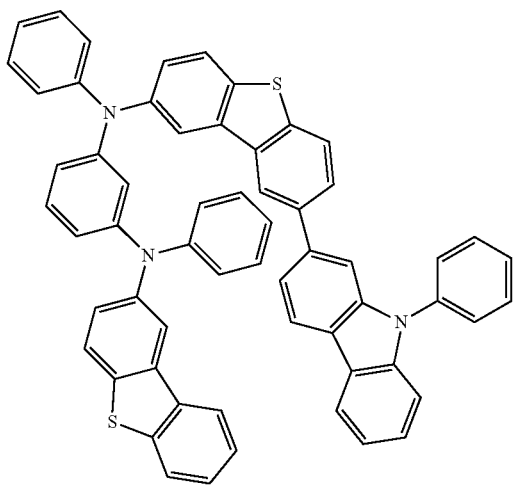
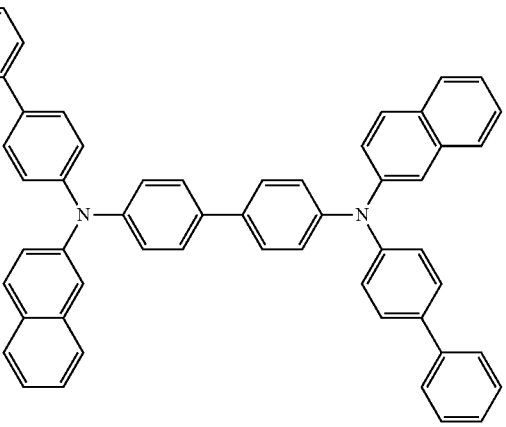
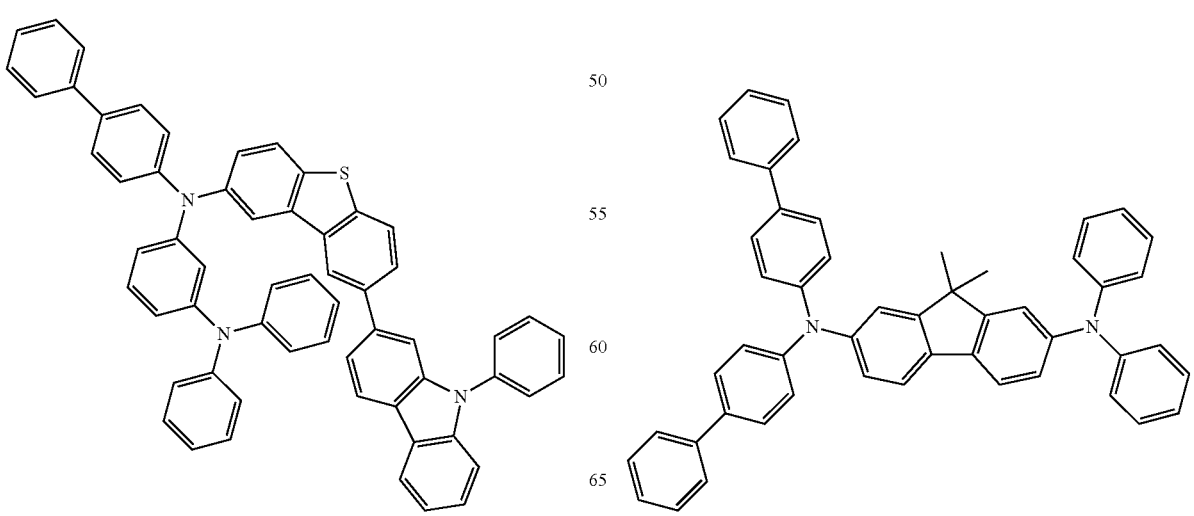

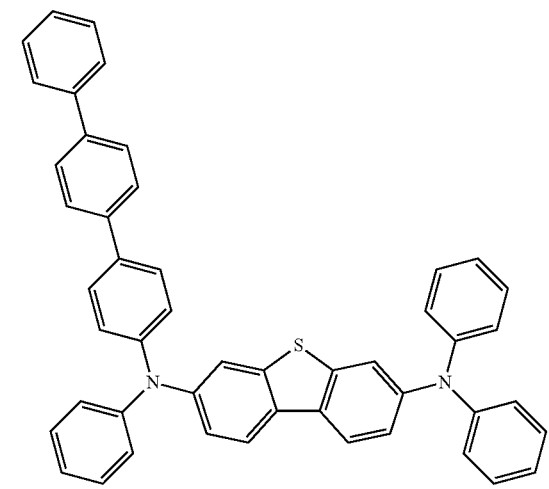
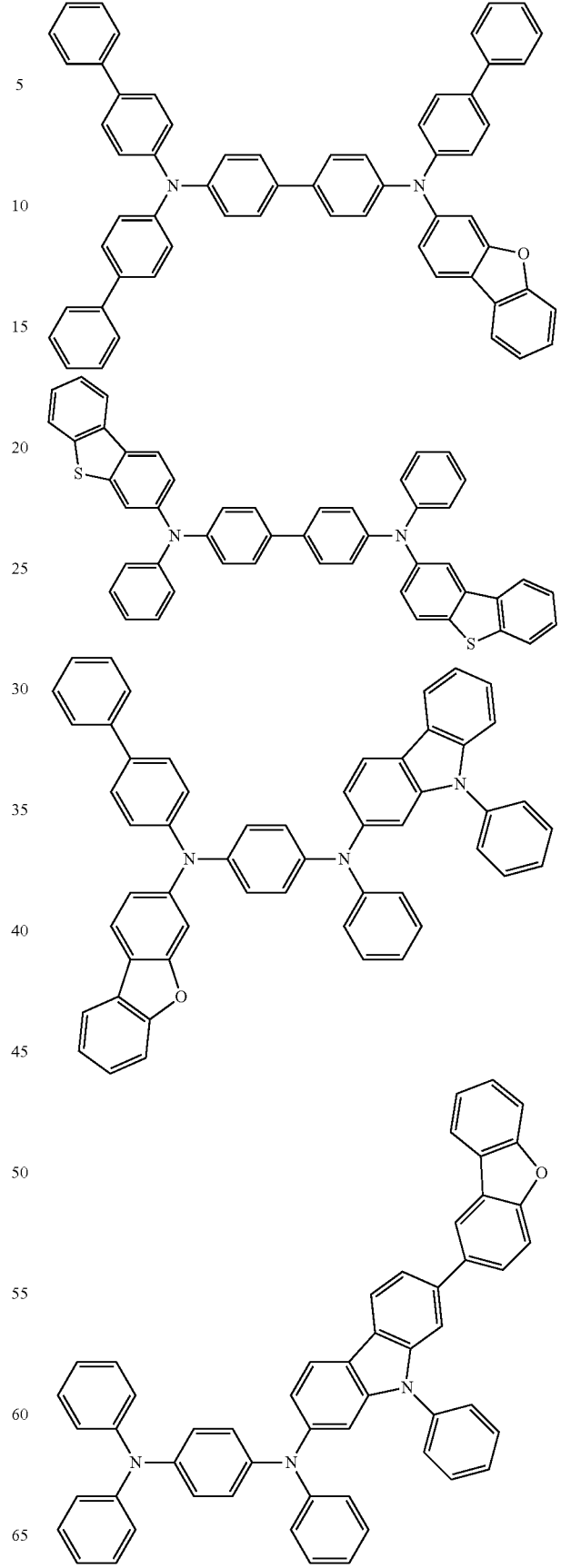

125
-continued
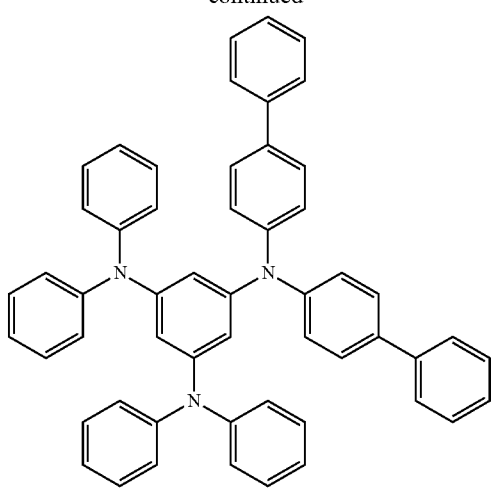
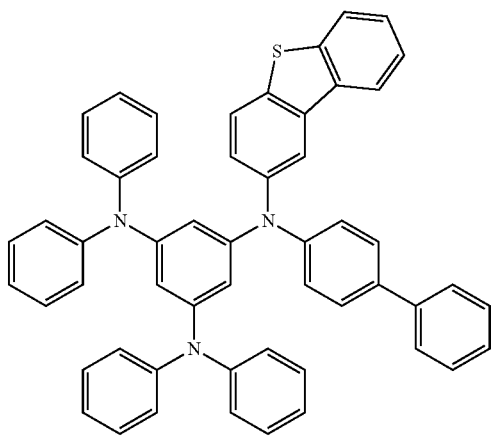
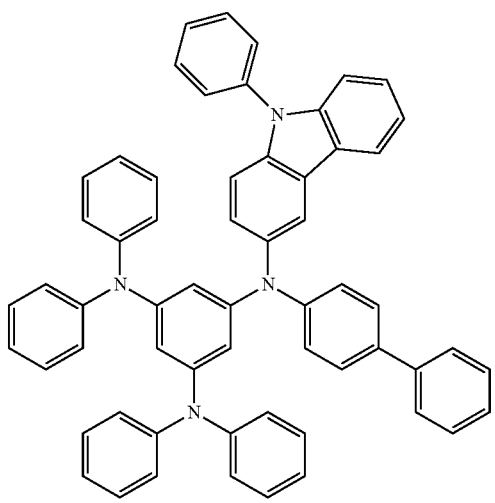
126
-continued
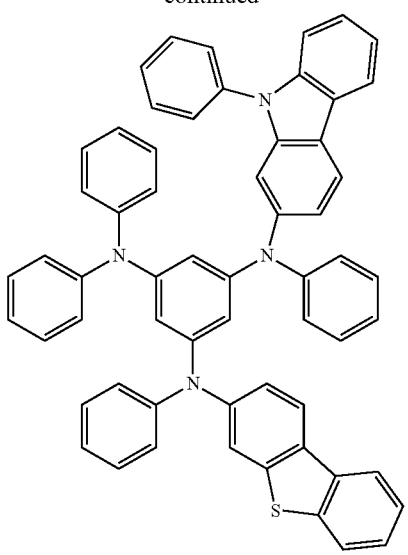
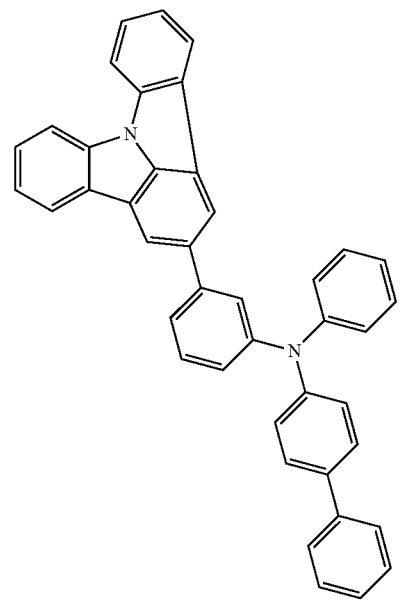
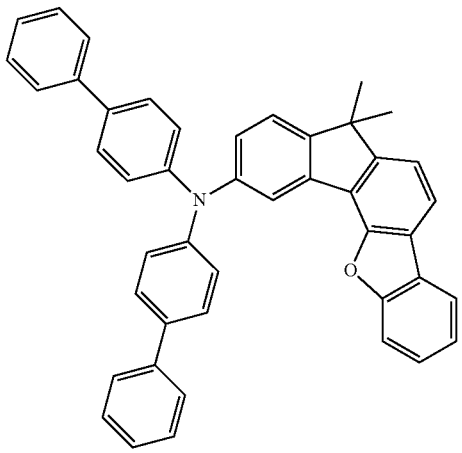

127
-continued
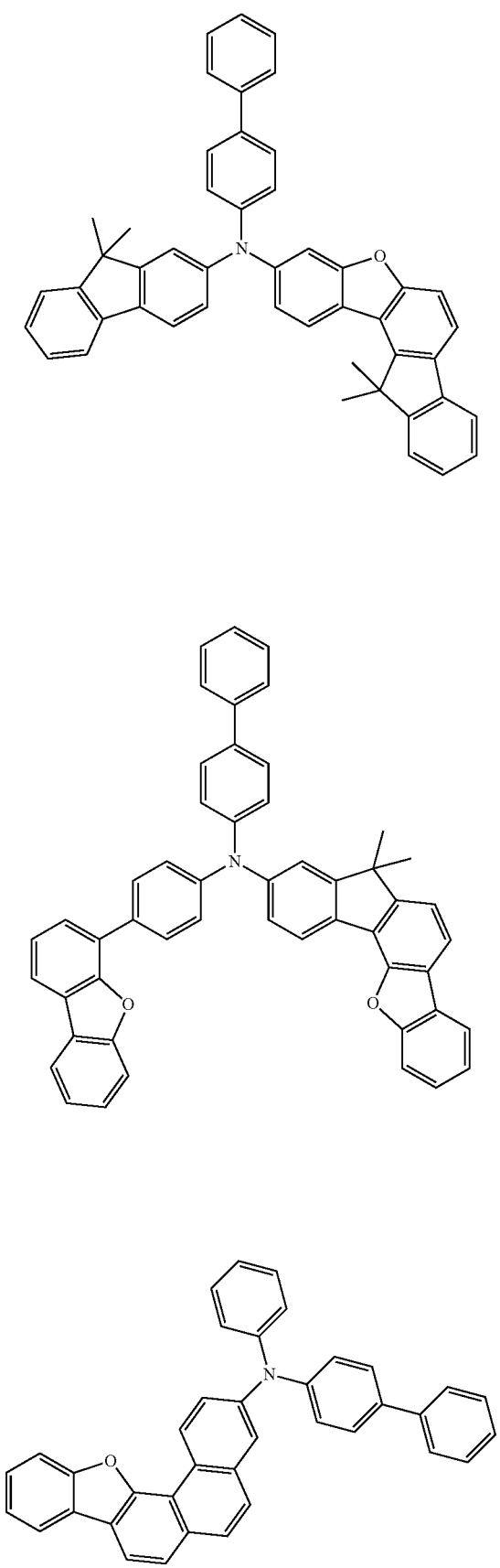
128
-continued
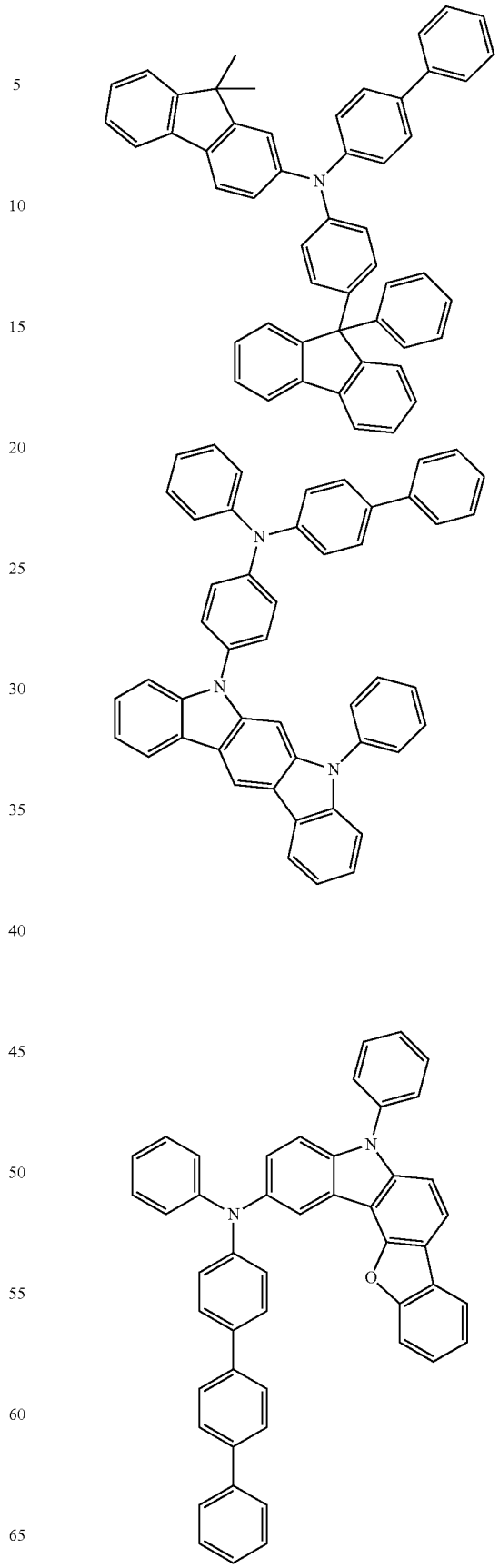

129
-continued
130
-continued
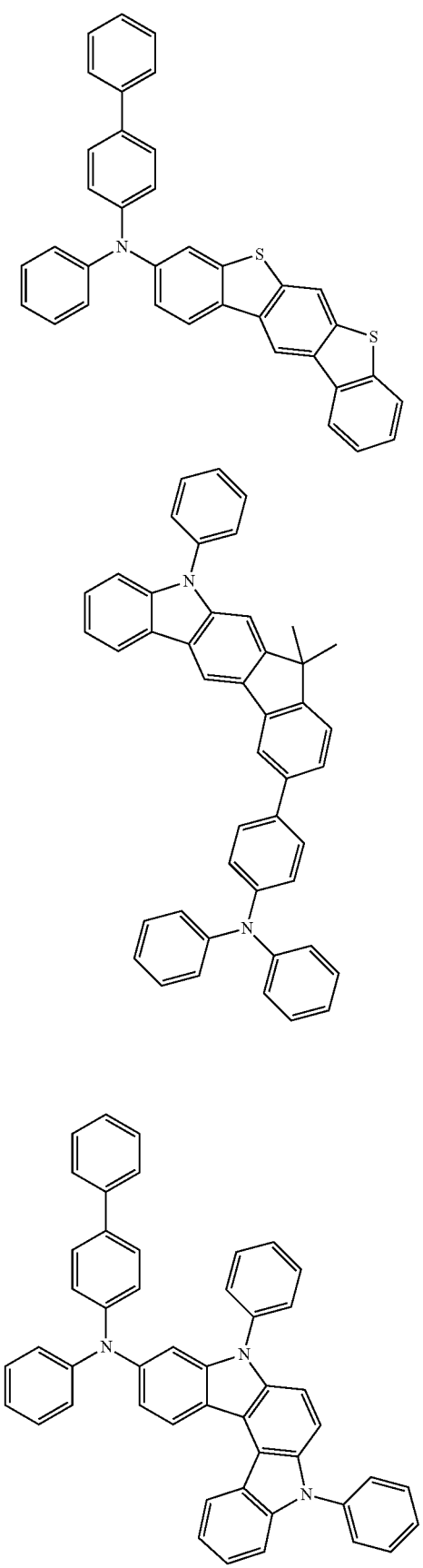
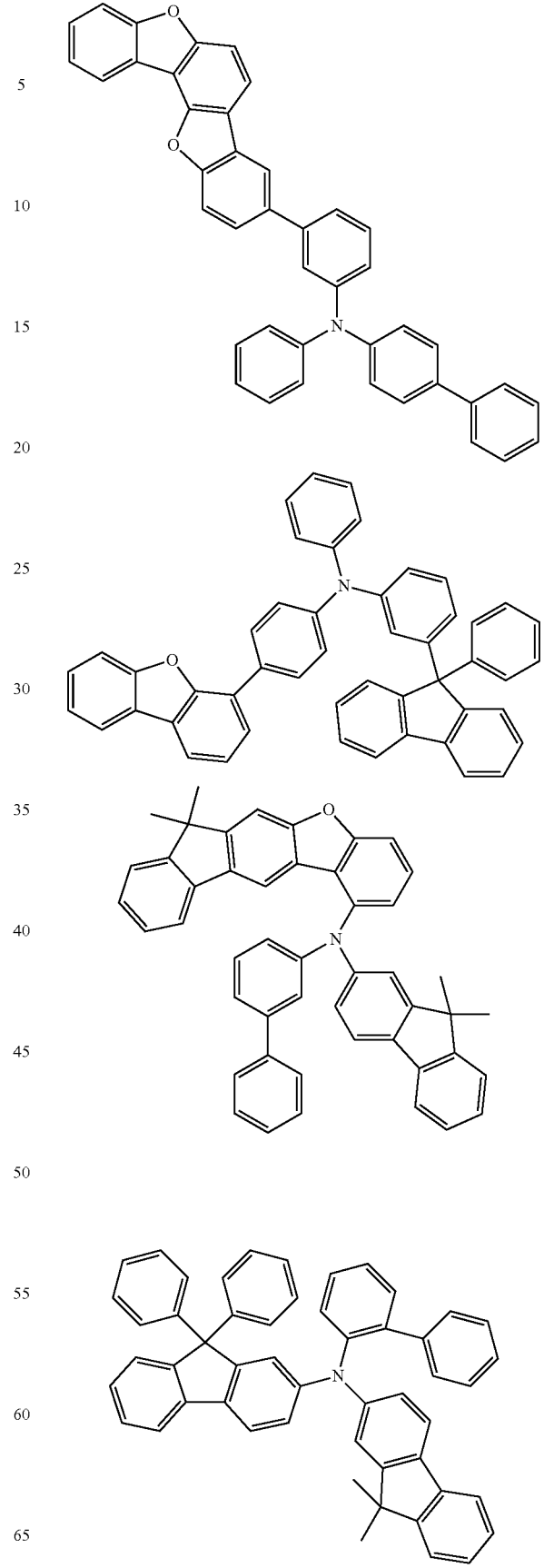

131
-continued
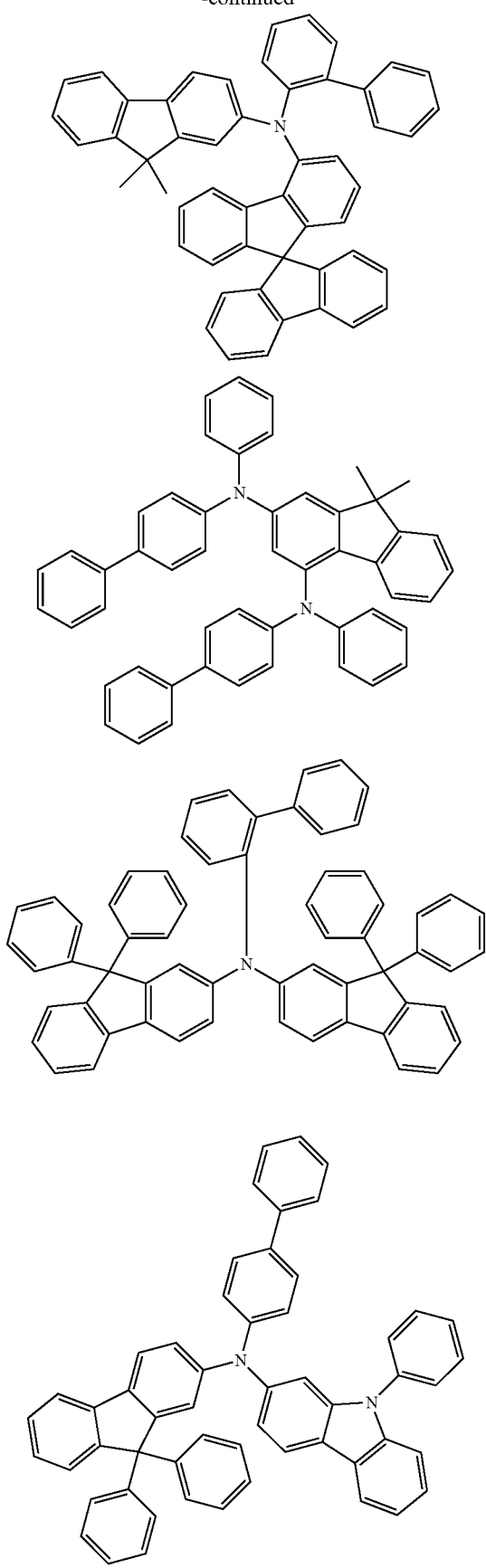
132
-continued
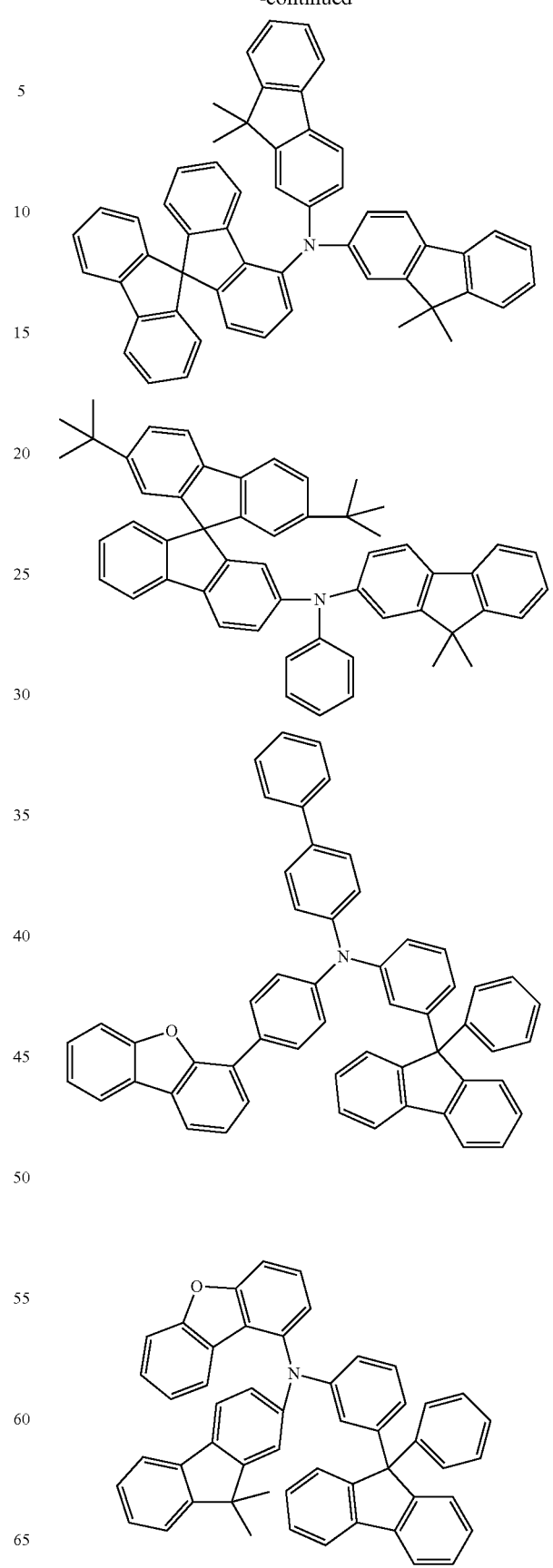

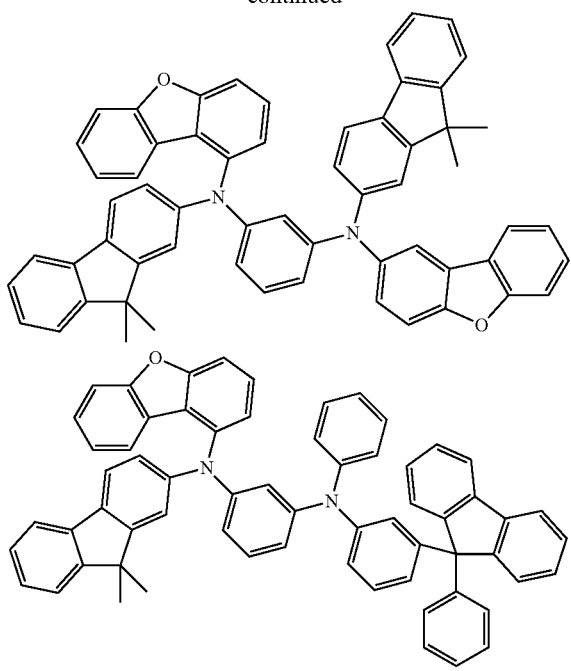
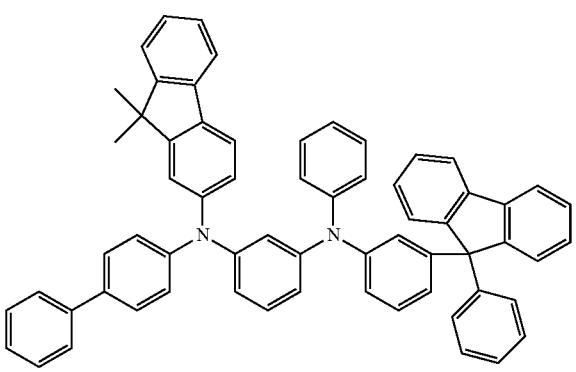
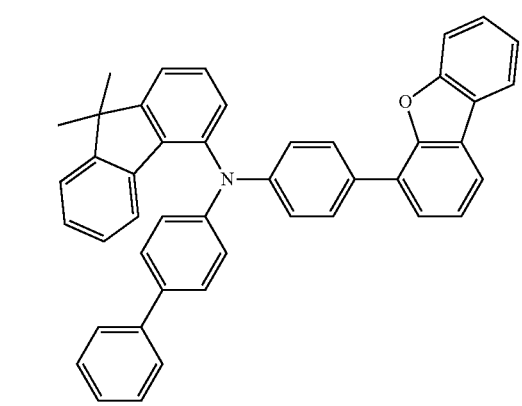
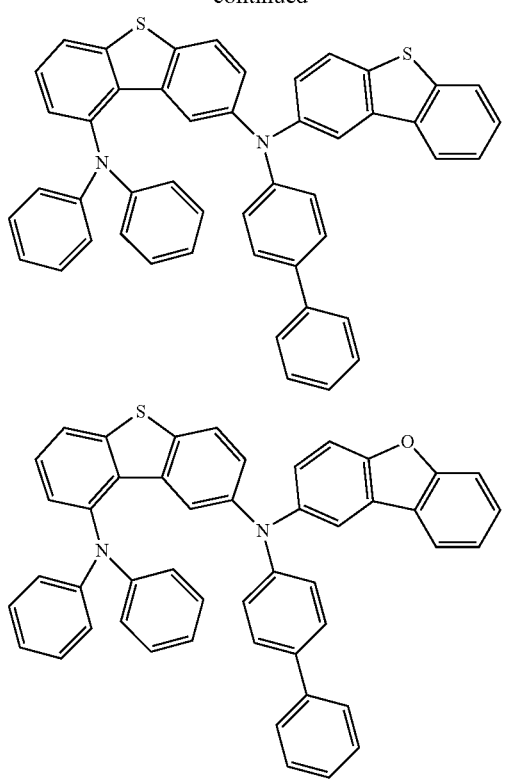
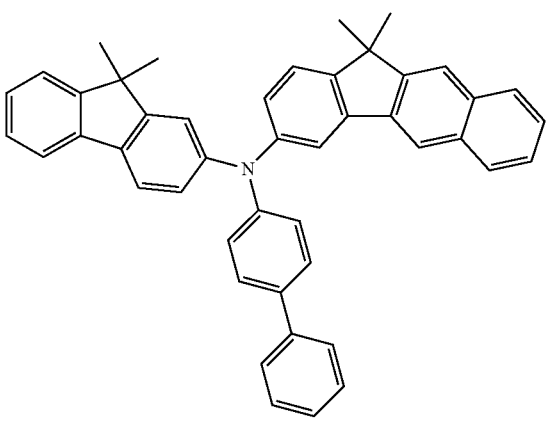
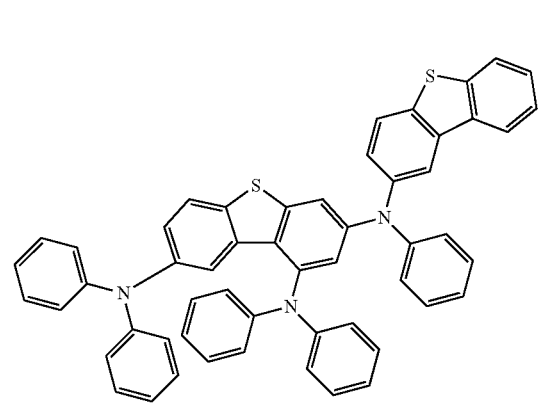

-continued

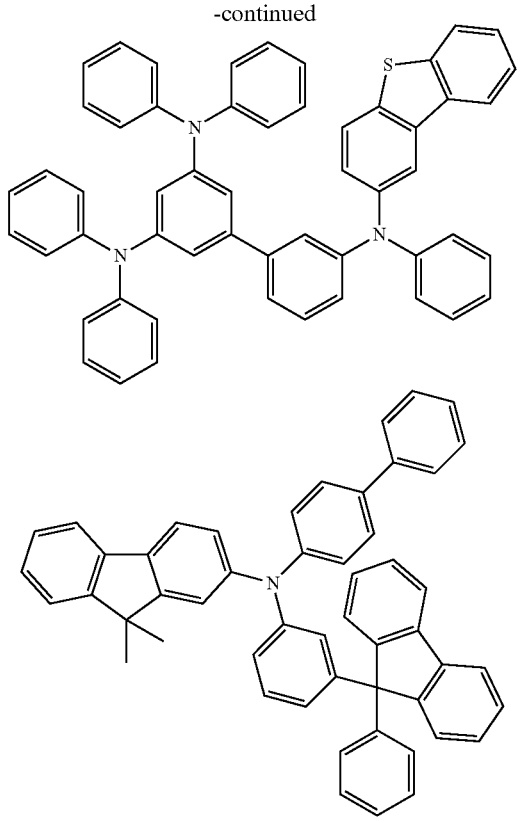

In the hole transport region, in addition to the compounds described above, other suitable compounds may also be used.

Figure 3:
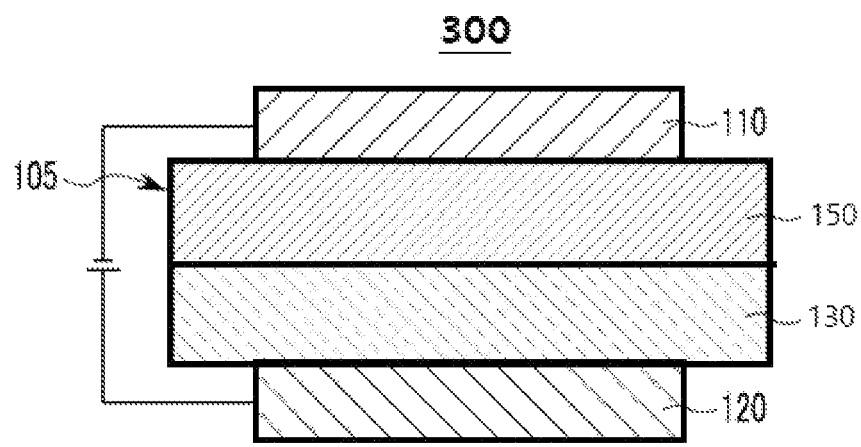

In an implementation, the charge transport region may be, e.g., the electron transport region 150 (see FIG. 3).

Referring to FIG. 3, the organic light emitting diode 300 may further include an electron transport region 150 in addition to the light emitting layer 130. The electron transport region 150 may help further increase electron injection and/or electron mobility and block holes between the cathode 110 and the light emitting layer 130.

In an implementation, the electron transport region 150 may include an electron transport layer between the cathode 110 and the light emitting layer 130, and an electron transport auxiliary layer between the light emitting layer 130 and the electron transport layer. In an implementation, a compound of Group F may be included in at least one of the electron transport layer and the electron transport auxiliary layer.

[Group F]

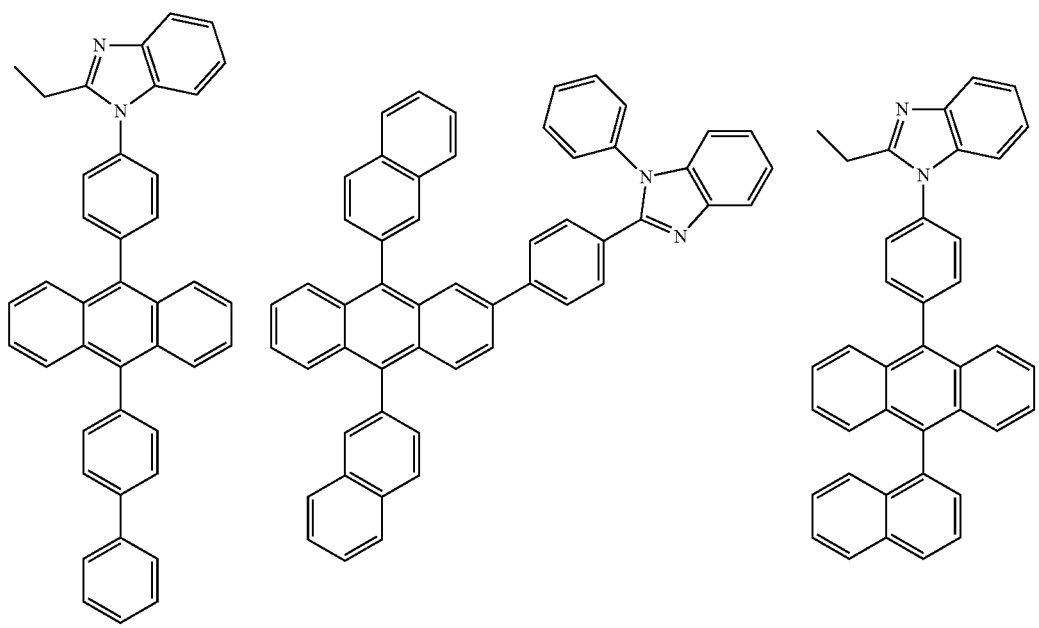

-continued
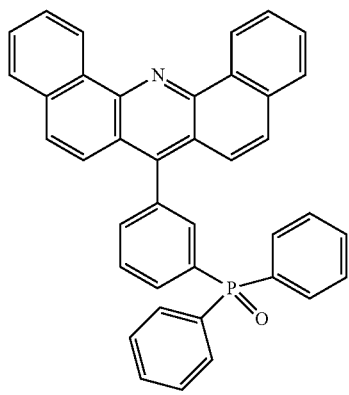
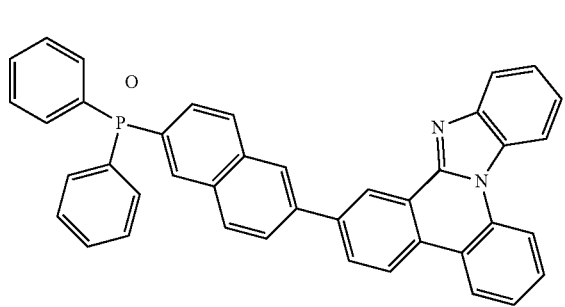
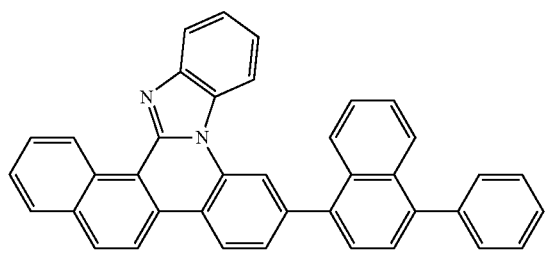
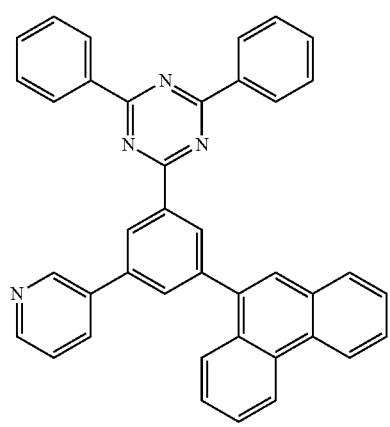
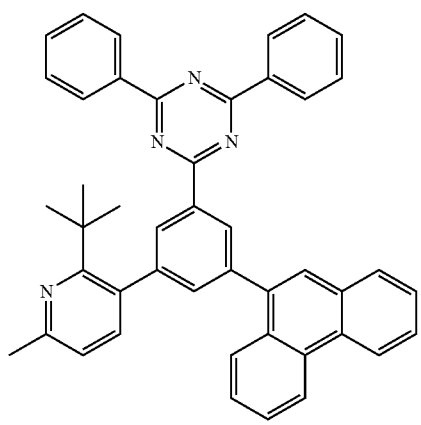
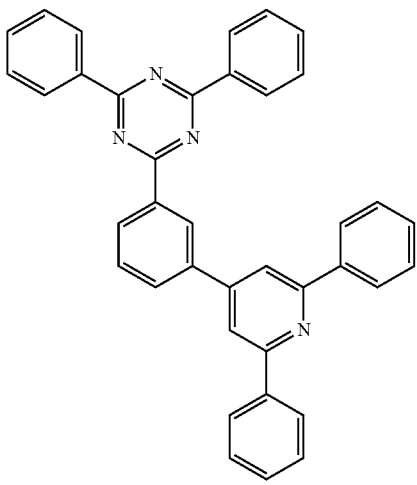
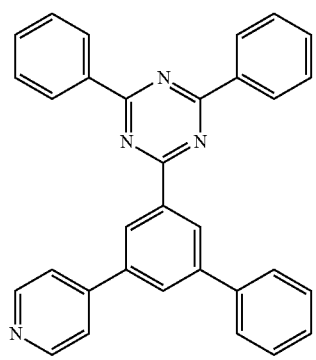
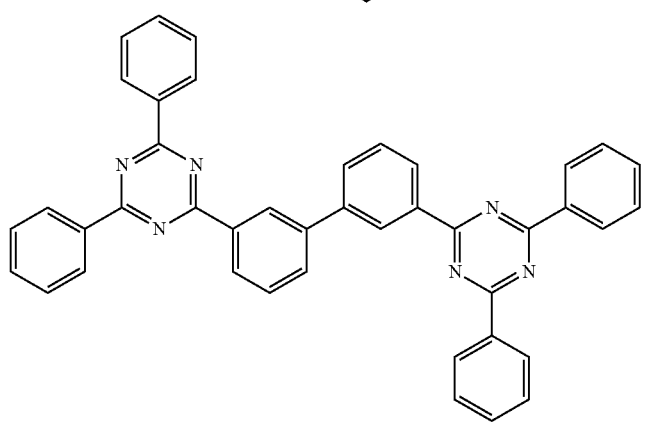

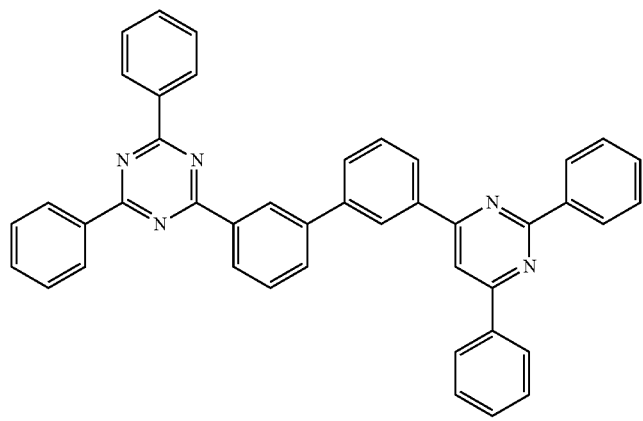
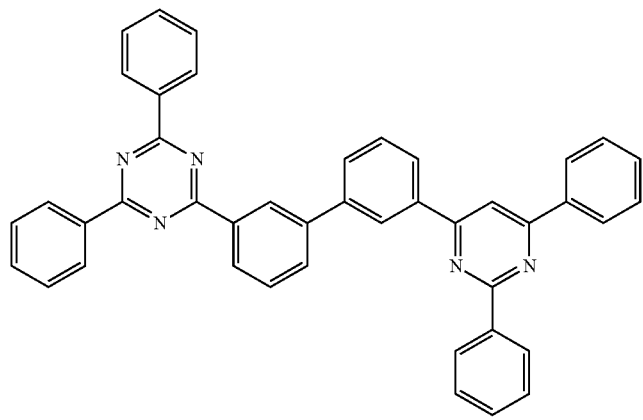
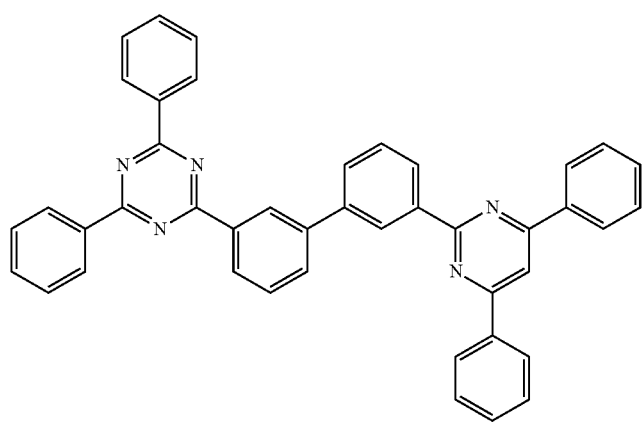
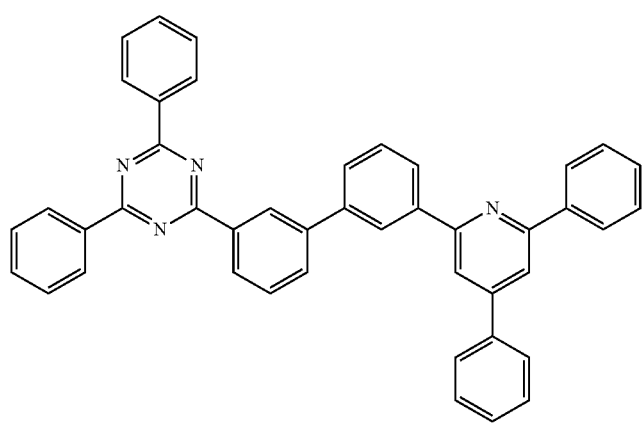

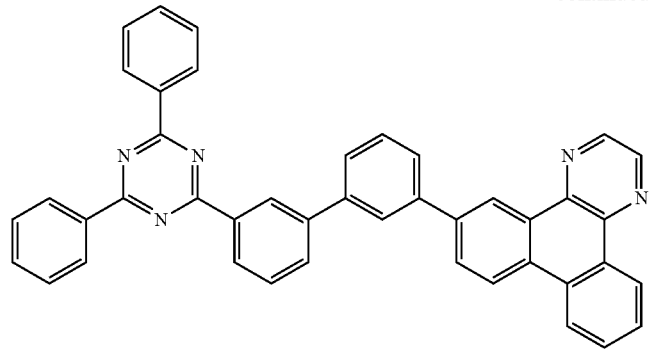
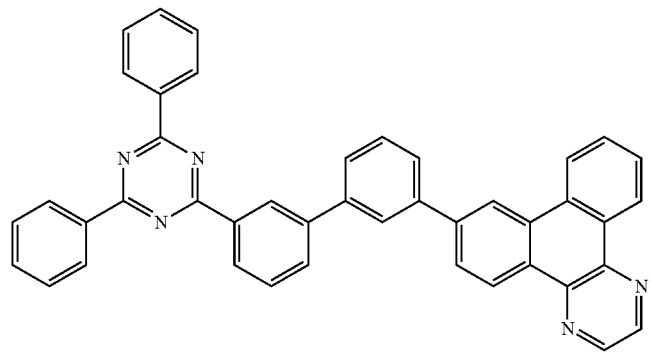
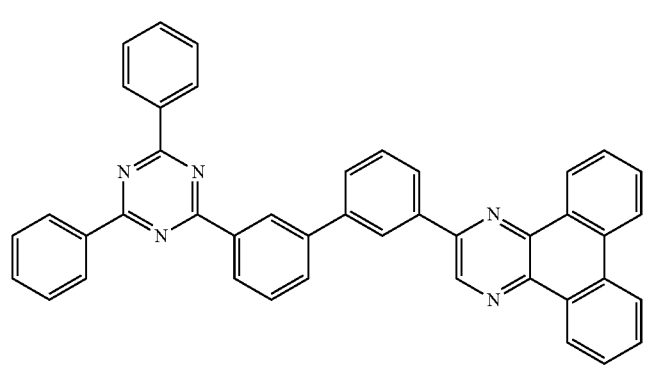
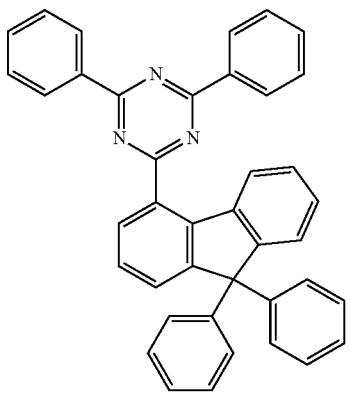
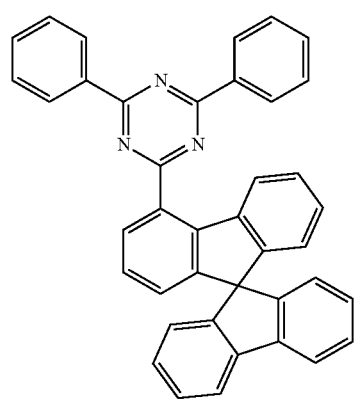
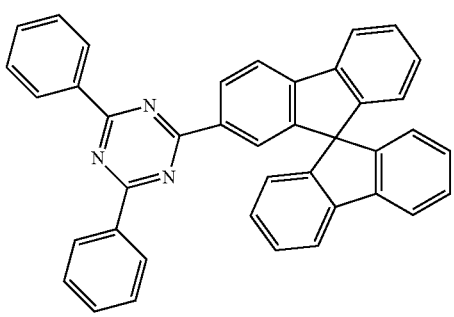

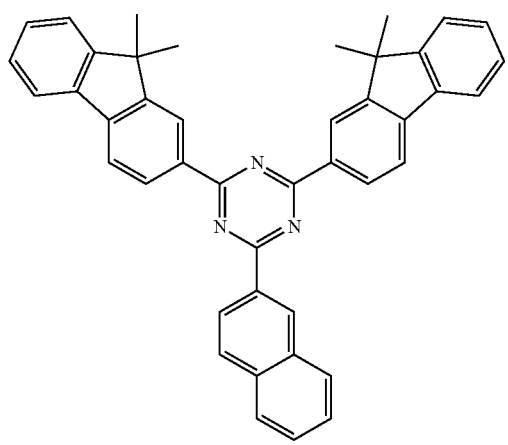
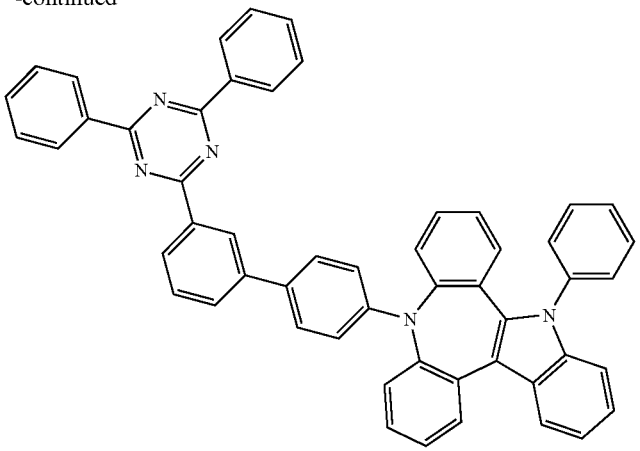
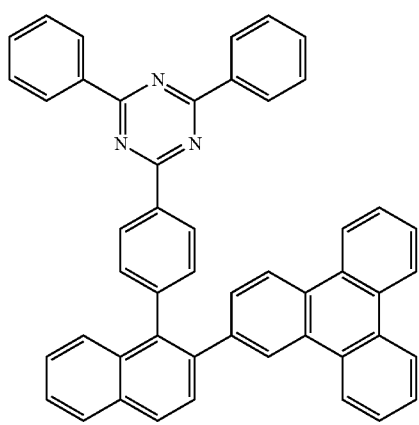
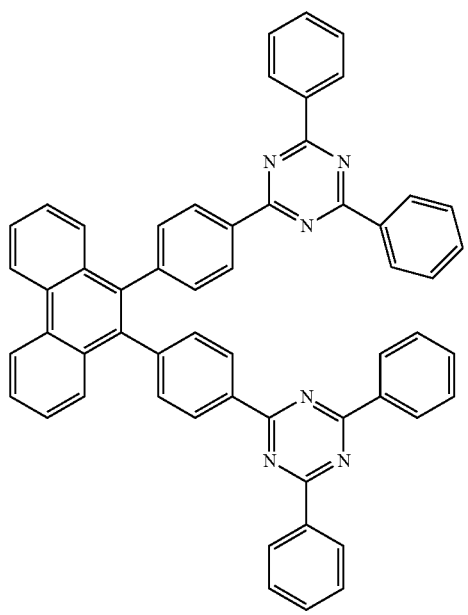
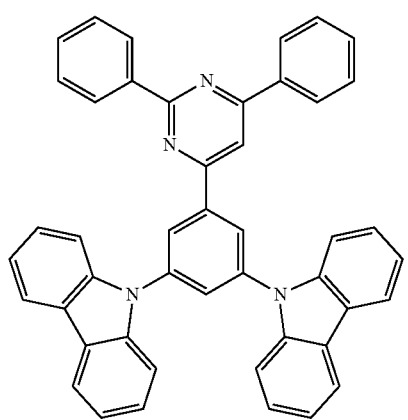
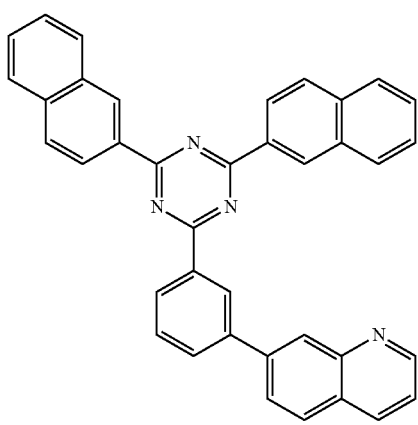

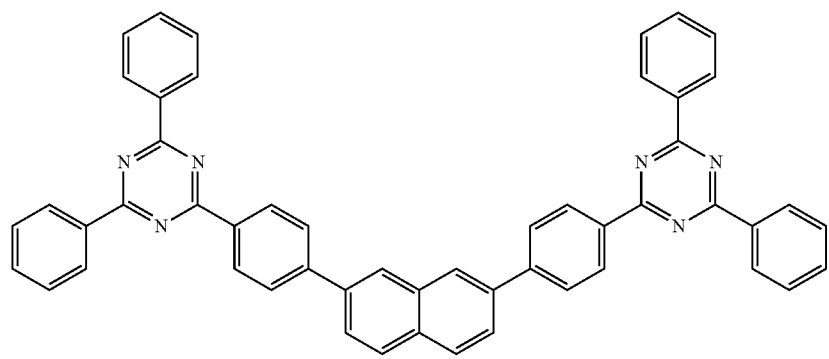
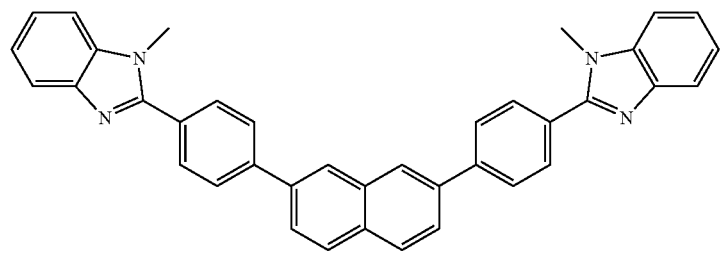
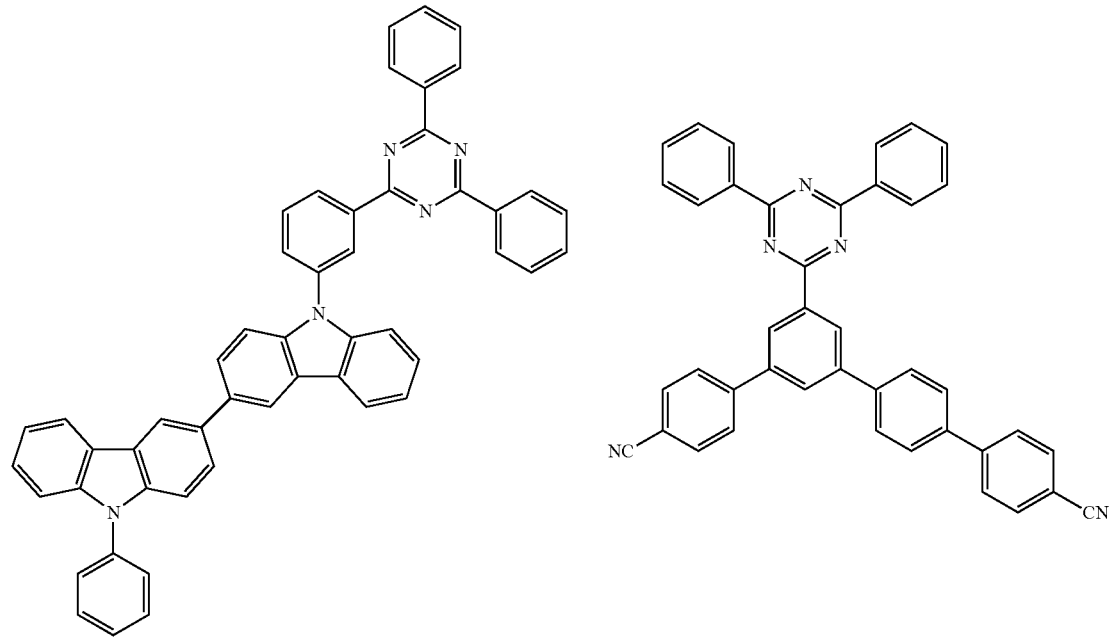

-continued
147
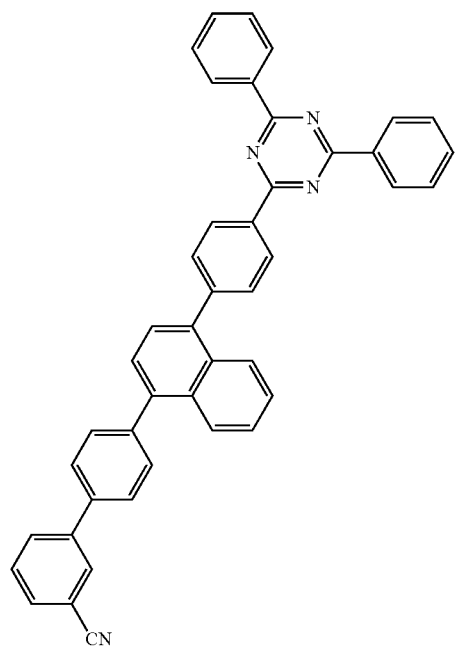
148
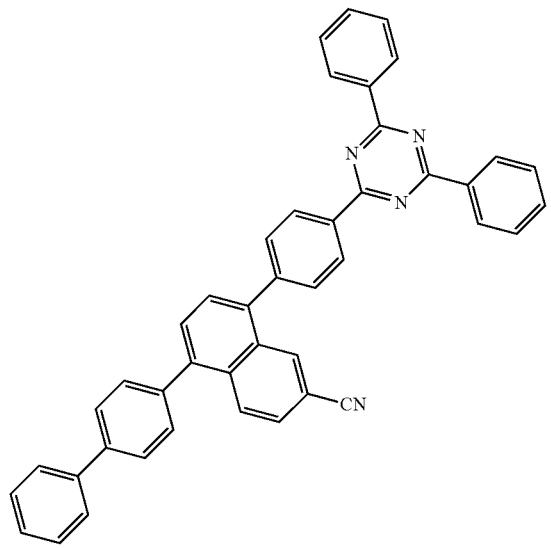
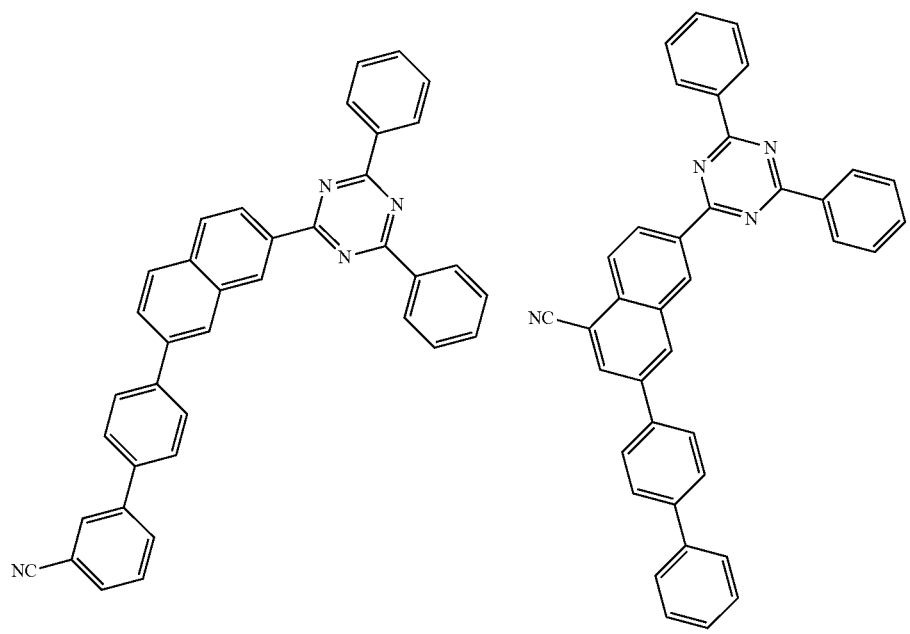

149 150
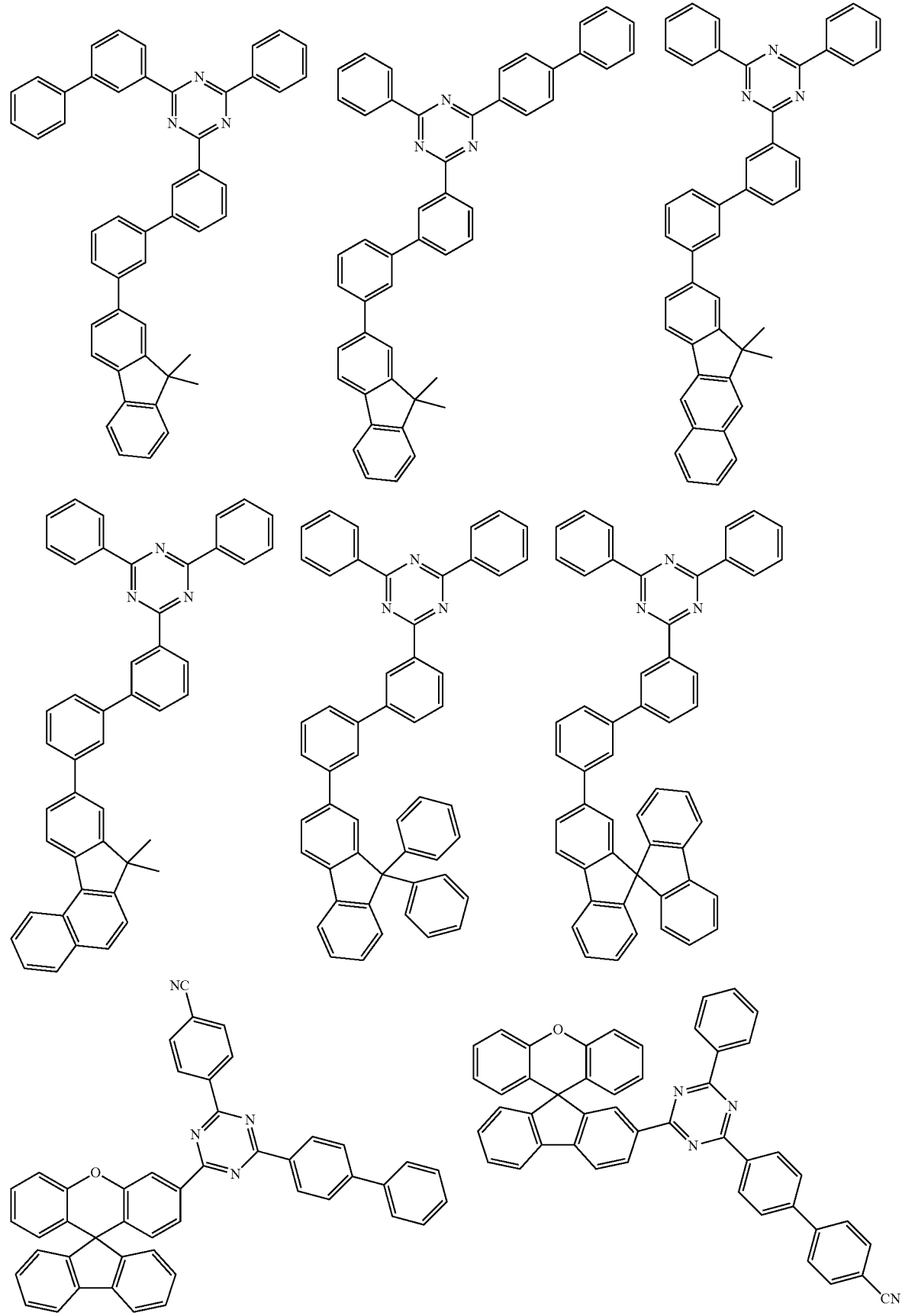
-continued

-continued
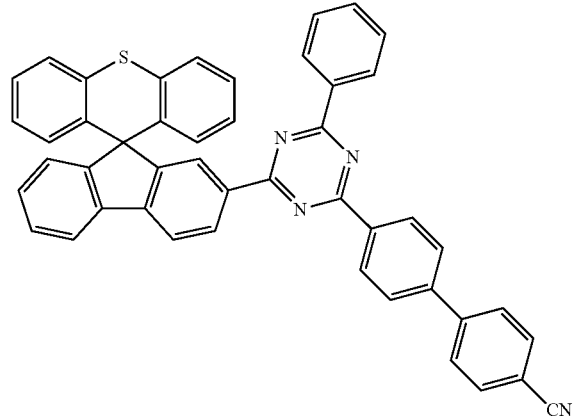
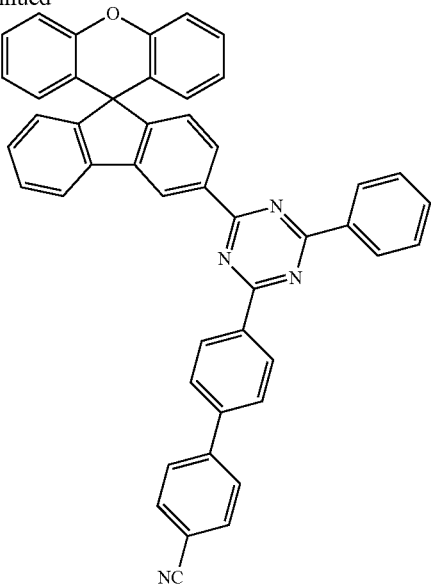
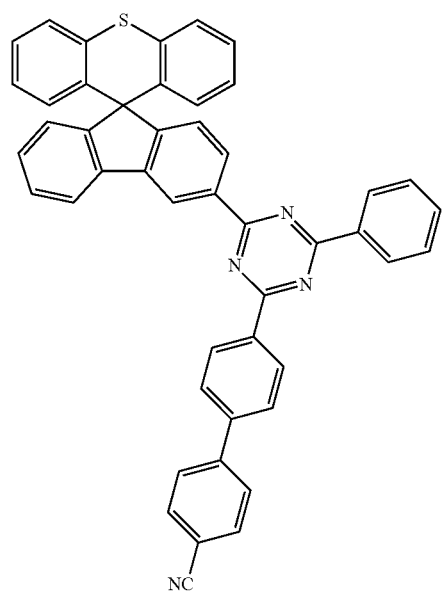
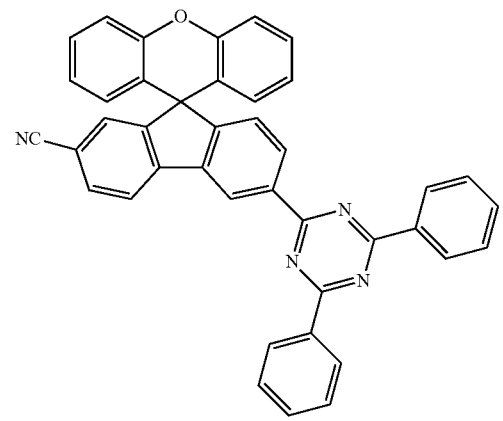
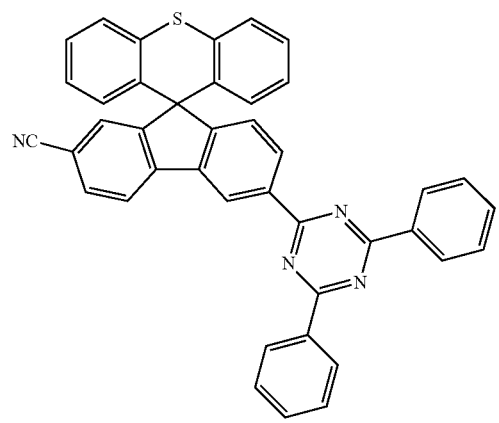

An embodiment may provide an organic light emitting diode including the light emitting layer 130 as the organic layer 105 as shown in FIG. 1.

Another embodiment may provide an organic light emitting diode including a hole transport region 140 in addition to the light emitting layer 130 as the organic layer 105, as shown in FIG. 2.

Another embodiment may provide an organic light emitting diode including an electron transport region 150 in addition to the light emitting layer 130 as the organic layer 105 as shown in FIG. 3.

Figure 4:
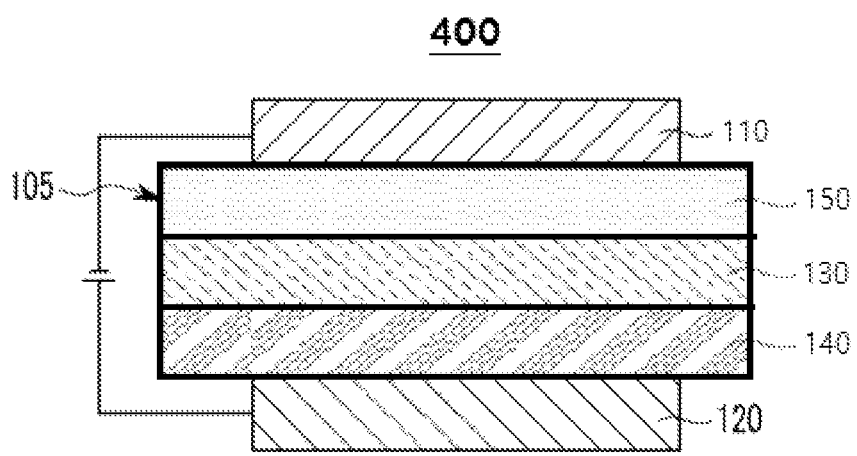

Another embodiment may provide an organic light emitting diode including a hole transport region 140 and an electron transport region 150 in addition to the light emitting layer 130 as the organic layer 105, as shown in FIG. 4.

In another embodiment, an organic light emitting diode may further include an electron injection layer, a hole injection layer, or the like, in addition to the light emitting layer 130 as the organic layer 105 in each of FIGS. 1 to 4.

The organic light emitting diodes 100, 200, 300, and 400 may be manufactured by forming an anode or a cathode on a substrate, and then forming an organic layer by a dry film method such as vacuum deposition, sputtering, plasma plating and ion plating, and forming a cathode or an anode thereon.

The aforementioned organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., Tokyo chemical industry or P&H tech as far as there is no particular comment or were synthesized by suitable methods.

(Preparation of Compound for Organic Optoelectronic Device)

Compounds were synthesized through the following steps.

<Synthesis of Core-1>

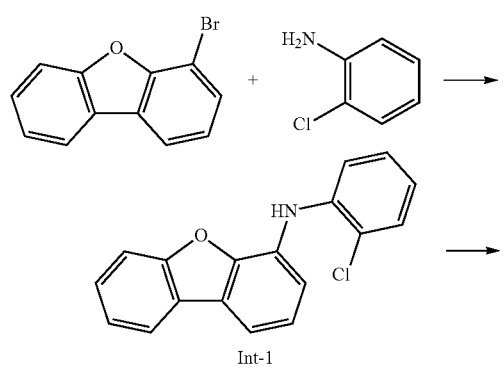

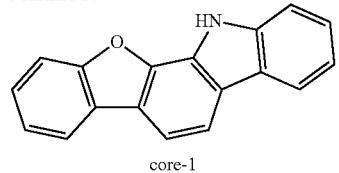

core-1

Synthesis Example 1: Synthesis of Int-1

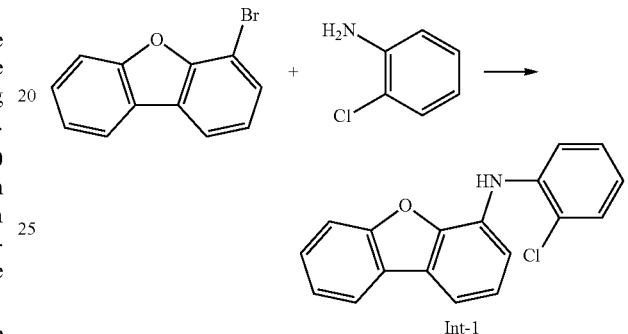

Int-1

4-bromo-dibenzofuran (25 g, 101.18 mmol), 2-chloroaniline (19.36 g, 151.77 mmol), Pd$_2$(dba)$_3$ (4.63 g, 5.06 mmol), P(t-Bu)$_3$ (3.7 ml, 15.18 mmol), and NaO(t-Bu) (11.67 g, 121.41 mmol) were put in a round-bottomed flask and then, stirred under reflux in a toluene (350 ml) solvent at 130° C. for 12 hours. When a reaction was completed, the resultant was treated through column chromatography, obtaining 15 g (50%) of Intermediate (Int-1).

Synthesis Example 2: Synthesis of Core-1

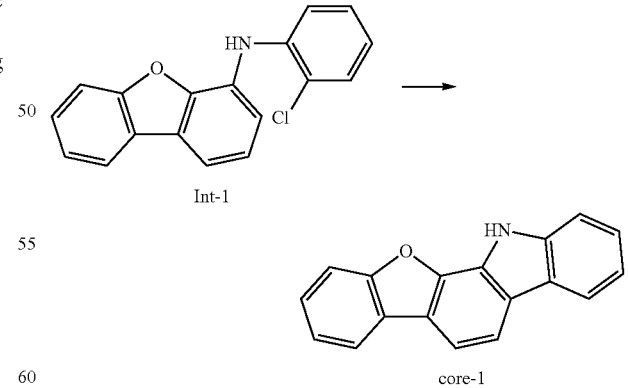

Int-1 core-1

Int-1 (20 g, 68.09 mmol), Pd$_2$(dba)$_3$ (3.12 g, 3.4 mmol), Cs$_2$CO$_3$ (44.34 g, 136.17 mmol), PCy3·HBF$_4$ (3.7 ml, 15.18 mmol), and NaO(t-Bu) (11.67 g, 121.41 mmol) were put in a round-bottomed flask and then, stirred under reflux in a DMAc (220 ml) solvent at 160° C. for 12 hours. When a reaction was completed, the resultant was treated through column chromatography, obtaining 8.1 g (46%) of Intermediate Core-1.

<Synthesis of Core-2>

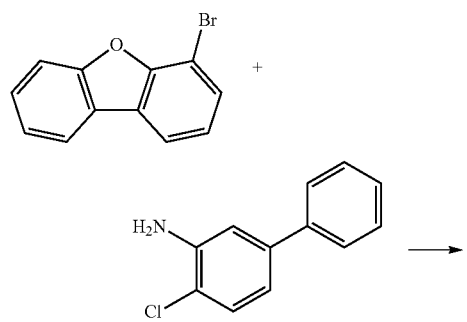

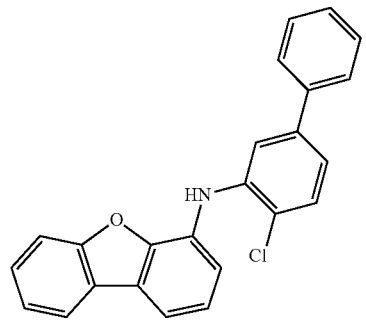

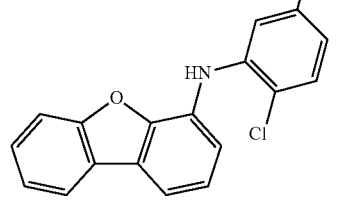

core-2

Core-2 was synthesized according to the same method as in Core-1 except that 4-chloro-[1,1'-biphenyl]-3-amine was used instead of the 2-chloroaniline.

<Synthesis of Core-3>

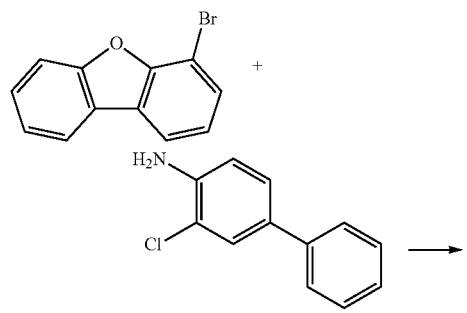

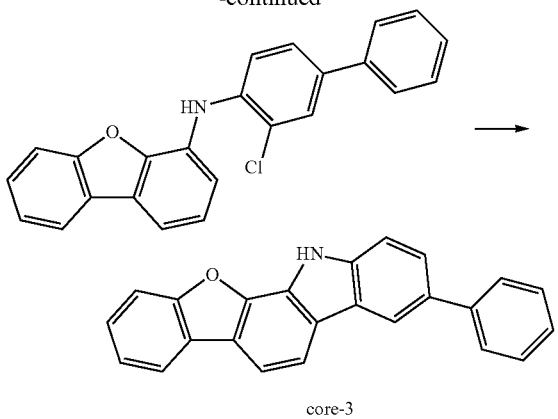

core-3

Core-3 was synthesized according to the same method as in Core-1 except that 3-chloro-[1,1'-biphenyl]-4-amine was used instead of the 2-chloroaniline.

<Synthesis of Core-4>

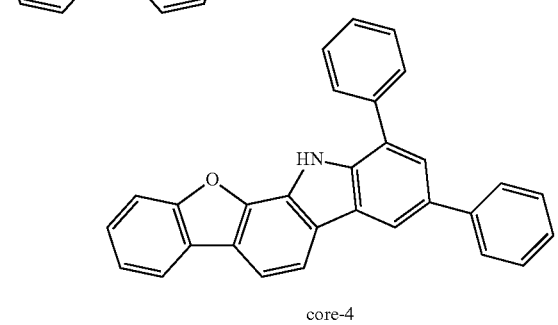

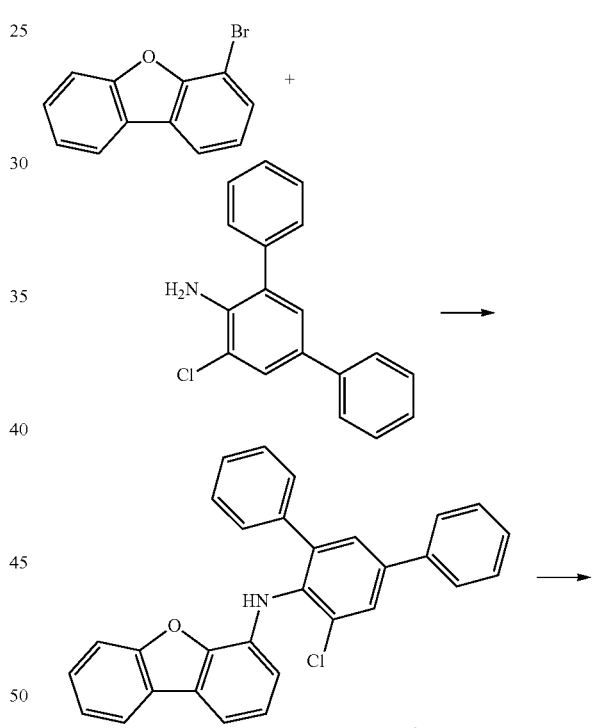

core-4

Core-4 was synthesized according to the same method as in Core-1 except that 5'-chloro-[1,1':3',1''-terphenyl]-4'-amine was used instead of the 2-chloroaniline.

<Synthesis of Core-5>

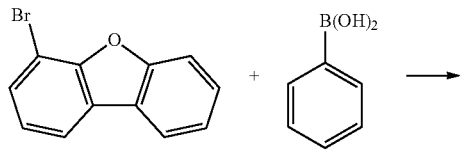

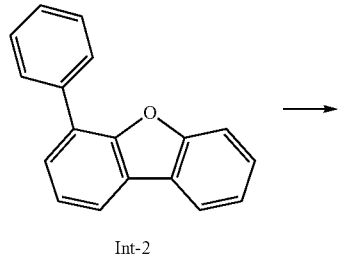

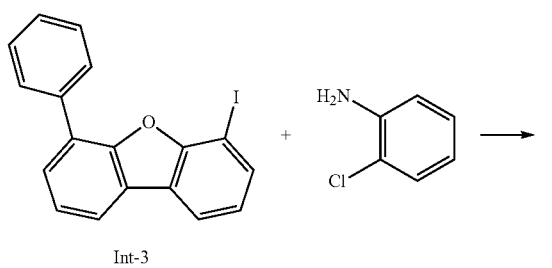

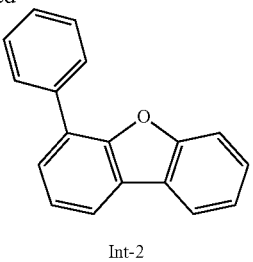

Int-2

4-bromo-dibenzofuran (80 g, 509.41 mmol), phenylboronic acid (90 g, 424.51 mmol), K$_2$CO$_3$ (117.34 g, 849.02 mmol), and Pd(PPh$_3$)$_4$ (24.53 g, 21.23 mmol) were put in a round-bottomed flask, and THF (1,000 ml) and distilled water (500 ml) were added thereto and then, the resultant was stirred under reflux at 80° C. for 12 hours. When a reaction was completed, after removing an aqueous layer therefrom, 93 g (91%) of Intermediate Int-2 was obtained using column chromatography.

Synthesis Example 4: Synthesis of Int-3

[Reaction Scheme 4]

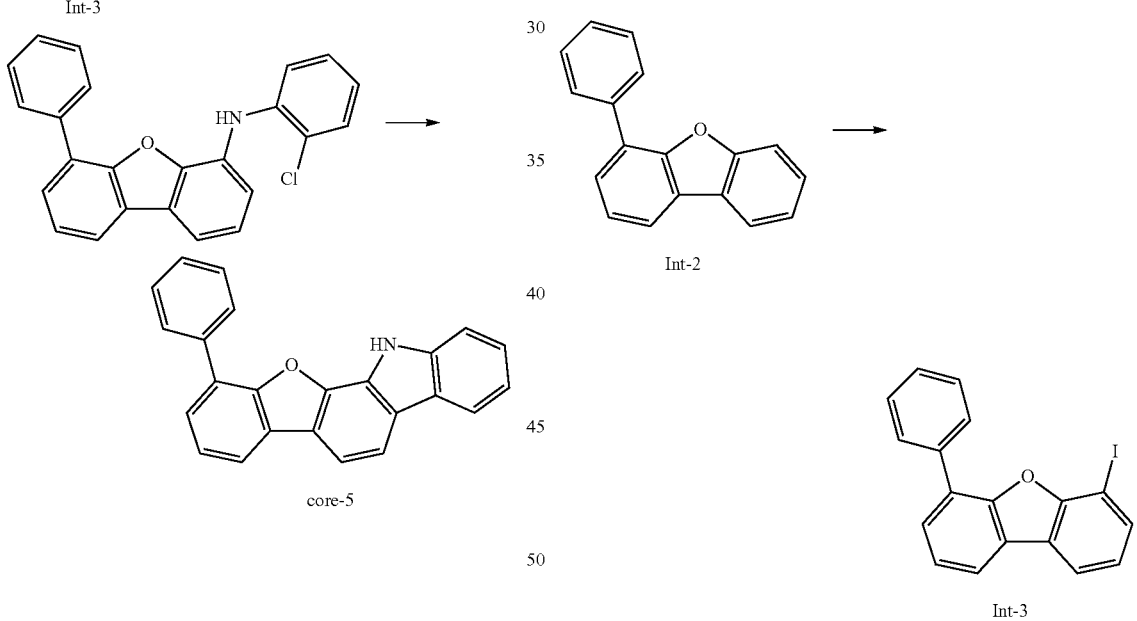

Synthesis Example 3: Synthesis of Int-2

[Reaction Scheme 3]

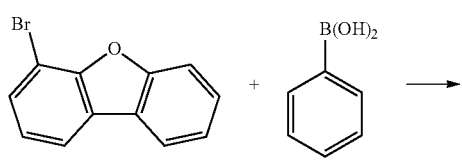

Int-2 (93 g, 380.70 mmol) was dissolved in THF (300 ml) and then, cooled down to −78° C., and N-BuLi (243.64 ml, 609.11 mmol) was slowly added thereto and then, the resultant was stirred for 6 hours, while the temperature was increased up to ambient temperature. When the stirring was completed, the resultant was cooled down to −78° C., and I$_2$ (111.12 g, 437.80 mmol) dissolved in THF (300 ml) was slowly added thereto and then, the resultant was stirred at ambient temperature for 12 hours. When a reaction was completed, after quenched by adding water thereto and then, removing an aqueous layer therefrom, 120 g (85%) of Intermediate Int-3 was obtained using column chromatography.

Synthesis Example 5: Synthesis of Core-5

[Reaction Scheme 5]

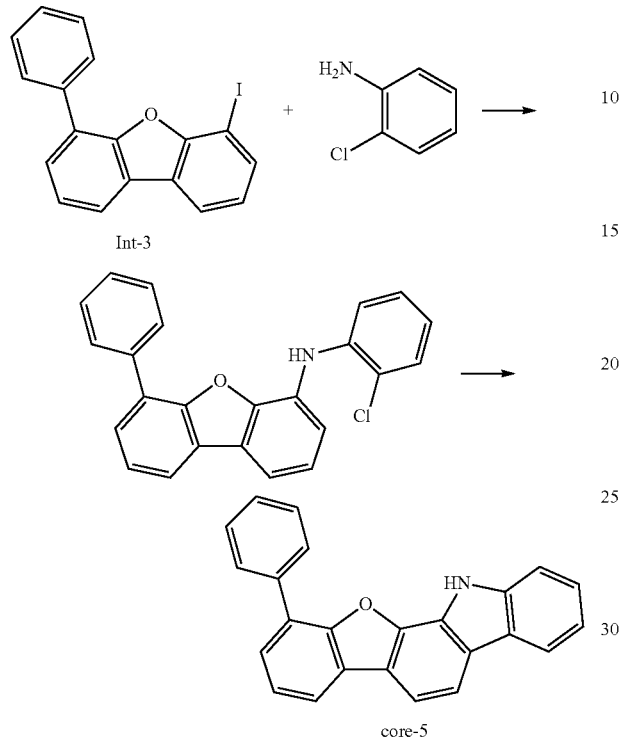

Core-5 was synthesized according to the same method as in Core-1 except that Int-3 was used instead of the intermediate of 4-bromo-dibenzofuran.

Synthesis Example 6: Synthesis of Int-4

[Reaction Scheme 6]

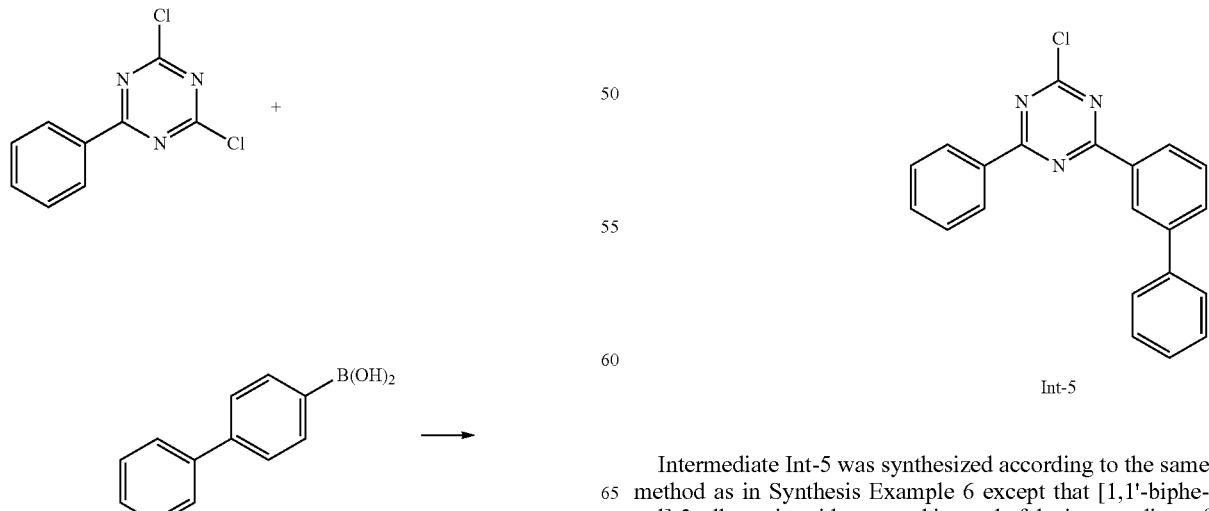

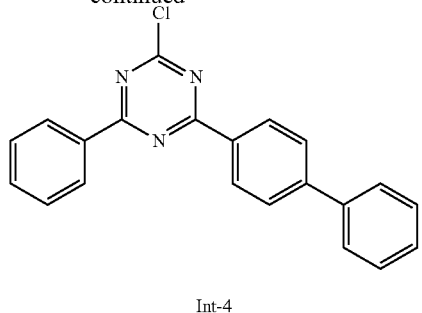

2,4-dichloro-6-phenyl-1,3,5-triazine (17.12 g, 75.75 mmol), [1,1'-biphenyl]-4-ylboronic acid (10 g, 50.50 mmol), $K_2CO_3$ (13.96 g, 138.21 mmol), and $Pd(PPh_3)_4$ (2.92 g, 2.52 mmol) were put in a round-bottomed flask, and THF (100 ml) and distilled water (50 ml) were added thereto and then, the resultant was stirred under reflux at 80° C. for 12 hours.

When a reaction was completed, the mixture was added to 300 mL of methanol, and a solid crystallized therein was filtered, dissolved in monochlorobenzene, and filtered with silica gel/Celite, and after removing an appropriate amount of an organic solvent, recrystallized with methanol, obtaining 11.3 g (65%) of Intermediate Int-4.

Synthesis Example 7: Synthesis of Int-5

[Reaction Scheme 7]

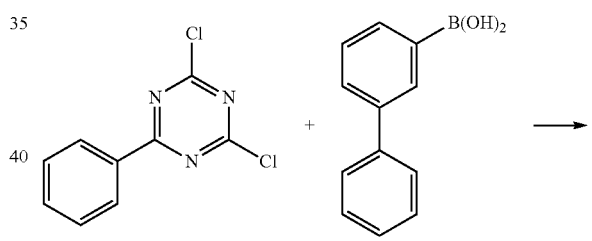

Intermediate Int-5 was synthesized according to the same method as in Synthesis Example 6 except that [1,1'-biphenyl]-3-ylboronic acid was used instead of the intermediate of [1,1'-biphenyl]-4-ylboronic acid.

Synthesis Example 8: Synthesis of Int-6

[Reaction Scheme 8]

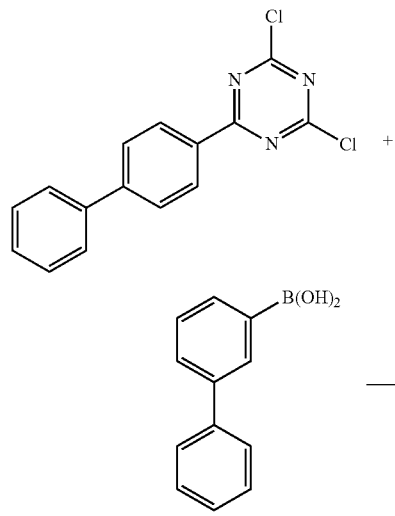

Intermediate Int-6 was synthesized according to the same method as in Synthesis Example 7 except that 2,4-dichloro-6-(biphenyl-4-yl)-1,3,5-triazine was used instead of the intermediate of 2,4-dichloro-6-phenyl-1,3,5-triazine.

Synthesis Example 9: Synthesis of Int-7

[Reaction Scheme 9]

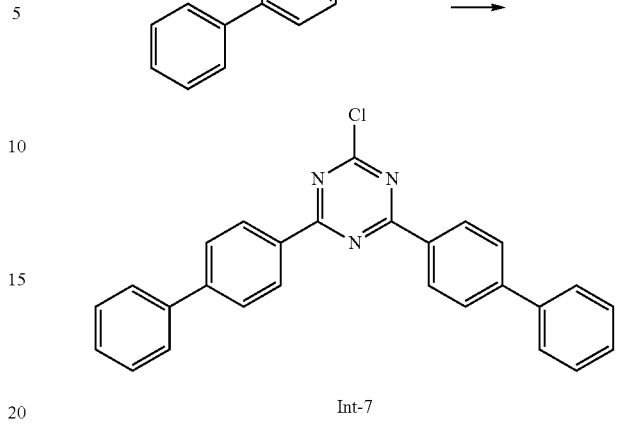

Intermediate Int-7 was synthesized according to the same method as in Synthesis Example 6 except that 2,4-dichloro-6-(biphenyl-4-yl)-1,3,5-triazine was used instead of the intermediate of 2,4-dichloro-6-phenyl-1,3,5-triazine.

Synthesis Example 10: Synthesis of Int-8

[Reaction Scheme 10]

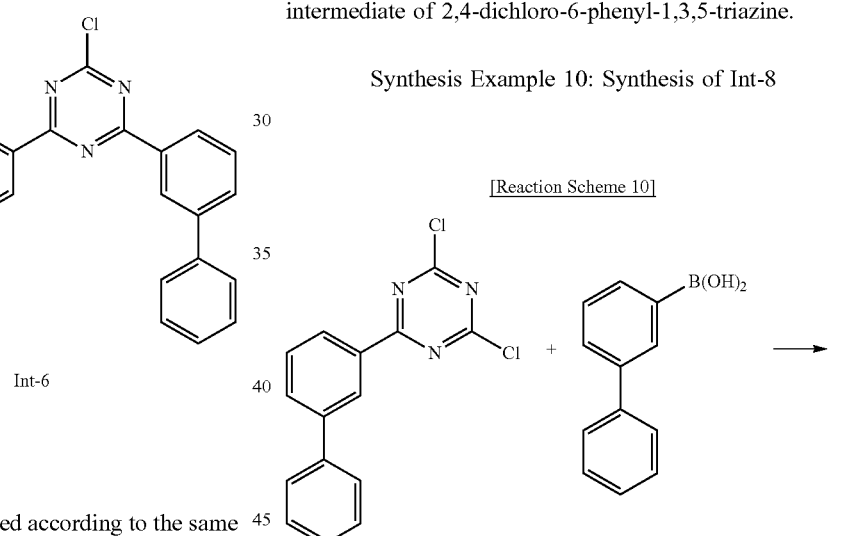

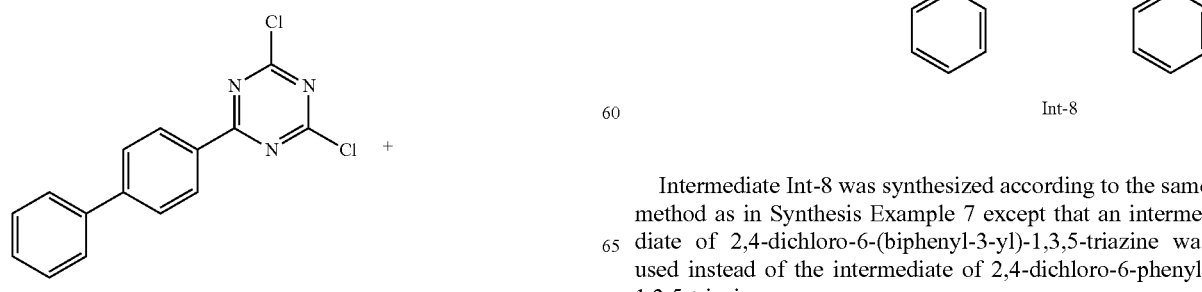

Intermediate Int-8 was synthesized according to the same method as in Synthesis Example 7 except that an intermediate of 2,4-dichloro-6-(biphenyl-3-yl)-1,3,5-triazine was used instead of the intermediate of 2,4-dichloro-6-phenyl-1,3,5-triazine.

Synthesis Example 11: Synthesis of Int-9

[Reaction Scheme 11]

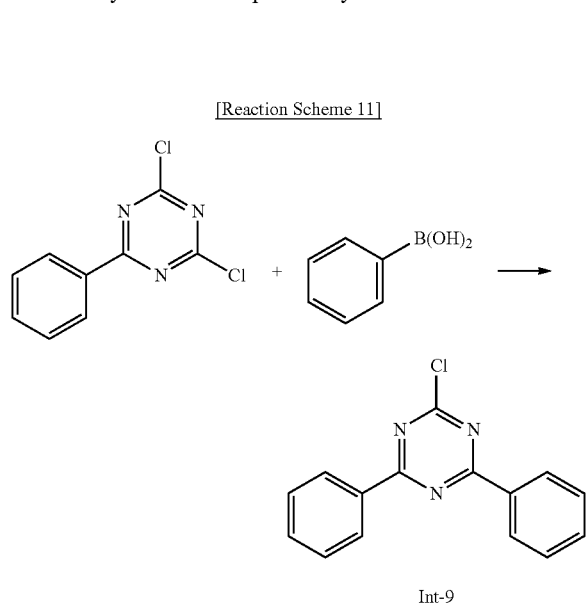

Int-9

Intermediate Int-9 was synthesized according to the same method as in Synthesis Example 6 except that phenylboronic acid was used instead of the intermediate of [1,1'-biphenyl]-4-ylboronic acid.

Synthesis Example 12: Synthesis of Compound 6

[Reaction Scheme 12]

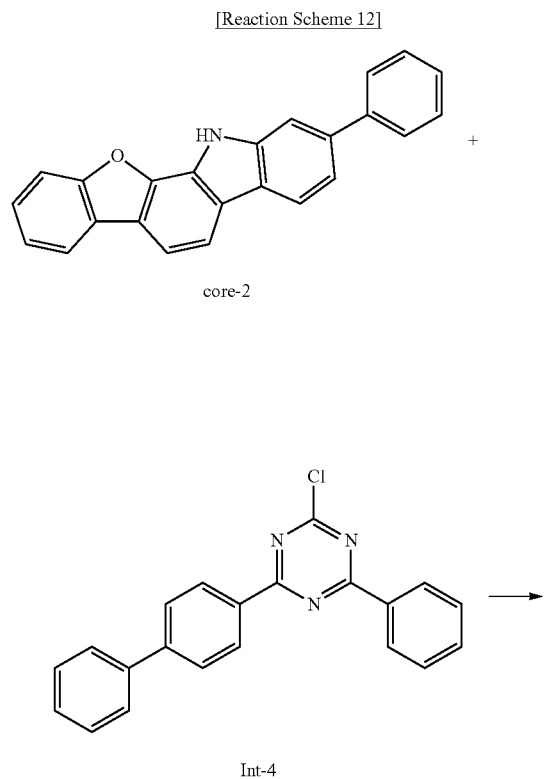

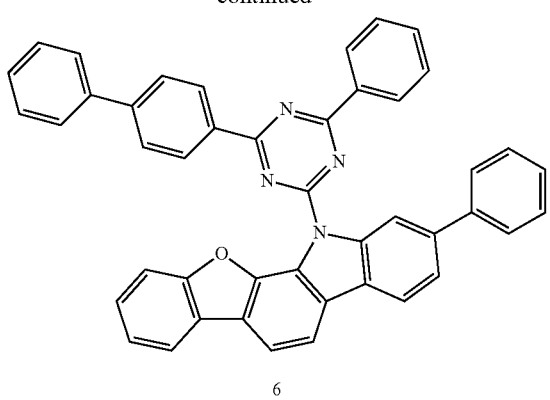

6

Core-2 (10 g, 30.0 mmol), Int-4 (10.83 g, 31.5 mmol), and NaH (1.58 g, 65.99 mmol) were put in a round-bottomed flask, and DMF (100 ml) was added thereto and then, the resultant was stirred at ambient temperature for 12 hours. When a reaction was completed, 300 mL of water was added to the mixture, and a solid crystallized therein was filtered, dissolved in monochlorobenzene, filtered with silica gel/Celite, and after removing an appropriate amount of an organic solvent, recrystallized with methanol, obtaining 17.1 g (88%) of Compound 6.

Compounds were synthesized according to the same method as in Synthesis Example 12 except that the intermediates were changed as shown in Table 1.

TABLE 1

| Synthesis Example | Core | Intermediate | Compound | Yield |
|---|---|---|---|---|
| 13 | Core-2 | Int-4 | 6 | 17.1 g (88%) |
| 14 | Core-2 | Int-5 | 42 | 15 g (70.1%) |
| 15 | Core-2 | Int-6 | 10 | 11.6 g (77.4%) |
| 16 | Core-2 | Int-7 | 14 | 13.6 g (80.1%) |
| 17 | Core-2 | Int-8 | 46 | 14.6 g (78.9%) |
| 18 | Core-3 | Int-4 | 7 | 15.6 g (77.4%) |
| 19 | Core-3 | Int-5 | 43 | 11.2 g (90%) |
| 20 | Core-3 | Int-6 | 11 | 10.7 g (87.3%) |
| 21 | Core-3 | Int-7 | 15 | 13.4 g (72.3%) |
| 22 | Core-3 | Int-8 | 47 | 18.5 g (85.6%) |
| 23 | Core-4 | Int-4 | 18 | 12.6 g (79.9%) |
| 24 | Core-4 | Int-6 | 19 | 13.1 g (78.6%) |
| 25 | Core-4 | Int-7 | 20 | 14.6 g (84.7%) |
| 26 | Core-5 | Int-4 | 25 | 16.3 g (80.7%) |
| 27 | Core-5 | Int-5 | 49 | 18 g (84.3%) |
| 28 | Core-5 | Int-6 | 29 | 16.1 g (82.1%) |
| 29 | Core-5 | Int-7 | 33 | 21.1 g (91.2%) |
| 30 | Core-5 | Int-8 | 53 | 10.1 g (87.8%) |
| 31 | Core-2 | Int-9 | 2 | 17.1 g (80%) |
| 32 | Core-3 | Int-9 | 3 | 15.0 g (71.4%) |
| 33 | Core-5 | Int-9 | 21 | 10.9 g (89.8%) |

Comparative Synthesis Example 1: Synthesis of Comparative Compound 1

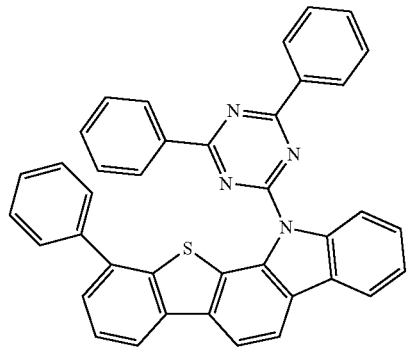 [SMILES: c1ccc(-c2nc(-c3ccccc3)nc(-n3c4ccccc4c4ccc5c6cccc(-c7ccccc7)c6sc5c43)n2)cc1]

Comparative Compound 1

Comparative Compound 1 was synthesized according to a method disclosed in KR2014-0067914.

Comparative Synthesis Example 2: Synthesis of Comparative Compound 2

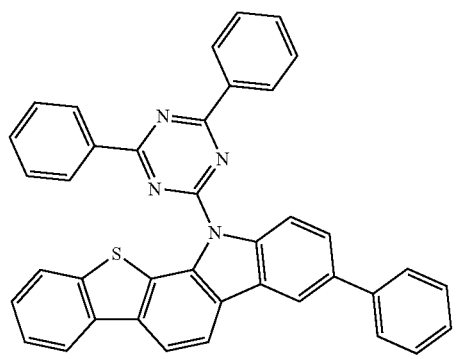 [SMILES: c1ccc(-c2ccc3c(c2)c2ccc4c5ccccc5sc4c2n3-c2nc(-c3ccccc3)nc(-c3ccccc3)n2)cc1]

Comparative Compound 2

Comparative Compound 2 was synthesized according to a method disclosed in KR2014-0067914.

Comparative Synthesis Example 3: Synthesis of Comparative Compound 3

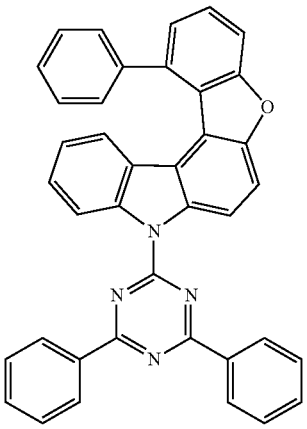 [SMILES: c1ccc(-c2nc(-c3ccccc3)nc(-n3c4ccccc4c4c5c(ccc43)oc3cccc(-c4ccccc4)c35)n2)cc1]

Comparative Compound 3

Comparative Compound 3 was synthesized according to a method disclosed in KR2014-0067914.

Comparative Synthesis Example 4: Synthesis of Comparative Compound 4

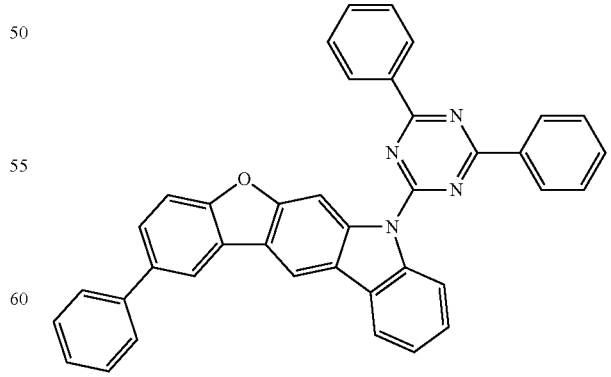

Comparative Compound 4

Comparative Compound 4 was synthesized according to a method disclosed in KR2020-0002020.

Comparative Synthesis Example 5: Synthesis of Comparative Compound 5

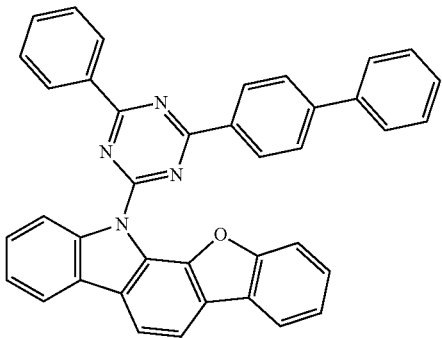 [SMILES: c1ccc(-c2ccc(-c3nc(-c4ccccc4)nc(-n4c5ccccc5c5ccc6c7ccccc7oc6c54)n3)cc2)cc1]

Comparative Compound 5

Comparative Compound 5 was synthesized in the same method as in Synthesis Example 12, except that Core-1 was used instead of Core-2.

Comparative Synthesis Example 6: Synthesis of Comparative Compound 6

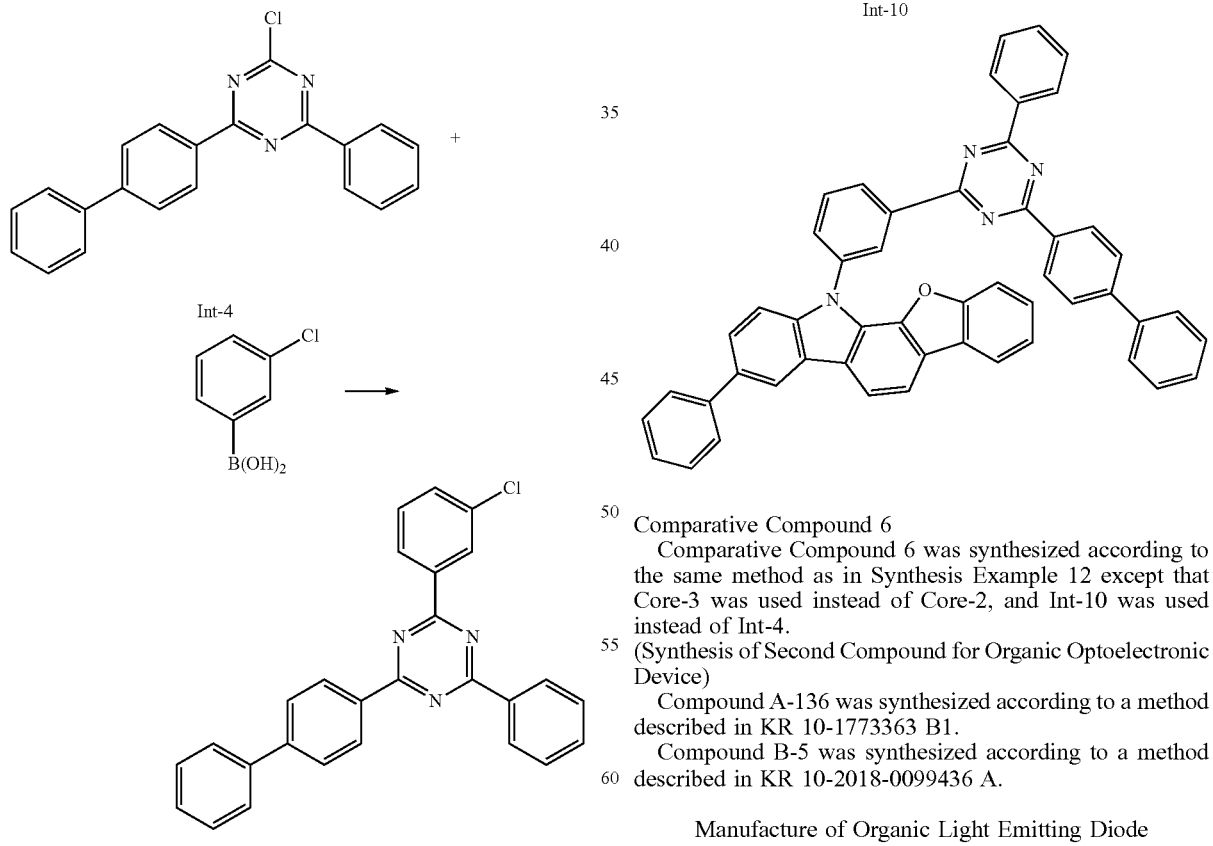

Intermediate Int-10 was synthesized according to the same method as in Synthesis Example 6 except that Int-4 was used instead of the 2,4-dichloro-6-phenyl-1,3,5-triazine, and 3-chloro-phenylboronic acid was used instead of the intermediate of [1,1'-biphenyl]-4-ylboronic acid.

Comparative Compound 6

Comparative Compound 6 was synthesized according to the same method as in Synthesis Example 12 except that Core-3 was used instead of Core-2, and Int-10 was used instead of Int-4.

(Synthesis of Second Compound for Organic Optoelectronic Device)

Compound A-136 was synthesized according to a method described in KR 10-1773363 B1.

Compound B-5 was synthesized according to a method described in KR 10-2018-0099436 A.

Manufacture of Organic Light Emitting Diode

Example 1

A glass substrate coated with 1,500 Å-thick ITO (Indium tin oxide) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 1,020 Å-thick to form a hole transport layer. On the hole transport layer, 400 Å-thick light emitting layer was formed by using Compound 21 as a host and doping 2 wt % of [Ir(piq)$_2$acac] as a dopant by a vacuum deposition. Subsequently, on the light emitting layer, a 300 Å-thick electron transport layer was formed by simultaneously vacuum-depositing Compound D and Liq in a weight ratio of 1:1, and on the electron transport layer, Liq and Al were sequentially vacuum-deposited to be 15 Å-thick and 1,200 Å-thick, manufacturing an organic light emitting diode.

The organic light emitting diode had a five-layered organic thin layer, and specifically the following structure.

ITO/Compound A (700 Å)/Compound B (50 Å)/Compound C (1,020 Å)/EML [Compound 21: [Ir(piq)$_2$acac] (2 wt %)] (400 Å)/Compound D:Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Example 2 and Comparative Examples 1 and 2

Each diode of Example 2 and Comparative Examples 1 and 2 was manufactured in the same manner as in Example 1, except that the host was changed as shown in Tables 2 and 3.

Examples 3 to 6 and Comparative Examples 3 to 7

Each diode according to Examples 3 to 6 and Comparative Examples 3 to 7 was manufactured according to the same method as in Example 1 except that the first host and the second host were changed as shown in Tables 4 to 7, and the first host and the second host were mixed in a weight ratio of 3:7.

Example 7 and Comparative Example 8

Each diode according to Example 7 and Comparative Example 8 was manufactured according to the same method as in Example 1 except that the first host and the second host were changed as shown in Table 8, and the first host and the second host were respectively mixed in a weight ratio of 4:6.

Evaluation: Confirmation of Life-Span Increase Effect

The luminous efficiency and life-span characteristics of the organic light emitting diodes according to Examples 1 to 7 and Comparative Examples 1 to 8 were evaluated. Specific measurement methods are as follows, and the results are shown in Tables 2 to 8.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 mA/cm$^2$) were calculated by using the luminance, current density, and voltage from the items (1) and (2).

(4) Measurement of Life-Span

T95 life-spans of the organic light emitting diodes according to Examples 1 to 7, and Comparative Examples 1 to 8 were measured as a time when their luminance decreased down to 95% relative to the initial luminance (cd/m$^2$) after emitting light with 6,000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm$^2$.

Relative evaluation values based on each measurement value of Comparative Examples 1 to 5, Example 6, and Comparative Example 8 are shown in Tables 2 to 8.

TABLE 2

|  | Single host | T95 (%) | Efficiency (%) | Driving voltage (%) |
|---|---|---|---|---|
| Example 1 | Compound 21 | 195% | 118% | 94% |
| Comparative Example 1 | Comparative Compound 1 | 100% | 100% | 100% |

TABLE 3

|  | Single host | T95 (%) | Efficiency (%) | Driving voltage (%) |
|---|---|---|---|---|
| Example 2 | Compound 7 | 141% | 104% | 98% |
| Comparative Example 2 | Comparative Compound 6 | 100% | 100% | 100% |

TABLE 4

|  | Hosts | | T95 (%) | Efficiency (%) | Driving voltage (%) |
|---|---|---|---|---|---|
|  | First host | Second host | | | |
| Example 3 | Compound 21 | A-136 | 155% | 124% | 96% |
| Comparative Example 3 | Comparative Compound 1 | A-136 | 100% | 100% | 100% |

TABLE 5

|  | Hosts | | T95 (%) | Efficiency (%) | Driving voltage (%) |
|---|---|---|---|---|---|
|  | First host | Second host | | | |
| Example 4 | Compound 25 | A-136 | 121% | 108% | 100% |
| Comparative Example 4 | Comparative Compound 5 | A-136 | 100% | 100% | 100% |

TABLE 6

| Hosts | | T95 (%) | Efficiency (%) | Driving voltage (%) |
|---|---|---|---|---|
| First host | Second host | | | |
| Example 5 | Compound 7 | A-136 | 138% | 111% | 96% |
| Comparative Example 5 | Comparative Compound 6 | A-136 | 100% | 100% | 100% |

TABLE 7

| Hosts | | T95 (%) |
|---|---|---|
| First host | Second host | |
| Example 6 | Compound 21 | A-136 | 100% |
| Comparative Example 6 | Comparative Compound 3 | A-136 | 69% |
| Comparative Example 7 | Comparative Compound 4 | A-136 | 78% |

TABLE 8

| Hosts | | T95 (%) | Efficiency (%) | Driving voltage (%) |
|---|---|---|---|---|
| First host | Second host | | | |
| Example 7 | Compound 25 | B-5 | 130% | 110% | 100% |
| Comparative Example 8 | Comparative Compound 5 | B-5 | 100% | 100% | 100% |

Referring to Tables 2 and 4, when a dibenzofuran moiety was fused, devices with improved life-span characteristics, efficiency, and driving voltage due to excellent hole characteristics were realized, compared with when a dibenzothiophene moiety was fused.

In addition, referring to Tables 3 and 6, when a linker was present, the devices lost a balance due to expansion of electron characteristics through the linker, and accordingly, the life-span characteristics, efficiency, and driving voltage thereof were deteriorated, compared with when no linker was present.

In addition, referring to Table 7, fused carbazole (in which a benzofuran moiety was fused at the $1^{st}$ and $2^{nd}$ positions of carbazole), compared with a fused carbazole (in which a benzofuran moiety was fused at the $2^{nd}$ and $3^{rd}$ positions of carbazole) and a fused carbazole (in which a benzofuran moiety was fused at the $3^{rd}$ and $4^{th}$ positions of carbazole), exhibited that HOMO/LUMO partitions were clearly separated, as a hole transport region was expanded, and a device life-span was significantly increased.

In addition, referring to Tables 5 and 8, when the fused carbazole was substituted with an aryl group, the hole transport region was expanded and thus improved the life-span characteristics and the efficiency, compared with when a fused carbazole was not substituted with an aryl group.

One or more embodiments may provide a composition for an organic optoelectronic device capable of implementing an organic optoelectronic device having high efficiency and a long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic optoelectronic device, the composition comprising:
a first compound represented by Chemical Formula 1, and
a second compound represented by:
Chemical Formula 2; or
a combination of Chemical Formula 3 and Chemical Formula 4,

[Chemical Formula 1]

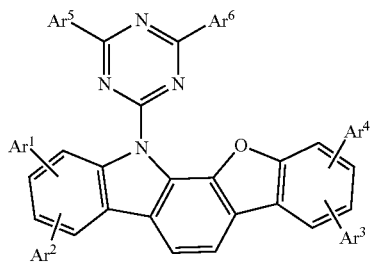

wherein, in Chemical Formula 1,
$Ar^1$ to $Ar^4$ are each independently hydrogen, deuterium, or a substituted or unsubstituted C6 to C18 aryl group, at least one of $Ar^1$ to $Ar^4$ being a substituted or unsubstituted C6 to C18 aryl group, and
$Ar^5$ and $Ar^6$ are each independently a substituted or unsubstituted C6 to C30 aryl group;

[Chemical Formula 2]

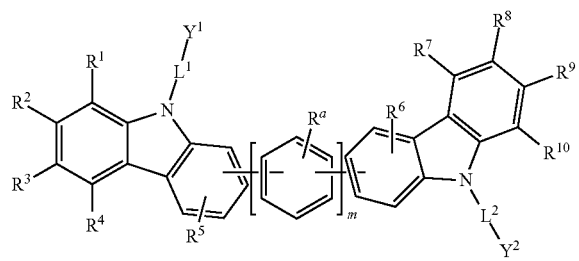

wherein, in Chemical Formula 2,
$Y^1$ and $Y^2$ are each independently a substituted or unsubstituted C6 to C20 aryl group or a substituted or unsubstituted C2 to C30 heterocyclic group,
$L^1$ and $L^2$ are each independently a single bond or a substituted or unsubstituted C6 to C20 arylene group,
$R^a$ and $R^1$ to $R^{10}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group, and m is an integer of 0 to 2;

[Chemical Formula 3]

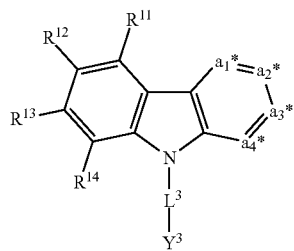

[Chemical Formula 4]

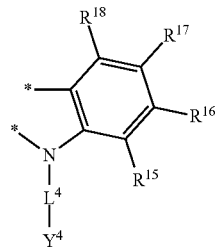

wherein, in Chemical Formulas 3 and 4, $Y^3$ and $Y^4$ are each independently a substituted or unsubstituted C6 to C20 aryl group or a substituted or unsubstituted C2 to C30 heterocyclic group, two adjacent ones of a1* to a4* of Chemical Formula 3 are linking carbons linked at * of Chemical Formula 4, the remaining two of a1* to a4* of Chemical Formula 3, not linked at * of Chemical Formula 4, are C-$L^a$-$R^b$, $L^a$, $L^3$ and $L^4$ are each independently a single bond or a substituted or unsubstituted C6 to C20 arylene group, and $R^b$ and $R^{11}$ to $R^{18}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

2. The composition as claimed in claim 1, wherein:

Chemical Formula 1 is represented by one of Chemical Formula 1-1 to Chemical Formula 1-12:

[Chemical Formula 1-1]

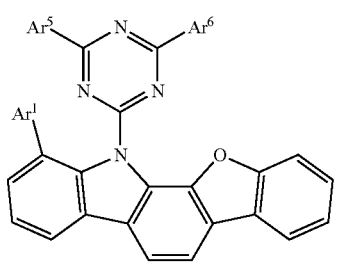

[Chemical Formula 1-2]

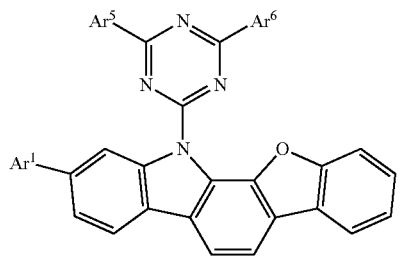

[Chemical Formula 1-3]

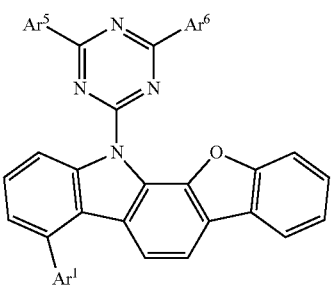

[Chemical Formula 1-4]

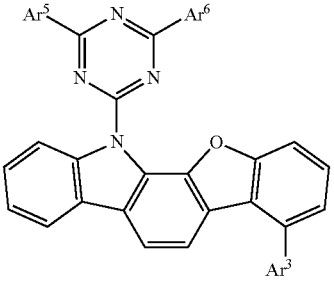

[Chemical Formula 1-5]

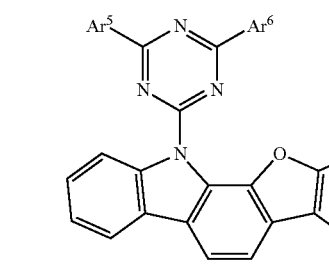

[Chemical Formula 1-6]

[Chemical Formula 1-7]

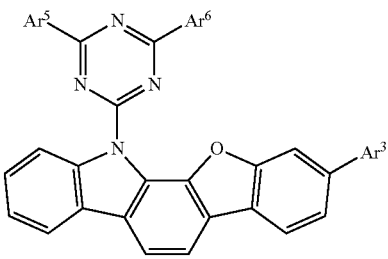

[Chemical Formula 1-8]

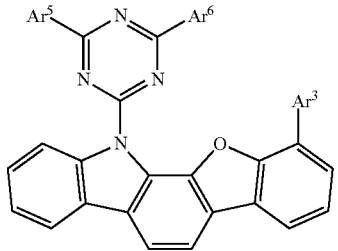

[Chemical Formula 1-9]

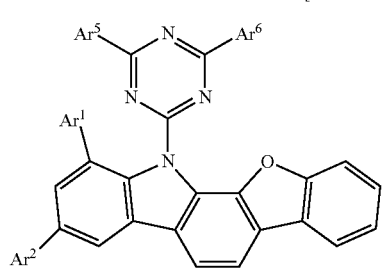

[Chemical Formula 1-10]

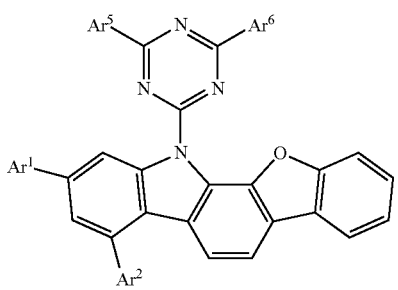

[Chemical Formula 1-11]

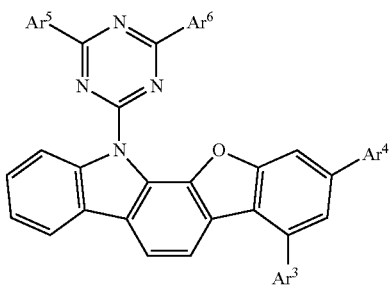

[Chemical Formula 1-12]

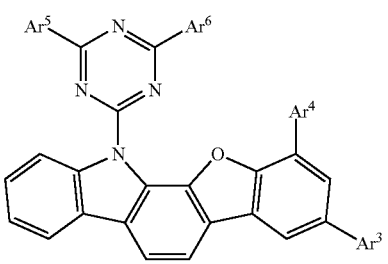

in Chemical Formula 1-1 to Chemical Formula 1-12, $Ar^1$ to $Ar^4$ are each independently a substituted or unsubstituted C6 to C18 aryl group, and $Ar^5$ and $Ar^6$ are each independently a substituted or unsubstituted C6 to C30 aryl group.

3. The composition as claimed in claim 2, wherein Chemical Formula 1 is represented by Chemical Formula 1-2, Chemical Formula 1-3, Chemical Formula 1-6, Chemical Formula 1-7, Chemical Formula 1-8, or Chemical Formula 1-9.

4. The composition as claimed in claim 1, wherein at least one of $Ar^1$ to $Ar^4$ of above Chemical Formula 1 is a substituted or unsubstituted C6 to C12 aryl group.

5. The composition as claimed in claim 1, wherein:

moiety

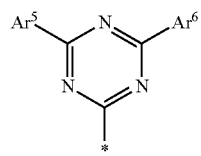

of Chemical Formula 1 is a moiety of Group I:

[Group I]

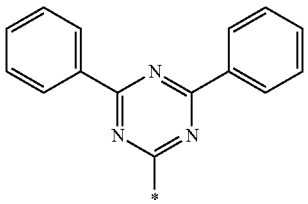

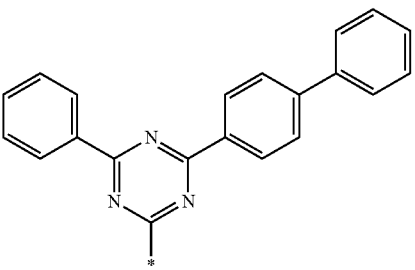

-continued
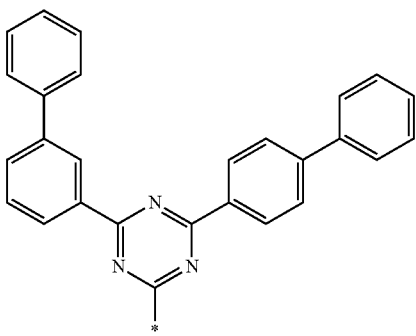
6. The composition as claimed in claim 1, wherein the first compound represented by Chemical Formula 1 is a compound of Group 1:
[Group 1]
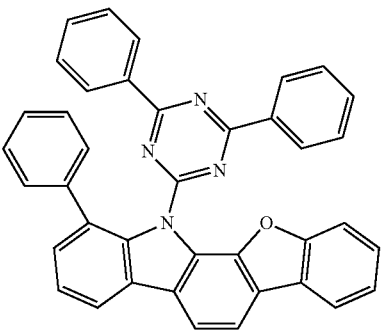
[1]
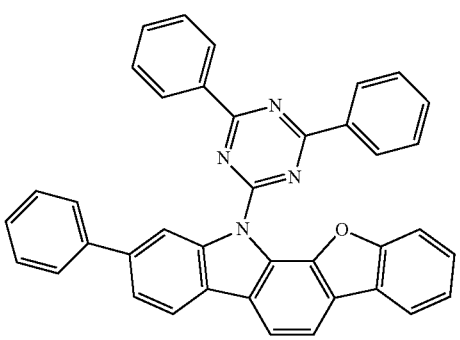
[2]
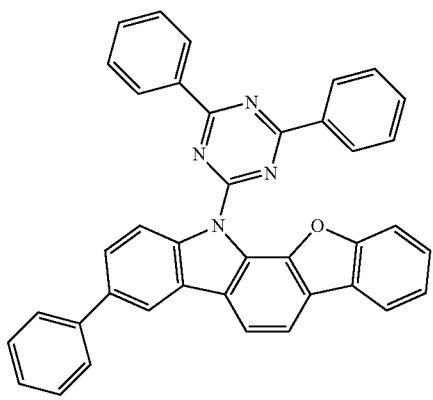
[3]
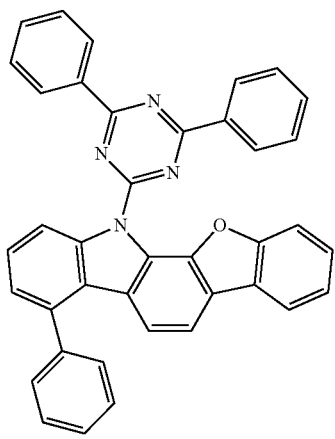
[4]
in Group I, * is a linking point.

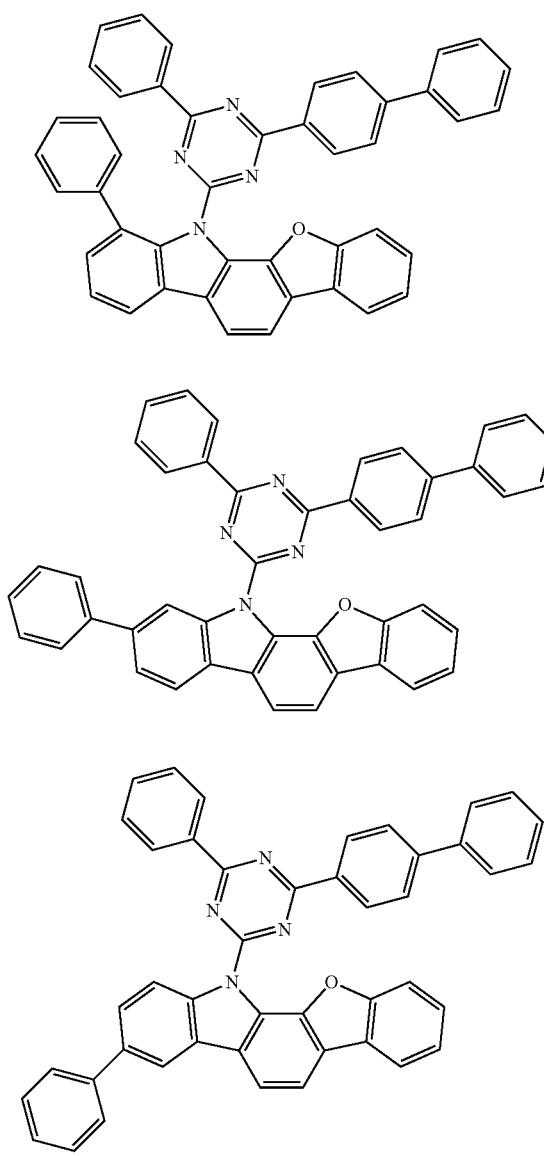
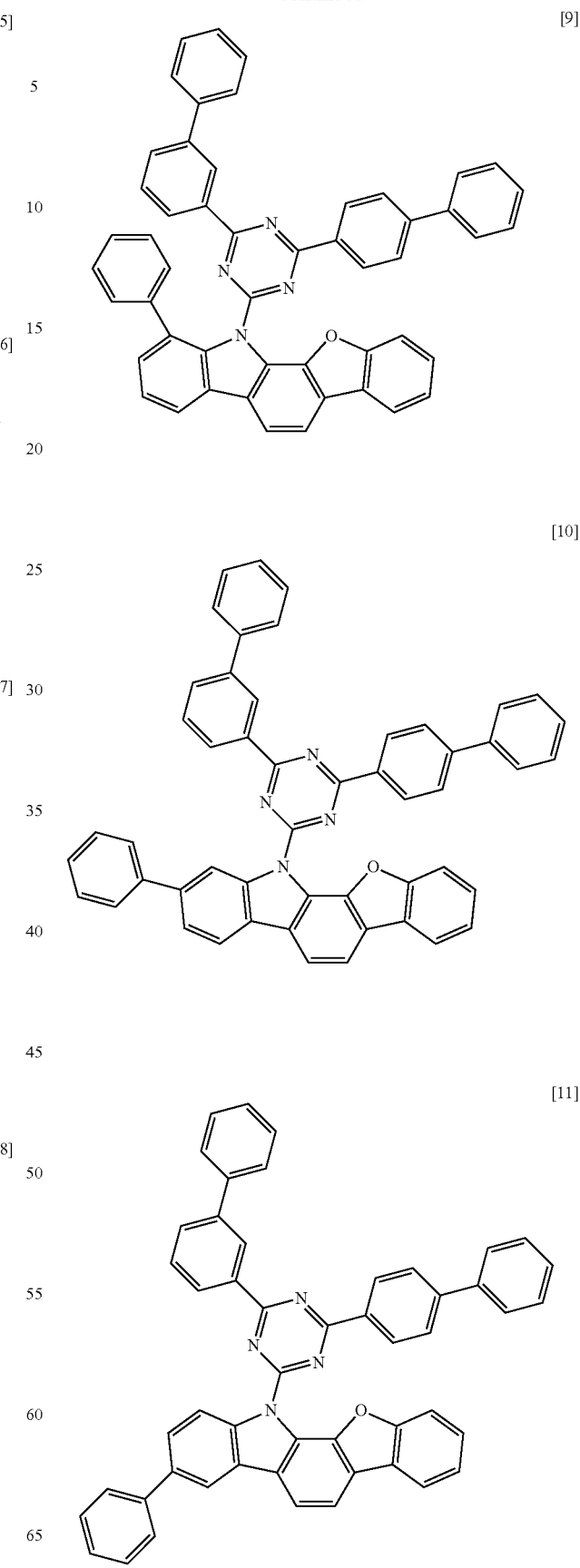

[12]
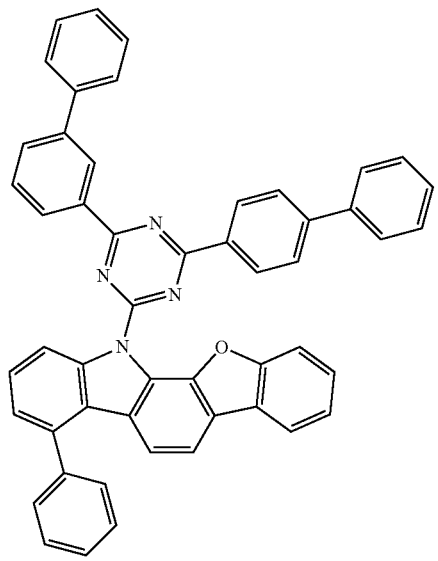
[13]
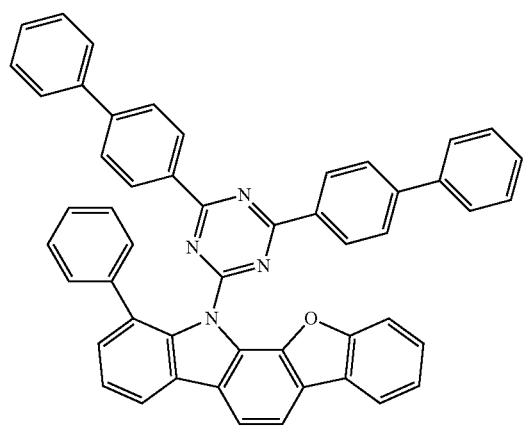
[14]
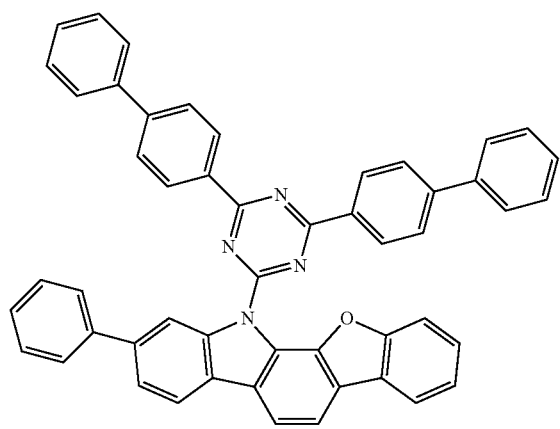
[15]
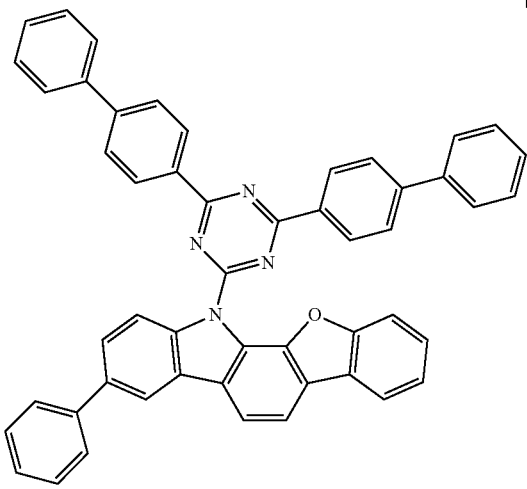
[16]
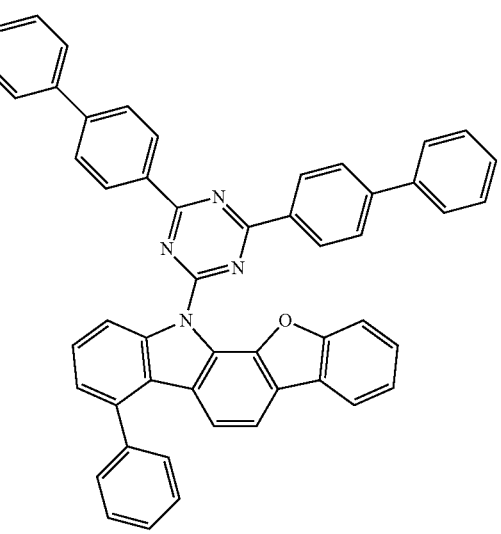
[17]
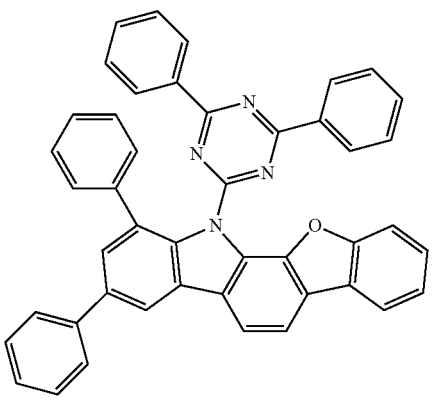

[18]
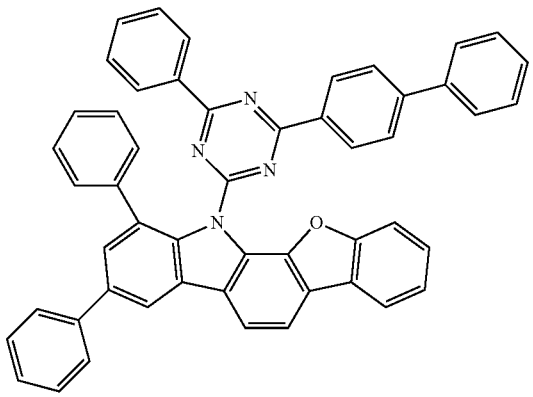
[19]
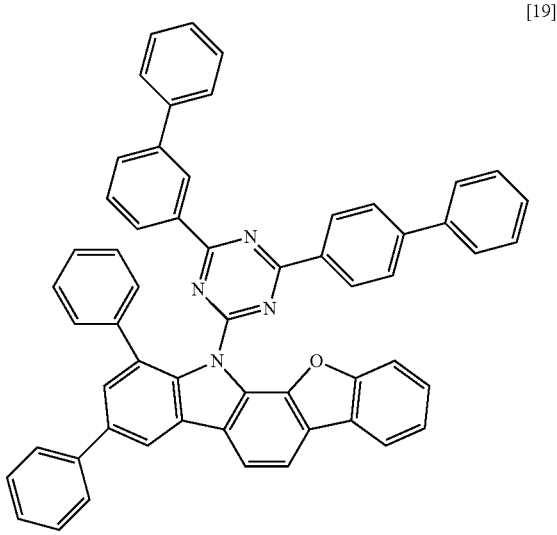
[20]
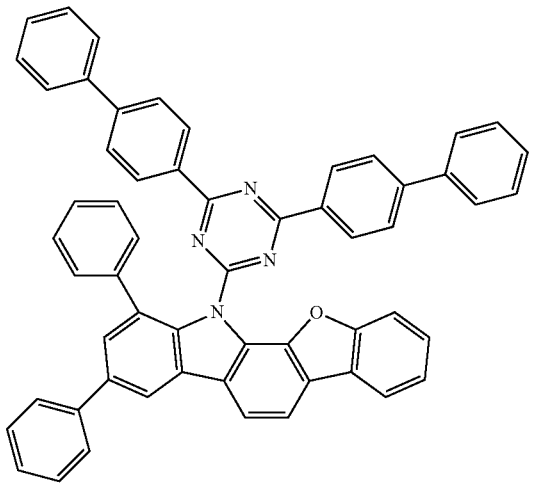
[21]
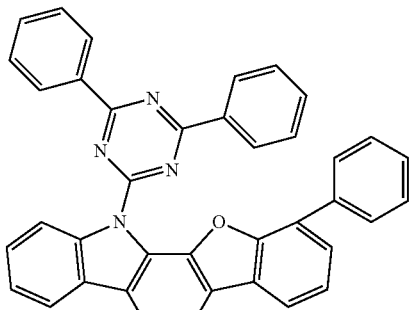
[22]
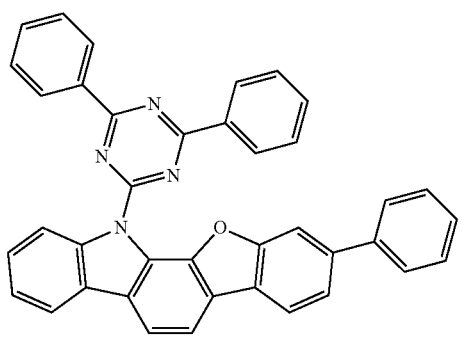
[23]
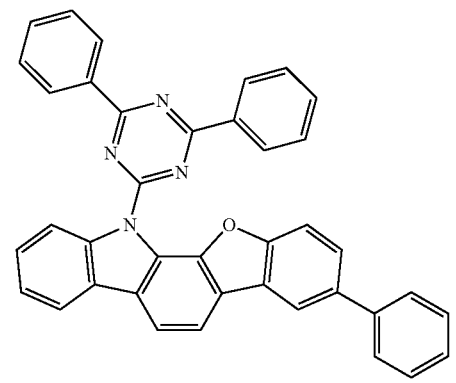
[24]
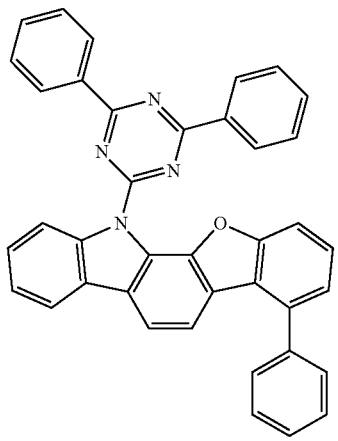

[25]
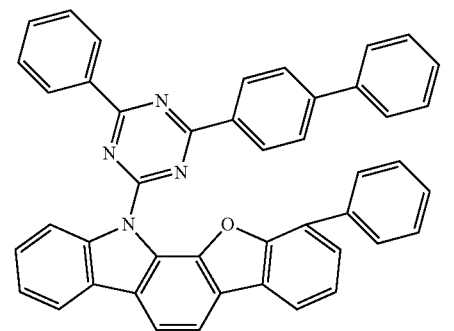
[26]
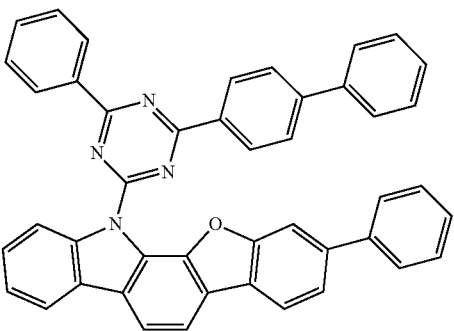
[27]
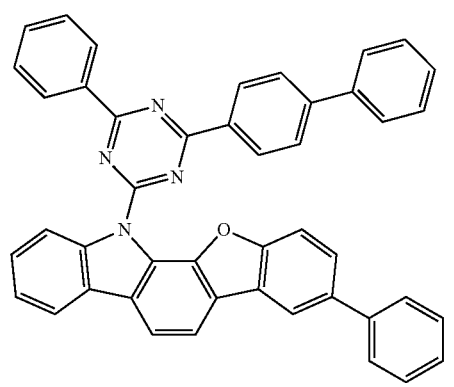
[28]
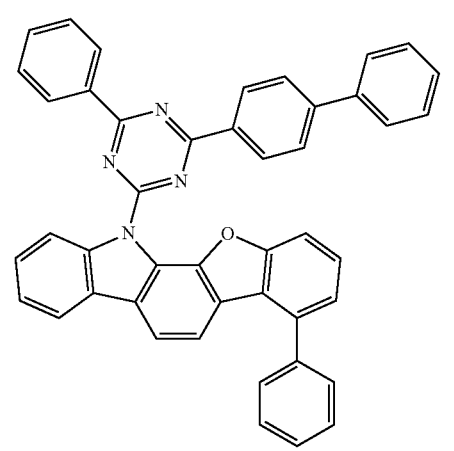
[29]
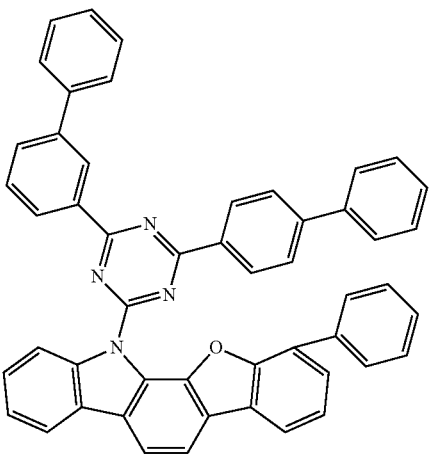
[30]
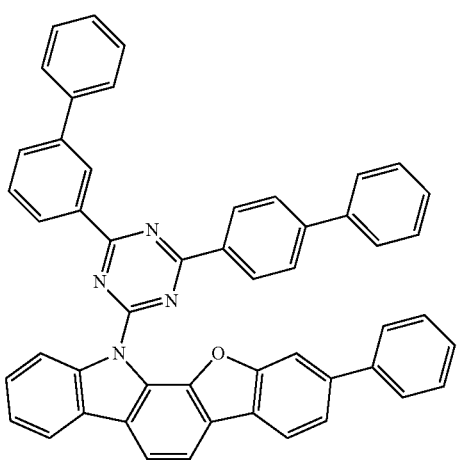
[31]
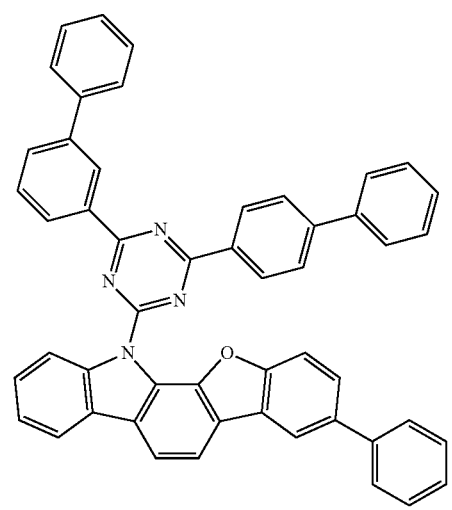

-continued
[32]
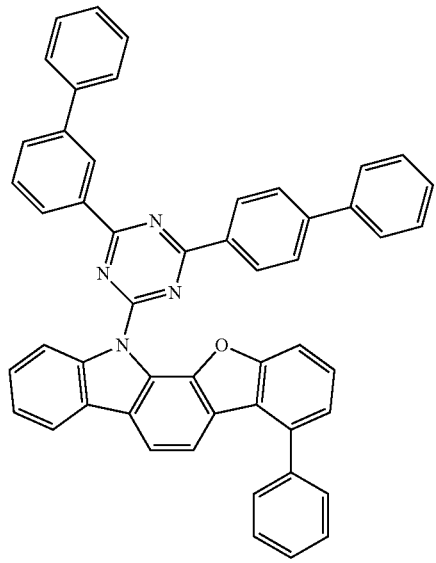
[33]
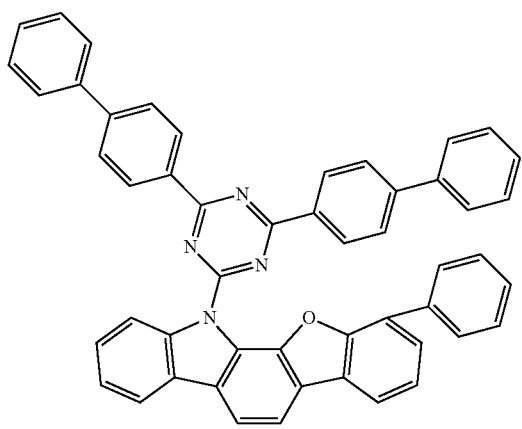
[34]
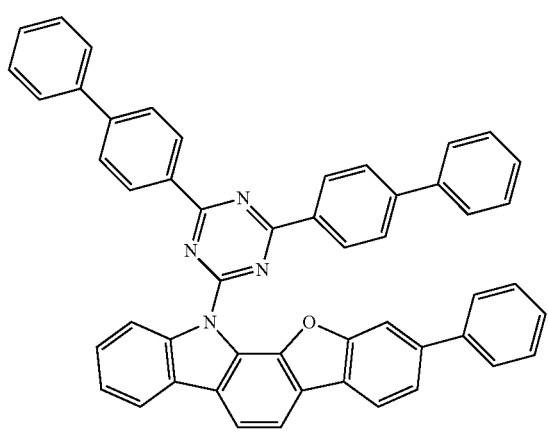
-continued
[35]
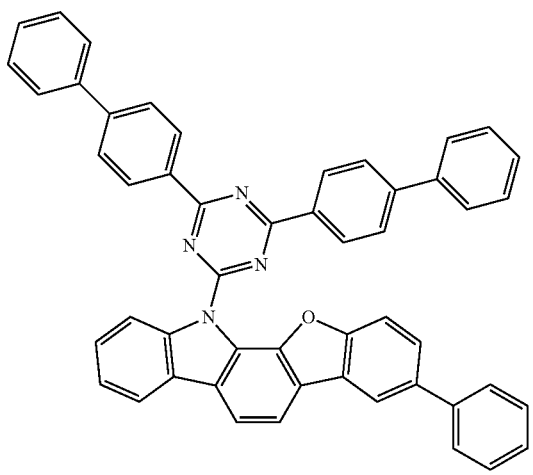
[36]
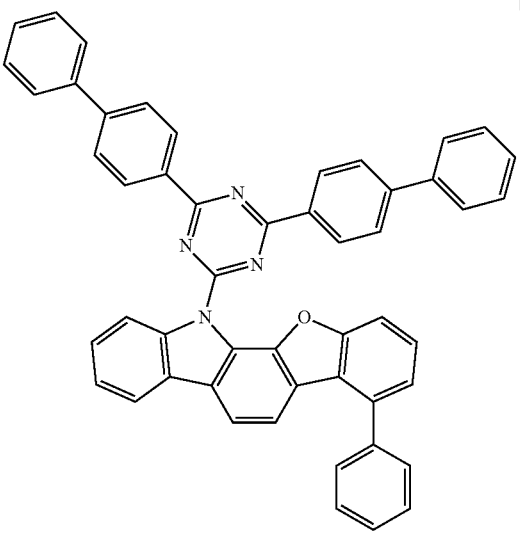
[37]
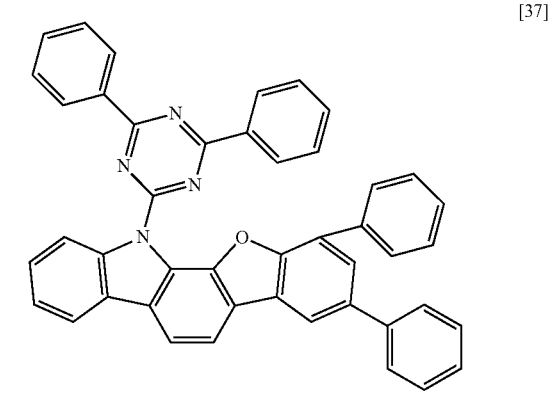

[38]
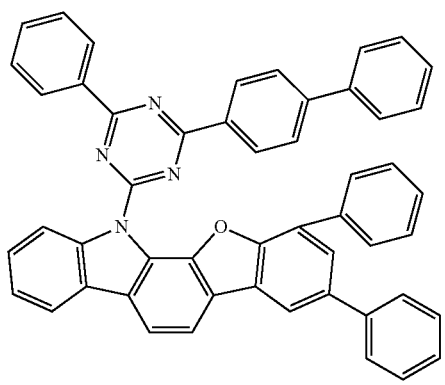
[39]
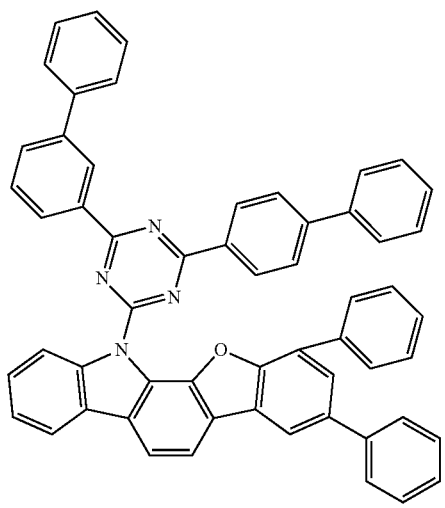
[40]
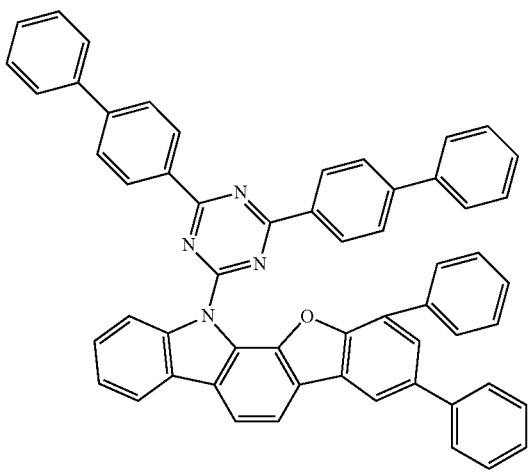
[41]
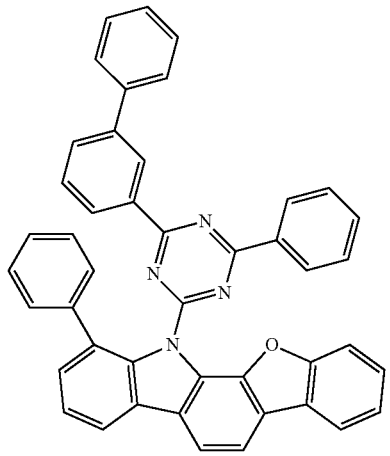
[42]
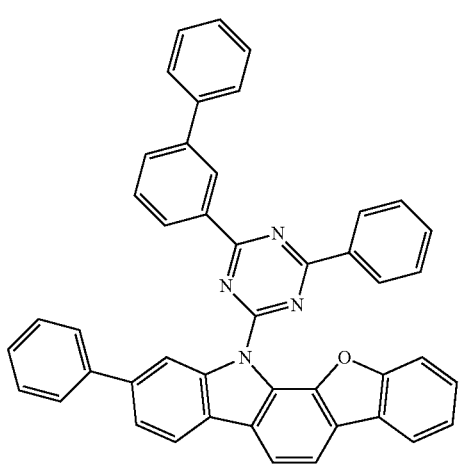
[43]
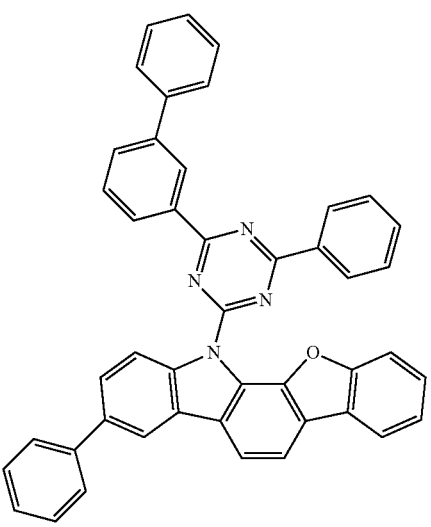

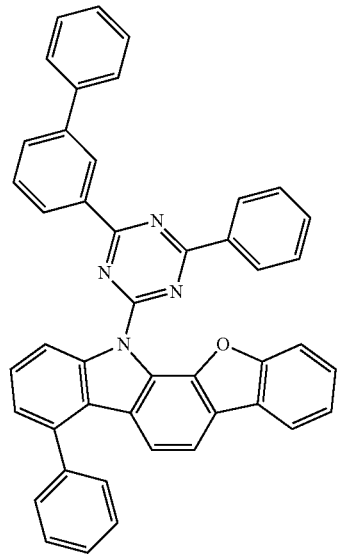
[44]
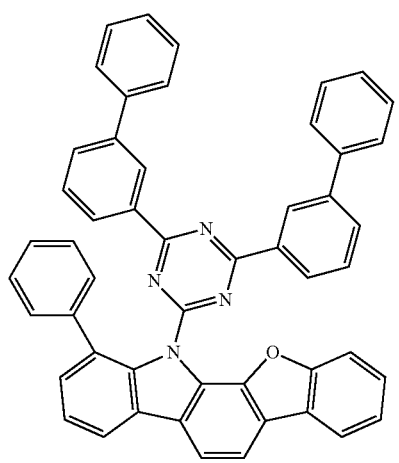
[45]
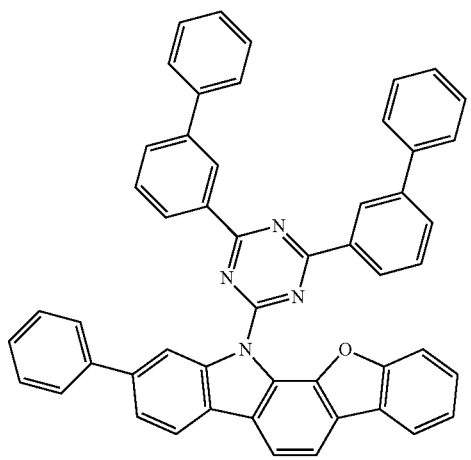
[46]
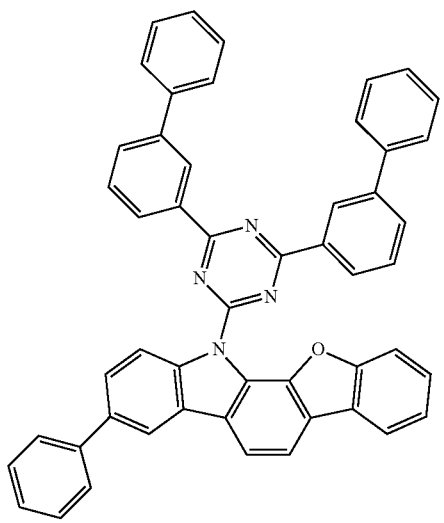
[47]
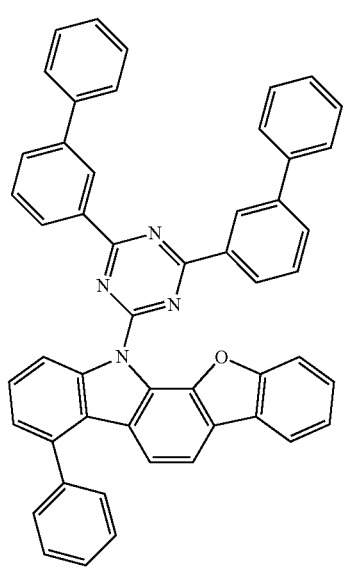
[48]
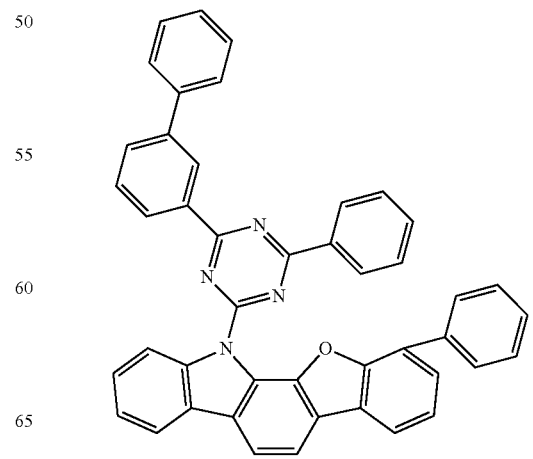
[49]

[50]
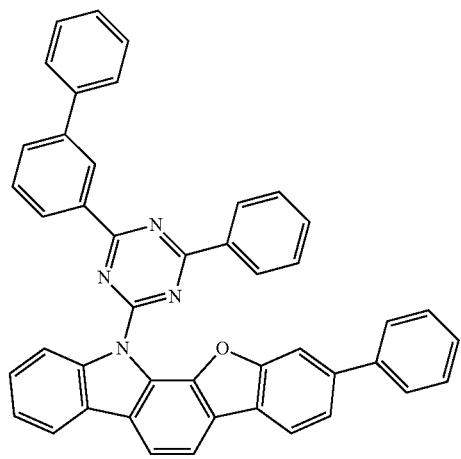
[51]
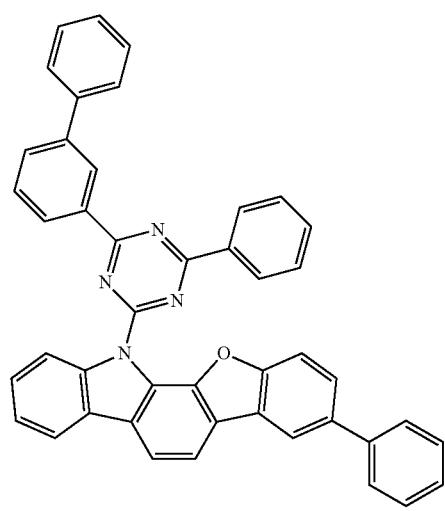
[52]
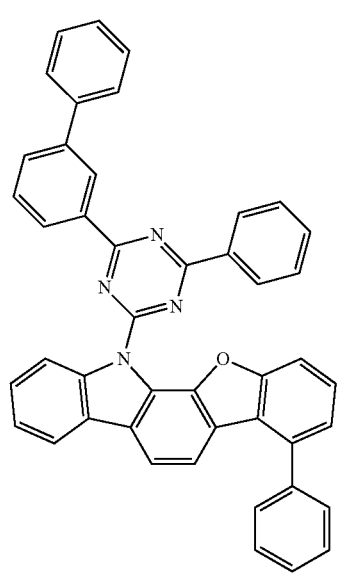
[53]
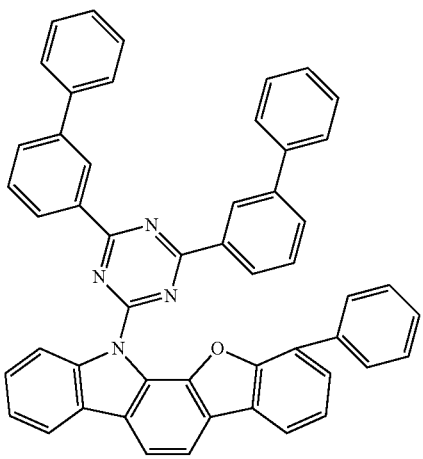
[54]
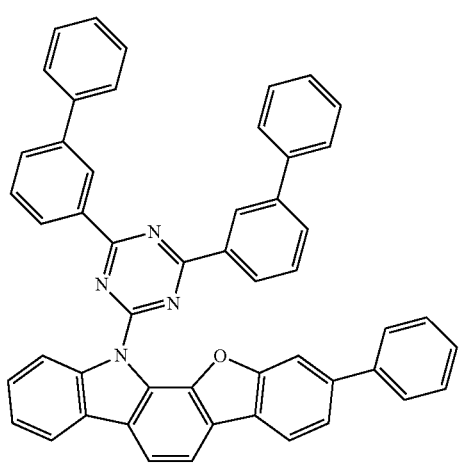
[55]
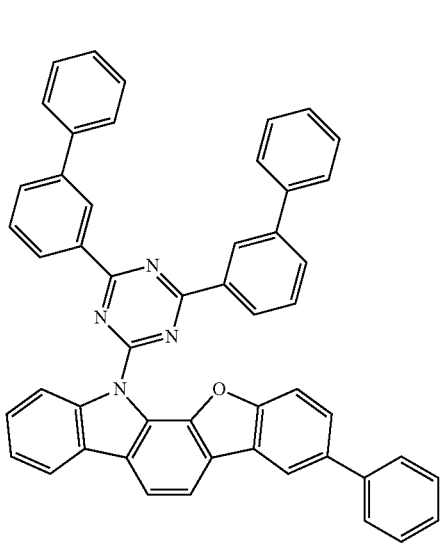

[56]
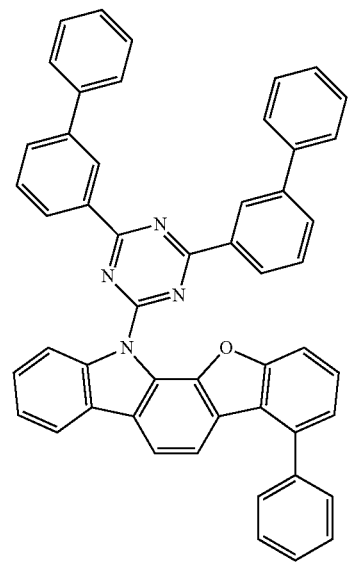
[57]
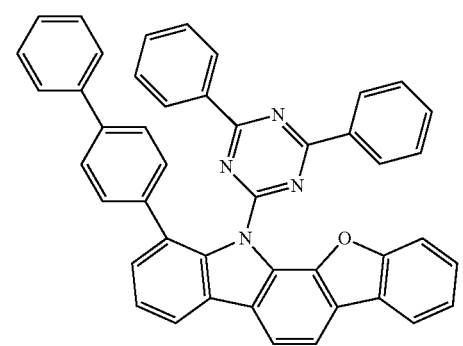
[58]
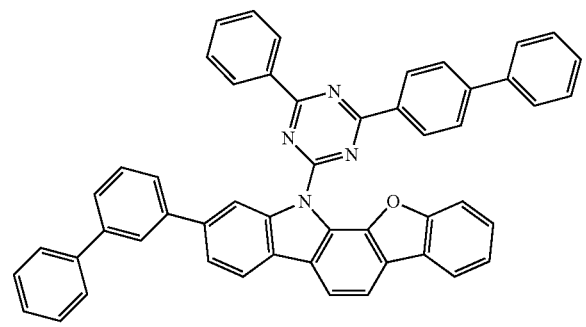
[59]
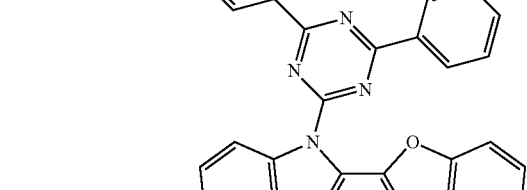
[60]
[61]
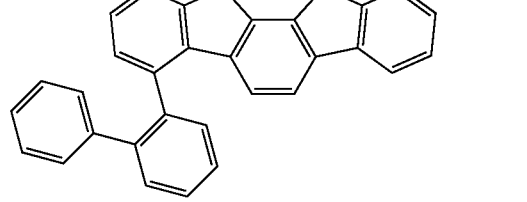

197
-continued
[62]
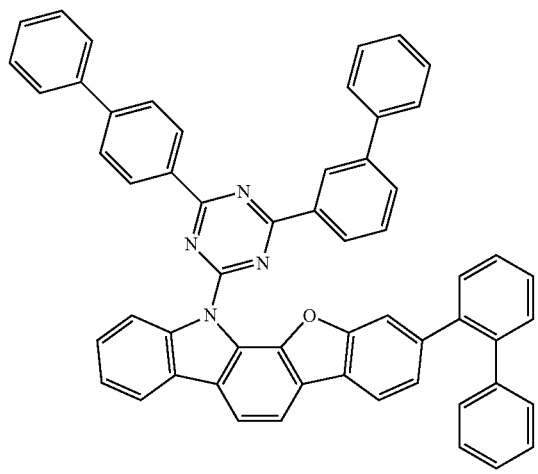
[63]
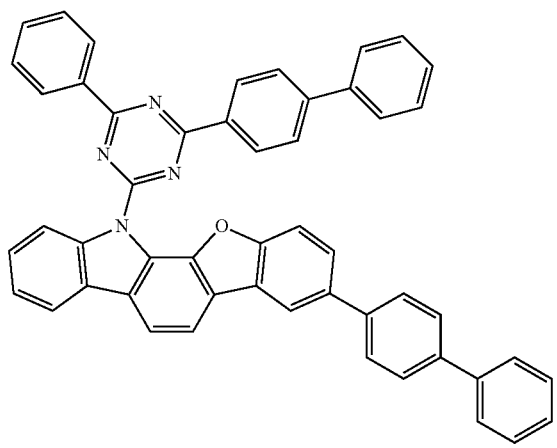
[64]
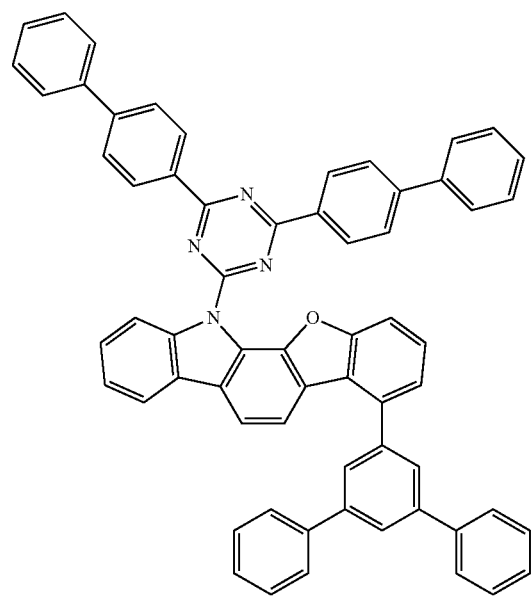
198
-continued
[65]
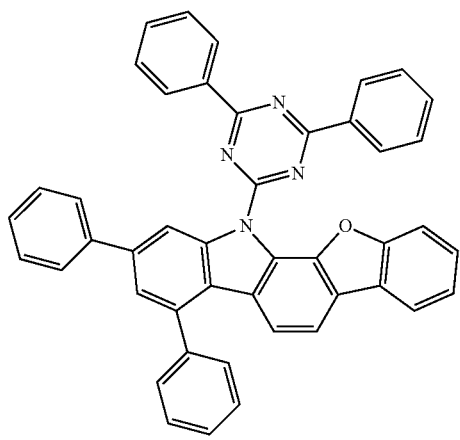
[66]
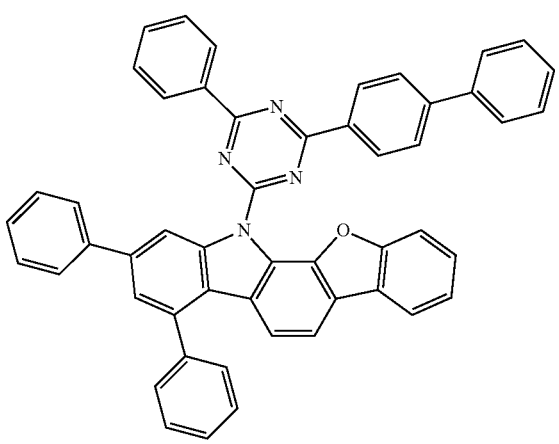
[67]
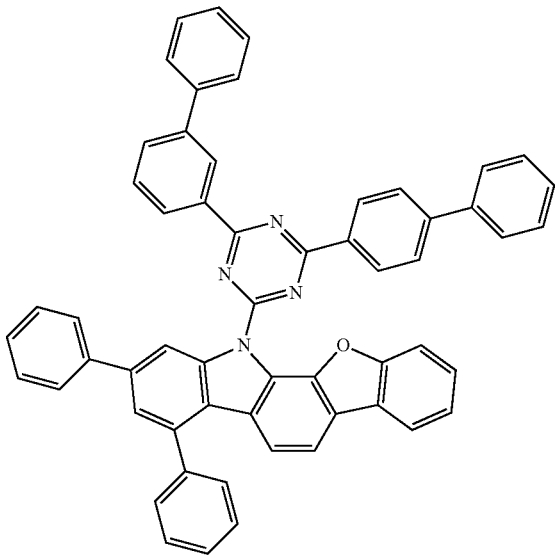

[68]
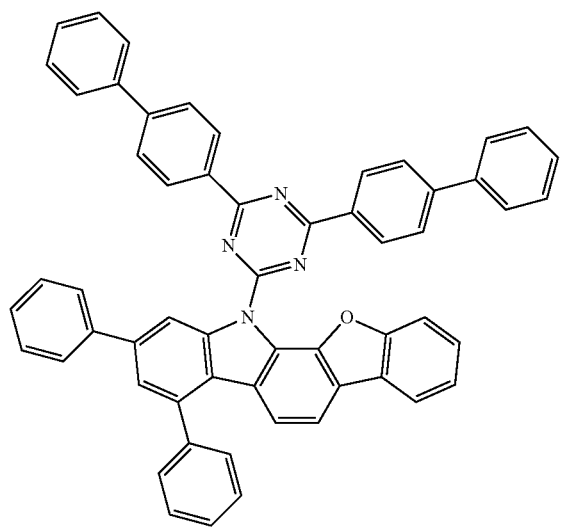
[69]
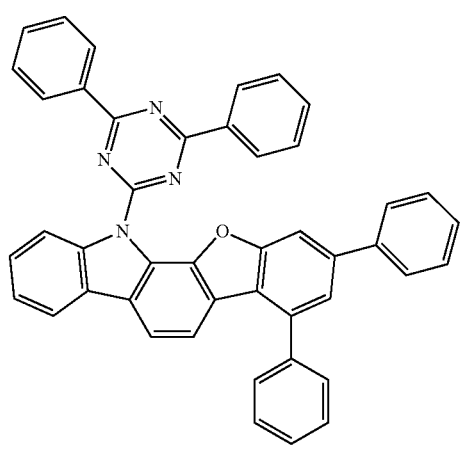
[70]
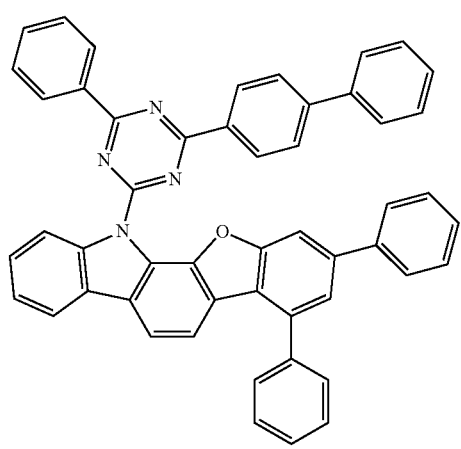
[71]
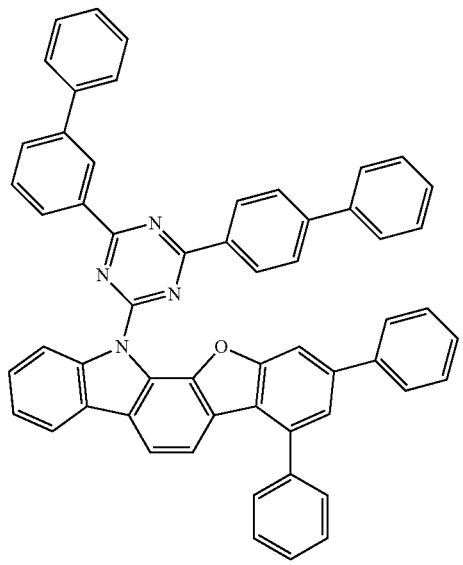
[72]
7. The composition as claimed in claim 1, wherein:
the second compound is represented by Chemical Formula 2, Chemical Formula 2 is represented by Chemical Formula 2-8:
[Chemical Formula 2-8]
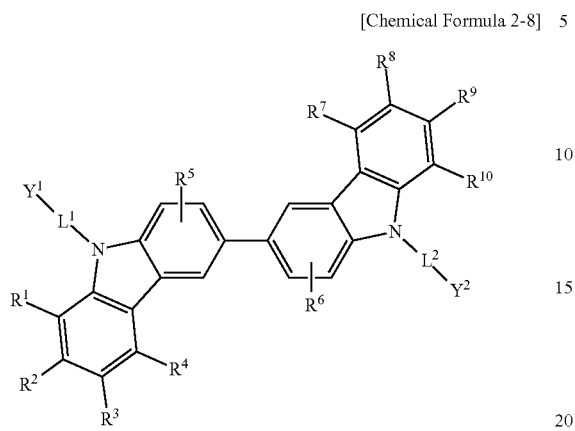
in Chemical Formula 2-8,
$R^1$ to $R^{10}$ are each independently hydrogen or a substituted or unsubstituted C6 to C12 aryl group, and
moieties *-$L^1$-$Y^1$ and *-$L^2$-$Y^2$ are each independently a moiety of Group II,
[Group II]
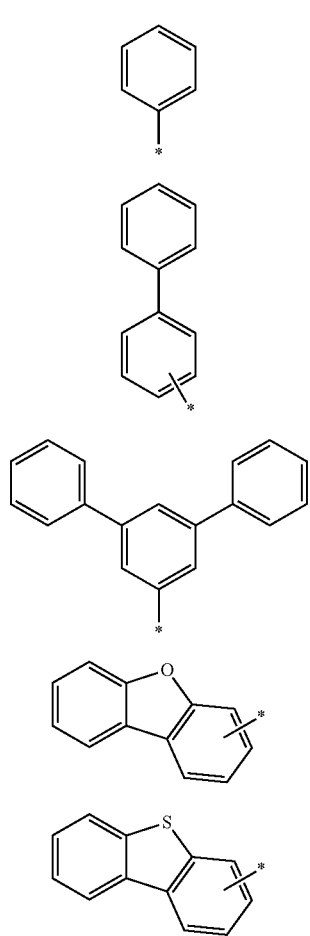
C-1
C-2
C-3
C-4
C-5
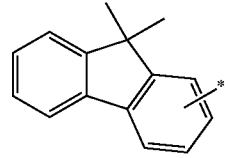
C-6
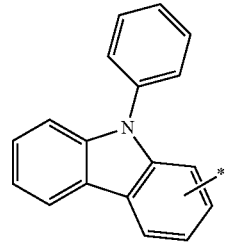
C-7
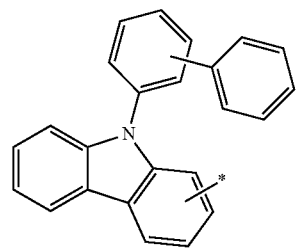
C-8
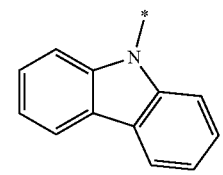
C-9
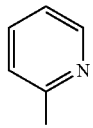
C-10
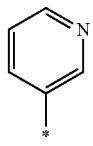
C-11
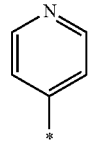
C-12
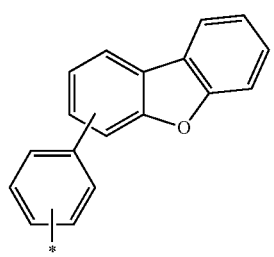
C-13

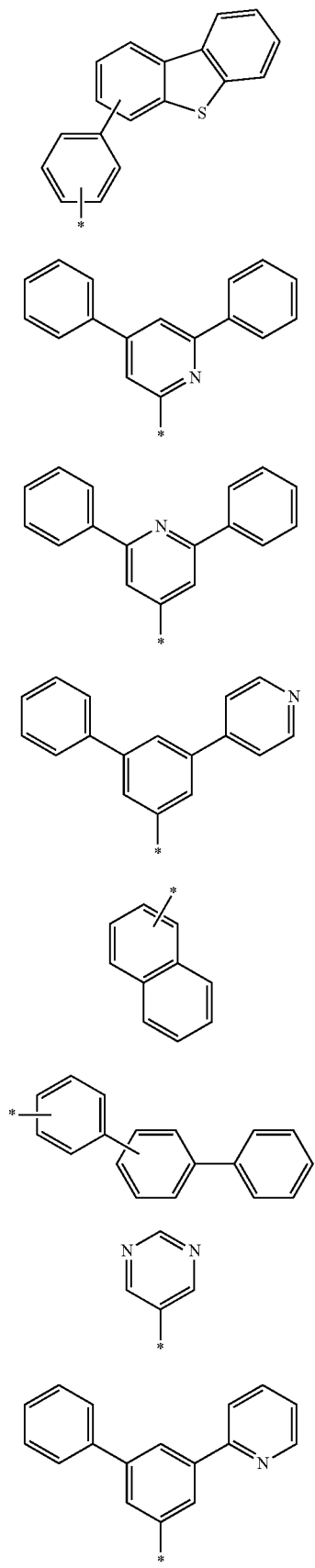
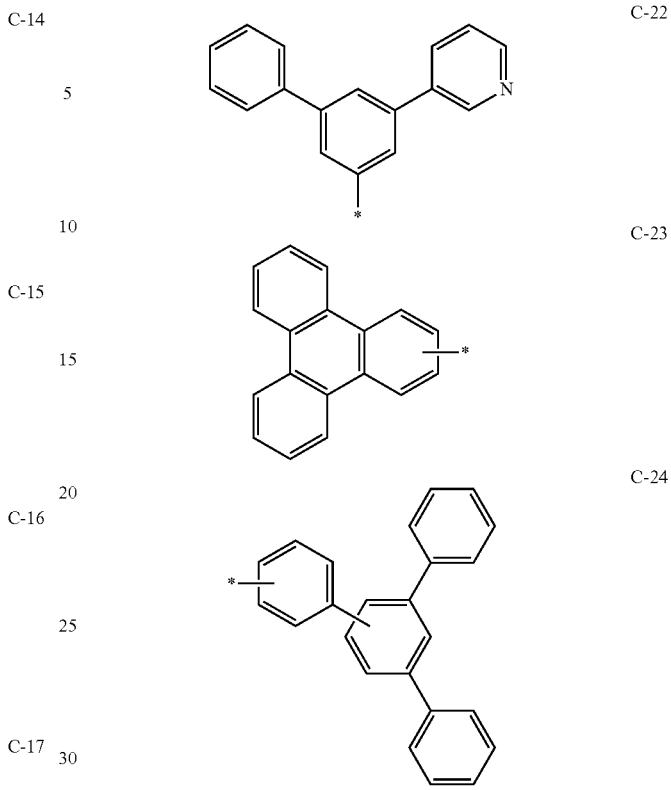

in Group II, * is a linking point.

8. The composition as claimed in claim 1, wherein:
the second compound is represented by the combination of Chemical Formula 3 and Chemical Formula 4,
the combination of Chemical Formula 3 and Chemical Formula 4 is represented by Chemical Formula 3C:

[Chemical Formula 3C]

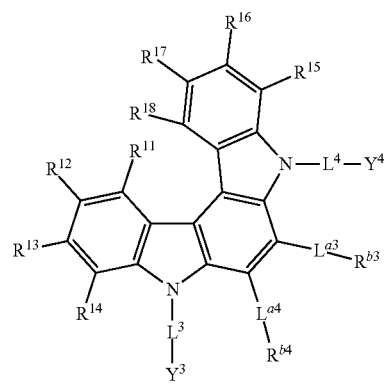

in Chemical Formula 3C,
$L^{a3}$ and $L^{a4}$ are each a single bond,
$L^3$ and $L^4$ are each independently a single bond or a substituted or unsubstituted C6 to C12 arylene group,
$R^{11}$ to $R^{18}$, $R^{b3}$, and $R^{b4}$ are each hydrogen, and
$Y^3$ and $Y^4$ are each independently a substituted or unsubstituted phenyl group, a substituted or unsubstituted naphthyl group, or a substituted or unsubstituted biphenyl group.

9. An organic optoelectronic device, comprising:
an anode and a cathode facing each other, and
at least one organic layer between the anode and the cathode,
wherein the at least one organic layer includes the composition for an organic optoelectronic device as claimed in claim 1.

10. The organic optoelectronic device as claimed in claim 9, wherein:
the organic layer includes a light emitting layer, and
the light emitting layer includes the composition for an organic optoelectronic device.

11. A display device comprising the organic optoelectronic device as claimed in claim 9.

* * * * *